(12) United States Patent
Webber et al.

(10) Patent No.: US 12,037,335 B2
(45) Date of Patent: *Jul. 16, 2024

(54) SUBSTITUTED PURINES AS TLR7 AGONISTS

(71) Applicant: Primmune Therapeutics, Inc., San Diego, CA (US)

(72) Inventors: Stephen E. Webber, San Diego, CA (US); James Richard Appleman, San Diego, CA (US)

(73) Assignee: Primmune Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/371,857

(22) Filed: Jul. 9, 2021

(65) Prior Publication Data

US 2022/0098198 A1  Mar. 31, 2022

Related U.S. Application Data

(63) Continuation of application No. 16/422,050, filed on May 24, 2019, now Pat. No. 11,059,824.

(60) Provisional application No. 62/676,433, filed on May 25, 2018.

(51) Int. Cl.
| | | |
|---|---|---|
| A61K 31/522 | (2006.01) |
| C07D 473/18 | (2006.01) |
| C07D 473/32 | (2006.01) |
| C07K 16/28 | (2006.01) |
| C07K 16/32 | (2006.01) |

(52) U.S. Cl.
CPC ......... C07D 473/18 (2013.01); C07D 473/32 (2013.01); *C07K 16/2887* (2013.01); *C07K 16/2893* (2013.01); *C07K 16/32* (2013.01); *C07K 2317/732* (2013.01)

(58) Field of Classification Search
CPC .............................. A61K 31/522; C07D 473/32
USPC ...................................................... 514/263.37
See application file for complete search history.

(56) References Cited

U.S. PATENT DOCUMENTS

| | | | |
|---|---|---|---|
| 5,011,828 | A | 4/1991 | Goodman et al. |
| 5,093,319 | A | 3/1992 | Higham et al. |
| 5,136,030 | A | 8/1992 | Chen |
| 5,476,659 | A | 12/1995 | Goodman et al. |
| 6,784,161 | B2 | 8/2004 | Ismaili et al. |
| 7,576,068 | B2 | 8/2009 | Averett |
| 7,858,637 | B2 | 12/2010 | Averett |
| 8,034,802 | B2 | 10/2011 | Averett |
| 8,097,718 | B2 | 1/2012 | Webber et al. |
| 8,211,863 | B2 | 7/2012 | Averett |
| 8,853,375 | B2 | 10/2014 | Kandimalla et al. |
| 2005/0090660 | A1 | 4/2005 | Watanabe et al. |
| 2011/0269707 | A1 | 11/2011 | Stuyver et al. |
| 2012/0028999 | A1 | 2/2012 | Averett |
| 2016/0194350 | A1 | 7/2016 | Chen et al. |
| 2016/0331758 | A1 | 11/2016 | Howbert et al. |
| 2018/0346572 | A1 | 12/2018 | Li |

FOREIGN PATENT DOCUMENTS

| | | | |
|---|---|---|---|
| WO | 9411003 A1 | 5/1994 | |
| WO | 9816184 A2 | 4/1998 | |
| WO | 2010111290 A1 | 9/2010 | |
| WO | 2013067597 A1 | 5/2013 | |
| WO | 2017118407 A1 | 7/2017 | |
| WO | WO-2019226977 A1 * | 11/2019 | ........... A61K 31/708 |

OTHER PUBLICATIONS

Jordan, V. C. Nature Reviews: Drug Discovery, 2, 2003, 205.*
Hackam, et al. JAMA, 296(14), 2006, 1731-1732.*
Bennett, et al. (1996) "Cecil Textbook of Medicine", 20th Edition, 1:1004-1010.
Cadena-Amaro, et al. (2005) "Synthesis and Incorporation into DNA Fragments of the Artificial Nucleobase, 2-Amino-8-Oxopurine", Bioorganic & Medicinal Chemistry Letters, 15(4):1069-1073.
Chen, et al. (1994) "Guanosine Derivatives as Immunostimulants. Discovery of Loxoribine", Nucleosides and Nucleotide, 13(1-3):551-562.
Dermer Gerald B. (Mar. 12, 1994) "Another Anniversary for the War on Cancer", Bio/Technology, 12:320 (4 pages).
Freshney (1983) "Culture of Animal Cells", Alan R. Liss Inc., 7 pages.
Golub, et al. (Oct. 15, 1999) "Molecular Classification of Cancer: Class Discovery and Class Prediction by Gene Expression Monitoring", Science, 286(5439):531-537.
Ohto, et al. (2014) "Structure and Function of toll-like Receptor 8", Microbes and Infection, 16:273-282.
Reitz, et al. (1994) "Small-Molecule Immunostimulants. Synthesis and Activity of 7,8-Disubstituted Guanosines and Structurally Related Compounds", Journal of Medicinal Chemistry, 37(21):3561-3578.

(Continued)

*Primary Examiner* — Douglas M Willis
(74) *Attorney, Agent, or Firm* — Mintz, Levin, Cohn, Ferris; Pooja Varshneya

(57) ABSTRACT

The present invention relates to TLR7 agonists according to Formula I and their use in the treatment of diseases such as cancer and infectious disease.

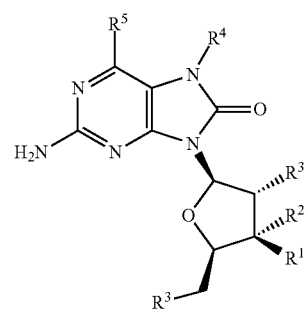

14 Claims, No Drawings

(56) References Cited

OTHER PUBLICATIONS

Yu, et al. (2013) "Dual Character of Toll-like Receptor Signaling: Pro-tumorigenic Effects and Anti-Tumor Functions", Biochimica et Biophysica Acta, 1835(2):144-154.
Zhao, et al. (Jul. 2014) "Toll-like Receptors and Prostate Cancer" Frontiers in Immunology, 6 pages.

* cited by examiner

SUBSTITUTED PURINES AS TLR7 AGONISTS

CROSS-REFERENCE

This Application is a Continuation of application Ser. No. 16/422,050 filed on May 24, 2019, which claims the benefit of U.S. Provisional Application Ser. No. 62/676,433 filed May 25, 2018. The entire contents of these applications are incorporated herein by reference.

FIELD OF THE INVENTION

The present invention provides TLR7 agonists and their uses in therapeutic applications. The invention provides methods for treating infections, immune disorders and cancer using TLR7 agonists.

BACKGROUND OF THE INVENTION

The ultimate goal of cancer immunotherapy is the eradication of tumor cells by the immune system. Both the innate and the adaptive arm of the immune system can contribute to eradication of tumor cells, with natural killer (NK) cells and T cells, respectively, as key players. Crucial in the adaptive immune response against tumor cells is the activation of CD8+ cytotoxic T lymphocytes (CTLs), able to exploit their cytotoxic potential against tumor cells after recognition of tumor-associated antigens (TAAs). Activation of naïve CD8+ cells occurs via antigen-presenting cells (APCs), with dendritic cells (DCs) considered as the most professional APCs. These cells capture and process TAAs, presenting the epitopes at their membrane in complex with major histocompatibility complex (MHC) molecules. Maturation of APCs by danger signals is essential for the presentation of epitopes in a stimulatory way to T cells.

Peripheral T-cell tolerance against TAAs prevents an effective immune response to tumors, despite the potential of TAA-specific T cells to eliminate tumor cells. The approaches to break this T-cell tolerance against TAAs can be divided into two groups: (a) active specific immunotherapy (also known as cancer vaccines) and (b) passive specific immunotherapy (by adoptive transfer of antitumor T cells or by monoclonal antibodies). Poor immunogenicity of tumor cells is also a potential problem in cancer immunotherapy. This low immunogenicity is a result of the fact that TAAs are mostly self-antigens, and also because of the downregulation of human leukocyte antigen and costimulatory molecules on the membranes of tumor cells. Moreover, tumor cells actively inhibit the immune system by the secretion of immunosuppressive factors that interfere with DC and T-cell function.

Toll-like receptors (TLRs) are a class of proteins that play a key role in the innate immune system. TLRs are a type of pattern recognition receptor (PRR) and recognize molecules that are broadly shared by pathogens but distinguishable from host molecules, collectively referred to as pathogen-associated molecular patterns (PAMPs). They are single, membrane-spanning, non-catalytic receptors usually expressed on sentinel cells such as macrophages and dendritic cells, that recognize structurally conserved molecules derived from microbes.

TLRs 3, 7, 8, and 9 form a group of intracellular TLRs and recognize bacterial or viral nucleic acids. The natural ligand for TLR7 and TLR8 is single-stranded RNA that is rich in guanosine and/or uridine. TLR7 and TLR8 are also activated by certain small synthetic compounds. The imidazoquinoline derivates imiquimod (R837) and resiquimod (R848) were described as TLR7 ligands in mice (Hemmi et al., 2002, Nat. Immunol. 3:196-200). Additionally, the guanosine analogue loxoribine was identified as a TLR7 ligand (Heil et al., 2003, Eur. J. Immunol. 33:2987-2997. Additional TLR7 and/or TLR8 ligands include CL097 (3M-001), 852A and CL075.

Despite the structural similarities between TLR7 and TLR8, their activation has distinct consequences on the innate immune cells and subsequent production of cytokines. TLR8 agonists are reportedly much more effective than TLR7 agonist at inducing pro-inflammatory cytokines and chemokines, such as tumor necrosis factor (TNF)-α, interleukin (IL)-12, and macrophage inflammatory protein (MIP)-1α, in peripheral blood mononuclear cells (PBMC). In contrast, TLR7 agonists reportedly activate plasmacytoid dendritic cells and induced the production of interferon (IFN)-α.

After the discovery of the effectiveness of the TLR7/8 agonist imiquimod to protect guinea pigs from herpes virus infection, imiquimod was also shown to be effective against several transplantable murine tumors. Clinical responsiveness to topical treatment with imiquimod (Aldara® 5% cream) was reportedly found to be effective for both primary skin tumors and cutaneous metastases. In these reports, no TAAs were added, and the immune-enhancing effects of imiquimod were sufficient to elicit an antitumor response. Imiquimod treatment was also reportedly associated with partial or total reversal of the aberrant expression of some genes in pre-malignant actinic keratoses, thereby demonstrating the ability of imiquimod to prevent the development of cancer.

Although treatment with TLR7 agonists in topical cancer show good anti-cancer effects, it has been challenging to administer these agonists by oral or systemic routes. In a clinical phase II study in hepatitis C virus infected patients, R848 was administered by the oral route and showed therapeutic effects on plasma hepatitis virus titers, but with dose-limiting toxicity. In another study, the TLR7 agonist 852A was tested in a phase II study in patients with metastatic melanoma with three weekly intravenous doses. The study showed prolonged disease stabilization in some patients, increased serum IFNα and IP-10, but dose-limiting toxicity in two patients. These studies indicate that systemic use of TLR7 agonists in patients may be a challenge due to a narrow therapeutic window.

SUMMARY OF THE INVENTION

The present invention generally relates to compounds useful as TLR7 agonists, compositions thereof, methods for their manufacture, and methods for their use.

In one embodiment the present invention is directed to TLR7 agonist compounds according to Formula I:

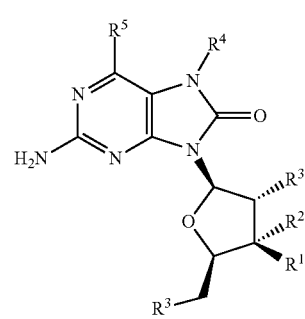

I wherein
R¹ is —H, —OH, —O—C(O)—R⁶ or —F,
R² is —H or —F,
R³ is independently —OH or —O—C(O)—R⁷,
R⁴ is —($C_1$-$C_8$)alkyl, —($C_1$-$C_8$)alkenyl, —($C_1$-$C_8$)alkynyl, —($C_1$-$C_8$)haloalkyl, —$(CH_2)_n$(cycloalkyl), —$(CH_2)_n$(heterocyclyl), —$(CH_2)_n$(aryl), —$(CH_2)_n$(heteroaryl) or —$(CH_2)_n$C(O)OR⁶,
R⁵ is —H, —OH, —OCH₃, —SH or —Cl,
R⁶ and R⁷ are independently —($C_1$-$C_8$)alkyl or aryl,
n is an integer 1, 2, 3, 4 or 5,
wherein each alkyl, cycloalkyl, alkenyl, alkynyl, haloalkyl, aryl, heteroaryl and heterocyclyl are independently optionally substituted by CN, NO₂, halogen, ($C_1$-$C_3$) alkyl, ($C_1$-$C_3$)haloalkyl, aryl, heteroaryl, OH, alkenyl, alkynyl, O—($C_1$-$C_3$)alkyl, O-(alkylene)aryl, O-(alkylene)heteroaryl, C(O)R⁸, S($C_1$-$C_8$)alkyl, S(O)alkyl, SO₂alkyl, C(O)OR⁸, C(O)NR⁸R⁸, C(O)NR⁸SO₂alkyl, NR⁸R⁸, NR⁸(CO)OR⁸, NH(CO)R⁸, NH(SO₂)alkyl or NH(SO₂)NR⁸R⁸, and R⁸ is independently —H, —OH, —($C_1$-$C_8$)alkyl, cycloalkyl, hetercyclyl, or the two R⁸'s of C(O)NR⁸R⁸ or NR⁸R⁸ combine together with the nitrogen atom to form a heterocycle;
or a pharmaceutically acceptable salt, pharmaceutically acceptable solvate or pharmaceutically acceptable hydrate thereof.

In other embodiments, the TLR7 agonist compound(s) of the invention may be used alone, or in association with other, further therapeutic agents and therapeutic procedures, for treating or preventing cancer or an infection or infectious disease in a subject in need of such treatment or prevention.

In other embodiments, the present invention provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient. Pharmaceutical compositions comprising a pharmaceutically acceptable carrier, diluent, or excipient, in association with further therapeutic agents are also part of the present invention.

The above embodiments and other aspects of the invention are readily apparent in the detailed description that follows. To this end, various references are set forth herein which describe in more detail certain background information, procedures, compounds and/or compositions, and are each hereby incorporated by reference in their entireties.

DETAILED DESCRIPTION

The present invention provides compounds as TLR7 agonists. The present invention includes TLR7 agonists that activate TLR7 without substantial activation of TLR8.
Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the therapeutic agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

"Amino" refers to the —NH₂ substituent.
"Aminocarbonyl" refers to the —C(O)NH₂ substituent.
"Carboxyl" refers to the —CO₂H substituent.
"Carbonyl" refers to a —C(O)— or —C(=O)— group. Both notations are used interchangeably within the specification.
"Cyano" refers to the —C≡N substituent.
"Acetyl" refers to the —C(O)CH₃ substituent.
"Hydroxy" or "hydroxyl" refers to the —OH substituent.
"Oxo" refers to a =O substituent.
"Thio" or "thiol" refer to a —SH substituent.
"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like. Moieties with which the alkyl group can be substituted with are selected from but not necessarily limited to the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Lower alkyl" has the same meaning as alkyl defined above but having from one to three carbon atoms ($C_1$-$C_3$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group. The aryl group can be substituted with, but not necessarily limited to, one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, 2 carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzoxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

The compounds of the invention may exhibit the phenomenon of tautomerism. While Formula I cannot expressly depict all possible tautomeric forms, it is to be understood that Formula I is intended to represent any tautomeric form of the depicted compound and not to be limited merely to a specific compound form depicted by the formula drawing. For example, when $R^5$ is OH it is understood for Formula I that regardless of whether or not the substituents are shown in their enol or keto form as shown below, they represent the same compound. It will be apparent to one skilled in the art, that compounds such as Compound 1:

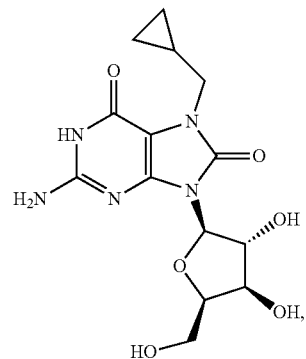

may exist in such tautomeric forms such as compounds 1A and 1B:

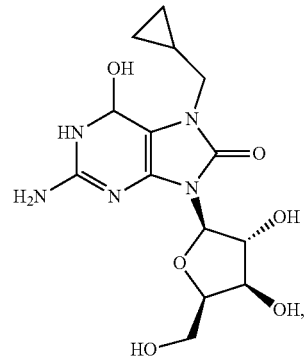

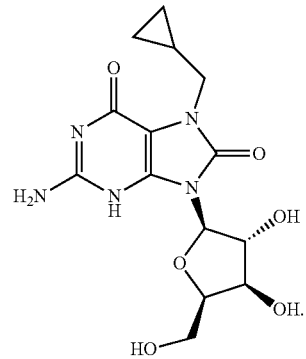

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

The term "in association with" indicates that the components administered in a method of the present invention can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

As used herein, the term "effective amount" refer to an amount of a TLR7 agonist compound of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of a compound or pharmaceutical composition thereof sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

A "subject" may be a mammal such as a human, dog, cat, horse, cow, mouse, rat, monkey (e.g., cynomolgous monkey, e.g., *Macaca fascicularis*) or rabbit. In preferred embodiments of the invention, the subject is a human subject.

TLR7 Agonists

One aspect of the invention comprises TLR7 agonist compounds of Formula I:

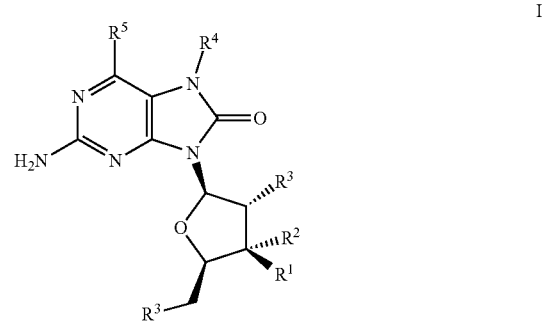

I wherein
$R^1$ is —H, —OH, —O—C(O)—$R^6$ or —F,
$R^2$ is —H or —F,
$R^3$ is independently —OH or —O—C(O)—$R^7$,
$R^4$ is —($C_1$-$C_8$)alkyl, —($C_1$-$C_8$)alkenyl, —($C_1$-$C_8$)alkynyl, —($C_1$-$C_8$)haloalkyl, —$(CH_2)_n$(cycloalkyl), —$(CH_2)_n$(heterocyclyl), —$(CH_2)_n$(aryl), —$(CH_2)_n$(heteroaryl) or —$(CH_2)_n$C(O)O$R^6$,
$R^5$ is —H, —OH, —O$CH_3$, —SH or —Cl,
$R^6$ and $R^7$ are independently —($C_1$-$C_8$)alkyl or aryl,
n is an integer 1, 2, 3, 4 or 5,
wherein each alkyl, cycloalkyl, alkenyl, alkynyl, haloalkyl, aryl, heteroaryl and heterocyclyl are independently optionally substituted by CN, $NO_2$, halogen, ($C_1$-$C_3$)alkyl, ($C_1$-$C_3$)haloalkyl, aryl, heteroaryl, OH, alkenyl, alkynyl, O—($C_1$-$C_3$)alkyl, O-(alkylene)aryl, O-(alkylene)heteroaryl, C(O)$R^8$, S($C_1$-$C_8$)alkyl, S(O)alkyl, $SO_2$alkyl, C(O)O$R^8$, C(O)N$R^8R^8$, C(O)N$R^8SO_2$alkyl, N$R^8R^8$, N$R^8$(CO)O$R^8$, NH(CO)$R^8$, NH($SO_2$)alkyl or NH($SO_2$)N$R^8R^8$, and $R^8$ is independently —H, —OH, —($C_1$-$C_8$)alkyl, cycloalkyl, hetercyclyl, or the two $R^8$'s of C(O)N$R^8R^8$ or N$R^8R^8$ combine together with the nitrogen atom to form a heterocycle;
or a pharmaceutically acceptable salt, pharmaceutically acceptable solvate or pharmaceutically acceptable hydrate thereof.
In an embodiment $R^1$ is —H, —OH, or —F.
In an embodiment $R^1$ is —OH.
In an embodiment $R^1$ is —H
In an embodiment $R^1$ is —F
In an embodiment $R^2$ is —H or —F.
In an embodiment $R^2$ is —H In an embodiment $R^2$ is —F In an embodiment $R^3$ is —OH or —O—C(O)—CH$_3$.

In an embodiment $R^3$ is —OH.

In an embodiment $R^3$ is —O—C(O)—CH$_3$.

In an embodiment $R^1$ and $R^3$ are independently —OH.

In an embodiment $R^1$ and $R^3$ are independently —O—C(O)—CH$_3$.

In an embodiment $R^4$ is —(CH$_2$)(cyclopropyl), —CH$_2$C≡CH, —(CH$_2$)$_3$CH$_3$ or —CH$_2$CF$_3$.

In an embodiment $R^4$ is —(CH$_2$)(cyclopropyl).

In an embodiment $R^4$ is —CH$_2$C≡CH.

In an embodiment $R^4$ is —(CH$_2$)$_3$CH$_3$.

In an embodiment $R^4$ is —CH$_2$CF$_3$.

In an embodiment $R^5$ is —H or —OH.

In an embodiment $R^5$ is —H.

In an embodiment $R^5$ is —OH.

In an embodiment $R^7$ is —(C$_1$-C$_8$)alkyl.

In an embodiment $R^7$ is —CH$_3$.

In an embodiment $R^8$ is —H, —OH, —CH$_3$, or —CH$_2$CH$_3$.

In an embodiment $R^8$ is —H.

In an embodiment $R^8$ is —OH.

In an embodiment $R^8$ is —CH$_3$.

In an embodiment $R^8$ is —CH$_2$CH$_3$.

In an embodiment the compound of Formula I is Compound 1 which may be referred to as 2-Amino-7-(cyclopropylmethyl)-9-((2R,3R,4R,5R)-3,4-dihydroxy-5-(hydroxymethyl)-tetrahydrofuran-2-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 2 which may be referred to as 7-Allyl-2-amino-9-((2R,3R,4R,5R)-3,4-dihydroxy-5-(hydroxymethyl)-tetrahydrofuran-2-yl)-7,9-dihydro-1H-purine-6,8-dione; or 7-Allyl-2-amino-9-(β-D-xylofurosyl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 3 which may be referred to as 2-Amino-7-(cyclopropylmethyl)-9-((2R,3R,4R,5R)-3,4-dihydroxy-5-(hydroxymethyl)-tetrahydrofuran-2-yl)-7,9-dihydro-purin-8-one, or a pharmaceutically acceptable salt, pharmaceutically acceptable solvate or pharmaceutically acceptable hydrate thereof.

In another embodiment the compound of Formula I is Compound 4 which may be referred to as (2R,3R,4R,5R)-2-(Acetoxymethyl)-5-(2-amino-7-(cyclopropylmethyl)-8-oxo-7,8-dihydro-9H-purin-9-yl) tetrahydrofuran-3,4-diyl diacetate, or a pharmaceutically acceptable salt, pharmaceutically acceptable solvate or pharmaceutically acceptable hydrate thereof.

In another embodiment the compound of Formula I is Compound 27 which may be referred to as 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 30 which may be referred to as 2-Amino-9-((2R,3R,5S)-3-hydroxy-5-(hydroxymethyl)tetrahydrofuran-2-yl)-7-(prop-2-yn-1-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 29 which may be referred to as ((2S,4R,5R)-4-Acetoxy-5-(2-amino-8-oxo-7-(prop-2-yn-1-yl)-7,8-dihydro-9H-purin-9-yl)tetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 26 which may be referred to as 2-Amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 32 which may be referred to as 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 31 which may be referred to as ((2R,3R,4S,5R)-4-Acetoxy-5-(2-amino-8-oxo-7-(prop-2-yn-1-yl)-7,8-dihydro-9H-purin-9-yl)-3-fluorotetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 28 which may be referred to as 2-Amino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 32S which may be referred to as 2-Amino-9-((2R,3S,4R,5R)-4-fluoro-3-hydroxy-5-(hydroxymethyl)tetrahydrofuran-2-yl)-7-(prop-2-yn-1-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 31S which may be referred to as ((2R,3S,4S,5R)-4-Acetoxy-5-(2-amino-8-oxo-7-(prop-2-yn-1-yl)-7,8-dihydro-9H-purin-9-yl)-3-fluorotetrahydrofuran-2-yl) methyl acetate, or a pharmaceutically acceptable salt, pharmaceutically acceptable solvate or pharmaceutically acceptable hydrate thereof.

In another embodiment the compound of Formula I is Compound 135 which may be referred to as 2-Amino-7-butyl-9-((2R,3S,4S,5R)-4-fluoro-3-hydroxy-5-(hydroxymethyl)tetrahydrofuran-2-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 337 which may be referred to as 2-Amino-7-butyl-9-((2R,3S,4S,5R)-4-fluoro-3-hydroxy-5-(hydroxymethyl)tetrahydrofuran-2-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 336 which may be referred to as ((2R,3R,4S,5R)-4-Acetoxy-5-(2-amino-7-butyl-8-oxo-7,8-dihydro-9H-purin-9-yl)-3-fluorotetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 37 which may be referred to as 2-Amino-7-butyl-9-((2R,3R,5S)-3-hydroxy-5-(hydroxymethyl)tetrahydrofuran-2-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 225 which may be referred to as 2-Amino-7-butyl-9-((2R,3R,5S)-3-hydroxy-5-(hydroxymethyl)tetrahydrofuran-2-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 224 which may be referred to as ((2S,4R,5R)-4-Acetoxy-5-(2-amino-7-butyl-8-oxo-7,8-dihydro-9H-purin-9-yl)tetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 138 which may be referred to as 2-Amino-9-((2R,3S,4S,5R)-4-fluoro-3-hydroxy-5-(hydroxymethyl)tetrahydrofuran-2-yl)-7-(2,2,2-trifluoroethyl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 343 which may be referred to as 2-Amino-9-((2R,3S,4S,5R)-4-fluoro-3-hydroxy-5-(hydroxymethyl)tetrahydrofuran-2-yl)-7-(2,2,2-trifluoroethyl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 342 which may be referred to as ((2R,3R,4S,5R)-4-Acetoxy-5-(2-amino-8-oxo-7-(2,2,2-trifluoroethyl)-7,8-dihydro-9H-purin-9-yl)-3-fluorotetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 80 which may be referred to as 2-Amino-9-((2R,3R,5S)-3-hydroxy-5-(hydroxymethyl)tetrahydrofuran-2-yl)-7-(2,2,2-trifluoroethyl)-7,9-dihydro-1H-purine-6,8-dione or a pharmaceutically acceptable salt, pharmaceutically acceptable solvate or pharmaceutically acceptable hydrate thereof.

In another embodiment the compound of Formula I is Compound 231 which may be referred to as 2-Amino-9-((2R,3R,5S)-3-hydroxy-5-(hydroxymethyl)tetrahydrofuran-2-yl)-7-(2,2,2-trifluoroethyl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 230 which may be referred to as ((2S,4R,5R)-4-Acetoxy-5-(2-amino-8-oxo-7-(2,2,2-trifluoroethyl)-7,8-dihydro-9H-purin-9-yl)tetrahydrofuran-2-yl)methyl acetate, or a pharmaceutically acceptable salt, pharmaceutically acceptable solvate or pharmaceutically acceptable hydrate thereof.

In another embodiment the compound of Formula I is Compound 134 which may be referred to as 2-Amino-7-(cyclopropylmethyl)-9-((2R,3S,4S,5R)-4-fluoro-3-hydroxy-5-(hydroxymethyl)tetrahydrofuran-2-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 335 which may be referred to as 2-Amino-7-(cyclopropylmethyl)-9-((2R,3S,4S,5R)-4-fluoro-3-hydroxy-5-(hydroxymethyl)tetrahydrofuran-2-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 334 which may be referred to as ((2R,3R,4S,5R)-4-Acetoxy-5-(2-amino-7-(cyclopropylmethyl)-8-oxo-7,8-dihydro-9H-purin-9-yl)-3-fluorotetrahydrofuran-2-yl) methyl acetate, or a pharmaceutically acceptable salt, pharmaceutically acceptable solvate or pharmaceutically acceptable hydrate thereof.

In another embodiment the compound of Formula I is Compound 77 which may be referred to as 2-Amino-7-(cyclopropylmethyl)-9-((2R,3R,5S)-3-hydroxy-5-(hydroxymethyl)tetrahydrofuran-2-yl)-7,9-dihydro-1H-purine-6,8-dione, or a pharmaceutically acceptable salt, pharmaceutically acceptable solvate or pharmaceutically acceptable hydrate thereof.

In another embodiment the compound of Formula I is Compound 223 which may be referred to as 2-Amino-7-(cyclopropylmethyl)-9-((2R,3R,5S)-3-hydroxy-5-(hydroxymethyl)tetrahydrofuran-2-yl)-7,9-dihydro-8H-purin-8-one, or a pharmaceutically acceptable salt, pharmaceutically acceptable solvate or pharmaceutically acceptable hydrate thereof.

In another embodiment the compound of Formula I is Compound 222 which may be referred to as ((2S,4R,5R)-4-Acetoxy-5-(2-amino-7-(cyclopropylmethyl)-8-oxo-7,8-dihydro-9H-purin-9-yl)tetrahydrofuran-2-yl)methyl acetate, or a pharmaceutically acceptable salt, pharmaceutically acceptable solvate or pharmaceutically acceptable hydrate thereof.

In another embodiment the compound of Formula I is selected from Table 1, with loxoribine as a comparative.

TABLE 1

Compounds of Formula I

| COMPOUND | $R^1$ | $R^2$ | $R^3$ | $R^4$ | $R^5$ |
| --- | --- | --- | --- | --- | --- |
| Loxoribine | —H | —OH | —OH | —CH$_2$—CH=CH$_2$ | —OH |
| Compound 1 | —OH | —H | —OH | —(CH$_2$)(cyclopropyl) | —OH |
| Compound 2 | —OH | —H | —OH | —CH$_2$—CH=CH$_2$ | —OH |
| Compound 3 | —OH | —H | —OH | —(CH$_2$)(cyclopropyl) | —H |
| Compound 4 | —O—C(O)—CH3 | —H | —O—C(O)—CH3 | —(CH$_2$)(cyclopropyl) | —H |
| Compound 26 | —H | —H | —OH | —CH$_2$C≡CH | —OH |
| Compound 30 | —H | —H | —OH | —CH$_2$C≡CH | —H |
| Compound 29 | —H | —H | —O—C(O)—CH3 | —CH$_2$C≡CH | —H |
| Compound 27 | —H | —F | —OH | —CH$_2$C≡CH | —OH |

TABLE 1-continued

Compounds of Formula I

| COMPOUND | R$^1$ | R$^2$ | R$^3$ | R$^4$ | R$^5$ |
|---|---|---|---|---|---|
| Compound 32 | —H | —F | —OH | —CH$_2$C≡CH | —H |
| Compound 31 | —H | —F | —O—C(O)—CH3 | —CH$_2$C≡CH | —H |
| Compound 28 | —F | —H | —OH | —CH$_2$C≡CH | —OH |
| Compound 32S | —F | —H | —OH | —CH$_2$C≡CH | —H |
| Compound 31S | —F | —H | —O—C(O)—CH3 | —CH$_2$C≡CH | —H |
| Compound 135 | —H | —F | —OH | —(CH$_2$)$_3$CH$_3$ | —OH |
| Compound 337 | —H | —F | —OH | —(CH$_2$)$_3$CH$_3$ | —H |
| Compound 336 | —H | —F | —O—C(O)—CH3 | —(CH$_2$)$_3$CH$_3$ | —H |
| Compound 37 | —H | —H | —OH | —(CH$_2$)$_3$CH$_3$ | —OH |
| Compound 225 | —H | —H | —OH | —(CH$_2$)$_3$CH$_3$ | —H |
| Compound 224 | —H | —H | —O—C(O)—CH3 | —(CH$_2$)$_3$CH$_3$ | —H |
| Compound 138 | —H | —F | —OH | —CH$_2$CF$_3$ | —OH |
| Compound 343 | —H | —F | —OH | —CH$_2$CF$_3$ | —H |
| Compound 342 | —H | —F | —O—C(O)—CH3 | —CH$_2$CF$_3$ | —H |
| Compound 80 | —H | —H | —OH | —CH$_2$CF$_3$ | —OH |
| Compound 231 | —H | —H | —OH | —CH$_2$CF$_3$ | —H |
| Compound 230 | —H | —H | —O—C(O)—CH3 | —CH$_2$CF$_3$ | —H |
| Compound 134 | —H | —F | —OH | —(CH$_2$)(cyclopropyl) | —OH |
| Compound 335 | —H | —F | —OH | —(CH$_2$)(cyclopropyl) | —H |
| Compound 334 | —H | —F | —O—C(O)—CH3 | —(CH$_2$)(cyclopropyl) | —H |
| Compound 77 | —H | —H | —OH | —(CH$_2$)(cyclopropyl) | —OH |
| Compound 223 | —H | —H | —OH | —(CH$_2$)(cyclopropyl) | —H |
| Compound 222 | —H | —H | —O—C(O)—CH3 | —(CH$_2$)(cyclopropyl) | —H |

General Experimental

Compounds of Formula I can be prepared via the general methods described below.

In one method (Scheme 1) the synthetic preparation may originate from a guanosine nucleoside analog II where R$^1$ can be H, OH, F and R$^2$ is H or F and R$^3$ is OH. The C-8 of the guanine base can be brominated under conditions described by Holmes, et al., JACS, 1964, p. 1242 and Sheu et al., JACS, 1995, p. 6439 to give an 8-bromo-guanosine derivative III. Oxygen can be introduced at C-8 by the S$_N$Ar displacement of the bromine of III with an alkoxide of benzyl alcohol described by Holmes, et al., JACS, 1965, p. 1772 and Sheu et al., JACS, 1995, p. 6439 to give an 8-benzyloxo-guano sine derivative IV. Before debenzylation of the oxygen at C-8 it is necessary to protect the nitrogen at the N-1 position in order to achieve selective alkylation of N-7. Broom et al., JOC, 1969, p. 1025 describes the amination of the N-1 of guanosine that in essence acts as a protecting group. Thus, intermediate IV can be exposed to hydroxylamine-O-sulfonic acid under basic conditions to give an N-1 amino-guanosine derivative V. The benzyl group can then be removed from the C-8 oxygen under a number of de-etherification reaction conditions, preferably via catalytic hydrogenation with palladium metal to give cyclic urea intermediate VI. N-7 alkylation of intermediate VI can be accomplished under basic conditions with R$^4$-Lv to give an N-7 alkyl intermediate VII. R$^4$ is a C$_1$-C$_8$ alkyl group and Lv is defined as a leaving group such as a halogen atom, OSO$_2$CH$_3$ (mesylate), OSO$_2$CF$_3$ (triflate), or OSO$_2$Ar where Ar is 4-methylphenyl (tosylate). The final step in the synthesis is an N-1 deamination of VII achieved by forming a diazonium salt with sodium nitrite under aqueous acidic conditions as described in U.S. Pat. No. 5,093,318 to give the desired compounds of Formula I, where R$^5$ is OH.

Scheme 1

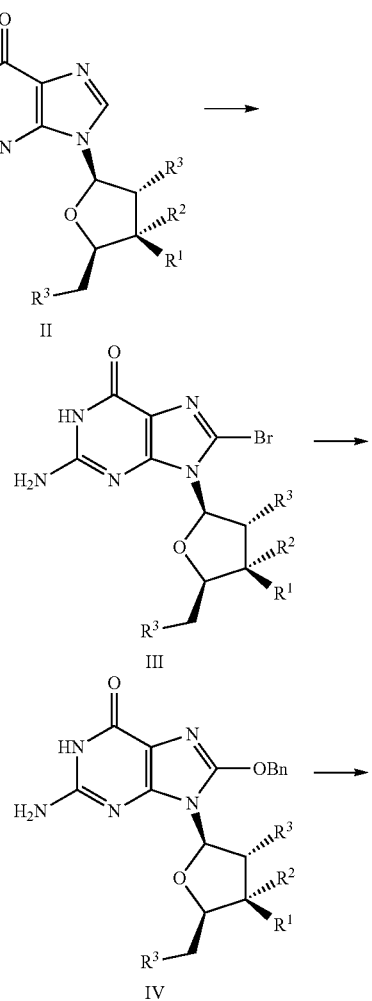

-continued

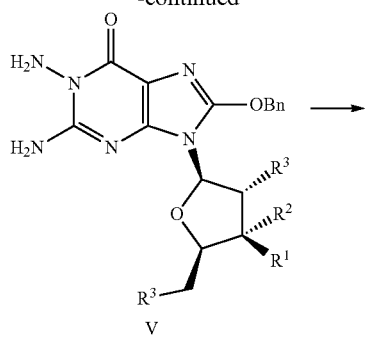

V

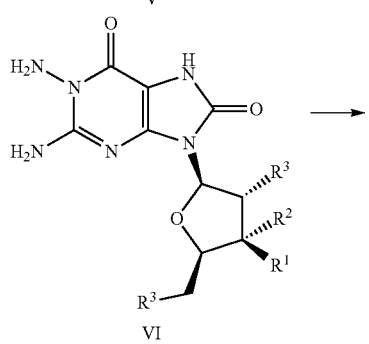

VI

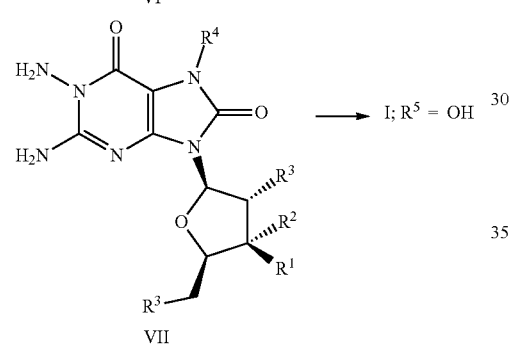

VII

→ I; $R^5$ = OH

Scheme 2

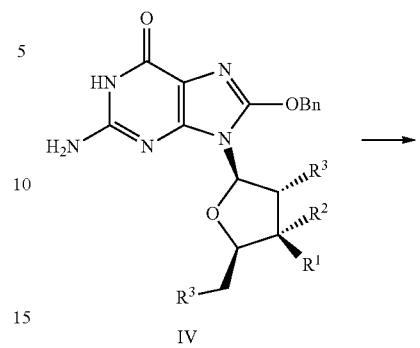

IV

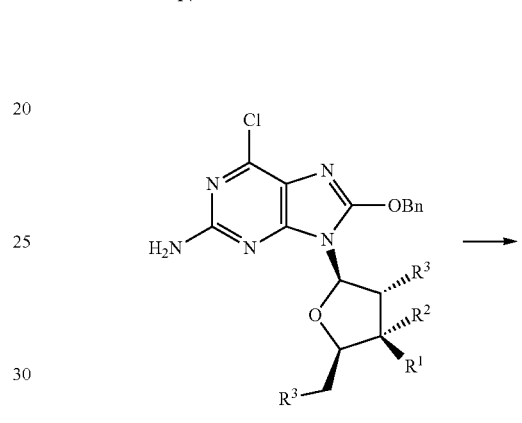

VIII

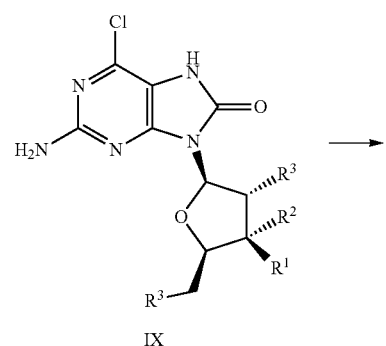

IX

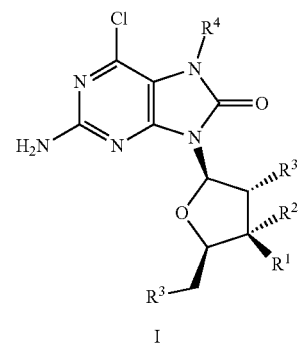

I

An alternate method (Scheme 2) begins with intermediate IV (described above) where the amide oxygen can be converted to the 6-chlorine purine intermediate VIII typically with phosphorus oxychloride. The benzyl ether at C-8 can then selectively be removed by catalytic hydrogenation or with a boron tri-halide such as $BCl_3$ to give intermediate IX. N-7 alkylation of intermediate IX can be accomplished under basic conditions with $R^4$-Lv to give an N-7 alkyl compounds of Formula I. $R^4$ and Lv are defined in Method A.

Compounds of Formula I where $R^5$ is a chlorine may be further transformed into other compounds of Formula I where $R^5$ is H, OH or $OCH_3$. To obtain compounds of Formula I where $R^3$ is H, a hydro-dehalogenation reaction may be utilized. This transformation can usually be conducted under hydrogenation conditions with Pd of Pt or with activated zinc in acetic acid. Displacement of the C-6 chlorine to a hydroxyl group can be accomplished under aqueous basic or acidic conditions. This chlorine can also be displaced with methoxide anion to produce compounds of Formula I where $R^5$ is $OCH_3$.

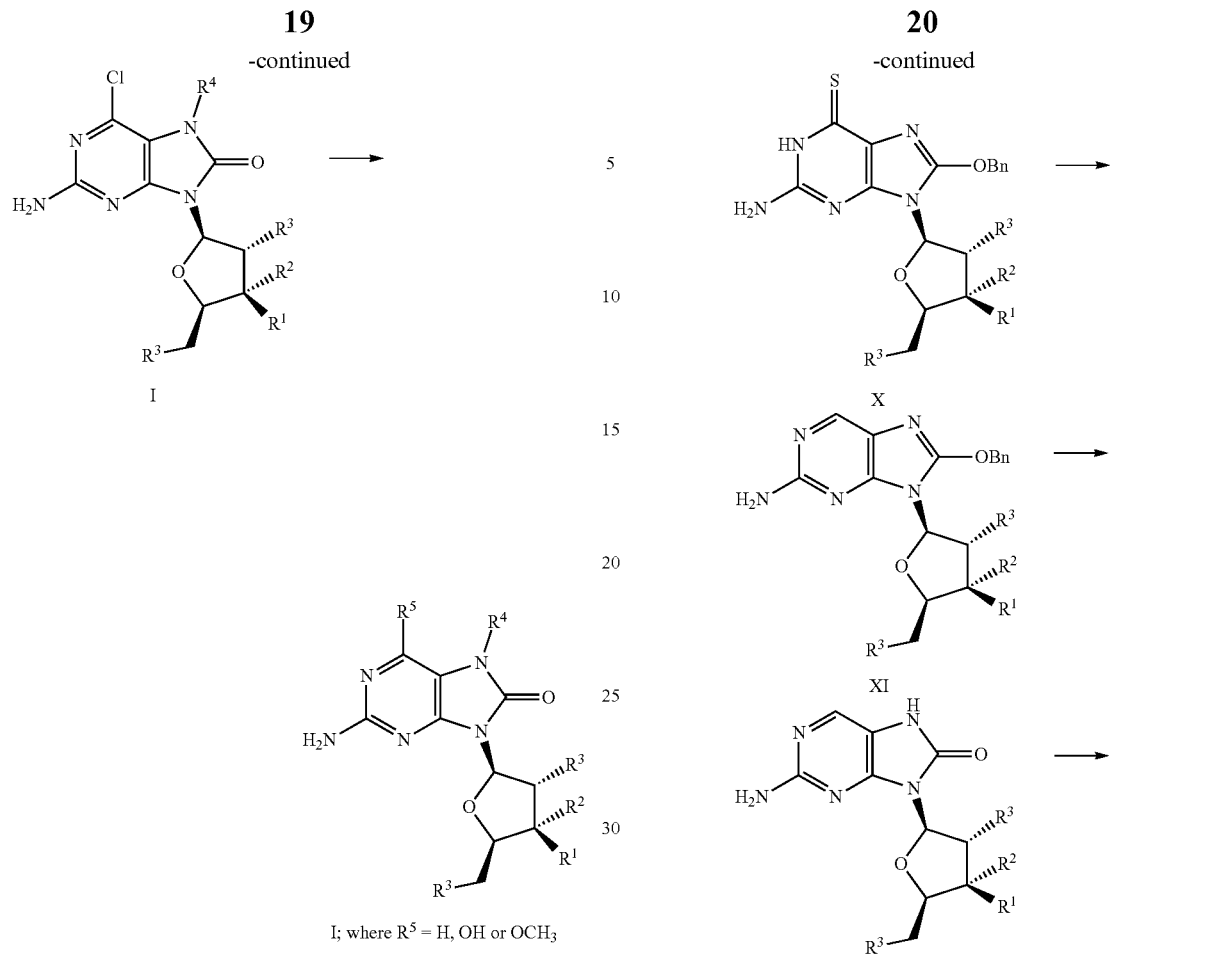

I; where R⁵ = H, OH or OCH₃

Yet another method (Scheme 3) begins with intermediate IV (described above) where the amide oxygen can be converted to the 6-thio purine intermediate X typically with phosphorus pentasulfide, Lawesson's reagent or equivalent. The thio group can be reduced with Raney nickel to afford intermediate XI. The benzyl ether at C-8 can then selectively be removed by catalytic hydrogenation or with a boron tri-halide such as BCl₃ to give intermediate XII. N-7 alkylation of intermediate XII can be accomplished under basic conditions with R⁴-Lv to give N-7 alkyl compounds of Formula I. R⁴ and Lv are defined above.

Scheme 3

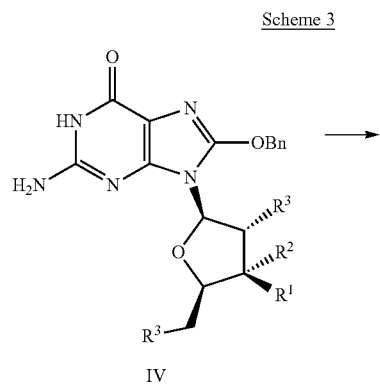

IV

In yet another method (Scheme 4), 6-chloro-2,4-diaminopyrimidine [156-83-2] can be halogenated with either bromine, N-bromosuccinimide or N-iodosuccinimide to give the 5-halo-6-chloro-2,4-diaminopyrimidine XIII. Exposing intermediate XIII to an alkylisocyanate can form the corresponding urea XIV. Intramolecular cyclization of intermediate XIV can be accomplished under reaction conditions with an appropriate Pd catalyst and phosphine ligand or by heating with copper (I) iodide in a polar aprotic solvent with an amine base to afford the 2-amino-6-chloro-7-alkyl-7,9-dihydro-8H-purin-8-ones of Formula XV. The 6-chloro group can then be hydro-dehalogenated with hydrogen and Pd or Pt metal to form XVI where R⁵ is H. To form the 6,8-dioxypurine XVII where R⁵ is OH, XV can be exposed to either aqueous HCl or NaOH. The 6-chloro group of XV can also be displacement with methoxide anion to give XVIII where R⁵ is OCH₃, or with sodium hydrogensulfide to give XIX where $R^5$ is SH. In general, purine intermediates XV-XIX can then be exposed to a sugar derivative XX under a variety nucleoside forming reaction conditions, followed by hydroxyl deprotection to give 9-β-furano-purine nucleoside analogs of Formula I. For a comprehensive review of the synthetic conditions to form nucleosides see Romeo, et al., *Chem. Rev.* 2010, 110, p. 3337-3370.

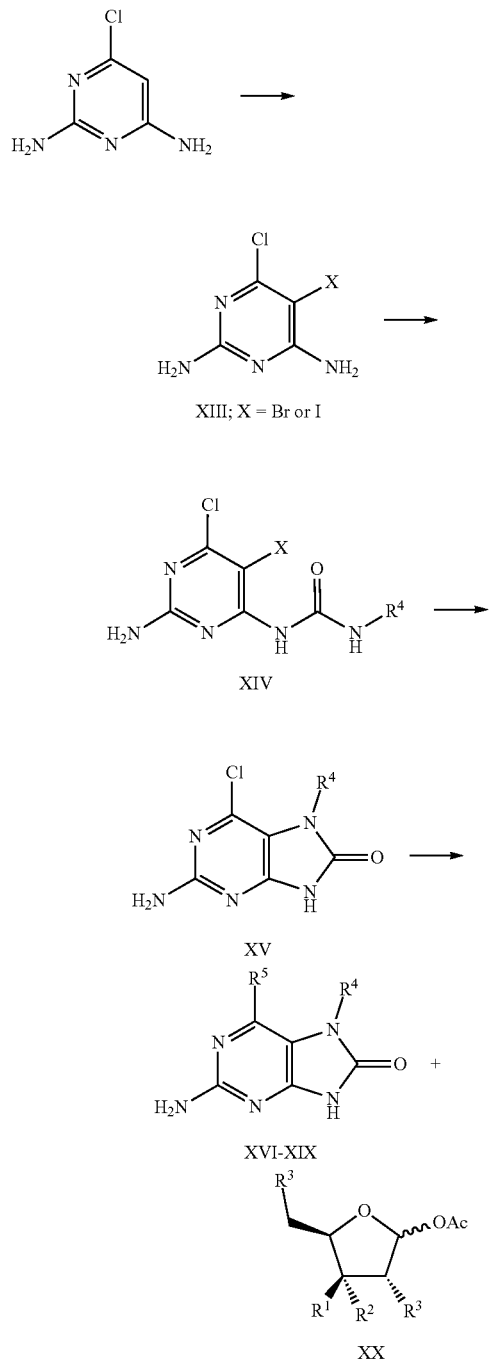

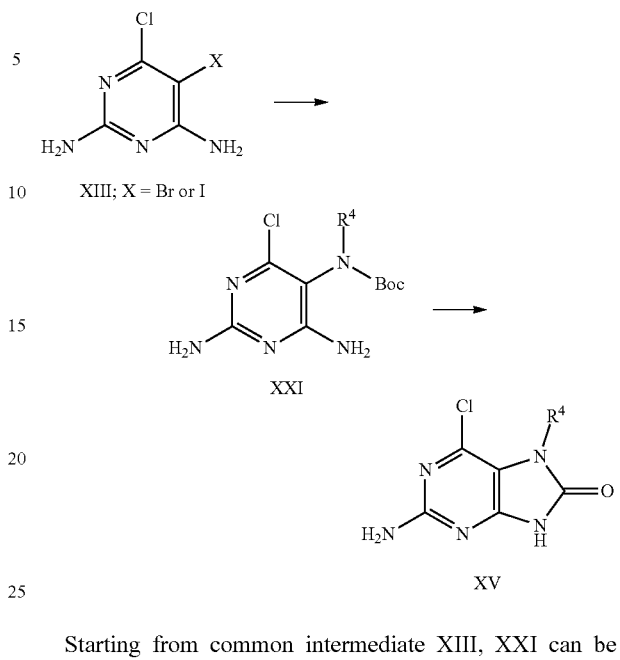

Starting from common intermediate XIII, XXI can be generated from a tert-butyl alkyl carbamate under reaction conditions with an appropriate Pd catalyst and phosphine ligand. This carbamate intermediate can then undergo intramolecular cyclization under thermal conditions to form purines of Formula XV.

Alternatively intermediate XXI may be prepared in a similar 2 step process by the formation of XXII from XIII and tert-butyl carbamate under reaction conditions with an appropriate Pd catalyst and phosphine ligand (Scheme 6). The carbamate nitrogen can then be alkylated with $R^4$-Lv under basic conditions to yield XXI.

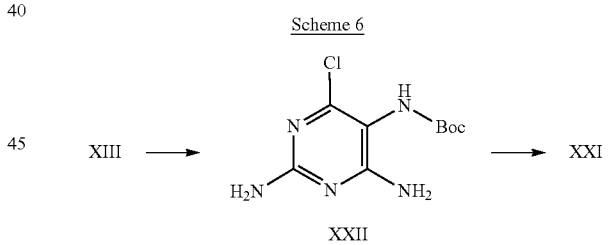

2-Amino-6-chloro-7-alkyl-7,9-dihydro-8H-purin-8-ones of Formula XV can also be synthesized in a 2 step process from XXI as shown below (Scheme 7).

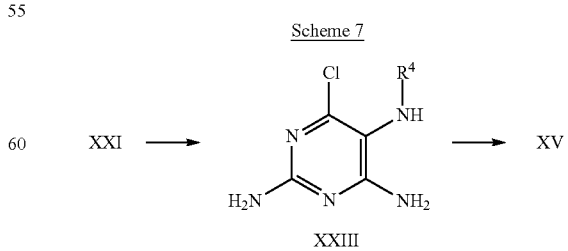

Another approach to prepare 2-amino-6-chloro-7-alkyl-7,9-dihydro-8H-purin-8-ones of Formula XV is outlined below (Scheme 5).

Exposing XXI to trifluoroacetic acid can give pyrimidine XXIII which can further be converted to XV with carbonyl diimidazole or bis(trichloromethyl) carbonate or bis(4-nitrophenyl) carbonate or other appropriate urea forming reagent.

An alternative approach to prepare intermediate XVII is depicted schematically below (Scheme 8). The chlorine of pyrimidine XIII can be directly displaced with the sodium salt of benzyl alcohol to form XXIV. Under appropriate reaction conditions with a Pd catalyst and phosphine ligand and an alkyl amine the 6-(benzyloxy)-$N^5$-alkyl substituted 2,4,5-pyrimidine XXV can be formed. XXVI can be generated from carbonyl diimidazole or bis(trichloromethyl) carbonate or bis(4-nitrophenyl) carbonate or other appropriate urea forming reagent. Purine intermediate XXVI can be reacted under catalytic hydrogenation or other ether cleaving conditions to form XVII.

can then undergo intramolecular cyclization under thermal conditions to form purines of Formula XXVI.

Alternatively, exposing XXVII to trifluoroacetic acid can give XXV which can then be converted to XXVI with carbonyl diimidazole or bis(trichloromethyl) carbonate or bis(4-nitrophenyl) carbonate or other appropriate urea forming reagent (Scheme 8).

Using conditions described above (Scheme 4) to glycosylate the N-9 of the purine base, XXVI and XX can be utilized to generate XXVII (Scheme 10). The benzylic ether can successively be removed via catalytic hydrogenation or with a boron trihalide reagent to give compounds of Formula I where $R^5$ is OH.

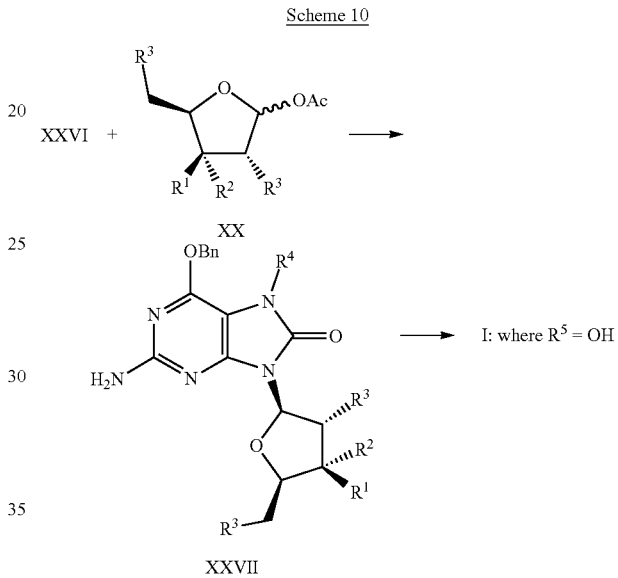

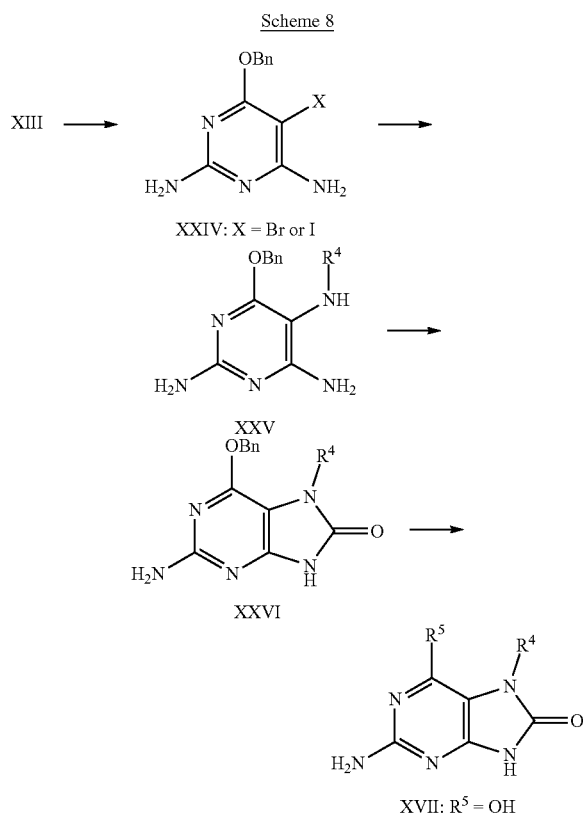

A different route that one may use to synthesize purine intermediate XXVI involves exposing intermediate XXIV to an alkylisocyanate which can form the corresponding urea XXVIII (Scheme 11). Intramolecular cyclization of intermediate XXVIII can be accomplished under reaction conditions with an appropriate Pd catalyst and phosphine ligand or by heating with copper (I) iodide in a polar aprotic solvent with an amine base to afford the 2-amino-6-benzyloxy-7-alkyl-7,9-dihydro-8H-purin-8-ones of Formula XXVI.

A second approach to prepare 2-amino-6-benzyloxo-7-alkyl-7,9-dihydro-8H-purin-8-ones of Formula XXVI is outlined below (Scheme 9).

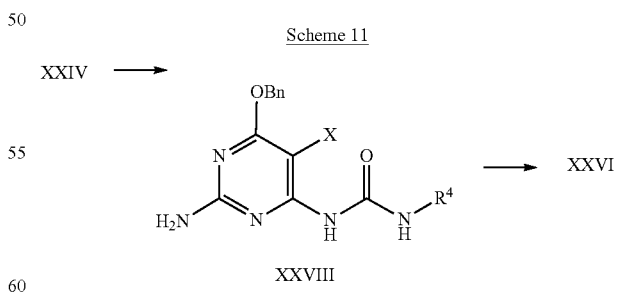

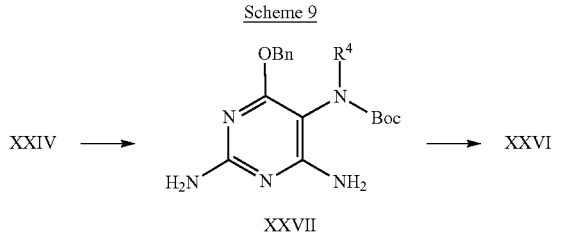

Using appropriate reaction conditions with a Pd catalyst, phosphine ligand and a tert-butyl alkyl carbamate, intermediate XXVII can be formed. This carbamate intermediate In yet another method (Scheme 12), a chlorine atom of the symmetrical 4,6-dichloropyrimidine-2,5-diamine [55583-59-0] can be displaced with a benzylic amine such as 4-methoxyl benzyl amine to form XXIX. Exposing intermediate XXIX to phosgene or a phosgene equivalent such as carbonyl diimidazole can form the corresponding cyclic urea XXX. The primary amino group may then be protected to form XXXI where P is a protecting group such as acyl or carbamyl. Intermediate XXXI may be hydro-dehalogenated with hydrogen and Pd or Pt metal or with activated Zn under acidic conditions to form XXXII. Alternatively the chlorine atom of XXXI may be displaced with an appropriate alcohol, preferably benzylic to form XXXIII. The N-protected-N-9-benzylic-7,9-dihydro-8H-purin-8-ones XXXI, XXXII and XXXIII can further be alkylated at N-7 under basic conditions with $R^4$-Lv to give N-7 alkyl compounds XXXIV, XXXV and XXXVI respectively. $R^4$ and Lv are defined previously above. After N-7 alkylation, N-9 of XXXIV and XXXV may by deprotected under the appropriate conditions. Depending upon what protecting group is used on the primary amine, this group may also be simultaneously removed. For instance, under acidic conditions such as trifluoroacetic combined with trifluoromethane sulfonic acid intermediates XV and XVI may be formed from XXXIV and XXXV respectively. Under similar acid condition XVII can be formed from XXXVI. In a similar fashion, intermediates XVIII and XIX may be synthesized using the general methods described in Scheme 12. Purine intermediates XV-XIX can then be exposed to a sugar derivative XX under a variety nucleoside forming reaction conditions followed by hydroxyl deprotection if required to give 9-β-furano-purine nucleoside analogs of Formula I. Also, the primary amino group of intermediates XV-XVII may be protected to form XXXVII-XLI, where P is a protecting group such as acyl or carbamyl. Purine intermediates XXXVII-XLI can then be exposed to a sugar derivative XX under a variety nucleoside forming reaction conditions followed by deprotection to give 9-β-furano-purine nucleoside analogs of Formula I.

Scheme 12

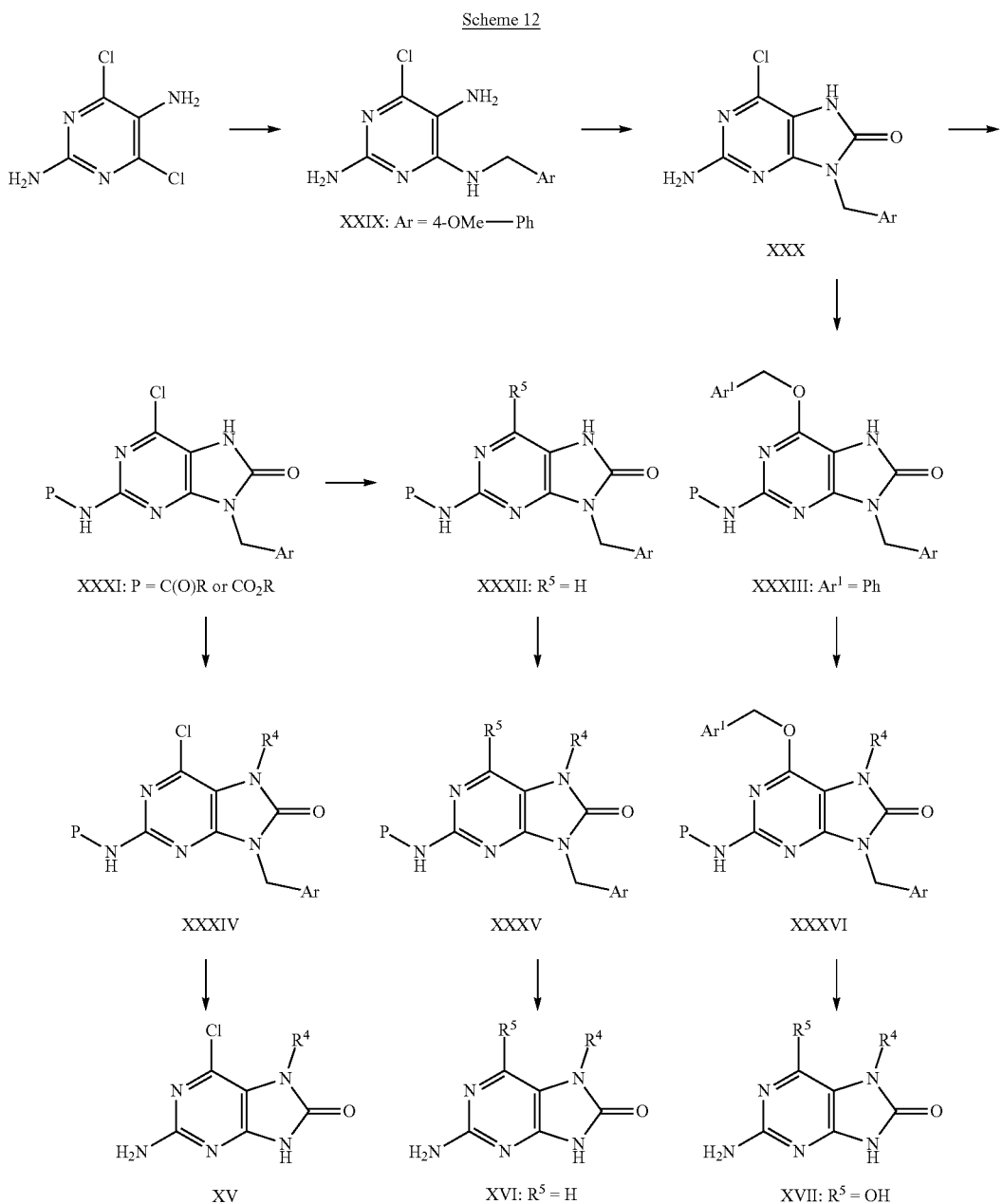

-continued

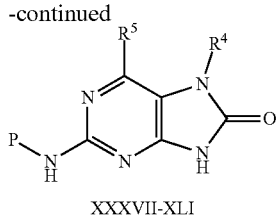
XV-XIX

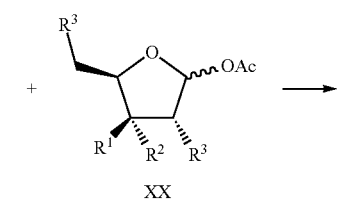
XXXVII-XLI

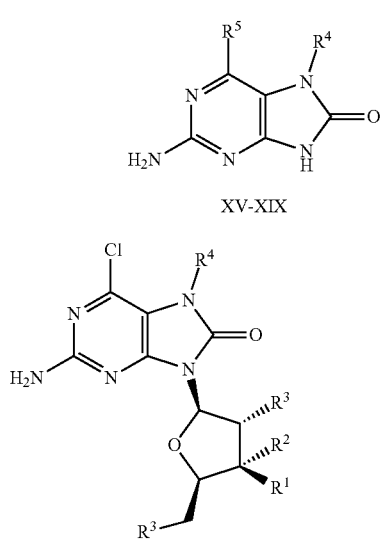

I where $R^1$ = H, OH or F
$R^2$ = H or F
$R^3$ = OH

Therapeutic Uses of TLR7 Agonists

TLR7 activation of innate immunity is principally mediated through plasmacytoid dendritic cells (pDCs). These cells are the primary physiological producers of type I interferons—up to 1,000 times that of any other cell type. Activation of TLR7 is therefore an important "gatekeeper" to overall induction of the innate immune response. TLR7 has significant advantages as a therapeutic target when compared to other TLRs. For example, it can be activated by small molecules which enables oral administration. Unlike several other TLRs, systemic activation of TLR7 avoids stimulation of excessive TNF production.

Administration of a TLR7 agonist directly and indirectly engages a variety of anti-tumor mechanisms including: production of cytokines and chemokines that have direct anti-tumor activity; activation of natural killer (NK) cells, the primary effector cell of the innate immune system for control of cancer, which are then capable of lysing tumor cells by both antibody-dependent (antibody-dependent cellular cytotoxicity, or ADCC) and independent mechanisms; activation of T-cells and reversal of T-cell exhaustion through antigen presentation by direct cell-cell interactions with, and production of cytokines and chemokines from pDCs, all leading to increased T-cell mediated attack on tumor cells; increased proliferation and maturation of normal B-cells and their precursors, which can enhance endogenous production of antibodies with antitumor activities; and direct activity against aberrant B-cells through the activation of TLR7 on these cells which can induce apoptosis and hypersensitization to chemotherapy.

In one embodiment, the TLR7 agonist compound(s) of the invention may be used alone, or in association with other, further therapeutic agents and therapeutic procedures, for treating or preventing cancer or an infection or infectious disease in a subject in need of such treatment or prevention.

In an embodiment, the TLR7 agonist compound(s) of the invention may be used alone, or in association with tumor vaccines.

In an embodiment, the TLR7 agonist compound(s) of the invention may be used alone, or in association with chemotherapeutic agents.

In an embodiment, the TLR7 agonist compound(s) of the invention may be used alone, or in association with radiation therapy.

In an embodiment, the TLR7 agonist compound(s) of the invention may be used alone, or in association with targeted therapies. Examples of targeted therapies include: hormone therapies, signal transduction inhibitors (e.g., EGFR inhibitors, such as cetuximab (Erbitux) and erlotinib (Tarceva)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators, apoptosis inducers (e.g., bortezomib (Velcade) and carfilzomib (Kyprolis)), angiogenesis inhibitors (e.g., bevacizumab (Avastin) and ramucirumab (Cyramza), monoclonal antibodies attached to toxins (e.g., brentuximab vedotin (Adcetris) and ado-trastuzumab emtansine (Kadcyla)).

In an embodiment, the TLR7 agonist compound(s) of the invention may be used in combination with an anti-cancer therapeutic agent or immunomodulatory drug such as an immunomodulatory receptor inhibitor or an antibody or antigen-binding fragment thereof that specifically binds to the receptor.

In an embodiment, the TLR7 agonist compound(s) of the invention may be used in combination with an immune checkpoint inhibitor, an OX40 agonist, a 4-1BB agonist, an ICOS agonist, a GITR agonist or an IL2-receptor agonist.

In an embodiment, the TLR7 agonist compound(s) of the invention may be used in combination with an inhibitor or antagonist of PD-1, PD-L1, CTLA4, TIM3, LAG3, SIRPα, CD47, VISTA, BTLA or TIGIT.

In an embodiment, the TLR7 agonist compound(s) of the invention may be used in combination with a therapeutic antibody with anti-tumor activity mediated at least in part through ADCC.

In an embodiment, the TLR7 agonist compound(s) of the invention may be used in combination with a therapeutic antibody with anti-tumor activity mediated at least in part through ADCC, including rituximab, trastuzumab and alemtuzumab.

In an embodiment of the invention, a TLR7 agonist compound of the invention is in association with an anti-OX40 antibody, including MOXR0916 and GSK3174998, or other pathway agonist.

In an embodiment of the invention, a TLR7 agonist compound of the invention is in association with an anti-4-1BB antibody, including urelumab, utomilumab, or other pathway agonist.

In an embodiment of the invention, a TLR7 agonist compound of the invention is in association with an anti-ICOS antibody or other pathway agonist.

In an embodiment of the invention, a TLR7 agonist compound of the invention is in association with an anti-GITR antibody or other pathway agonist.

In an embodiment of the invention, a TLR7 agonist compound of the invention is in association with an IL-2-receptor or other pathway agonist.

In an embodiment of the invention, a TLR7 agonist compound of the invention is in association with an anti-PD1 or anti-PDL1 antibody, including nivlumab (Opdivo), pembrolizumab (Keytruda), atezoluzimab (Tecentriq), durvalumab (Imfinzi) or avelumab (Bavencio)).

In an embodiment of the invention, a TLR7 agonist compound of the invention is in association with a CTLA-4/CD80-CD86 antagonist, including ipilimumab (Yervoy).

In an embodiment of the invention, a TLR7 agonist compound of the invention is in association with a Tim-3 pathway antagonist, including MBG453 and TSR-022.

In an embodiment of the invention, a TLR7 agonist compound of the invention is in association with a LAG-3 pathway antagonist, including BMS-986016, GSK2831781 and IMP321.

In an embodiment of the invention, a TLR7 agonist compound of the invention is in association with an anti-SIRPα antibody.

In an embodiment of the invention, a TLR7 agonist compound of the invention is in association with an anti-CD47 antibody.

In an embodiment of the invention, a TLR7 agonist compound of the invention is in association with a Vista pathway antagonist.

In an embodiment of the invention, a TLR7 agonist compound of the invention is in association with a BTLA pathway antagonist.

In an embodiment of the invention, a TLR7 agonist compound of the invention is in association with a TIGIT pathway antagonist.

In another embodiment, the TLR7 agonist compound(s) of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject.

Additional agents which are beneficial to raising a cytolytic T cell response may be used in combination with the TLR7 agonist compound of the present invention. These include, without limitation, B7 costimulatory molecule, interleukin-2 (e.g., NKTR-214), interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions.

In an embodiment of the invention, a TLR7 agonist compound of the invention is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, NJ), diphenhydramine (sold as Benadryl® by Pfizer; New York, NY), hydroxyzine (sold as Atarax® by Pfizer; New York, NY), metoclopramide (sold as Reglan® by AH Robins Co, Richmond, VA), lorazepam (sold as Ativan® by Wyeth; Madison, NJ), alprazolam (sold as Xanax® by Pfizer; New York, NY), haloperidol (sold as Haldol® by Ortho-McNeil; Raritan, NJ), droperidol (Inapsine®), dronabinol (sold as Marinol® by Solvay Pharmaceuticals, Inc.; Marietta, GA), dexamethasone (sold as Decadron® by Merck and Co.; Rahway, NJ), methylprednisolone (sold as Medrol® by Pfizer; New York, NY), prochlorperazine (sold as Compazine® by Glaxosmithkline; Research Triangle Park, NC), granisetron (sold as Kytril® by Hoffmann-La Roche Inc.; Nutley, NJ), ondansetron (sold as Zofran® by Glaxosmithkline; Research Triangle Park, NC), dolasetron (sold as Anzemet® by Sanofi-Aventis; New York, NY), tropisetron (sold as Navoban® by Novartis; East Hanover, NJ).

Other side effects of cancer treatment include red and white blood cell deficiency. Accordingly, in an embodiment of the invention, a TLR7 agonist compound is in association with an agent which treats or prevents such a deficiency, including filgrastim, PEG-filgrastim, erythropoietin, epoetin alfa and darbepoetin alfa.

In another embodiment, the present invention relates to compositions comprising one or more TLR7 agonist compounds of the present invention and a pharmaceutically acceptable carrier or diluent. Such compositions can further comprise one or more other therapeutically active ingredients such as an agonistic antibody or antigen-binding fragment thereof, or a soluble fusion, of a TNF receptor protein, an immunoglobulin-like protein, a cytokine receptor, an integrin, a signaling lymphocytic activation molecules (SLAM proteins), OX40, 4-1BB (CD137), ICOS (CD278), GITR, IL2R beta (CD122) and/or IL2R gamma.

The present invention includes compositions comprising a TLR7 agonist compound of the present invention in association with one or more antibodies that target the PD-1/PD-L1 interaction or CTLA-4/CD80-CD86 interaction. Non-limiting examples of such antibodies include pembrolizumab, nivolumab, avelumab, REGN2810, MEDI-0680, PDR-001, SHR-1210, BGB-A317, PF-06801591, TSR-042, atezoluzimab, durvalumab, BMS-936559, ipilimumab and tremelimumab.

Compositions for inducing a T cell immune response which preferentially stimulate a cytolytic T cell response versus an antibody response are preferred, although those that stimulate both types of response can be used as well.

In another embodiment compositions comprising one or more TLR7 agonist compounds can further comprise one or more other therapeutically active ingredients that are an immune checkpoint inhibitor, an OX40 agonist, a 4-1BB agonist, an ICOS agonist, a GITR agonist or an IL2-receptor agonist.

In another embodiment compositions comprising one or more TLR7 agonist compounds can further comprise one or more other therapeutically active ingredients that are an inhibitor or antagonist of PD-1, PD-L1, CTLA4, TIM3, LAG3, SIRPα, CD47, VISTA, BTLA or TIGIT.

In another embodiment compositions comprising one or more TLR7 agonist compounds can further comprise one or more other therapeutically active ingredients that are a therapeutic antibody with anti-tumor activity mediated at least in part through ADCC.

In another embodiment compositions comprising one or more TLR7 agonist compounds can further comprise one or more other therapeutically active ingredients that are a therapeutic antibody with anti-tumor activity mediated at least in part through ADCC, including rituximab, trastuzumab and alemtuzumab.

Further provided in the invention are methods for treating or preventing cancer or an infection or infectious disease in a subject in need of such treatment or prevention, in subjects, including human subjects, with the TLR7 agonist compound(s) disclosed herein. In one embodiment of the invention, such subject suffers from cancer or a precancerous condition. In another embodiment of the invention, such subject suffers from an infection or an infectious disease.

In another embodiment the present invention also relates to methods of treating or preventing cancer in a human subject, comprising administering to the subject an effective amount of one or more TLR7 agonist compounds of the present invention, optionally in association with a further therapeutic agent or therapeutic procedure; and to methods of treating an infection or infectious disease in a human subject, comprising administering to the subject an effective amount of one or more TLR7 agonist compounds of the present invention, optionally in association with a further therapeutic agent or therapeutic procedure.

In yet another embodiment the present invention relates to a method of increasing the activity of an immune cell, comprising administering to a subject in need thereof an effective amount of one or more TLR7 agonist compounds of the present invention for treating or preventing cancer; treating an infection or infectious disease; acting as a vaccine adjuvant; or increasing immune cell activation.

In an embodiment, the invention provides methods for treating subjects using a TLR7 agonist compound of the invention, wherein the subject suffers from cancer or a precancerous condition. In an embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating subjects using a TLR7 agonist compound of the invention, wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using a TLR7 agonist compound of the invention, wherein the subject suffers from a bacterial infection. In one embodiment, the bacterial infection is infection with a bacterium selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella, bacilli, Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using a TLR7 agonist compound of the invention, wherein the subject suffers from a fungal infection. In one embodiment, the fungal infection is infection with a fungus selected from the group consisting of *Candida* (*albicans, krusei, glabrata, tropicalis*, etc.), *Cryptococcus neoformans, Aspergillus* (*fumigatus, niger*, etc.), *Genus Mucorales* (*mucor, absidia, rhizopus*), *Sporothrix schenkii, Blastomyces dermatitidis, Paracoccidioides brasiliensis, Coccidioides immitis* and *Histoplasma capsulatum*.

In an embodiment, the invention provides methods for treating subjects using a TLR7 agonist compound of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

The present invention includes methods for treating or preventing cancer in a subject comprising administering an effective amount of the TLR7 agonist compound of the present invention and one or more antibodies that target the PD-1/PD-L1 or CTLA-4/CD80-CD86 interaction to the subject. In an embodiment of the invention, a TLR7 agonist compound of the invention is in association with an anti-PD1 or anti-PDL1 antibody.

The present invention includes methods for treating or preventing cancer in a subject comprising administering an effective amount of the TLR7 agonist compound of the present invention in combination with an immune checkpoint inhibitor, an OX40 agonist, a 4-1BB agonist, an ICOS agonist, a GITR agonist or an IL2-receptor agonist.

The present invention includes methods for treating or preventing cancer in a subject comprising administering an effective amount of the TLR7 agonist compound of the present invention in combination with an inhibitor or antagonist of PD-1, PD-L1, CTLA4, TIM3, LAG3, SIRPα, CD47, VISTA, BTLA or TIGIT.

The present invention includes methods for treating or preventing cancer in a subject comprising administering an effective amount of the TLR7 agonist compound of the present invention in combination with a therapeutic antibody with anti-tumor activity mediated at least in part through ADCC.

The present invention includes methods for treating or preventing cancer in a subject comprising administering an effective amount of the TLR7 agonist compound of the present invention in combination with a therapeutic antibody with anti-tumor activity mediated at least in part through ADCC, including rituximab, trastuzumab and alemtuzumab.

The present invention includes methods for treating or preventing cancer in a subject comprising administering an effective amount of the TLR7 agonist compound of the present invention in association with an anti-OX40 antibody, including MOXR0916 and GSK3174998, or other pathway agonist.

The present invention includes methods for treating or preventing cancer in a subject comprising administering an effective amount of the TLR7 agonist compound of the present invention in association with an anti-4-1BB antibody, including urelumab, utomilumab, or other pathway agonist.

The present invention includes methods for treating or preventing cancer in a subject comprising administering an effective amount of the TLR7 agonist compound of the present invention in association with an anti-ICOS antibody or other pathway agonist.

The present invention includes methods for treating or preventing cancer in a subject comprising administering an effective amount of the TLR7 agonist compound of the present invention in association with an anti-GITR antibody or other pathway agonist.

The present invention includes methods for treating or preventing cancer in a subject comprising administering an effective amount of the TLR7 agonist compound of the present invention in association with an IL-2-receptor or other pathway agonist.

The present invention includes methods for treating or preventing cancer in a subject comprising administering an effective amount of the TLR7 agonist compound of the present invention in association with an anti-PD1 or anti-PDL1 antibody, including nivlumab (Opdivo), pembrolizumab (Keytruda), atezoluzimab (Tecentriq), durvalumab (Imfinzi) or avelumab (Bavencio)).

The present invention includes methods for treating or preventing cancer in a subject comprising administering an effective amount of the TLR7 agonist compound of the present invention in association with a CTLA-4/CD80-CD86 antagonist, including ipilimumab (Yervoy).

The present invention includes methods for treating or preventing cancer in a subject comprising administering an effective amount of the TLR7 agonist compound of the present invention in association with a Tim-3 pathway antagonist, including MBG453 and TSR-022.

The present invention includes methods for treating or preventing cancer in a subject comprising administering an effective amount of the TLR7 agonist compound of the present invention in association with a LAG-3 pathway antagonist, including BMS-986016, GSK2831781 and IMP321.

The present invention includes methods for treating or preventing cancer in a subject comprising administering an effective amount of the TLR7 agonist compound of the present invention in association with an anti-SIRPα antibody.

The present invention includes methods for treating or preventing cancer in a subject comprising administering an effective amount of the TLR7 agonist compound of the present invention in association with an anti-CD47 antibody.

The present invention includes methods for treating or preventing cancer in a subject comprising administering an effective amount of the TLR7 agonist compound of the present invention in association with a Vista pathway antagonist.

The present invention includes methods for treating or preventing cancer in a subject comprising administering an effective amount of the TLR7 agonist compound of the present invention in association with a BTLA pathway antagonist.

The present invention includes methods for treating or preventing cancer in a subject comprising administering an effective amount of the TLR7 agonist compound of the present invention in association with a TIGIT pathway antagonist.

Pharmaceutical Compositions and Administration

The present invention also provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient. Pharmaceutical compositions comprising a pharmaceutically acceptable carrier, diluent, or excipient, in association with further therapeutic agents are also part of the present invention.

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in *Remington, The Science and Practice of Pharmacy* $21^{st}$ *Edition* (Mack Publishing Co., Easton, PA) and Nielloud and Marti-Mestres, Pharmaceutical Emulsions and Suspensions: $2^{nd}$ Edition (Marcel Dekker, Inc, New York). To prepare pharmaceutical or sterile compositions of the TLR7 agonist compound(s) of the invention, the compound(s) is(are) admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the compounds or compositions of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with a TLR7 agonist compound of the invention in accordance with the Physicians' Desk Reference 2003 (Thomson Healthcare; 57th edition (Nov. 1, 2002)).

The mode of administration can vary. For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Intra-tumoral (directly into the tumor mass) or peri-tumoral (around the tumor mass) administration of the compound(s) of the present invention are also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

The present invention provides a vessel (e.g., a plastic or glass vial, e.g., with a cap or a chromatography column, hollow bore needle or a syringe cylinder) comprising one or more compounds of the invention or a pharmaceutical composition thereof. The present invention also provides an injection device comprising one or more compounds of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., one or more compounds of the invention or a pharmaceutical composition thereof), a needle for piecing skin and/or blood vessels for injection of the fluid; and a plunger for pushing the fluid out of the cylinder and through the needle bore. In an embodiment of the invention, an injection device that comprises one or more compounds of the invention or a pharmaceutical composition thereof is an intravenous (IV) injection device. Such a device includes one or more compounds of the invention or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. The one or more compounds of the invention or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the one or more compounds of the invention or a pharmaceutical composition thereof to a patient's body. External infusion pumps are medical devices that deliver a pharmaceutical composition into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The compounds and pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the TLR7 agonist compound of the invention in a local rather than systemic manner, for example, via injection of the compound into a tumor. Furthermore, one may administer the TLR7 agonist compound of the invention in a targeted drug delivery system, for example, in a liposome coated with a tissue-specific antibody, targeting, for example, a tumor characterized by immunopathology. The liposomes will be targeted to and taken up selectively by the corresponding tissue. Such methods and liposomes are part of the present invention.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e., the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compound(s) of the invention are preferably pharmaceutically acceptable. Suitable pharmaceutically acceptable salts include those described by P. Heinrich Stahl and Camille G. Wermuth in *Handbook of Pharmaceutical Salts: Properties, Selection, and Use*, $2^{nd}$ ed. (Wiley-VCH: 2011) and also *Remington's Pharmaceutical Sciences*, $18^{th}$ ed. (Mack Publishing, Easton PA: 1990) and also *Remington: The Science and Practice of Pharmacy*, $19^{th}$ ed. (Mack Publishing, Easton PA: 1995).

Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, trifluoroacetate, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

Salts of a compound of the present invention may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like.

A pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

If a compound containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of a compound or a pharmaceutically acceptable salt, pharmaceutically acceptable solvate or pharmaceutically acceptable hydrate thereof, as described herein, for a particular patient may vary depending on factors such as the condition being treated, the overall health of the patient, the route and dose of administration and the severity of side effects.

"A pharmaceutically acceptable prodrug" is a compound that may be converted under physiological conditions or by solvolysis to the specified compound or to a pharmaceutically acceptable salt of such compound prior to exhibiting its pharmacological effect(s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g. toxicity). The prodrug can be readily prepared from the compounds of Formula I using methods known in the art, such as those described by Burger's Medicinal Chemistry and Drug Chemistry, 1, 172-178, 949-982 (1995). See also Bertolini et al., J. Med. Chem., 40, 2011-2016 (1997); Shan, et al, J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds. Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al. Xenobiol., 3, 1031-112 (1992).

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, NY; Poole and Peterson (eds.) (2001) Pharmacotherapeutics for Advanced Practice:A Practical Approach, Lippincott, Williams & Wilkins, Phila., PA; Chabner and Longo (eds.) (2001) Cancer Chemotherapy and Biotherapy, Lippincott, Williams & Wilkins, Phila., PA). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g., same formulation) such that they are administered at the same time by the same route of administration.

Generally, each administration of a compound of the invention comprises between about 10 mg to about 2000 mg in an individual, e.g., from about 10 mg to about 50 mg, from about 50 mg to about 100 mg, from about 100 mg to about 250 mg, from about 250 mg to about 500 mg, from about 500 mg to about 1000 mg, from about 1000 mg to about 2000 mg.

General Methods

All synthetic chemistry was performed in standard laboratory glassware unless indicated otherwise in the examples. Commercial reagents were used as received. Microwave reactions were performed in a Biotage Initiator using the instrument software to control heating time and pressure. Analytical LC/MS was performed on an Agilent 1290 infinity, Mass:6150 SQD(ESI/APCI) or an Agilent 1200 SERIES, Mass:6130SQD(ESI/APCI); variable wavelength detector and Agilent 6130 single quadrupole mass spectrometer, alternating positive and negative ion scans using Chemistation software. Retention times were determined from the extracted 220 nm UV chromatogram. HPLC was performed on a Waters 2695 system with a variable wavelength detector using Empower software. Retention times were determined from the extracted 210 nm and 300 nm UV chromatograms. $^1$H NMR was performed on a Bruker Avance 400 at 400 MHz or a Bruker Avance DRX-500 at 500 MHz using Topspin software. For complicated splitting patterns, the apparent splitting was tabulated. Analytical thin layer chromatography was performed on silica (Macherey-Nagel ALUGRAM Xtra SIL G, 0.2 mm, $UV_{254}$ indicator) and was visualized under UV light. Silica gel chromatography was performed manually, or with Grace automated chromatography for gradient elution. Melting points were collected using a Büchi B-540 melting point apparatus.

Standard methods in molecular biology are described Sambrook, Fritsch and Maniatis (1982 & 1989 $2^{nd}$ Edition, 2001 $3^{rd}$ Edition) Molecular Cloning, A Laboratory Manual, Cold Spring Harbor Laboratory Press, Cold Spring Harbor, NY; Sambrook and Russell (2001) Molecular Cloning, $3^{rd}$ ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Standard methods of histology of the immune system are described (see, e.g., Muller-Harmelink (ed.) (1986) Human Thymus: Histopathology and Pathology, Springer Verlag, New York, NY; Hiatt, et al. (2000) Color Atlas of Histology, Lippincott, Williams, and Wilkins, Phila, PA; Louis, et al. (2002) Basic Histology: Text and Atlas, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

EXAMPLES

Example 1: 2-Amino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione, Compound 1

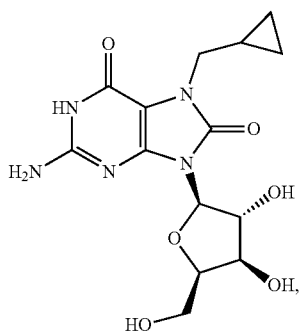 [SMILES: Nc1nc2c(c(=O)[nH]1)n(CC1CC1)c(=O)n2[C@@H]1O[C@H](CO)[C@H](O)[C@H]1O]

Compound 1 was made according to the following multi-step procedure.

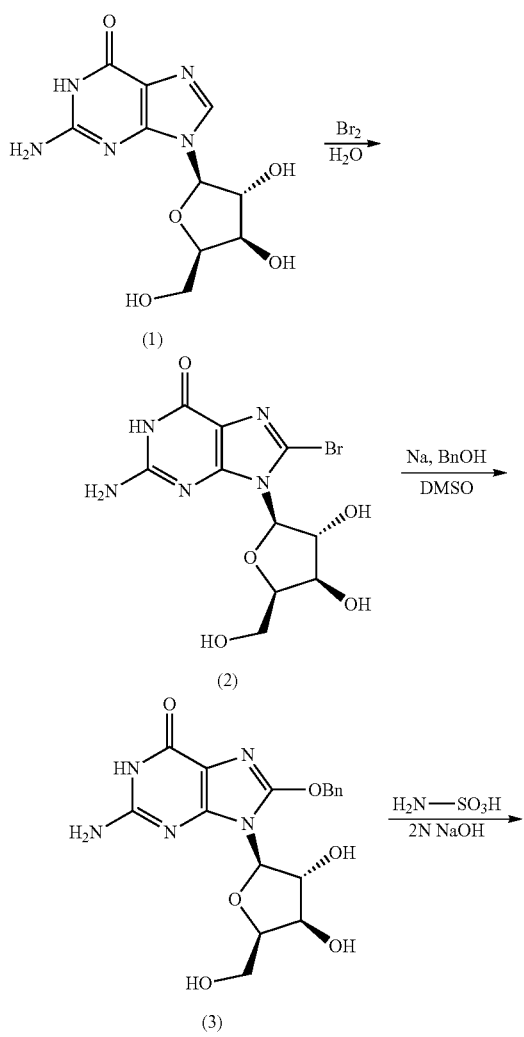

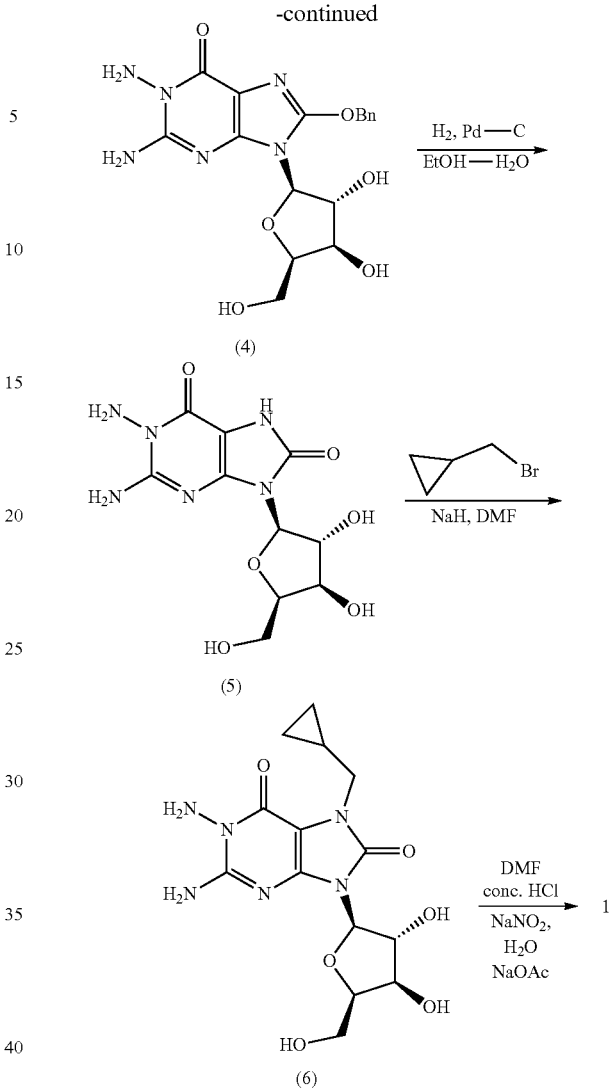

Step 1: 2-Amino-8-bromo-9-((2R,3R,4R,5R)-3,4-dihydroxy-5-(hydroxymethyl)tetrahydrofuran-2-yl)-1,9-dihydro-6H-purin-6-one (2)

To a stirred solution of 2-amino-9-((2R,3R,4R,5R)-3,4-dihydroxy-5-(hydroxymethyl)tetrahydrofuran-2-yl)-1,9-dihydro-6H-purin-6-one (1) [27462-39-1], prepared according to the procedures of Zou, et al, *Can. J. Chem.*, 1987, p. 1436 and Robins et al, *JOC*, 1996, p. 9207, (15.0 g, 53 mmol) in 250 mL of water was added aqueous bromine solution (4.5 mL, 1.5 eq) slowly at room temperature. In the closed round-bottom flask the reaction mixture was stirred at room temperature overnight. Aqueous sodium thiosulfate solution was added to destroy the excess bromine. The reaction mixture was filtered, and the filtrate was washed with water and acetone. The solid was dried under vacuum giving 15.4 g desired product 2-amino-8-bromo-9-((2R,3R,4R,5R)-3,4-dihydroxy-5-(hydroxymethyl)tetrahydrofuran-2-yl)-1,9-dihydro-6H-purin-6-one (2) as an off-white solid in 80% yield.

Step 2: 2-Amino-8-(benzyloxy)-9-((2R,3R,4R,5R)-3,4-dihydroxy-5-(hydroxymethyl)tetrahydrofuran-2-yl)-1,9-dihydro-6H-purin-6-one (3)

Pieces of sodium (6.0 gm, 260.9 mmol) was added to 60 mL of benzyl alcohol in a round-bottom flask. The mixture was stirred at room temperature for 0.5 h, and then heated until sodium went to solution. A solution of 2-amino-8-bromo-9-((2R,3R,4R,5R)-3,4-dihydroxy-5-(hydroxymethyl)tetrahydrofuran-2-yl)-1,9-dihydro-6H-purin-6-one (2) (15.4 g, 42 mmol) in 60 mL of DMSO was added to the stirred solution obtained above. It was stirred for 10 h. Glacial acetic acid was added to the stirred reaction mixture to adjust to neutral. The mixture was treated with ether. The ether layer was decanted, and the material left was treated with acetone. The solid was filtered and washed with water. The crude product was recrystallized with ethanol-water (1:1) to give 11.0 g of 2-amino-8-(benzyloxy)-9-((2R,3R,4R,5R)-3,4-dihydroxy-5-(hydroxymethyl)tetrahydrofuran-2-yl)-1,9-dihydro-6H-purin-6-one (3) as an off-white solid in 67% yield.

Step 3: 1,2-Diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4)

2-Amino-8-(benzyloxy)-9-((2R,3R,4R,5R)-3,4-dihydroxy-5-(hydroxymethyl)tetrahydrofuran-2-yl)-1,9-dihydro-6H-purin-6-one (3) (11.0 g, 28 mmol) was dissolved in 150 mL of 2N sodium hydroxide aqueous solution. Hydroxylamine-O-sulfonic acid (9.35 g, 82 mmol, 3 eq) was added. The reaction mixture was stirred at room temperature overnight, and filtered. The solid was washed with acetone giving 5.8 g white solid product 1,2-diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4) in 51% yield.

Step 4: 1,2-Diamino-9-((2R,3R,4R,5R)-3,4-dihydroxy-5-(hydroxymethyl)tetrahydrofuran-2-yl)-7,9-dihydro-1H-purine-6,8-dione (5)

1,2-Diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4) (5.8 g, 14 mmol) was dissolved in 200 mL of ethanol and 200 mL of water in the hydrogenation flask by heating to 90° C. 1 g of 5% Pd/C was added. In the Parr reactor the reaction mixture was kept under an atmosphere of hydrogen at 40-50 psi overnight. Hydrogen was evacuated from the reactor and the catalyst was filtered off and washed with hot water. The filtrate was concentrated under reduced pressure giving crude product that was recrystallized from water giving 3.6 g of 1,2-diamino-9-((2R,3R,4R,5R)-3,4-dihydroxy-5-(hydroxymethyl)tetrahydrofuran-2-yl)-7,9-dihydro-1H-purine-6,8-dione (5) as a white solid in 81% yield.

Step 5: 1,2-Diamino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione (6)

1,2-Diamino-9-((2R,3R,4R,5R)-3,4-dihydroxy-5-(hydroxymethyl)tetrahydrofuran-2-yl)-7,9-dihydro-1H-purine-6,8-dione (5) (3.6 g, 11.4 mmol, 1.0 eq) was dissolved in 50 mL of anhydrous DMF. NaH (0.5 g, 12.6 mmol, 1.1 eq) was added to the stirred solution, and it was further stirred for 1 hr. Cyclopropylmethyl bromide (1.70 g, 12.6 mmol, 1.1 eq) was added to the reaction mixture and stirring was continued at room temperature overnight. The reaction mixture was concentrated under reduced pressure. The residue was purified by flash chromatography on a silica gel column using dichloromethane-methanol (15:1) as an eluent. 1,2-Diamino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione (6) (2.5 g) was obtained as a white solid in 65% yield.

Step 6: 2-Amino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione, Compound 1

1,2-Diamino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione (6) (0.50 g, 1.4 mmol) was added to the flask containing 10 mL of DMF. Concentrated hydrochloric acid (1.0 mL) was added at 0° C. An aqueous solution of sodium nitrite (113 mg, 1.7 mmol) in 5 mL of water was added under stirring. After stirring for 30 min, sodium acetate (0.50 g, 6.3 mmol) was added. The reaction mixture was stirred for 25 min and concentrated under reduced pressure. The residue was purified by flash chromatography on a silica gel column using dichloromethane-methanol (10:1) as an eluent giving 0.30 g of product 2-amino-7-(cyclopropylmethyl)-9-((2R,3R,4R,5R)-3,4-dihydroxy-5-(hydroxymethyl)tetrahydrofuran-2-yl)-7,9-dihydro-1H-purine-6,8-dione, Compound 1, as a white solid in 63% yield. HPLC purity 99.5%. $^1$H NMR (DMSO-$d_6$, 400 MHz) δ 11.03 (s, 1H), 6.64 (s, 2H), 5.69-5.77 (m, 2H), 5.51 (d, 1H, J=4 Hz), 4.63 (t, 1H, J=8 Hz), 4.46-4.54 (m, 1H), 3.83-3.94 (m, 2H), 3.61-3.73 (m, 3H), 3.51-3.60 (m, 1H), 1.12-1.25 (m, 1H), 0.31-0.46 (m, 4H). MS (ESI), m/z 354.3 [M+H]$^+$.

Example 2: 7-Allyl-2-amino-9-((2R,3R,4R,5R)-3,4-dihydroxy-5-(hydroxymethyl)tetrahydrofuran-2-yl)-7,9-dihydro-1H-purine-6,8-dione, Compound 2

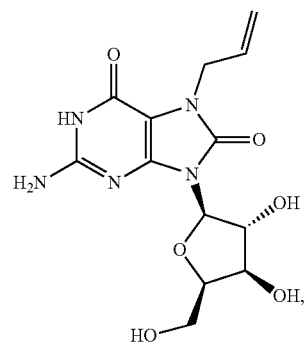 [SMILES: C=CCn1c(=O)n([C@@H]2O[C@H](CO)[C@H](O)[C@H]2O)c2nc(N)[nH]c(=O)c21]

Compound 2 was made according to the following multi-step procedure.

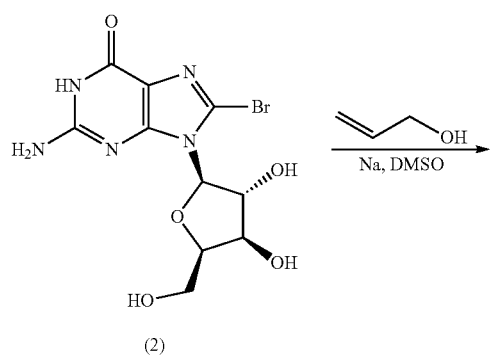

(2)

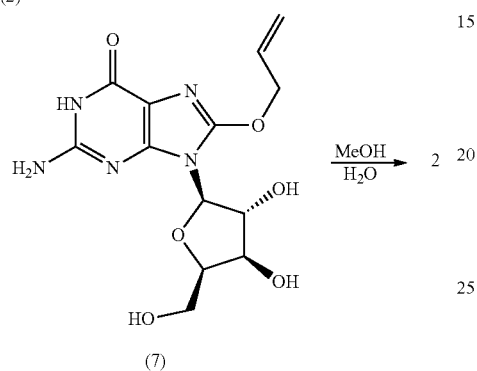

(7)

Step 1: 8-(Allyloxy)-2-amino-9-((2R,3R,4R,5R)-3,4-dihydroxy-5-(hydroxymethyl)tetrahydrofuran-2-yl)-1,9-dihydro-6H-purin-6-one (7)

Small pieces of sodium metal (0.4 g, 17.4 mmol) was added portion-wise to stirred allyl alcohol (10 mL, 8.5 g, 146 mmol) with stirring and continue until all the sodium was completed dissolved and hydrogen gas ceased to evolve. Anhydrous DMSO (10 mL) was added followed by the addition of 2-amino-8-bromo-9-((2R,3R,4R,5R)-3,4-dihydroxy-5-(hydroxymethyl)tetrahydrofuran-2-yl)-1,9-dihydro-6H-purin-6-one (2)(Example 1) (1.0 g, 2.8 mmol). The reaction mixture was heated to 65° C. under stirring and continued until the 8-bromo purine starting material was consumed as shown by TLC (dichloromethane-methanol: 2:1; $R_f$=0.6). The solvents were concentrated under reduce pressure, and the residue was treated with ethyl ether. The ethyl ether layer was decanted and the residue was purified by flash chromatography on a silica gel column using dichloromethane-methanol: 8:1 as eluent giving 190 mg 8-(allyloxy)-2-amino-9-((2R,3R,4R,5R)-3,4-dihydroxy-5-(hydroxymethyl)tetrahydrofuran-2-yl)-1,9-dihydro-6H-purin-6-one (7) as an off-white solid in 21% yield.

Step 2: 7-Allyl-2-amino-9-((2R,3R,4R,5R)-3,4-dihydroxy-5-(hydroxymethyl)tetrahydrofuran-2-yl)-7,9-dihydro-1H-purine-6,8-dione, Compound 2

8-(Allyloxy)-2-amino-9-((2R,3R,4R,5R)-3,4-dihydroxy-5-(hydroxymethyl)tetrahydrofuran-2-yl)-1,9-dihydro-6H-purin-6-one (7) (190 mg, 0.6 mmol) was dissolved in 15 mL of methanol and 150 mL of water. The reaction mixture was heated to reflux for 5 h. The solvent was concentrated under reduced pressure, and the residue was purified by flash chromatography on a silica gel column using dichloromethane-methanol: 10:1 as eluent giving 134 mg of 7-allyl-2-amino-9-((2R,3R,4R,5R)-3,4-dihydroxy-5-(hydroxymethyl)tetrahydrofuran-2-yl)-7,9-dihydro-1H-purine-6,8-dione, Compound 2, as an off-white foam in 70.5% yield; $^1$H NMR (DMSO-$d_6$, 400 MHz) δ 5.86-5.95 (m, 1H), 5.67-5.74 (m, 2H), 5.50 (d, 1H, J=3.2 Hz), 5.02-5.12 (m, 2H), 4.60-4.63 (m, 1H), 4.41-4.50 (m, 3H), 3.85-3.92 (m, 2H), 3.64-3.69 (m, 1H), 3.53-3.58 (m, 1H), MS (ESI), m/z 340.2 [M+H]$^+$.

Example 3: (2R,3S,4R,5R)-2-(Acetoxymethyl)-5-(2-amino-7-(cyclopropylmethyl)-8-oxo-7,8-dihydro-9H-purin-9-yl)tetrahydrofuran-3,4-diyl diacetate, Compound 3

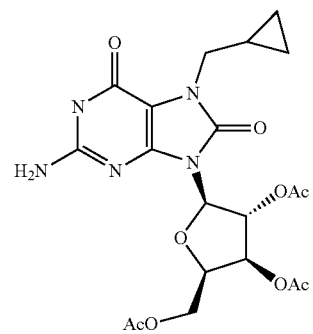 [SMILES: CC(=O)OC[C@H]1O[C@@H](n2c(=O)n(CC3CC3)c3c(=O)[nH]c(N)nc32)[C@H](OC(C)=O)[C@H]1OC(C)=O]

Compound 3 was made according to the following multi-step procedure.

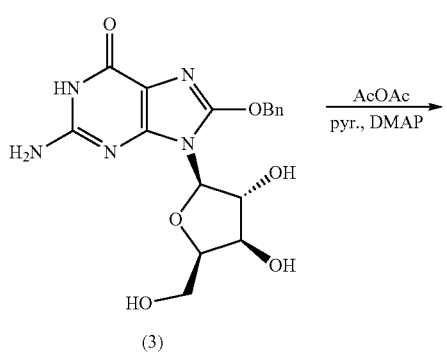

(3)

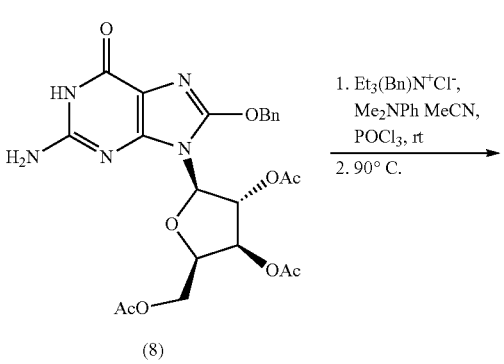

(8)

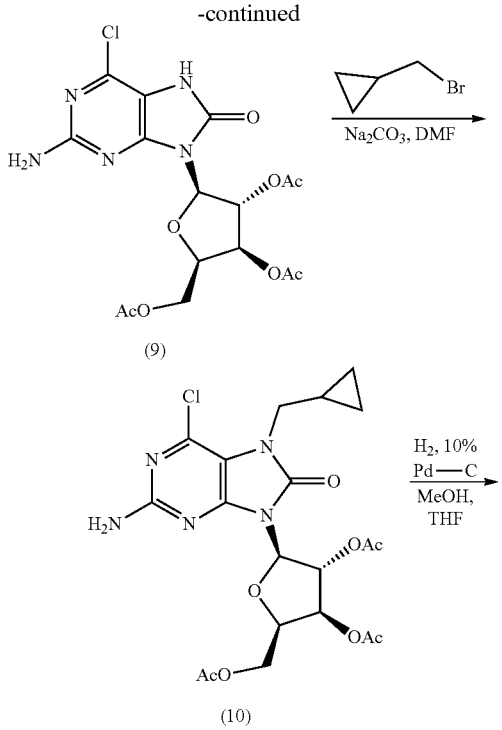

(9)

(10)

Step 1: (2R,3S,4R,5R)-2-(Acetoxymethyl)-5-(2-amino-8-(benzyloxy)-6-oxo-1,6-dihydro-9H-purin-9-yl)tetrahydrofuran-3,4-diyl diacetate (8)

A solution of 2-amino-8-(benzyloxy)-9-((2R,3R,4R,5R)-3,4-dihydroxy-5-(hydroxymethyl)tetrahydrofuran-2-yl)-1,9-dihydro-6H-purin-6-one (3) (16.0 g, 41.1 mmol) in anhydrous pyridine (250 mL) was treated with acetic anhydride (15.5 mL, 164.4 mmol, 4.0 eq) and catalytic amount of DMAP (50 mg, 0.41 mmol, 0.01 eq). The reaction mixture was stirred at room temperature overnight. Upon completion of the reaction as monitored by TLC, the reaction mixture was diluted with ethyl acetate (300 mL) and poured into 500 mL of water. The layers were separated, and the aqueous layer was extracted twice with ethyl acetate. The combined organic layer was washed with saturated brines solution, dried over anhydrous sodium sulfate and concentrated under reduced pressure. The resulting residue was purified by column chromatography on a silica gel column using dichloromethane-methanol (20:1) as an eluent to give 10 g of (2R,3S,4R,5R)-2-(acetoxymethyl)-5-(2-amino-8-(benzyloxy)-6-oxo-1,6-dihydro-9H-purin-9-yl)tetrahydrofuran-3,4-diyl diacetate (8) as a white foam in 47.2% yield; $R_f$=0.30 (dichloromethane-methanol=18:1).

Step 2: (2R,3S,4R,5R)-2-(Acetoxymethyl)-5-(2-amino-6-chloro-8-oxo-7,8-dihydro-9H-purin-9-yl)tetrahydrofuran-3,4-diyl diacetate (9)

In an oven-dried flask, (2R,3S,4R,5R)-2-(acetoxymethyl)-5-(2-amino-8-(benzyloxy)-6-oxo-1,6-dihydro-9H-purin-9-yl)tetrahydrofuran-3,4-diyl diacetate (8) (10 g, 19.4 mmol), benzyltriethylammonium chloride (8.8 g, 38.8 mmol, 2.0 eq) and N, N-dimethylaniline (2.7 mL, 21.3 mmol, 1.1 eq) were dissolved in 300 mL dry MeCN. Then phosphorus oxychloride (9.0 mL, 97 mmol, 5.0 eq) was added with stirring at room temperature. The reaction mixture was stirred at room temperature for 1 h or upon disappearance of starting material (8) as shown by TLC. At this time the reaction mixture was moved to pre-heated oil bath at 90° C. and heated for 3 h. Upon completion of the reaction as monitored by TLC, the reaction mixture was concentrated in vacuo. The resulting residue was dissolved in ethyl acetate (200 mL) and poured into 200 mL of saturated sodium bicarbonate solution. The aqueous layer was extracted with ethyl acetate and the combined organic layer was washed with saturated brines solution, and then dried over anhydrous sodium sulfate and concentrated under reduced pressure. The resulting residue was purified by column chromatography using dichloromethane-methanol (30:1) as an eluent to give 1.8 g of product (2R,3S,4R,5R)-2-(acetoxymethyl)-5-(2-amino-6-chloro-8-oxo-7,8-dihydro-9H-purin-9-yl)tetrahydrofuran-3,4-diyl diacetate (9) as a white foam in 22% yield. $R_f$=0.60 (dichloromethane-methanol=18:1)

Step 3: (2R,3S,4R,5R)-2-(Acetoxymethyl)-5-(2-amino-6-chloro-7-(cyclopropylmethyl)-8-oxo-7,8-dihydro-9H-purin-9-yl)tetrahydrofuran-3,4-diyl diacetate (10)

(2R,3S,4R,5R)-2-(Acetoxymethyl)-5-(2-amino-6-chloro-8-oxo-7,8-dihydro-9H-purin-9-yl)tetrahydrofuran-3,4-diyl diacetate (9) (1.4 g, 3.2 mmol, 1.0 eq) was dissolved in 50 mL of anhydrous DMF. $K_2CO_3$ (655 mg, 4.7 mmol, 1.5 eq) was added to the stirred solution, and it was stirred further for 10 min. Then cyclopropylmethyl bromide (0.37 mL, 3.84 mmol, 1.2 eq) was added to the reaction mixture, and stirring was continued at room temperature overnight. Upon completion of the reaction as monitored by TLC, the reaction mixture was diluted with ethyl acetate (100 mL) and treated with 100 mL water. The aqueous layer was extracted with ethyl acetate and the combined organic layer was washed with saturated brines solution, dried over anhydrous sodium sulfate and concentrated under reduced pressure. The resulting residue was purified by column chromatography using dichloromethane-methanol (50:1) as eluent to give 1.18 g of (2R,3S,4R,5R)-2-(acetoxymethyl)-5-(2-amino-6-chloro-7-(cyclopropylmethyl)-8-oxo-7,8-dihydro-9H-purin-9-yl)tetrahydrofuran-3,4-diyl diacetate (10) as a white foam in 75% yield. $R_f$=0.70 (dichloromethane-methanol=30:1)

Step 4: (2R,3S,4R,5R)-2-(Acetoxymethyl)-5-(2-amino-7-(cyclopropylmethyl)-8-oxo-7,8-dihydro-9H-purin-9-yl)tetrahydrofuran-3,4-diyl diacetate, Compound 3

(2R,3S,4R,5R)-2-(Acetoxymethyl)-5-(2-amino-6-chloro-7-(cyclopropylmethyl)-8-oxo-7,8-dihydro-9H-purin-9-yl)tetrahydrofuran-3,4-diyl diacetate (10) (1.0 g, 2.0 mmol) was dissolved in a mixture of anhydrous methanol (50 mL) and tetrahydrofuran (10 mL). 10% Pd/C (120 mg, was added, and the mixture was stirred for 5 h under $H_2$ (50 Psi) atmosphere at room temperature for 2 days. Upon completion of the reaction as monitored by TLC, the catalyst was removed by filteration through a pad of Celite. The solvent was evaporated, and the crude product was purified by flash chromatography on a silica gel column using dichloromethane-methanol (50:1) as eluent providing 650 mg of (2R,3S,4R,5R)-2-(acetoxymethyl)-5-(2-amino-7-(cyclopropylmethyl)-8-oxo-7,8-dihydro-9H-purin-9-yl)tetrahydrofuran-3,4-diyl diacetate, Compound 3 as a white solid in 70% yield with an HPLC purity of 98.2%. $R_f$=0.20 (dichloromethane-methanol=30:1). $^1$H NMR (CDCl$_3$, 400 MHz) δ 7.87 (s, 1H), 6.41-6.46 (m, 1H), 5.85 (d, 1H, J=6.0 Hz), 5.48 (t, 1H, J=4.8 Hz), 4.83 (s, 2H), 4.50-4.56 (m, 2H), 4.36-4.44 (m, 1H), 3.64-3.69 (m, 1H), 2.17 (s, 3H), 2.03 (s, 3H), 2.06 (s, 3H), 1.08-1.19 (m, 1H), 0.55-0.65 (m, 2H), 0.35-0.41 (m, 2H); MS (ESI), m/z 464.2 [M+H]$^+$.

Example 4: 2-Amino-7-(cyclopropylmethyl)-9-((2R,3R,4R,5R)-3,4-dihydroxy-5-(hydroxymethyl)tetrahydrofuran-2-yl)-7,9-dihydro-8H-purin-8-one, Compound 4

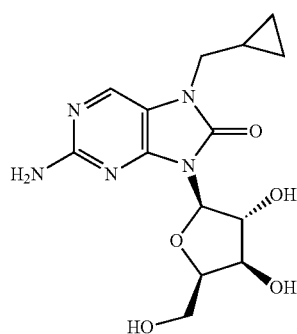 [SMILES: Nc1ncc2c(n1)n([C@@H]1O[C@H](CO)[C@H](O)[C@H]1O)c(=O)n2CC1CC1]

Compound 4 was prepared from Compound 3 according to the following procedure.

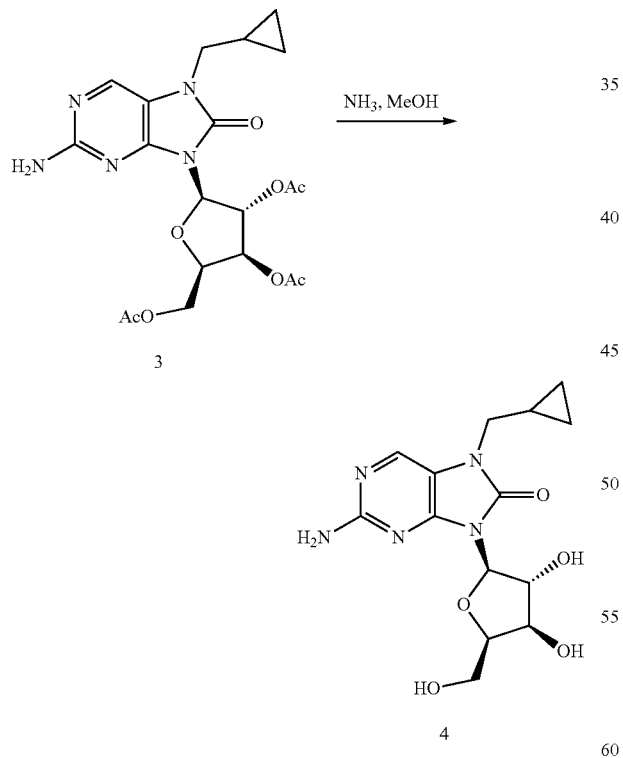

(2R,3S,4R,5R)-2-(Acetoxymethyl)-5-(2-amino-7-(cyclopropylmethyl)-8-oxo-7,8-dihydro-9H-purin-9-yl)tetrahydrofuran-3,4-diyl diacetate, Compound 3 (400 mg, 0.86 mmol) was dissolved in NH$_3$-MeOH (20 mL). The mixture was allowed to stir at room temperature overnight and then concentrated under reduced pressure. The residue was purified on a silica gel column to give 240 mg of 2-amino-7-(cyclopropylmethyl)-9-((2R,3R,4R,5R)-3,4-dihydroxy-5-(hydroxymethyl)tetrahydrofuran-2-yl)-7,9-dihydro-8H-purin-8-one, Compound 4 as a white solid in 82% yield with an HPLC purity of 97.9%; R$_f$=0.30 (dichloromethane-methanol=10:1). $^1$H NMR (DMSO-d$_6$, 400 MHz) δ 8.14 (s, 1H), 6.34 (s, 2H), 5.72 (d, 1H, J=4.8 Hz), 5.61-5.67 (m, 1H), 5.57 (d, 1H, J=4.0 Hz), 4.61-4.66 (m, 1H), 4.57 (t, 1H, J=5.6 Hz), 3.91-3.99 (m, 2H), 3.55-3.75 (m, 4H), 1.10-1.20 (m, 1H), 0.45-0.53 (m, 2H), 0.32-0.40 (m, 2H); MS (ESI), m/z 338.4 [M+H]$^+$, 360.4 [M+Na]$^+$.

Example 5: 2-Amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5

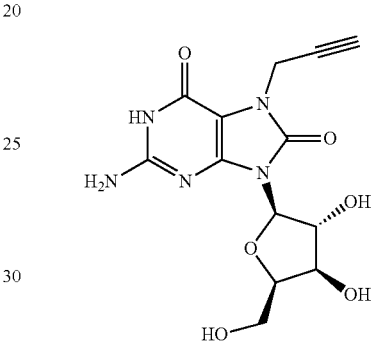

Compound 5 was prepared using a modified method used to synthesize Compound 1 according to the following procedure.

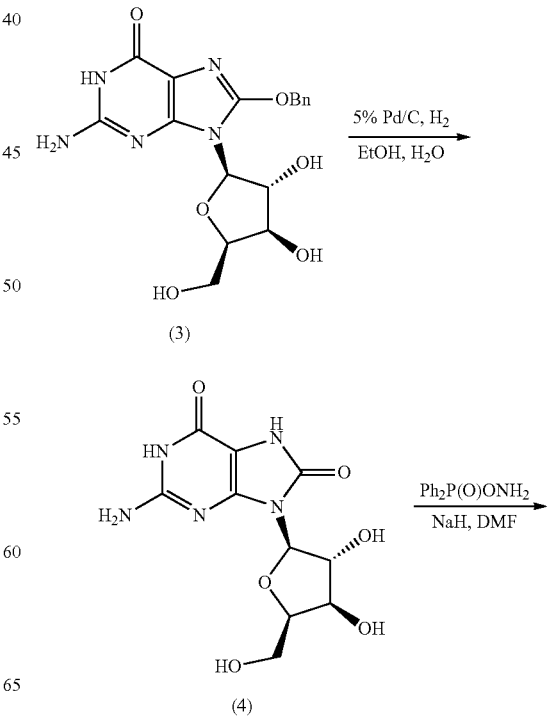

-continued

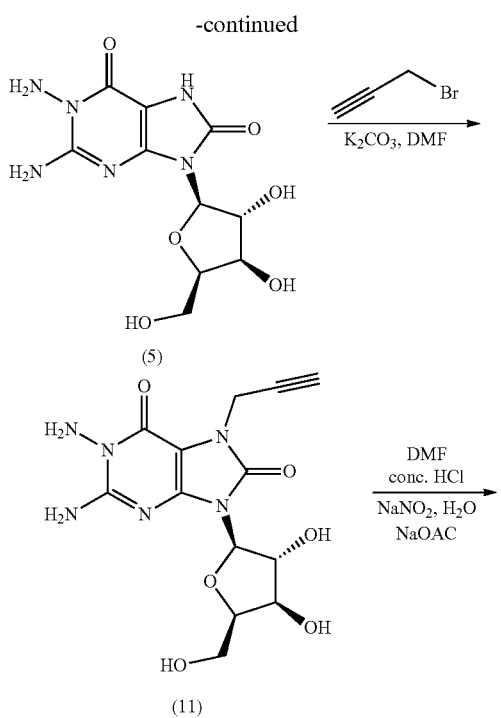

Step 1: 1,2-Diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4)

To a stirred solution of 2-amino-8-(benzyloxy)-9-((2R,3R,4R,5R)-3,4-dihydroxy-5-(hydroxymethyl)tetrahydrofuran-2-yl)-1,9-dihydro-6H-purin-6-one (3) (5.1 g, 13 mmol) in 100 mL of dry DMF was added NaH (0.7 g, 16.9 mmol, 1.3 eq) slowly at 0° C. The reaction mixture was stirred for 30 min, and O-(diphenylphosphinyl)hydroxylamine (4.5 g, 19.5 mmol. 1.5 eq) was added. The reaction mixture was stirred at room temperature until completion as monitored by TLC (dichloromethane-methanol: 3:1). The precipitate was filtered and dried under vacuum to give 3.7 g of 1,2-diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4) as an off-white solid in 70% yield.

Step 2: 1,2-Diamino-9-((2R,3R,4R,5R)-3,4-dihydroxy-5-(hydroxymethyl)tetrahydrofuran-2-yl)-7,9-dihydro-1H-purine-6,8-dione (5)

1,2-Diamino-8-(benzyloxy)-9-((2R,3R,4R,5R)-3,4-dihydroxy-5-(hydroxymethyl)tetrahydrofuran-2-yl)-1,9-dihydro-6H-purin-6-one (4) (3.7 g, 9.1 mmol) was dissolved in 500 mL of ethanol and 500 mL of water in a hydrogenation flask by heating to 90° C. 0.8 g of 5% Pd/C was added. In the Parr reactor the reaction mixture was kept under an atmosphere of hydrogen at 40-50 psi overnight. Hydrogen was evacuated from the reactor and the catalyst was filtered off and washed with hot water. The filtrate was concentrated under reduced pressure giving crude product that was recrystallized from water giving 2.1 g of 1,2-diamino-9-((2R,3R,4R,5R)-3,4-dihydroxy-5-(hydroxymethyl)tetrahydrofuran-2-yl)-7,9-dihydro-1H-purine-6,8-dione (5) as a white solid in 72% yield.

Step 3: 1,2-Diamino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione (11)

1,2-Diamino-9-((2R,3R,4R,5R)-3,4-dihydroxy-5-(hydroxymethyl)tetrahydrofuran-2-yl)-7,9-dihydro-1H-purine-6,8-dione (5) (850 mg, 2.7 mmol, 1.0 eq) was dissolved in 30 mL of anhydrous DMF. $K_2CO_3$ (410 mg, 3.8 mmol, 1.4 eq) was added to the stirred solution, and it was further stirred for 30 min. 3-Bromo-1-propyne (453 mg, 4.8 mmol, 1.8 eq) was added to the reaction mixture, and it was stirred at room temperature overnight. The reaction mixture was concentrated under reduced pressure. The residue was taken up with methanol and purified by flash chromatography on a silica gel column using dichloromethane-methanol (20:1) as an eluent to give 610 mg of 1,2-diamino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione (11) as a white solid in 74% yield.

Step 4: 2-Amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5

1,2-Diamino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione (11) (610 mg, 1.7 mmol) was added to a flask containing 10 mL of DMF. Concentrated hydrochloric acid (0.65 mL) was added at 0° C. An aqueous solution of sodium nitrite (132 mg, 2.04 mmol, 1.2 eq) in 3 mL of water was added under stirring. After stirring for 30 min at 0° C. the reaction mixture was concentrated under reduced pressure. The residue was purified by flash chromatography on a silica gel column using dichloromethane-methanol (10:1) as an eluent to give 408 mg of 2-amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5 as a white solid in 71% yield; $^1$H NMR (DMSO-$d_6$, 400 MHz) δ 11.33 (s, 1H), 6.78 (br, 2H), 5.73-5.76 (m, 2H), 5.48-5.47 (d, 1H, J=3.2 Hz), 4.62-4.63 (m, 2H), 4.50 (s, 1H), 3.9 (s, 2H), 3.30-3.65 (m, 2H), 3.25 (s, 1H). MS (ESI) m/z 338.1 (M+H)$^+$, 360.1 [M+Na]$^+$.

The syntheses of Compounds 6-8, 10-19, and 21-23 was accomplished using the same methods as described for Compounds 1 or 5. Compounds 9 and 20 were originally prepared via the concurrent hydrolysis of a nitrile group under acidic conditions in the final N-1-deamination step. Compounds 10 and 21 may also be prepared from Compounds 9 and 20 by esterification respectively.

Example 6: 2-Amino-7-(but-2-yn-1-yl)-9-((2R,3R,4R,5R)-3,4-dihydroxy-5-(hydroxymethyl)tetrahydrofuran-2-yl)-7,9-dihydro-1H-purine-6,8-dione, Compound 6

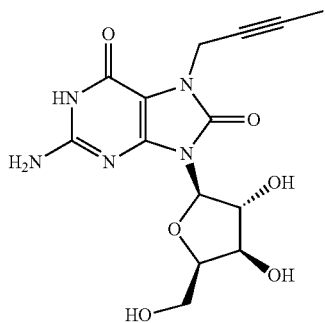 [SMILES: CC#CCn1c(=O)n([C@@H]2O[C@H](CO)[C@H](O)[C@H]2O)c2nc(N)[nH]c(=O)c21]

Off-white solid: $^1$H NMR (DMSO-$d_6$, 400 MHz) δ: 7.02 (s, 2H), 5.82-5.83 (d, 1H, J=4.0 Hz), 5.66-5.68 (d, 1H, J=8.0 Hz), 5.46-5.47 (d, 1H, J=4.0 Hz), 4.66 (t, 1H), 4.57 (t, 1H, J=5.6 Hz), 4.56 (m, 1H), 3.9 (m, 2H), 3.11-3.37 (m, 2H), 1.75 (s, 3H). MS (ESI) m/z 352.2 (M+H)$^+$, 374.1 [M+Na]$^+$.

Example 7: 2-Amino-7-((E)-but-2-en-1-yl)-9-((2R,3R,4R,5R)-3,4-dihydroxy-5-(hydroxymethyl)tetrahydrofuran-2-yl)-7,9-dihydro-1H-purine-6,8-dione, Compound 7

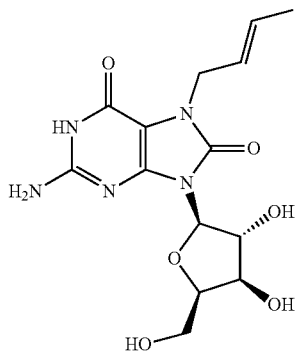 [SMILES: C/C=C/Cn1c(=O)n([C@@H]2O[C@H](CO)[C@H](O)[C@H]2O)c2nc(N)[nH]c(=O)c21]

Off-white solid: MS (ESI) m/z 354.2 (M+H)$^+$, 376.1 [M+Na]$^+$.

Example 8: 2-Amino-9-((2R,3R,4R,5R)-3,4-dihydroxy-5-(hydroxymethyl)tetrahydrofuran-2-yl)-7-((E)-4-hydroxybut-2-en-1-yl)-7,9-dihydro-1H-purine-6,8-dione, Compound 8

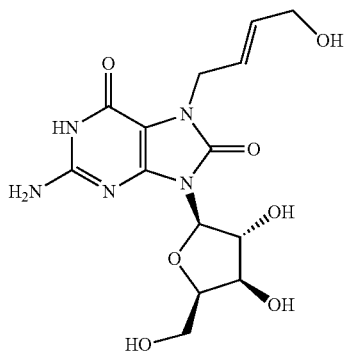 [SMILES: Nc1nc2c(c(=O)[nH]1)n(C/C=C/CO)c(=O)n2[C@@H]1O[C@H](CO)[C@H](O)[C@H]1O]

Off-white solid: $^1$H NMR (DMSO-$d_6$, 400 MHz) δ 6.71 (s, 2H), 5.75 (d, 1H, J=4.8 Hz), 5.66-5.73 (m, 2H), 5.46 (m, 1H), 4.74 (t, 1H, J=5.6 Hz), 4.62 (t, 1H, J=5.6 Hz), 4.41-4.48 (m, 1H), 4.40-4.41 (m, 2H), 3.80-3.98 (m, 4H), 3.51-3.70 (m, 2H), 3.17 (d, 1H, J=5.2 Hz). MS (ESI) m/z 370.1 (M+H)$^+$, 392.1 [M+Na]$^+$.

Example 9: (E)-4-(2-Amino-9-((2R,3R,4R,5R)-3,4-dihydroxy-5-(hydroxymethyl)tetrahydrofuran-2-yl)-6,8-dioxo-1,6,8,9-tetrahydro-7H-purin-7-yl)but-2-enoic acid, Compound 9

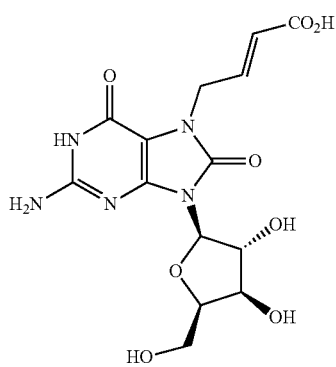 [SMILES: Nc1nc2c(c(=O)[nH]1)n(C/C=C/C(=O)O)c(=O)n2[C@@H]1O[C@H](CO)[C@H](O)[C@H]1O]

Off-white solid: $^1$H NMR (DMSO-$d_6$, 400 MHz) δ 11.15 (s, 1H), 6.64-7.08 (m, 3H), 5.59-5.69 (m, 1H), 5.49 (d, 1H, J=3.2 Hz), 4.48-4.68 (m, 3H), 3.82-4.01 (m, 2H), 3.49-3.74 (m, 2H). MS (ESI) m/z 384.1 (M+H)$^+$, 422.0 [M+K]$^+$.

Example 10: Methyl (E)-4-(2-amino-9-((2R,3R,4R,5R)-3,4-dihydroxy-5-(hydroxymethyl)tetrahydrofuran-2-yl)-6,8-dioxo-1,6,8,9-tetrahydro-7H-purin-7-yl)but-2-enoate, Compound 10

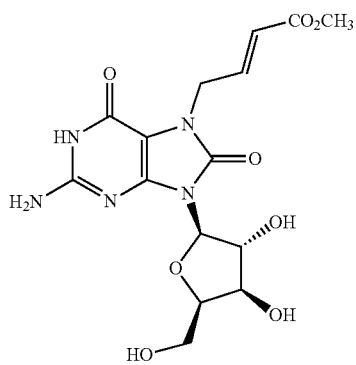 [SMILES: COC(=O)/C=C/Cn1c(=O)n([C@@H]2O[C@H](CO)[C@H](O)[C@H]2O)c2nc(N)[nH]c(=O)c21]

Off-white solid: MS (ESI) m/z 398.1 (M+H)$^+$, 420.1 [M+Na]$^+$.

Example 11: 2-Amino-9-((2R,3R,4R,5R)-3,4-dihydroxy-5-(hydroxymethyl)tetrahydrofuran-2-yl)-7-(4-hydroxybut-2-yn-1-yl)-7,9-dihydro-1H-purine-6,8-dione, Compound 11

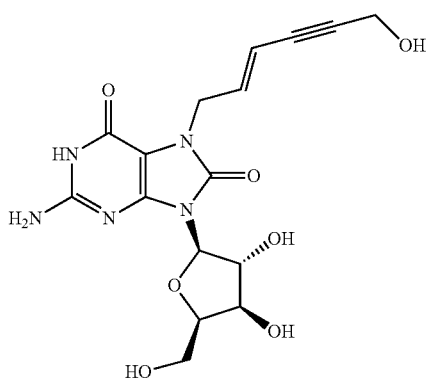 [SMILES: Nc1nc2c(c(=O)[nH]1)n(C/C=C/C#CCO)c(=O)n2[C@@H]1O[C@H](CO)[C@H](O)[C@H]1O]

Off-white solid: MS (ESI) m/z 368.1 (M+H)⁺, 390.1 [M+Na]⁺.

Example 12: Methyl 2-(2-amino-9-((2R,3R,4R,5R)-3,4-dihydroxy-5-(hydroxymethyl)tetrahydrofuran-2-yl)-6,8-dioxo-1,6,8,9-tetrahydro-7H-purin-7-yl)acetate, Compound 12

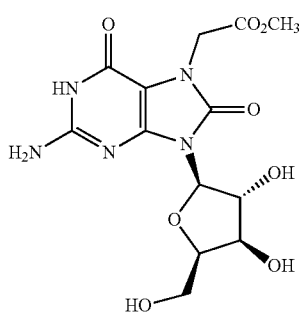 [SMILES: COC(=O)Cn1c(=O)n([C@@H]2O[C@H](CO)[C@H](O)[C@H]2O)c2nc(N)[nH]c(=O)c21]

Off-white solid: MS (ESI) m/z 372.1 (M+H)⁺.

Example 13: 2-Amino-9-((2R,3R,4R,5R)-3,4-dihydroxy-5-(hydroxymethyl)tetrahydrofuran-2-yl)-7-(2,2,2-trifluoroethyl)-7,9-dihydro-1H-purine-6,8-dione, Compound 13

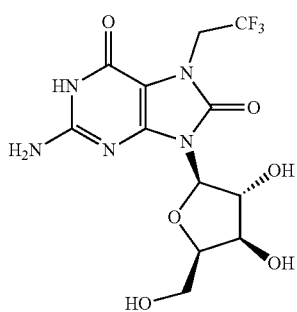 [SMILES: Nc1nc2c(c(=O)[nH]1)n(CC(F)(F)F)c(=O)n2[C@@H]1O[C@H](CO)[C@H](O)[C@H]1O]

Off-white solid: $^1$H NMR (DMSO-$d_6$, 400 MHz) δ 11.09 (s, 1H), 6.86 (s, 2H), 5.78 (d, 1H, J=4 Hz), 5.54 (d, 1H, J=4 Hz), 5.48 (d, 1H, J=4 Hz), 4.55-4.67 (m, 4H), 3.90-3.92 (m, 2H), 3.64-3.69 (m, 1H), 3.54-3.60 (m, 1H). MS (ESI) m/z 382.1 (M+H)⁺, 404.2 [M+Na]⁺.

Example 14: 2-Amino-7-(2,2-difluoroethyl)-9-((2R,3R,4R,5R)-3,4-dihydroxy-5-(hydroxymethyl)tetrahydrofuran-2-yl)-7,9-dihydro-1H-purine-6,8-dione, Compound 14

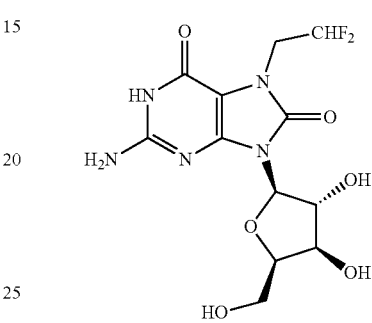

Off-white solid: $^1$H NMR (DMSO-$d_6$, 400 MHz) δ 11.09 (s, 1H), 6.67 (s, 2H), 6.14-6.44 (m, 1H), 5.74 (d, 1H, J=4 Hz), 5.57 (d, 1H, J=8 Hz), 5.48 (d, 1H, J=4 Hz), 4.61 (d, 1H, J=4 Hz), 4.53 (s, 1H), 4.18-4.26 (m, 2H), 3.88-3.93 (m, 2H), 3.64-3.69 (m, 1H), 3.53-3.59 (m, 1H). MS (ESI) m/z 386.0 [M+Na]⁺.

Example 15: 2-Amino-9-((2R,3R,4R,5R)-3,4-dihydroxy-5-(hydroxymethyl)tetrahydrofuran-2-yl)-7-methyl-7,9-dihydro-1H-purine-6,8-dione, Compound 15

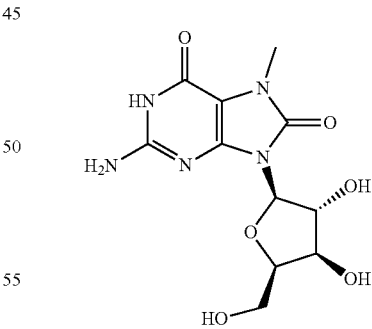

Off-white solid: $^1$H NMR (DMSO-$d_6$, 400 MHz) δ 11.14 (s, 1H), 6.79 (s, 2H), 5.74-5.78 (m, 2H), 5.51 (d, 1H, J=4 Hz), 4.63 (t, 1H, J=8 Hz), 4.48-4.52 (m, 1H), 3.85-3.92 (m, 2H), 3.63-3.69 (m, 1H), 3.51-3.57 (m, 1H), 3.36 (s, 3H). MS (ESI) m/z 314.1 (M+H)⁺, 336.0 [M+Na]⁺.

Example 16: 2-Amino-9-((2R,3R,4R,5R)-3,4-dihydroxy-5-(hydroxymethyl)tetrahydrofuran-2-yl)-7-ethyl-7,9-dihydro-1H-purine-6,8-dione, Compound 16

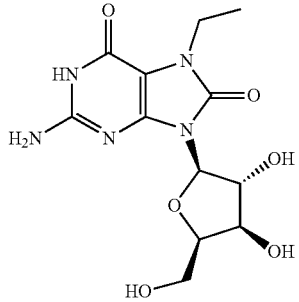 [SMILES: CCn1c(=O)n([C@@H]2O[C@H](CO)[C@H](O)[C@H]2O)c2nc(N)[nH]c(=O)c21]

Off-white solid: $^1$H NMR (DMSO-d$_6$, 400 MHz) δ 11.01 (s, 1H), 6.61 (s, 2H), 5.72-5.76 (m, 2H), 5.51 (d, 1H, J=4 Hz), 4.63 (t, 1H, J=8 Hz), 4.47-4.49 (m, 1H), 3.81-3.91 (m, 4H), 3.64-3.69 (m, 1H), 3.52-3.58 (m, 1H), 1.20 (t, 3H, J=8 Hz). MS (ESI) m/z 328.1 (M+H)$^+$.

Example 17: 2-Amino-9-((2R,3R,4R,5R)-3,4-dihydroxy-5-(hydroxymethyl)tetrahydrofuran-2-yl)-7-propyl-7,9-dihydro-1H-purine-6,8-dione, Compound 17

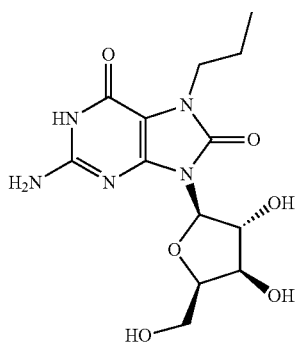 [SMILES: CCCn1c(=O)n([C@@H]2O[C@H](CO)[C@H](O)[C@H]2O)c2nc(N)[nH]c(=O)c21]

Off-white solid: $^1$H NMR (DMSO-d$_6$, 400 MHz) δ 10.95 (s, 1H), 6.58 (s, 2H), 5.71-5.74 (m, 2H), 5.51 (d, 1H, J=4 Hz), 4.63 (t, 1H, J=8 Hz), 4.47-4.49 (m, 1H), 3.84-3.92 (m, 2H), 3.76 (t, 2H, J=8 Hz), 3.64-3.69 (m, 1H), 3.52-3.58 (m, 1H), 1.60-1.69 (m, 2H), 0.83 (t, 3H, J=8 Hz). MS (ESI) m/z 342.2 (M+H)$^+$, 364.1 [M+Na]$^+$.

Example 18: 2-Amino-7-butyl-9-((2R,3R,4R,5R)-3,4-dihydroxy-5-(hydroxymethyl)tetrahydrofuran-2-yl)-7,9-dihydro-1H-purine-6,8-dione, Compound 18

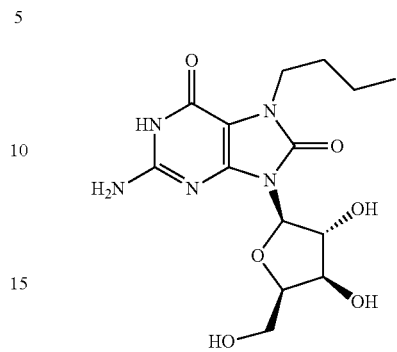

Tan solid: $^1$H NMR (DMSO-d$_6$, 400 MHz) δ 11.02 (s, 1H), 6.58 (s, 2H), 5.71-5.74 (m, 2H), 5.51 (d, 1H, J=4 Hz), 4.63 (t, 1H, J=8 Hz), 4.47-4.49 (m, 1H), 3.84-3.92 (m, 2H), 3.76 (t, 2H, J=8 Hz), 3.64-3.69 (m, 1H), 3.52-3.58 (m, 1H), 1.58-1.65 (m, 2H), 1.21-1.30 (m, 2H), 0.88 (t, 3H, J=8 Hz). MS (ESI) m/z 356.1 (M+H)$^+$, 378.1 [M+Na]$^+$.

Example 19: 2-Amino-9-((2R,3R,4R,5R)-3,4-dihydroxy-5-(hydroxymethyl)tetrahydrofuran-2-yl)-7-(4-hydroxybutyl)-7,9-dihydro-1H-purine-6,8-dione, Compound 19

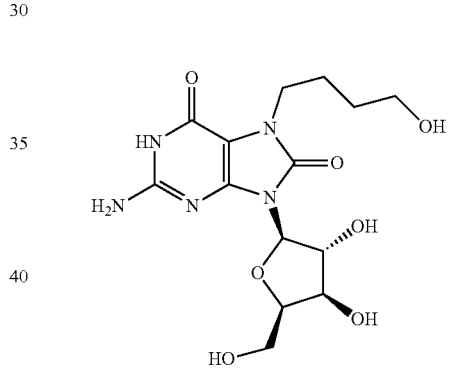

Off-white solid: MS (ESI) m/z 372.4 (M+H)$^+$, 394.4 [M+Na]$^+$.

Example 20: 4-(2-Amino-9-((2R,3R,4R,5R)-3,4-dihydroxy-5-(hydroxymethyl)tetrahydrofuran-2-yl)-6,8-dioxo-1,6,8,9-tetrahydro-7H-purin-7-yl)butanoic acid, Compound 20

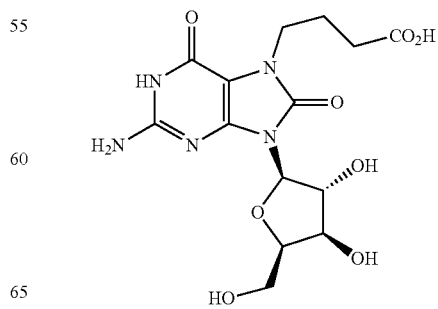

Off-white solid: ¹H NMR (DMSO-d₆, 400 MHz) δ 11.06 (s, 1H), 6.69 (bs, 2H), 5.50 (d, 1H J=3.2 Hz), 5.48-4.65 (b, 3H), 4.49 (dd, 1H, J=3.0, 1.8 Hz), 4.89 (m, 4H), 3.85 (ddd, 1H, J=10.4, 6.4, 4.8, 1.6 Hz), 3.61 (dd, 1H, J=6.4, 4.8 Hz), 2.21 (t, 2H, J=7.2 Hz), 1.88 (m, 2H). MS (ESI) m/z 386.1 (M+H)⁺, 324.1[M+K]⁺.

Example 21: Methyl 4-(2-amino-9-((2R,3R,4R,5R)-3,4-dihydroxy-5-(hydroxymethyl)tetrahydrofuran-2-yl)-6,8-dioxo-1,6,8,9-tetrahydro-7H-purin-7-yl)butanoate, Compound 21

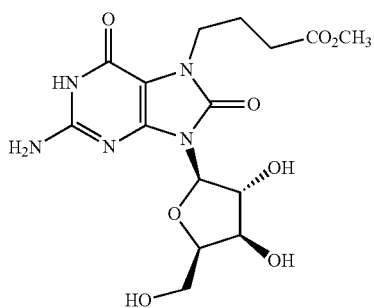 [SMILES: COC(=O)CCCn1c(=O)n([C@@H]2O[C@H](CO)[C@H](O)[C@H]2O)c2nc(N)[nH]c(=O)c21]

Off-white solid: MS (ESI) m/z 400.2 (M+H)⁺, 422.1 [M+Na]⁺.

Example 22: 2-Amino-9-((2R,3R,4R,5R)-3,4-dihydroxy-5-(hydroxymethyl)tetrahydrofuran-2-yl)-7-(2-methoxyethyl)-7,9-dihydro-1H-purine-6,8-dione, Compound 22

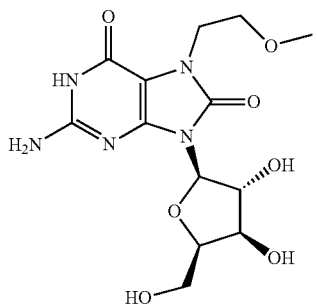 [SMILES: COCCn1c(=O)n([C@@H]2O[C@H](CO)[C@H](O)[C@H]2O)c2nc(N)[nH]c(=O)c21]

Off-white solid: MS (ESI) m/z 358.2 (M+H)⁺.

Example 23: 2-Amino-7-(2-aminoethyl)-9-((2R,3R,4R,5R)-3,4-dihydroxy-5-(hydroxymethyl)tetrahydrofuran-2-yl)-7,9-dihydro-1H-purine-6,8-dione hydrochloride, Compound 23

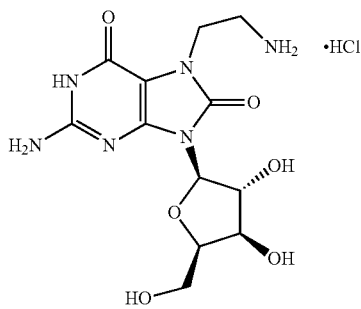 [SMILES: NCCn1c(=O)n([C@@H]2O[C@H](CO)[C@H](O)[C@H]2O)c2nc(N)[nH]c(=O)c21 ; Cl]

Off-white solid: ¹H NMR (DMSO-d₆, 400 MHz) δ 5.63 (s, 1H, J=4.0 Hz), 4.71 (m, 1H), 4.13-4.21 (m, 4H), 3.72-3.85 (m, 2H), 3.25-3.33 (m, 2H). MS (ESI) m/z 343.1 (M+H)⁺.

Example 24: (2R,3S,4R,5R)-2-(Acetoxymethyl)-5-(2-amino-8-oxo-7-(prop-2-yn-yl)-7,8-dihydro-9H-purin-9-yl)tetrahydrofuran-3,4-diyl diacetate, Compound 24

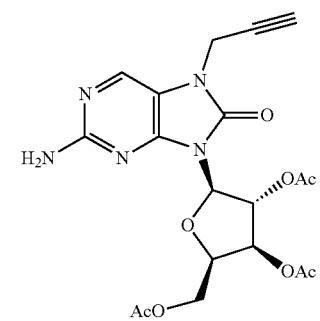 [SMILES: C#CCn1c(=O)n([C@@H]2O[C@H](COC(C)=O)[C@H](OC(C)=O)[C@H]2OC(C)=O)c2nc(N)ncc21]

Compound 24 was made according to the following synthetic procedure from (2R,3S,4R,5R)-2-(acetoxymethyl)-5-(2-amino-6-chloro-8-oxo-7,8-dihydro-9H-purin-9-yl)tetrahydrofuran-3,4-diyl diacetate (9).

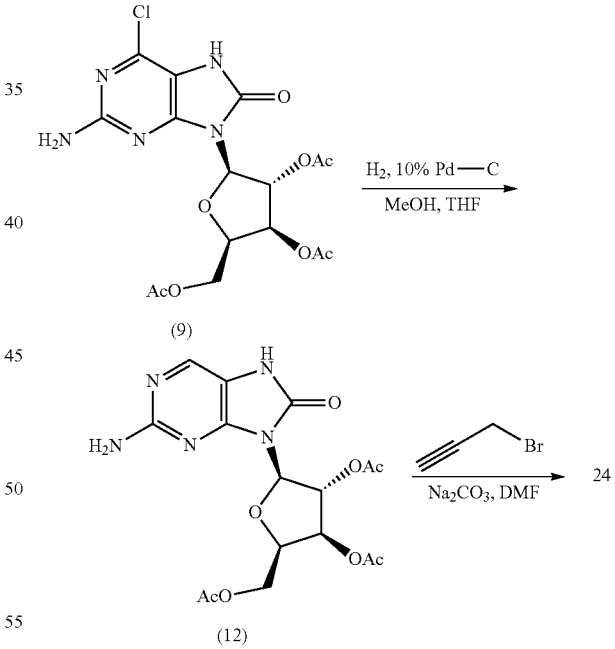

Step 1: (2R,3S,4R,5R)-2-(Acetoxymethyl)-5-(2-amino-8-oxo-7,8-dihydro-9H-purin-9-yl)tetrahydrofuran-3,4-diyl diacetate (12)

(2R,3S,4R,5R)-2-(Acetoxymethyl)-5-(2-amino-6-chloro-8-oxo-7,8-dihydro-9H-purin-9-yl)tetrahydrofuran-3,4-diyl diacetate (9) (6.0 g, 13.6 mmol) was dissolved in a mixture of anhydrous methanol (100 mL) and tetrahydrofuran (10 mL). Catalyst Pd/C (150 mg, 10%) was added, and the mixture was stirred for 5 h under H₂ (50 Psi) atmosphere at room temperature. The catalyst was filtered off through Celite. The solvent was evaporated, and the crude product was used in the next step without further purification.

Step 2: (2R,3S,4R,5R)-2-(Acetoxymethyl)-5-(2-amino-8-oxo-7-(prop-2-yn-1-yl)-7,8-dihydro-9H-purin-9-yl)tetrahydrofuran-3,4-diyl diacetate, Compound 24

(2R,3S,4R,5R)-2-(Acetoxymethyl)-5-(2-amino-8-oxo-7, 8-dihydro-9H-purin-9-yl)tetrahydrofuran-3,4-diyl diacetate (12) (13.6 mmol) was dissolved in 150 mL of anhydrous DMF. Potassium carbonate (2.8 g, 20.4 mmol, 1.5 eq) was added to the stirred solution, and it was further stirred for 5 min. At this time 3-bromopropyne (1.9 mg, 16.32 mmol, 1.2 eq) was added to the reaction mixture and stirred at 45° C. for 5 h. The mixture was concentrated under reduced pressure and the resulting residue was purified by column chromatography using dichloromethane-methanol (70:1) as eluent to give 3.5 g of (2R,3S,4R,5R)-2-(acetoxymethyl)-5-(2-amino-8-oxo-7-(prop-2-yn-yl)-7,8-dihy1dro-9H-purin-9-yl)tetrahydrofuran-3,4-diyl diacetate, Compound 24, as a white foam in 60% yield for two steps with an HPLC purity of 98%. R$_f$=0.50 (dichloromethane-methanol=30:1). ¹H NMR (CDCl₃, 400 MHz) δ 8.01 (s, 1H), 6.35-6.43 (m, 1H), 5.83 (d, 1H, J=5.6 Hz), 6.43-6.51 (m, 1H), 4.91 (s, 2H), 4.59 (t, 1H, J=1.6 Hz), 4.46-4.56 (m, 2H), 4.36-4.45 (m, 1H), 2.37 (t, 1H, J=2.4 Hz), 2.17 (s, 3H), 2.07 (s, 3H), 2.06 (s, 3H). MS (ESI) m/z 448.2 [M+H]⁺, 470.2 [M+Na]⁺.

Example 25: 2-Amino-9-((2R,3R,4R,5R)-3,4-dihydroxy-5-(hydroxymethyl)tetrahydrofuran-2-yl)-7-(prop-2-yn-1-yl)-7,9-dihydro-8H-purin-8-one, Compound 25

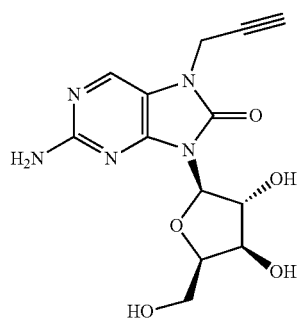 [SMILES: C#CCn1c(=O)n([C@@H]2O[C@H](CO)[C@H](O)[C@H]2O)c2nc(N)ncc21]

Compound 25 was prepared from Compound 24 using the method outlined to prepare Compound 4 from Compound 3.

(2R,3S,4R,5R)-2-(Acetoxymethyl)-5-(2-amino-8-oxo-7-(prop-2-yn-yl)-7,8-dihy1dro-9H-purin-9-yl)tetrahydrofuran-3,4-diyl diacetate, Compound 24 (600 mg, 1.3 mmol) was dissolved in saturated NH₃ in MeOH (50 mL). The mixture was allowed to stir at room temperature overnight and then concentrated under reduced pressure. The residue was purified on a silica gel column to give 300 mg 2-amino-9-((2R,3R,4R,5R)-3,4-dihydroxy-5-(hydroxymethyl)tetrahydrofuran-2-yl)-7-(prop-2-yn-1-yl)-7,9-dihydro-8H-purin-8-one, Compound 25 as a white solid in 72% yield with an HPLC purity of 98.8%; R$_f$=0.50 (dichloromethane-methanol=6:1). ¹H NMR (CDCl₃, 400 MHz) δ 8.08 (s, 1H), 6.44 (s, 2H), 5.72 (d, 1H, J=4.8 Hz), 5.49-5.60 (m, 2H), 4.46-4.76 (m, 4H), 3.92-4.03 (m, 2H), 3.55-3.71 (m, 2H), 3.41 (t, 1H, J=2.4 Hz). MS (ESI) m/z 322.1 (M+H)⁺, 344.1 [M+Na]⁺.

Example 26: 2-Amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26

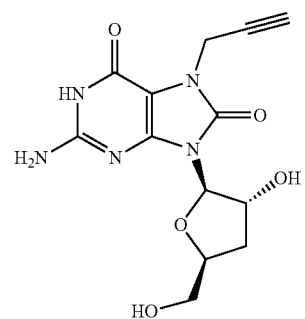 [SMILES: C#CCn1c(=O)n([C@@H]2O[C@H](CO)C[C@H]2O)c2nc(N)[nH]c(=O)c21]

Using the general procedure to synthesize 2-amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5, 2-amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26 was prepared starting from the known 3'-deoxy-guanosine [3608-58-0] and its' corresponding 3'-deoxy-8-bromo-guanosine [847649-68-7] as shown in the following synthetic scheme.

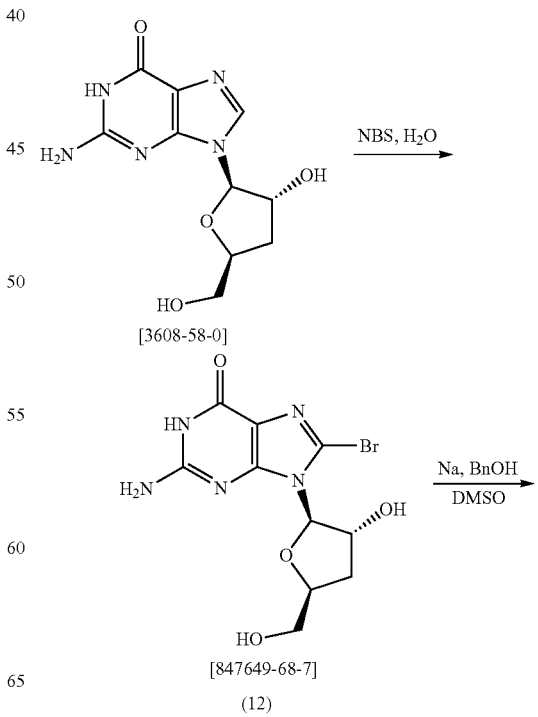

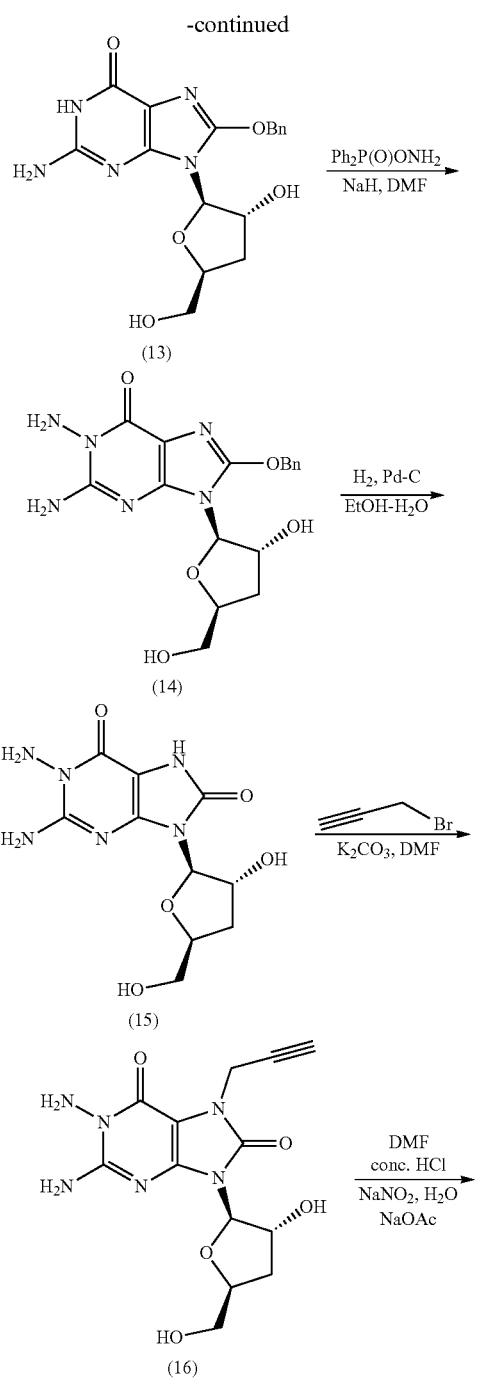

Step 1: 2-Amino-8-bromo-9-((2R,3R,5S)-3-hydroxy-5-(hydroxymethyl)tetrahydrofuran-2-yl)-1,9-dihydro-6H-purin-6-one (12)

To a solution 3'-deoxy-guanosine (2 g, 7.49 mmol, 1 eq) in H$_2$O (20 mL) was added NBS (2.6 g, 14.98 mmol, 2 eq) at 0° C., the reaction mixture was stirred at 0° C. for 1 h. The reaction was monitored by TLC. The reaction mixture was diluted with water (50 mL) and extracted with n-butyl alcohol (3×100 ml); the organic layer was washed with water (100 mL), brine (100 mL), and concentrated. The residue was triturated with diethyl ether filtered, dried under reduced pressure to afford 1.7 g of (65%) 2-amino-8-bromo-9-((2R,3R,5S)-3-hydroxy-5-(hydroxymethyl)tetrahydrofuran-2-yl)-1,9-dihydro-6H-purin-6-one (12) as an off-white solid. $^1$H NMR (400 MHz, DMSO-d$_6$): δ 10.81 (brs, 1H), 6.53 (s, 2H), 5.62 (d, J=3.2 Hz, 1H), 5.54 (s, 1H), 4.94 (s, 1H), 4.80 (s, 1H), 4.24-4.18 (m, 1H), 3.50 (d, J=3.6 Hz, 2H), 2.47-2.43 (m, 1H), 1.91-1.86 (m, 1H). (ESI) m/z 344.0, 346.0 (M−H)⁻.

Step 2: 2-Amino-8-(benzyloxy)-9-((2R,3R,5S)-3-hydroxy-5-(hydroxymethyl)tetrahydrofuran-2-yl)-1,9-dihydro-6H-purin-6-one (13)

Sodium metal (339 mg, 14.78 mmol, 3 eq) was dissolved in benzyl alcohol (7.9 g, 73.91 mmol, 15 eq) and heated to 65° C. until a clear solution was observed. The reaction mixture was then brought to room temperature and to it was added a solution of 2-amino-8-bromo-9-((2R,3R,5S)-3-hydroxy-5-(hydroxymethyl)tetrahydrofuran-2-yl)-1,9-dihydro-6H-purin-6-one in DMSO (8 mL) (1.7 g, 4.92 mmol, 1 eq) dropwise at room temperature. The reaction mixture was then stirred at 80° C. for 5 h. The reaction was monitored by TLC. The reaction mixture was diluted with water (50 mL) and washed with diethyl ether (2×100 mL), the aqueous layer was extracted with n-butyl alcohol (3×100 mL). The organic layer was washed with water (100 mL), brine (100 mL), and concentrated to get crude which on trituration with diethyl ether afforded 1.6 g (87%) of 2-amino-8-(benzyloxy)-9-((2R,3R,5S)-3-hydroxy-5-(hydroxymethyl)tetrahydrofuran-2-yl)-1,9-dihydro-6H-purin-6-one (13) as an off-white solid. $^1$H NMR (500 MHz, DMSO-d$_6$): δ 11.65 (brs, 1H), 7.48 (d, J=7 Hz, 2H), 7.42-7.30 (m, 3H), 6.31 (brs, 2H), 5.54 (d, J=3.5 Hz, 1H), 5.48 (s, 1H), 5.39 (d, J=4 Hz, 2H), 5.31 (brs, 1H), 4.75 (s, 1H), 4.16-4.11 (m, 1H), 3.45-3.43 (m, 2H), 2.21-2.15 (m, 1H), 1.85-1.80 (m, 1H). (ESI) m/z 374.1 (M+H)⁺.

Step 3: 1,2-Diamino-8-(benzyloxy)-9-((2R,3R,5S)-3-hydroxy-5-(hydroxymethyl)tetrahydrofuran-2-yl)-1,9-dihydro-6H-purin-6-one (14)

To a solution of 2-amino-8-(benzyloxy)-9-((2R,3R,5S)-3-hydroxy-5-(hydroxymethyl)tetrahydrofuran-2-yl)-1,9-dihydro-6H-purin-6-one (1.6 g, 4.28 mmol, 1 eq) in DMF (20 mL) was added 60% NaH (2.5 mg, 5.14 mmol, 1.2 eq) at 0° C. After stirring for 30 min, O-(diphenylphosphoryl)hydroxylamine (1.59 g, 6.86 mmol, 1.6 eq) was added portionwise at the same temperature. The reaction mixture was stirred at room temperature for 2 h and the precipitate formed was removed by filtration. The filtrate was diluted with water (50 mL) and extracted with n-butyl alcohol (3×100 mL). The organic layer was washed with water (100 mL), brine solution (100 mL), and concentrated to get crude solid which upon trituration with diethyl ether afforded 1.3 g (78%) of 1,2-diamino-8-(benzyloxy)-9-((2R,3R,5S)-3-hydroxy-5-(hydroxymethyl)tetrahydrofuran-2-yl)-1,9-dihydro-6H-purin-6-one (14) as an off-white solid. $^1$H NMR (400 MHz, DMSO-d$_6$): δ 7.49 (d, J=8 Hz, 2H), 7.43-7.35 (m, 3H), 6.97 (s, 2H), 5.58-5.56 (m, 2H), 5.40 (s, 2H), 5.38 (s, 2H), 4.79-4.77 (m, 1H), 4.72-4.71 (m, 1H), 4.14-4.09 (m, 1H), 3.39-3.35 (m, 2H), 2.20-2.13 (m, 1H), 1.80-1.75 (m, 1H). (ESI) m/z 389.1 (M+H)⁺.

Step 4: 1,2-Diamino-9-((2R,3R,5S)-3-hydroxy-5-(hydroxymethyl)tetrahydrofuran-2-yl)-7,9-dihydro-1H-purine-6,8-dione (15)

To a solution of 1,2-diamino-9-((2R,3R,5S)-3-hydroxy-5-(hydroxymethyl)tetrahydrofuran-2-yl)-7,9-dihydro-1H- purine-6,8-dione (1.3 g, 3.35 mmol, 1 eq) in EtOH:H$_2$O (1:1; 60 mL), was added 10% Pd/C (400 mg) in a Parr shaker vessel. The reaction mixture was shaken with hydrogen (70 psi) at room temperature for 2 h. Progress of the reaction was monitored by TLC. Once starting material was consumed the reaction mixture was filtered through celite bed and washed with ethanol. The combined filtrate was concentrated and the residue was triturated with diethyl ether to afforded 1.2 g (crude) of 1,2-diamino-9-((2R,3R,5S)-3-hydroxy-5-(hydroxymethyl)tetrahydrofuran-2-yl)-7,9-dihydro-1H-purine-6,8-dione (15) as an off-white solid. The product was used as is or may be recrystallized from water. $^1$H NMR (400 MHz, DMSO-d$_6$): δ 10.64 (s, 1H), 7.04 (s, 2H), 5.50 (d, J=4.4 Hz, 1H), 5.41-5.36 (m, 1H), 5.37 (s, 2H), 4.82-4.80 (m, 1H), 4.73 (t, J=5.6 Hz, 1H), 4.13-4.12 (m, 1H), 3.50-3.38 (m, 2H), 2.40-2.32 (m, 1H), 1.85-1.79 (m, 1H). (ESI) m/z 299.1 (M+H)$^+$.

Step 5: 1,2-Diamino-9-((2R,3R,5S)-3-hydroxy-5-(hydroxymethyl)tetrahydrofuran-2-yl)-7-(prop-2-yn-1-yl)-7,9-dihydro-1H-purine-6,8-dione (16)

1,2-Diamino-9-((2R,3R,5S)-3-hydroxy-5-(hydroxymethyl)tetrahydrofuran-2-yl)-7,9-dihydro-1H-purine-6,8-dione (15) (650 mg, 2.18 mmol, 1.0 eq) was dissolved in 50 mL of anhydrous DMF. K$_2$CO$_3$ (402 mg, 3.05 mmol, 1.4 eq) was added to the stirred solution, and it was further stirred for 30 min. 3-Bromo-1-propyne (458 mg, 3.92 mmol, 1.8 eq) was added to the reaction mixture, and it was stirred at room temperature overnight. The reaction mixture was concentrated under reduced pressure and the remaining residue was taken up with methanol and purified by flash chromatography on a silica gel column using dichloromethane-methanol (20:1) as an eluent to give 505 mg of 1,2-diamino-9-((2R,3R,5S)-3-hydroxy-5-(hydroxymethyl)tetrahydrofuran-2-yl)-7-(prop-2-yn-1-yl)-7,9-dihydro-1H-purine-6,8-dione (16) as a white solid in 69% yield. MS (ESI) m/z 337.1 (M+H)$^+$.

Step 6: 2-Amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26

1,2-Diamino-9-((2R,3R,5S)-3-hydroxy-5-(hydroxymethyl)tetrahydrofuran-2-yl)-7-(prop-2-yn-1-yl)-7,9-dihydro-1H-purine-6,8-dione (16) (400 mg, 1.19 mmol) was added to the flask containing 10 mL of DMF. Concentrated hydrochloric acid (0.44 mL) was added at 0° C. An aqueous solution of sodium nitrite (98 mg, 0.98 mmol, 1.2 eq) in 2 mL of water was added under stirring. After stirred for 30 min at 0° C. The reaction mixture was concentrated under reduced pressure. The residue was purified by flash chromatography on a silica gel column using dichloromethane-methanol (10:1) as an eluent to give 240 mg of 2-amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26 as a white solid in 67% yield; $^1$H NMR (400 MHz, DMSO-d$_6$): δ 10.98 (s, 1H), 6.55 (s, 2H), 5.51 (d, J=3.6 Hz, 1H), 5.39 (d, J=4.4 Hz, 1H), 4.81-4.77 (m, 1H), 4.68 (t, J=5.6 Hz, 1H), 4.56 (d, J=2 Hz, 2H), 4.16-4.12 (m, 1H), 3.48-3.41 (m, 2H), 3.22 (s, 1H), 2.38-2.31 (m, 1H), 1.85-1.79 (m, 1H). MS (ESI) m/z 322.1 (M+H)$^+$, 344.1 [M+Na]$^+$.

Example 27: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27

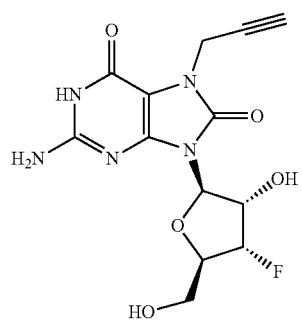 [SMILES: C#CCn1c(=O)n([C@@H]2O[C@H](CO)[C@@H](F)[C@H]2O)c2nc(N)[nH]c(=O)c21]

Using the general procedure to synthesize 2-amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5, 2-amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27 was prepared starting from the known 3'-deoxy-(3'S)-fluoro-guanosine [123402-21-1] and its' corresponding 3'-deoxy-(3'S)-fluoro-8-bromoguanosine [847649-50-7] as shown in the following synthetic scheme.

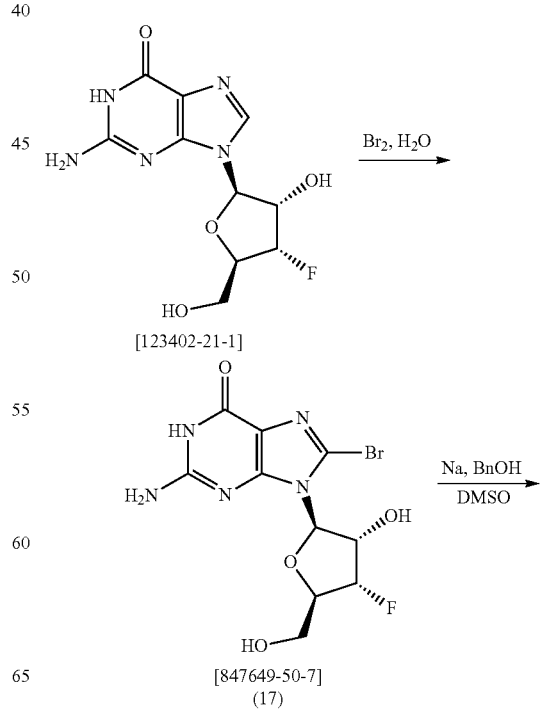

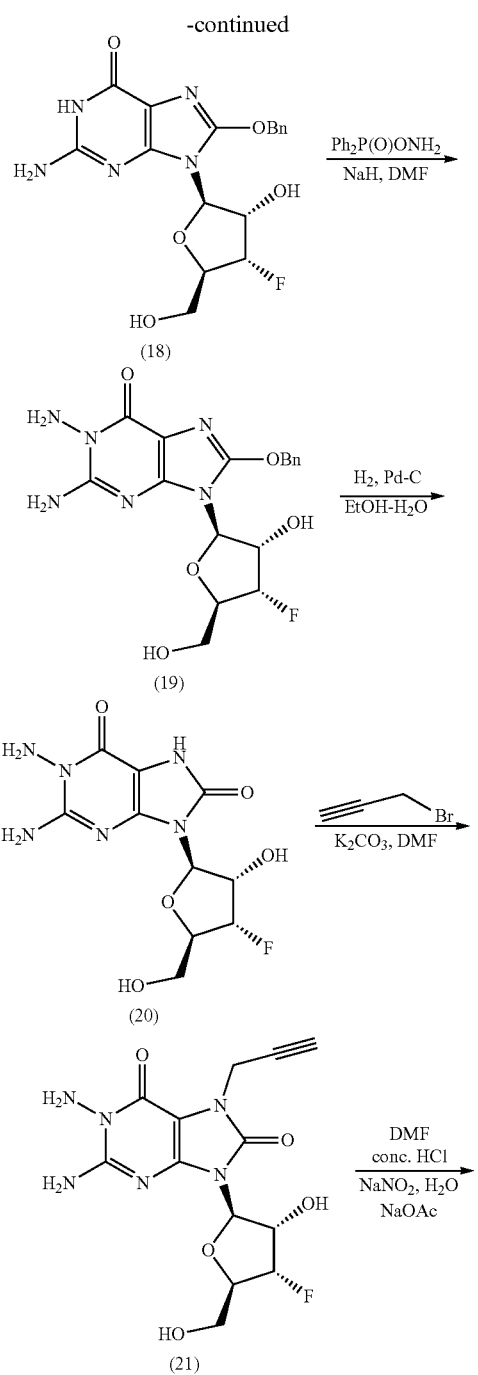

the filtrate was washed with water and acetone. The solid was dried under vacuum to give 13 g of 2-amino-8-bromo-9-((2R,3S,4S,5R)-4-fluoro-3-hydroxy-5-(hydroxymethyl)tetrahydrofuran-2-yl)-1,9-dihydro-6H-purin-6-one (17) as an off-white solid in 68% yield.

Step 2: 2-Amino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (18)

Small pieces of sodium (1.2 g) were added to 28 mL of benzyl alcohol in a round-bottom flask. The mixture was stirred at room temperature for 0.5 h, and then heated to 65° C. until sodium went into solution. A solution of 2-amino-8-bromo-9-((2R,3S,4S,5R)-4-fluoro-3-hydroxy-5-(hydroxymethyl)tetrahydrofuran-2-yl)-1,9-dihydro-6H-purin-6-one (17) (7 g, 19.2 mmol) in 28 mL of DMSO was added to the stirred solution obtained above. The reaction mixture was stirred for 5 h until completion as monitored by TLC. Glacial acetic acid was added to the stirred reaction mixture to adjust the pH to 7. The mixture was poured into 1 L of ether with vigorously stirring. The upper ether layer was decanted, and the remaining material was added to a large amount of acetone (800 mL) under stirring. The solid was filtered, and the crude product was washed with water. The crude product was heated in a mixture of ethanol-water (1:1). The mixture was cooled to room temperature. The precipitate was filtered and dried under vacuum to give 4 g of 2-amino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (18) as an off-white solid product 23 in 53% yield.

Step 3: 1,2-Diamino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (19)

To a stirred solution of 2-amino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (18) (2 g, 5.1 mmol) in 40 mL of dry DMF was added NaH (0.24 g, 6.1 mmol) slowly at 0° C. The mixture was stirred for 30 min, and O-(diphenylphosphinyl)hydroxylamine (1.9 g, 8.2 mmol) was added. The reaction mixture was stirred at room temperature until consumption of starting material as indicated by TLC monitoring. The precipitate was filtered and dried under reduced pressure. The residue was purified by flash chromatography on a silica gel column using dichloromethane-methanol (10:1) as an eluent giving 1 g of 1,2-diamino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (19) as a white solid in 50% yield.

Step 4: 1,2-Diamino-9-((2R,3S,4S,5R)-4-fluoro-3-hydroxy-5-(hydroxymethyl)tetrahydrofuran-2-yl)-7,9-dihydro-1H-purine-6,8-dione (20)

1,2-Diamino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (19 (1 g, 2.5 mmol) was dissolved in 1000 mL of ethanol and 1000 mL of water by heating to 90° C. 10% Pd/C (0.2 g) was added. The reaction mixture was Step 1: 2-Amino-8-bromo-9-((2R,3S,4S,5R)-4-fluoro-3-hydroxy-5-(hydroxymethyl)tetrahydrofuran-2-yl)-1,9-dihydro-6H-purin-6-one (17)

In a fume hood an aqueous bromine solution (5.4 mL, 2 eq) was slowly added to a stirred solution of 3'-deoxy-(3'S)-fluoro-guanosine [123402-21-1] (15 g, 52.6 mmol) in 300 mL at room temperature. The reaction mixture was stirred overnight in a closed round-bottom flask at room temperature overnight or until completion as monitored by TLC. An aqueous sodium thiosulfate solution was added to destroy the excess bromine. The reaction mixture was filtered, and hydrogenated under 1 atm hydrogen atmosphere overnight. The catalyst was filtered off and washed with hot water. The filtrate was concentrated under reduced pressure and the remaining crude solid was recrystallized from water giving 0.65 g of 1,2-diamino-9-((2R,3S,4S,5R)-4-fluoro-3-hydroxy-5-(hydroxymethyl)tetrahydrofuran-2-yl)-7,9-dihydro-1H-purine-6,8-dione (20) as a white solid in 84% yield.

Step 5: 1,2-Diamino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione (21)

1,2-Diamino-9-((2R,3S,4S,5R)-4-fluoro-3-hydroxy-5-(hydroxymethyl)tetrahydrofuran-2-yl)-7,9-dihydro-1H-purine-6,8-dione (20) (650 mg, 2 mmol, 1.0 eq) was dissolved in 20 mL of anhydrous DMF. $K_2CO_3$ (414 mg, 3 mmol, 1.5 eq) was added, and it was further stirred for 30 min. 3-Bromopropyne (476 mg, 4 mmol, 2 eq) was added to the reaction mixture, and it was stirred at room temperature overnight. The reaction mixture was concentrated under reduced pressure. The residue was taken up with methanol and purified by flash chromatography on a silica gel column using dichloromethane-methanol (15:1) as an eluent to yield 580 mg of 1,2-diamino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione (21) as a white solid in 79%.

Step 6: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27

1,2-Diamino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione (21) (580 mg, 1.63 mmol) was added to the flask containing 10 mL of DMF. Concentrated hydrochloric acid (0.6 mL) was added at 0° C. An aqueous solution of sodium nitrite (135 mg, 1.96 mmol, 1.2 eq) in 5 mL of water was added under stirring. Stirring was continued at 0° C. for 30 min and the reaction mixture was then concentrated under reduced pressure. The residue was purified by flash chromatography on a silica gel column using dichloromethane-methanol (10:1) as an eluent giving 465 mg of 2-amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27 as a white solid in 83% yield. HPLC purity 96.5%; $^1$H NMR (DMSO-$d_6$, 400 MHz) δ 11.07 (s, 1H), 6.81 (s, 2H), 5.81 (d, 1H, J=4 Hz), 5.63 (d, 1H, J=8 Hz), 5.19-5.11 (m, 1H), 5.10-4.97 (m, 2H), 4.60 (s, 2H), 4.14-4.08 (m, 1H), 3.59-3.52 (m, 2H), 3.25 (s, 1H). ESI-MS m/z 340.1 [M+H]$^+$, 362.1 [M+Na]$^+$.

Example 28: 2-Amino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 28

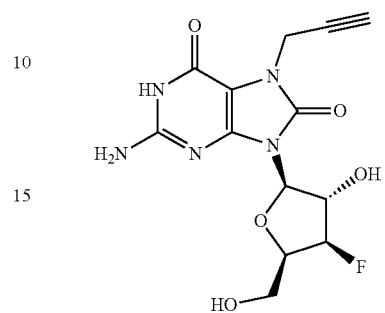

Using the general procedure to synthesize 2-amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5, 2-amino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 28 was prepared starting from the known 3'-deoxy-(3'R)-fluoro-guanosine [125291-15-8] as shown in the following synthetic scheme.

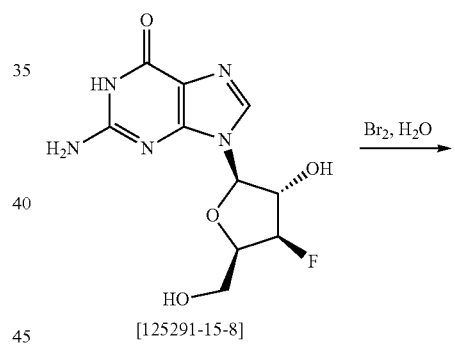

[125291-15-8]

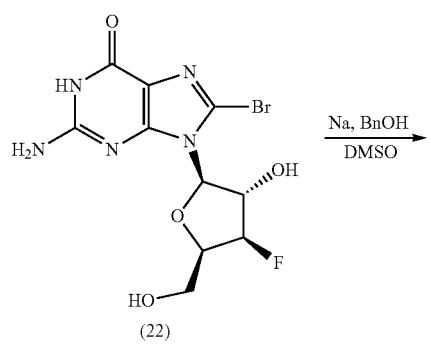

(22)

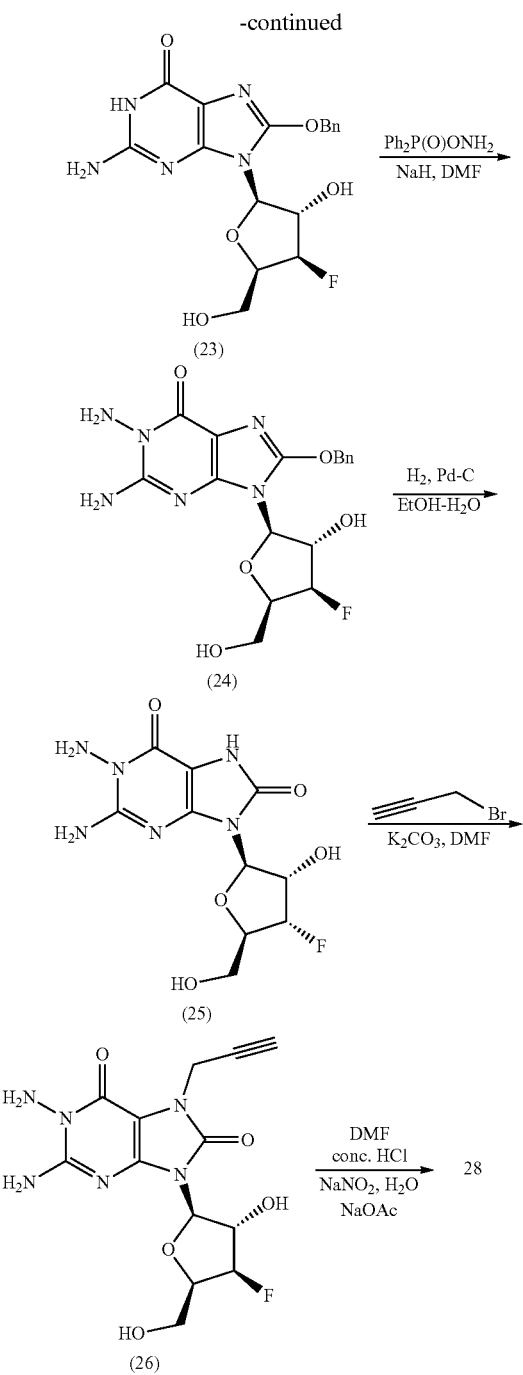

dried under vacuum giving 6.5 g of 2-amino-8-bromo-9-((2R,3S,4R,5R)-4-fluoro-3-hydroxy-5-(hydroxymethyl)tetrahydrofuran-2-yl)-1,9-dihydro-6H-purin-6-one (22) as an off-white solid in 76% yield.

Step 2: 2-Amino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (23)

Small pieces of sodium (1.2 g, 3 eq) was added to 25 mL of benzyl alcohol in a round-bottom flask. The mixture was stirred at room temperature for 0.5 h, and then heated to 65° C. until the disappearance of sodium. A solution of 2-amino-8-bromo-9-((2R,3S,4R,5R)-4-fluoro-3-hydroxy-5-(hydroxymethyl)tetrahydrofuran-2-yl)-1,9-dihydro-6H-purin-6-one (22) (6.5 g, 17.8 mmol) in 30 mL of DMSO was added to the stirred sodium alkoxide solution obtained above. It was stirred at 65° C. for 10 h until consumption of (22) as determined by TLC. Glacial acetic acid was added to the stirred reaction mixture to adjust the pH to 7. The mixture was poured into 1.5 L of ether with vigorously stirring. The solids were filtered, and the crude product was washed with water. The crude product was heated in a mixture of ethanol-water (1:1) and then cooled to room temperature. The precipitate was filtered and dried under vacuum to give 3.8 g of 2-amino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (23) as an off-white solid in 54% yield.

Step 3: 1,2-Diamino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (24)

To a stirred solution of 2-amino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (23) (3.8 g, 9.7 mmol) in 80 mL of dry DMF was added NaH (0.46 g, 11.6 mmol) slowly at 0° C. The reaction mixture was stirred for 30 min, and O-(diphenylphosphinyl)hydroxylamine (3.3 g, 14.5 mmol) was added and stirring at room temperature was continued until completion was determined by TLC. The precipitate was filtered and dried under reduced pressure. The residue was purified by flash chromatography on a silica gel column using dichloromethane-methanol (10:1) as an eluent giving 2 g of 1,2-diamino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (24) as a white solid in 51% yield.

Step 4: 1,2-Diamino-9-((2R,3S,4R,5R)-4-fluoro-3-hydroxy-5-(hydroxymethyl)tetrahydrofuran-2-yl)-7,9-dihydro-1H-purine-6,8-dione (25)

1,2-Diamino-8-(benzyloxy)-9-((2R,3S,4R,5R)-4-fluoro-3-hydroxy-5-(hydroxymethyl)tetrahydrofuran-2-yl)-1,9-dihydro-6H-purin-6-one (24) (2 g, 5 mmol) was dissolved in 1200 mL of ethanol and 1200 mL of water by heating to 90° C. 0.4 g of Pd/C catalyst (10%) was added. The reaction mixture was maintained under 1 atmosphere of hydrogen overnight. The catalyst was filtered through Celite and washed with hot water. The filtrate was concentrated under reduced pressure giving a solid that was recrystallized from water yielding 1.3 g of 1,2-diamino-9-((2R,3S,4R,5R)-4-fluoro-3-hydroxy-5-(hydroxymethyl)tetrahydrofuran-2-yl)-7,9-dihydro-1H-purine-6,8-dione (25) as a white solid in 84%.

Step 1: 2-Amino-8-bromo-9-((2R,3S,4R,5R)-4-fluoro-3-hydroxy-5-(hydroxymethyl)tetrahydrofuran-2-yl)-1,9-dihydro-6H-purin-6-one (22)

In a fume hood an aqueous bromine solution (2.4 mL, 2 eq) was slowly added to a stirred solution of 3'-deoxy-(3'R)-fluoro-guanosine [125291-15-8] (6.7 g, 23 mmol) in 100 mL of water at room temperature. The reaction mixture was sealed in a round-bottom flask and stirred at room temperature overnight or until completion as indicated by TLC. An aqueous sodium thiosulfate solution was added to destroy the excess bromine, the reaction mixture was filtered and the filtrate was washed with water and acetone. The solid was Step 5: 1,2-Diamino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione (26)

1,2-Diamino-9-((2R,3S,4R,5R)-4-fluoro-3-hydroxy-5-(hydroxymethyl)tetrahydrofuran-2-yl)-7,9-dihydro-1H-purine-6,8-dione (25) (1.3 g, 4.1 mmol, 1.0 eq) was dissolved in 40 mL of anhydrous DMF. K₂CO₃ (854 mg, 6.1 mmol, 1.5 eq) was added to the stirred solution, and it was further stirred for 30 min. 3-Bromopropyne (976 mg, 8.2 mmol, 2 eq) was added, and the reaction mixture was stirred at room temperature overnight. The reaction mixture was concentrated under reduced pressure whereupon the residue was taken up with methanol and purified by flash chromatography on a silica gel column using dichloromethane-methanol (15:1) as an eluent giving 1.2 g of 1,2-diamino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione (26) as a white solid in 82% yield.

Step 6: 2-Amino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 28

1,2-Diamino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione (26) (1.2 g, 3.39 mmol) was added to the flask containing 20 mL of DMF. Concentrated hydrochloric acid (1.2 mL) was added at 0° C. An aqueous solution of sodium nitrite (280 mg, 4.07 mmol, 1.2 eq) in 10 mL of water was added under stirring. After stirring at 0° C. for 30 min, the reaction mixture was concentrated under reduced pressure. The residue was purified by flash chromatography on a silica gel column using dichloromethane-methanol (10:1) as an eluent giving 960 mg of 2-amino-9-((2R,3S,4R,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 28 as a white solid in 83% yield. HPLC purity 96.3%; ¹H NMR (DMSO-d₆, 400 MHz) δ 10.98 (s, 1H), 6.60 (s, 2H), 5.95 (s, 1H), 5.35-5.37 (m, 2H), 4.74-5.08 (m, 2H), 4.60 (s, 2H), 4.00-4.08 (m, 1H), 3.56-3.63 (m, 2H), 3.24 (t, 1H, J=4 Hz). ESI-MS m/z 340.1 [M+H]⁺, 362.1 [M+Na]⁺.

Example 29: ((2S,4R,5R)-4-Acetoxy-5-(2-amino-8-oxo-7-(prop-2-yn-1-yl)-7,8-dihydro-9H-purin-9-yl)tetrahydrofuran-2-yl)methyl acetate, Compound 29

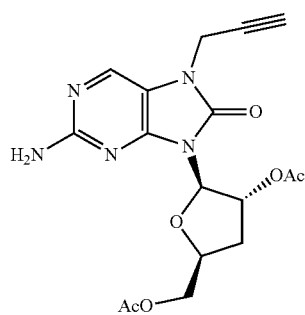 [SMILES: C#CCn1c(=O)n([C@@H]2O[C@H](COC(C)=O)C[C@H]2OC(C)=O)c2nc(N)ncc21]

Compound 29 was made according to the following multi-step procedure.

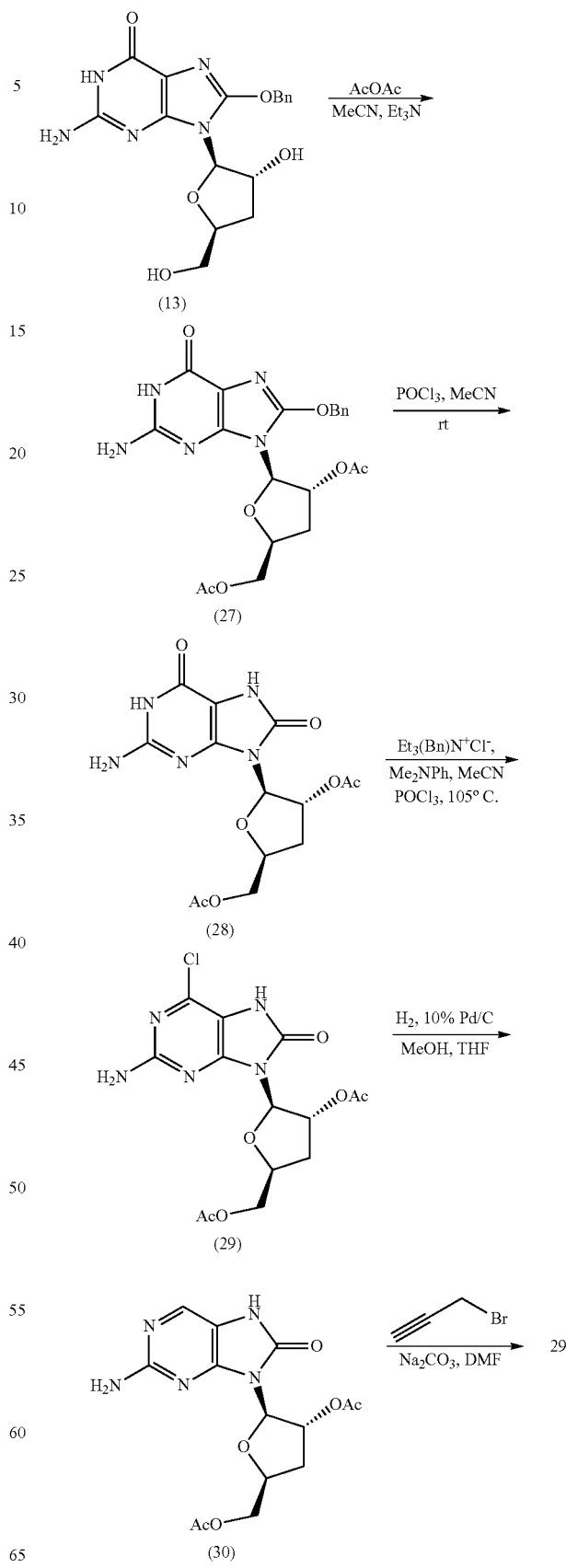

Step 1: ((2S,4R,5R)-4-Acetoxy-5-(2-amino-8-(benzyloxy)-6-oxo-1,6-dihydro-9H-purin-9-yl)tetrahydrofuran-2-yl)methyl acetate (27)

A solution of 2-amino-8-(benzyloxy)-9-((2R,3R,5S)-3-hydroxy-5-(hydroxymethyl)tetrahydrofuran-2-yl)-1,9-dihydro-6H-purin-6-one (13) (22 g, 58.9 mmol) in anhydrous MeCN (300 mL) containing triethylamine (40.8 mL) was treated with acetic anhydride (12.3 mL, 129.7 mmol, 2.2 eq). The reaction mixture was stirred at room temperature overnight. The reaction mixture was diluted with dichloromethane (800 mL) and poured into 800 mL of water. The layers were separated, and the aqueous layer was extracted twice with dichloromethane. The combined organic layer was washed with brines, dried over anhydrous $Na_2SO_4$, and concentrated under reduced pressure. The resulting residue was purified by column chromatography on a silica gel column using dichloromethane-methanol (50:1) as an eluent to give 18.1 g of ((2S,4R,5R)-4-acetoxy-5-(2-amino-8-(benzyloxy)-6-oxo-1,6-dihydro-9H-purin-9-yl)tetrahydrofuran-2-yl)methyl acetate (27) as a yellow solid in 67% yield; $R_f$=0.5 (dichloromethane-methanol=10:1).

Step 2: ((2S,4R,5R)-4-Acetoxy-5-(2-amino-6,8-dioxo-1,6,7,8-tetrahydro-9H-purin-9-yl)tetrahydrofuran-2-yl)methyl acetate (28)

In an oven-dried flask, ((2S,4R,5R)-4-acetoxy-5-(2-amino-8-(benzyloxy)-6-oxo-1,6-dihydro-9H-purin-9-yl)tetrahydrofuran-2-yl)methyl acetate (27) (18.1 g, 39.6 mmol) was dissolved in 200 mL of dry MeCN. Phosphorus oxychloride (3.6 mL, 39.6 mmol, 1.0 eq) was added, and it was stirred at room temperature for 1 h. The reaction mixture was diluted with dichloromethane (800 mL) and poured into saturated sodium bicarbonate aqueous solution. The aqueous layer was extracted with dichloromethane. The combined organic layer was dried over anhydrous $Na_2SO_4$, The resulting residue was purified by column chromatography using dichloromethane-methanol (30:1) as an eluent to give 13 g of ((2S,4R,5R)-4-acetoxy-5-(2-amino-6,8-dioxo-1,6,7,8-tetrahydro-9H-purin-9-yl)tetrahydrofuran-2-yl)methyl acetate (28) as a white solid in 89% yield, $R_f$=0.40 (dichloromethane-methanol=10:1).

Step 3: ((2S,4R,5R)-4-Acetoxy-5-(2-amino-6-chloro-8-oxo-7,8-dihydro-9H-purin-9-yl)tetrahydrofuran-2-yl)methyl acetate (29)

In an oven-dried flask ((2S,4R,5R)-4-acetoxy-5-(2-amino-6,8-dioxo-1,6,7,8-tetrahydro-9H-purin-9-yl)tetrahydrofuran-2-yl)methyl acetate (28) (13 g, 35.4 mmol), benzyl triethyl ammonium chloride (16.1 g, 70.8 mmol) and N,N-dimethylaniline (4.9 mL, 38.9 mmol) were dissolved in 400 mL of dry MeCN. $POCl_3$ (16.2 mL, 177.0 mmol) was added. The reaction mixture was stirred at 105° C. for 8 h. The reaction mixture was concentrated in vacuo. The resulting residue was dissolved in dichloromethane, washed with water followed by 5% aq. $NaHCO_3$ solution. The organic phase was dried over anhydrous $Na_2SO_4$ and concentrated under reduced pressure. The crude product was purified by column chromatography using dichloromethane-methanol (120:1) as an eluent to give 6.1 g of ((2S,4R,5R)-4-acetoxy-5-(2-amino-6-chloro-8-oxo-7,8-dihydro-9H-purin-9-yl)tetrahydrofuran-2-yl)methyl acetate (29) as a white solid in 45% yield. $R_f$=0.60 (dichloromethane-methanol=40:1)

Step 4: ((2S,4R,5R)-4-Acetoxy-5-(2-amino-8-oxo-7,8-dihydro-9H-purin-9-yl)tetrahydrofuran-2-yl) methyl acetate (30)

To ((2S,4R,5R)-4-acetoxy-5-(2-amino-6-chloro-8-oxo-7,8-dihydro-9H-purin-9-yl)tetrahydrofuran-2-yl)methyl acetate (29) (6.1 g, 15.8 mmol) dissolved in a mixture of THF (150 mL) and triethylamine (2.2 mL, 15.8 mmol) was added 10% Pd/C (610 mg). The mixture was stirred for 5 h under a hydrogen (50 psi) atmosphere at room temperature. The catalyst was then filtered through a pad of Celite and the solvent was evaporated giving the crude product which was purified by column chromatography using dichloromethane-methanol (60:1) as an eluent. ((2S,4R,5R)-4-Acetoxy-5-(2-amino-8-oxo-7,8-dihydro-9H-purin-9-yl)tetrahydrofuran-2-yl)methyl acetate (30)(3.2 g) was isolated as a white foam in 57% yield. $R_f$=0.4 (dichloromethane-methanol=20:1).

Step 5: ((2S,4R,5R)-4-Acetoxy-5-(2-amino-8-oxo-7-(prop-2-yn-1-yl)-7,8-dihydro-9H-purin-9-yl)tetrahydrofuran-2-yl)methyl acetate, Compound 29

To ((2S,4R,5R)-4-acetoxy-5-(2-amino-8-oxo-7,8-dihydro-9H-purin-9-yl)tetrahydrofuran-2-yl)methyl acetate (30) (2.2 g, 6.3 mmol) dissolved in 50 mL of anhydrous DMF was added $K_2CO_3$ (1.3 g, 9.4 mmol, 1.5 eq). The reaction mixture was stirred for 30 min. and 3-bromopropyne (0.98 mL, 12.6 mmol, 2 eq) was added. The stirred reaction mixture was maintained at 45° C. for 3 h. The mixture was then concentrated under reduced pressure and the resulting residue was purified by column chromatography using dichloromethane-methanol (160:1) as eluent to give 1.8 g of ((2S,4R,5R)-4-acetoxy-5-(2-amino-8-oxo-7-(prop-2-yn-1-yl)-7,8-dihydro-9H-purin-9-yl)tetrahydrofuran-2-yl)methyl acetate, Compound 29 as a white foam in 75% yield. HPLC purity (98.2%). $R_f$=0.50 (dichloromethane-methanol=40:1). $^1$H NMR ($CDCl_3$, 400 MHz) δ 8.00 (s, 1H), 5.98-5.99 (d, 1H, J=1.6 Hz), 5.80-5.82 (d, 1H, J=6.4 Hz), 4.91 (s, 2H), 4.59 (d, 2H, J=2.4 Hz), 4.44-4.51 (m, 2H), 4.16-4.21 (m, 1H), 2.39 (t, 1H, J=2.4 Hz), 2.12 (s, 3H), 2.07 (s, 3H). ESI-MS m/z 390.1 $[M+H]^+$, 412.1 $[M+Na]^+$.

Example 30: 2-Amino-9-((2R,3R,5S)-3-hydroxy-5-(hydroxymethyl)tetrahydrofuran-2-yl)-7-(prop-2-yn-1-yl)-7,9-dihydro-8H-purin-8-one, Compound 30

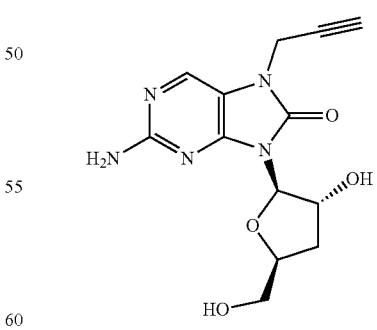

Compound 30 was prepared from Compound 29 using the method outlined to prepare Compound 4 from Compound 3.
((2S,4R,5R)-4-Acetoxy-5-(2-amino-8-oxo-7-(prop-2-yn-1-yl)-7,8-dihydro-9H-purin-9-yl)tetrahydrofuran-2-yl) methyl acetate, Compound 29 (1.37 g, 3.52 mmol) was treated with saturated ammonia in methanol. The flask was sealed, and the reaction mixture was heated at 40° C. and stirred overnight. Volatiles were evaporated under reduced pressure, and the residue purified by column chromatography using dichloromethane-methanol (30:1) as eluent to give 800 mg of 2-amino-9-((2R,3R,5S)-3-hydroxy-5-(hydroxymethyl)tetrahydrofuran-2-yl)-7-(prop-2-yn-1-yl)-7,9-dihydro-8H-purin-8-one, Compound 30 as a white solid in 75% yield with an HPLC purity of 98.9%. $R_f$=0.30 (dichloromethane-methanol=10:1). $^1$H NMR (DMSO, 400 MHz) δ 8.01 (s, 1H), 6.37 (s, 1H), 5.61 (d, 1H, J=2.8 Hz), 5.43-5.44 (d, 1H, J=4.4 Hz), 4.84-4.88 (m, 1H), 4.68-4.71 (t, 1H, J=2 Hz), 4.62-4.63 (d, 2H, J=2.4 Hz), 4.17-4.20 (m, 1H,), 3.42-3.49 (m, 2H,), 3.39-3.40 (t, 1H, J=2 Hz), 2.37-2.44 (m, 1H), 1.83-1.88 (m, 1H). ESI-MS m/z 306.1 [M+H]$^+$, 328.1 [M+Na]$^+$.

Example 31: ((2R,3R,4S,5R)-4-Acetoxy-5-(2-amino-8-oxo-7-(prop-2-yn-1-yl)-7,8-dihydro-9H-purin-9-yl)-3-fluorotetrahydrofuran-2-yl)methyl acetate, Compound 31

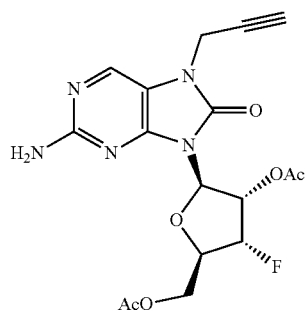 [SMILES: C#CCn1c(=O)n([C@@H]2O[C@H](COC(C)=O)[C@@H](F)[C@H]2OC(C)=O)c2nc(N)ncc21]

Compound 31 was made according to the following multi-step procedure.

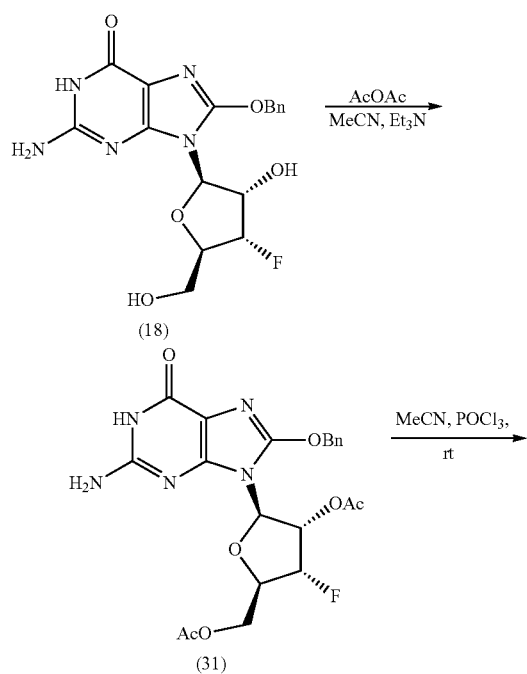

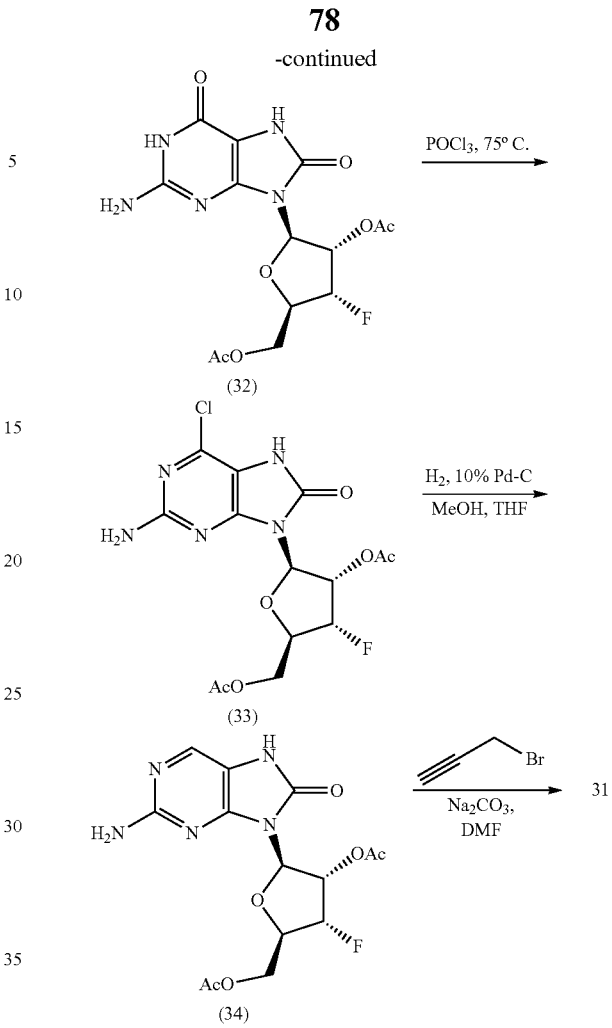

Step 1: ((2R,3R,4S,5R)-4-Acetoxy-5-(2-amino-8-(benzyloxy)-6-oxo-1,6-dihydro-9H-purin-9-yl)-3-fluorotetrahydrofuran-2-yl)methyl acetate (31)

A solution of 2-amino-8-(benzyloxy)-9-((2R,3S,4S,5R)-4-fluoro-3-hydroxy-5-(hydroxymethyl)tetrahydrofuran-2-yl)-1,9-dihydro-6H-purin-6-one (18) (11.2 g, 28.6 mmol) in anhydrous MeCN (150 mL) containing triethylamine (15.9 ml, 4.0 eq) was treated with acetic anhydride (6.8 mL, 71.6 mmol, 2.5 eq). The reaction mixture was stirred at room temperature overnight, diluted with ethyl acetate (500 mL) and poured into water. The layers were separated, and the aqueous layer was extracted twice with ethyl acetate. The combined organic layer was washed with brines, dried over anhydrous Na$_2$SO$_4$, and concentrated under reduced pressure. The resulting residue was purified by column chromatography on a silica gel column using dichloromethane-methanol (40:1) as an eluent to give 9.2 g of ((2R,3R,4S,5R)-4-acetoxy-5-(2-amino-8-(benzyloxy)-6-oxo-1,6-dihydro-9H-purin-9-yl)-3-fluorotetrahydrofuran-2-yl) methyl acetate (31) as a white foam in 67.6% yield; $R_f$=0.2 (dichloromethane-methanol=20:1).

Step 2: ((2R,3R,4S,5R)-4-Acetoxy-5-(2-amino-6,8-dioxo-1,6,7,8-tetrahydro-9H-purin-9-yl)-3-fluorotetrahydrofuran-2-yl)methyl acetate (32)

To ((2R,3R,4S,5R)-4-acetoxy-5-(2-amino-8-(benzyloxy)-6-oxo-1,6-dihydro-9H-purin-9-yl)-3-fluorotetrahydrofuran- 2-yl)methyl acetate (31) (8.5 g, 17.9 mmol) dissolved in 100 mL of dry MeCN was added phosphorus oxychloride (1.7 mL, 17.9 mmol, 1.0 eq) with stirring and continued at room temperature for 1 h. MeOH (10 mL) and excess solid NaHCO$_3$ were added to the reaction mixture. The mixture was stirred for 20 min and then concentrated in vacuo. The resulting residue was purified by column chromatography using dichloromethane-methanol (30:1) as an eluent to give 5.7 g of ((2R,3R,4S,5R)-4-acetoxy-5-(2-amino-6,8-dioxo-1,6,7,8-tetrahydro-9H-purin-9-yl)-3-fluorotetrahydrofuran-2-yl)methyl acetate (32) as a white foam in 82% yield, R$_f$=0.30 (dichloromethane-methanol=10:1).

Step 3: ((2R,3R,4S,5R)-4-Acetoxy-5-(2-amino-6-chloro-8-oxo-7,8-dihydro-9H-purin-9-yl)-3-fluorotetrahydrofuran-2-yl)methyl acetate (33)

In an oven-dried flask, ((2R,3R,4S,5R)-4-acetoxy-5-(2-amino-6,8-dioxo-1,6,7,8-tetrahydro-9H-purin-9-yl)-3-fluorotetrahydrofuran-2-yl)methyl acetate (32) (5.7 g, 14.8 mmol) was dissolved in 60 mL phosphorus oxychloride. The reaction mixture was stirred at 75° C. overnight and concentrated in vacuo. The resulting residue was purified by column chromatography using dichloromethane-methanol (100:1) as an eluent to give 2.7 g of ((2R,3R,4S,5R)-4-acetoxy-5-(2-amino-6-chloro-8-oxo-7,8-dihydro-9H-purin-9-yl)-3-fluorotetrahydrofuran-2-yl)methyl acetate (33) as a white foam in 45% yield. R$_f$=0.60 (dichloromethane-methanol=30:1).

Step 4: ((2R,3R,4S,5R)-4-Acetoxy-5-(2-amino-8-oxo-7,8-dihydro-9H-purin-9-yl)-3-fluorotetrahydrofuran-2-yl)methyl acetate (34)

To ((2R,3R,4S,5R)-4-acetoxy-5-(2-amino-6-chloro-8-oxo-7,8-dihydro-9H-purin-9-yl)-3-fluorotetrahydrofuran-2-yl)methyl acetate (33) (2.7 g, 6.7 mmol) dissolved in a mixture of anhydrous methanol (30 mL) and tetrahydrofuran (10 mL) was added 10% Pd/C (270 mg). The mixture was stirred for 5 h under a hydrogen (50 Psi) atmosphere at room temperature. The catalyst was filtered off through Celite, the solvent was evaporated, and the crude product was purified by column chromatography using dichloromethane-methanol (40:1) as an eluent to give 1 g of ((2R,3R,4S,5R)-4-acetoxy-5-(2-amino-8-oxo-7,8-dihydro-9H-purin-9-yl)-3-fluorotetrahydrofuran-2-yl)methyl acetate (34) as a white foam in 42% yield. R$_f$=0.2 (dichloromethane-methanol=20:1).

Step 5: ((2R,3R,4S,5R)-4-Acetoxy-5-(2-amino-8-oxo-7-(prop-2-yn-1-yl)-7,8-dihydro-9H-purin-9-yl)-3-fluorotetrahydrofuran-2-yl)methyl acetate, Compound 31

To ((2R,3R,4S,5R)-4-acetoxy-5-(2-amino-8-oxo-7,8-dihydro-9H-purin-9-yl)-3-fluorotetrahydrofuran-2-yl)methyl acetate (34) (1 g, 2.7 mmol) dissolved in 20 mL of anhydrous DMF was added K$_2$CO$_3$ (0.56 g, 4 mmol, 1.5 eq) with stirring. 3-Bromopropyne (0.43 mL, 5.4 mmol, 2 eq) was added to the reaction mixture, and stirring was continued for 5 h at 45° C. The mixture was concentrated under reduced pressure. The resulting residue was purified by column chromatography using dichloromethane-methanol (100:1) as eluent to give 750 mg of ((2R,3R,4S,5R)-4-acetoxy-5-(2-amino-8-oxo-7-(prop-2-yn-1-yl)-7,8-dihydro-9H-purin-9-yl)-3-fluorotetrahydrofuran-2-yl)methyl acetate, Compound 31 as a white foam in 70% yield with an HPLC purity of 98.4%. R$_f$=0.60 (dichloromethane-methanol=30:1). $^1$H NMR (CDCl$_3$, 400 MHz) δ 8.03 (s, 1H), 6.10-6.15 (m, 2H), 5.53-5.55 (m, 0.5H), 5.40-5.42 (m, 0.5H), 4.96 (s, 2H), 4.60 (d, 2H, J=4 Hz), 4.44-4.57 (m, 2H), 4.29-4.33 (m, 1H), 2.39 (t, 1H, J=4 Hz), 2.15 (s, 3H), 2.10 (s, 3H). ESI-MS m/z 408.1 [M+H]$^+$, 430.1 [M+Na]$^+$.

Example 32: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, Compound 32

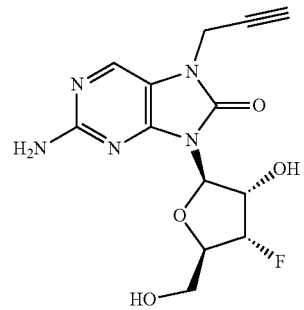 [SMILES: C#CCn1c(=O)n([C@@H]2O[C@H](CO)[C@@H](F)[C@H]2O)c2nc(N)ncc21]

Compound 32 was prepared from Compound 31 using the method outlined to prepare Compound 4 from Compound 3.

To ((2R,3R,4S,5R)-4-acetoxy-5-(2-amino-8-oxo-7-(prop-2-yn-1-yl)-7,8-dihydro-9H-purin-9-yl)-3-fluorotetrahydrofuran-2-yl)methyl acetate, Compound 31 (500 mg, 1.23 mmol) was added a saturated methanolic ammonia solution. The reaction mixture was heated at 40° C. and stirred overnight. Volatiles were evaporated under reduced pressure, and the solid residue was purified by column chromatography using dichloromethane-methanol (40:1) as eluent to give 300 mg of 2-amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, Compound 32 as a white solid in 76% yield with an HPLC purity of 98.6%. R$_f$=0.30 (dichloromethane-methanol=10:1). $^1$H NMR (DMSO, 400 MHz) δ 8.06 (s, 1H), 6.44 (s, 2H, NH$_2$), 5.85 (d, 1H, J=4 Hz, 1'-H), 5.71 (d, 1H, J=4 Hz, 2'-OH), 5.25-5.35 (m, 1H, 2'-H), 5.14-5.15 (m, 0.5H, 4'-H), 5.00-5.10 (m, 0.5H, half 4'-H), 4.96 (t, 1H, J=4 Hz, 5'-OH), 4.65 (d, 2H, J=4 Hz, CH$_2$), 4.09-4.19 (m, 1H, 3'-H), 3.51-3.62 (m, 2H, 5'-H), 3.41 (t, 1H, J=4 Hz). ESI-MS m/z 324.1 [M+H]$^+$, 346.1 [M+Na]$^+$.

Alternative Synthetic Procedures for Compounds 5, 26 and 27.

Example 5A: 2-Amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5

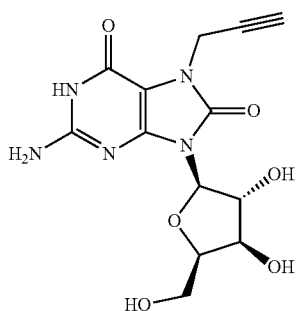 [SMILES: C#CCn1c(=O)n([C@@H]2O[C@H](CO)[C@H](O)[C@H]2O)c2nc(N)[nH]c(=O)c21]

Compound 5 was also synthesized according to the following alternative multi-step procedure.

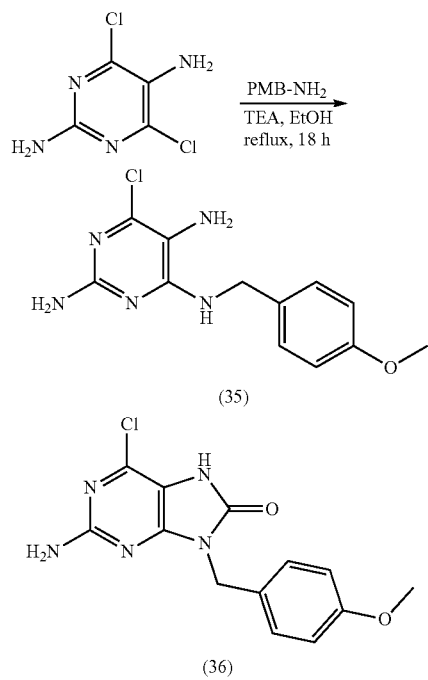

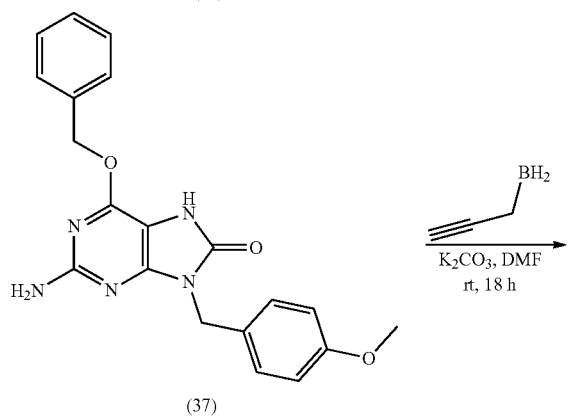

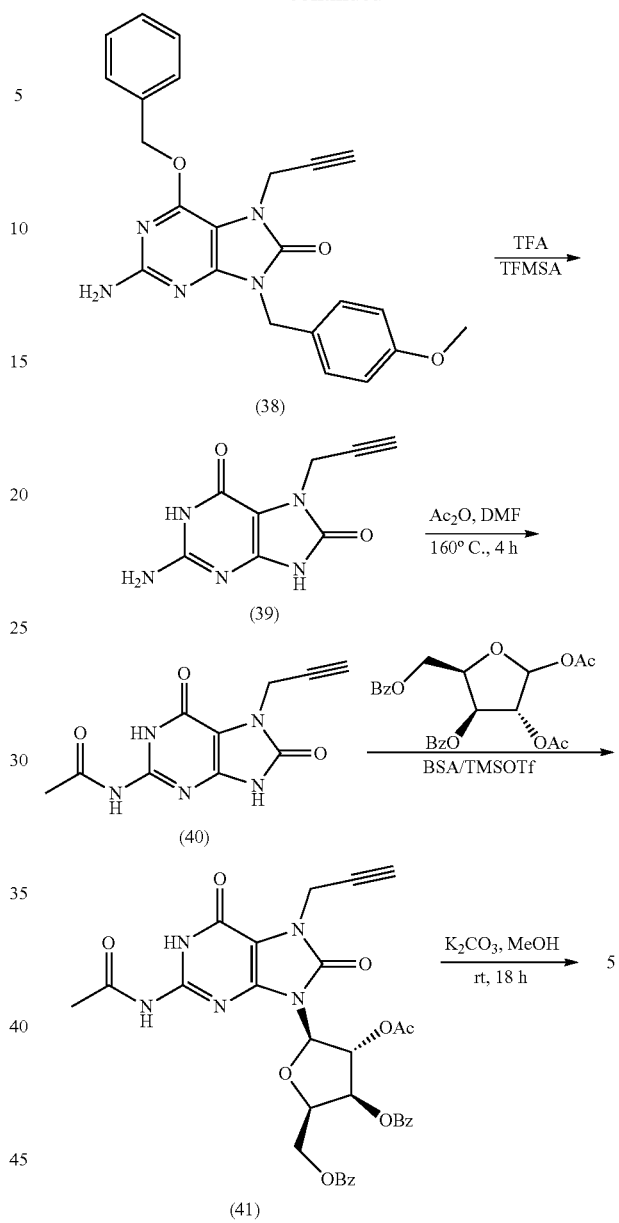

Step-1: 6-Chloro-N⁴-(4-methoxybenzyl)pyrimidine-2,4,5-triamine (35)

4-Methoxybenzyl amine (114.8 g, 83.728 mol) was added to a stirred solution mixture of 4,6-dichloropyrimidine-2,5-diamine [55583-59-0] (100 g, 55.81 mol) and TEA (169 mL, 167.45 mol) in ethanol (1.0 L) at 0° C. and the resulting reaction mixture was stirred at reflux temperature for 18 h. The solvent was evaporated under reduced pressure, the thick mass was poured into ice cold water and stirred for 30 min. The precipitated solid was collected by filtration, washed with water and dried under vacuum to afford 6-chloro-N⁴-(4-methoxybenzyl)pyrimidine-2,4,5-triamine (35) (100 g, 64%) as a brown solid. ES+, m/z 280.1 [M+H]⁺; $C_{12}H_{14}ClN_5O$; ¹H NMR (500 MHz, DMSO-$d_6$): δ 8.25 (d, J=8.5 Hz, 2H), 6.92 (t, J=6.0 Hz, 1H), 7.87 (d, J=8.5 Hz, 2H), 5.63 (s, 2H), 4.47 (d, J=5.5 Hz, 2H), 3.91 (s, 2H), 3.72 (s, 3H).

Step-2: 2-Amino-6-chloro-9-(4-methoxybenzyl)-7,9-dihydro-8H-purin-8-one (36)

A mixture of 6-chloro-N⁴-(4-methoxybenzyl)pyrimidine-2,4,5-triamine (35) (50 g, 17.92 mol) and 1,1'-carbonyldiimidazole (100 g, 61.64 mol) in acetonitrile (500 mL) was stirred at reflux temperature for 18 h. The reaction mixture was cooled to room temperature and concentrated under reduced pressure. To the resulting residue was added ice cold water and stirred for 30 min at room temperature. The precipitated solid was filtered, washed with water and dried to afford 2-amino-6-chloro-9-(4-methoxybenzyl)-7,9-dihydro-8H-purin-8-one (36) (50 g, 91%) as a brown solid; $C_{13}H_{12}C_1N_5O_2$; $^1H$ NMR (500 MHz, DMSO-$d_6$): δ 11.31 (s, 1H), 7.23 (d, J=9.0 Hz, 2H), 6.88 (d, J=5.0 Hz, 2H), 6.62 (s, 2H), 4.80 (s, 2H), 3.71 (s, 3H).

Step-3: 2-Amino-6-(benzyloxy)-9-(4-methoxybenzyl)-7,9-dihydro-8H-purin-8-one (37)

Sodium hydroxide (9.967 g, 262.29 mmol) was added to suspension of 2-amino-6-chloro-9-(4-methoxybenzyl)-7,9-dihydro-8H-purin-8-one (36) (40 g, 131.14 mmol) in benzyl alcohol (45.0 mL). The resulting reaction mixture was stirred at 120° C. for 18 h. The reaction mixture was quenched with ice water (200 mL), added diethyl ether (150 mL) and stirred for 15 min. The resulting precipitated solid was filtered, washed with water and dried to afford 2-amino-6-(benzyloxy)-9-(4-methoxybenzyl)-7,9-dihydro-8H-purin-8-one (30 g, 60%) as an brown solid. ES+, m/z 378.1 [M+H]⁺; $C_{20}H_{19}N_5O_3$; $^1H$ NMR (400 MHz, DMSO-$d_6$): δ 10.81 (s, 1H), 7.48 (d, J=7.2 Hz, 2H), 7.40-7.36 (t, J=7.6 Hz, 2H), 7.34-7.31 (t, J=5.2 Hz, 1H), 7.21 (d, J=8.4 Hz, 2H), 6.87 (d, J=8.4 Hz, 2H), 6.27 (s, 2H), 5.41 (s, 2H), 4.78 (s, 2H), 3.71 (s, 3H).

Step-4: 2-Amino-6-(benzyloxy)-9-(4-methoxybenzyl)-7-(prop-2-yn-1-yl)-7,9-dihydro-8H-purin-8-one (38)

Propargyl bromide (7.1 ml, 63.66 mmol) was added to a suspension of 2-amino-6-(benzyloxy)-9-(4-methoxybenzyl)-7,9-dihydro-8H-purin-8-one (37) (20 g, 53.05 mmol), $K_2CO_3$ (10.98 g, 79.57 mmol) in DMF (100 mL) at 0° C. and stirred at room temperature for 18 h. The reaction mixture was quenched with ice water (200 mL), added diethyl ether (150 mL) and stirred for 15 min. The resulting precipitated solid was filtered, washed with water and dried to afford 2-amino-6-(benzyloxy)-9-(4-methoxybenzyl)-7-(prop-2-yn-1-yl)-7,9-dihydro-8H-purin-8-one (38) (20 g, 91%) as a brown solid. ES+, m/z 416.1 [M+H]⁺; $C_{23}H_{21}N_5O_3$; $^1H$ NMR (400 MHz, DMSO-$d_6$): δ 7.52 (d, J=7.2 Hz, 2H), 7.38 (t, J=7.6 Hz, 2H), 7.32 (t, J=5.2 Hz, 1H), 7.22 (d, J=8.4 Hz, 2H), 6.81 (d, J=8.4 Hz, 2H), 6.27 (s, 2H), 5.44 (s, 2H), 4.82 (s, 2H), 4.56 (s, 2H), 3.71 (s, 3H), 3.32-3.26 (m, 1H).

Step-5: 2-Amino-7-(prop-2-yn-1-yl)-7,9-dihydro-1H-purine-6,8-dione (39)

Trifluoromethanesulfonic acid (27 g, 180.72 mmol) was added to a suspension of 2-amino-6-(benzyloxy)-9-(4-methoxybenzyl)-7-(prop-2-yn-1-yl)-7,9-dihydro-8H-purin-8-one (25 g, 60.24 mmol) in triflouroacetic acid (21 mL, 180.72 mmol) at 0° C. under argon atmosphere and the resulting reaction mixture was stirred at room temperature for 18 h under argon atmosphere. The reaction mixture was quenched with ice cold water, basified with saturated NaHCO₃ solution under vigorous stirring and filtered. The residual solid was taken into ethyl acetate, stirred for 30 min and filtered and dried to afford 2-amino-7-(prop-2-yn-1-yl)-7,9-dihydro-1H-purine-6,8-dione (12 g, 36%) as a brown solid. ES+, m/z 206.1 [M+H]⁺; $C_8H_7N_5O_2$; $^1H$ NMR (400 MHz, DMSO-$d_6$): δ 11.32 (s, 1H), 6.74 (s, 2H), 4.53 (s, 2H), 3.14 (s, 1H).

Step-6: N-(6,8-Dioxo-7-(prop-2-yn-1-yl)-6,7,8,9-tetrahydro-1H-purin-2-yl)acetamide (40)

Acetic anhydride (4.85 mL, 47.56 mmol) was added to a solution of 2-amino-7-(prop-2-yn-1-yl)-7,9-dihydro-1H-purine-6,8-dione (6.5 g, 31.70 mmol) in DMF (65 mL) at room temperature under argon atmosphere and the resulting reaction mixture was stirred at room temperature for 18 h under argon atmosphere. The reaction mixture was cooled to 0° C. (solid was formed under stirring) and stirred for 30 minutes. The product was filtered, washed with ethanol and dried under vacuum to afford N-(6,8-dioxo-7-(prop-2-yn-1-yl)-6,7,8,9-tetrahydro-1H-purin-2-yl)acetamide (4 g, 51.2%) as an brown solid. ES+, m/z 248.1 [M+H]⁺; $C_{10}H_9N_5O_3$; $^1H$ NMR (400 MHz, DMSO-$d_6$): δ 11.83 (s, 2H), 4.61 (s, 2H), 3.23 (s, 1H), 2.16 (s, 3H).

Step-6: (2R,3S,4R,5R)-5-(2-Acetamido-6,8-dioxo-7-(prop-2-yn-1-yl)-1,6,7,8-tetrahydro-9H-purin-9-yl)-4-acetoxy-2-((benzoyloxy)methyl)tetrahydrofuran-3-yl benzoate (41)

N-(6,8-dioxo-7-(prop-2-yn-1-yl)-6,7,8,9-tetrahydro-1H-purin-2-yl)acetamide (400 mg, 1.61 mmol), (3R,4S,5R)-4-(benzoyloxy)-5-((benzoyloxy)methyl)tetrahydrofuran-2,3-diyl diacetate (716 mg, 1.61 mmol) [85026-60-4] (See M. Popsavin, et al, *Bioorg. Med. Chem. Lett.,* 2012, 22, p. 6700 and G. Gosselin, et al, *J. Het. Chem.,* 1982, 19, p. 597), BSA (983 mg, 4.85 mmol) and MeCN (40 mL) were mixed vigorously for 45 min until a homogeneous solution was obtained. The reaction was then charged with TMSOTf (540 mg, 2.42 mmol) and placed into a preheated oil bath at 75° C. After 4 h the reaction was cooled to room temperature and the solvent was removed by rotary evaporation. The resultant solid was dissolved in ethyl acetate (100 mL) and extracted by saturated aqueous NaHCO₃ (2×30 mL). The organic phase was dried with Na₂SO₄ and concentrated. The crude product was purified by column chromatography (SiO₂, 0 to 40% ethyl acetate-pet-ether), to get 190 mg (18.64%) of (2R,3S,4R,5R)-5-(2-acetamido-6,8-dioxo-7-(prop-2-yn-1-yl)-1,6,7,8-tetrahydro-9H-purin-9-yl)-4-acetoxy-2-((benzoyloxy) methyl) tetrahydrofuran-3-yl benzoate as a light yellow solid. ES+, m/z 630.1 [M+H]⁺; $C_{31}H_{27}N_5O_{10}$; $^1H$ NMR (400 MHz, DMSO-$d_6$): δ 11.89 (s, 1H), 8.02 (d, J=6.8 Hz, 2H), 7.86 (d, J=7.2 Hz, 2H), 7.68-7.61 (m, 2H), 7.54-7.45 (m, 5H), 6.48-6.46 (m, 1H), 5.83-5.79 (m, 2H), 4.76 (d, J=6.0 Hz, 1H), 4.68 (s, 2H), 4.64 (d, J=4.8 Hz, 1H), 4.57-4.53 (m, 1H), 3.29 (s, 1H), 2.15 (s, 3H), 2.07 (s, 3H).

Step-7: 2-Amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5

(2R,3S,4R,5R)-5-(2-Acetamido-6,8-dioxo-7-(prop-2-yn-1-yl)-1,6,7,8-tetrahydro-9H-purin-9-yl)-4-acetoxy-2-((benzoyloxy)methyl)tetrahydrofuran-3-yl benzoate (500 mg, 0.79 mmol) was dissolved in methanol (10 mL). K₂CO₃

(164 mg, 1.19 mmol) was added, and the reaction was stirred at room temperature for 16 h. Acetic acid (96 mg, 1.58 mmol) was added, and the reaction was concentrated via rotary evaporation. The crude product was purified by GRACE reverse phase purification (MeCN-0.01% of HCO$_2$H in H$_2$O) to get 120 mg (45%) of 2-amino-9-((2R,3R,4R,5R)-3,4-dihydroxy-5-(hydroxymethyl)tetrahydrofuran-2-yl)-7-(prop-2-yn-1-yl)-7,9-dihydro-1H-purine-6,8-dione, Compound 5 as an off white solid. ES+, m/z 338.0 [M+H]$^+$; C$_{13}$H$_{15}$N$_5$O$_6$; $^1$H NMR (500 MHz, DMSO-d$_6$): δ 11.56 (s, 1H), 6.94 (s, 2H), 5.73 (s, 2H), 5.47 (d, J=2.8 Hz, 1H), 4.62 (d, J=2 Hz, 2H), 4.50 (s, 2H), 3.91-3.88 (m, 2H), 3.68-3.65 (m, 1H), 3.59-3.54 (m, 1H), 3.25-3.24 (m, 1H).

Example 26A: 2-Amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26

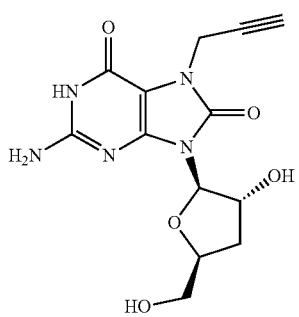 [SMILES: C#CCn1c(=O)n([C@@H]2O[C@H](CO)C[C@H]2O)c2nc(N)[nH]c(=O)c21]

Using the same general procedure as described for Example 5A, Compound 26 was also synthesized according to the following alternative multi-step procedure.

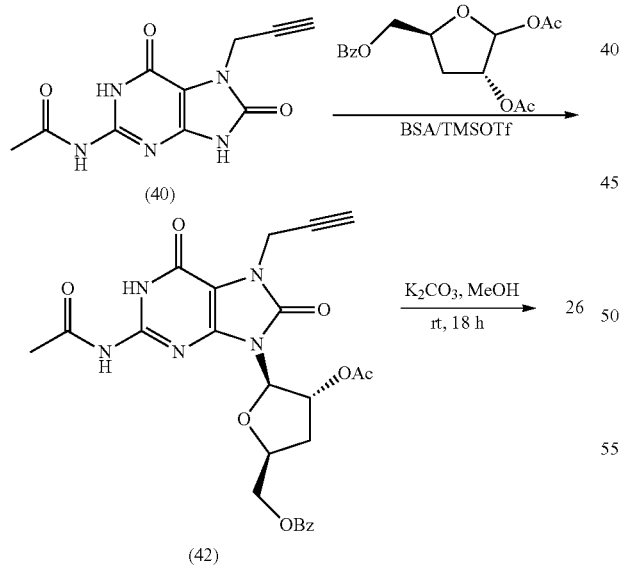

Step-1: ((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)methyl benzoate (42)

N-(6,8-Dioxo-7-(prop-2-yn-1-yl)-6,7,8,9-tetrahydro-1H-purin-2-yl)acetamide (1 g, 4.04 mmol), (2S,3R,5S)-5-((benzoyloxy)methyl)tetrahydrofuran-2,3-diyl diacetate [4613-71-2](See P. J. Bolon, et al, *Tetrahedron*, 1994, 50, p. 7747) (1.30 g, 4.04 mmol) and BSA (2.45 g, 12.14 mmol) in dichloromethane (100 mL) were stirred vigorously at 70° C. for 45 min until a homogeneous solution formed. The reaction mixture was cooled to room temperature and concentrated under vacuum. The crude concentrate was dissolved in MeCN (50 mL) then charged with TMSOTf (1.35 mL, 6.07 mmol) and placed into a preheated oil bath at 90° C. After 16 h the reaction was cooled to room temperature and the solvent was removed under rotary evaporation. The resultant solid was dissolved in EtOAc (200 mL) and extracted by saturated aqueous NaHCO$_3$ (2×50 mL). The organic phase was dried over Na$_2$SO$_4$ and concentrated. The crude product was purified by column chromatography (SiO$_2$, 0 to 40% EtOAc-pet-ether) to give 700 mg (33.98%) of ((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)methyl benzoate as a light yellow solid. ES+, m/z 510.1 [M+H]$^+$; C$_{24}$H$_{23}$N$_5$O$_8$.

Step 2: 2-Amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione, Compound 26

To ((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)methyl benzoate (1 g, 1.96 mmol) dissolved in methanol (20 mL) was added K$_2$CO$_3$ (407 mg, 2.9 mmol). The reaction mixture was stirred for 16 h at room temperature. Acetic acid (236 mg, 3.9 mmol) was added, and the mixture was concentrated via rotary evaporation. The crude product was purified by GRACE reverse phase purification (MeCN-0.01% of HCO$_2$H in H$_2$O), to give 200 mg (32%) of 2-amino-9-((2R,3R,5S)-3-hydroxy-5-(hydroxymethyl)tetrahydrofuran-2-yl)-7-(prop-2-yn-1-yl)-7,9-dihydro-1H-purine-6,8-dione as an off white solid. ES+, m/z 322.0 [M+H]$^+$; C$_{13}$H$_{15}$N$_5$O$_5$. $^1$H NMR (400 MHz, DMSO-d$_6$): δ 11.03 (s, 1H), 6.59 (s, 2H), 5.51 (d, J=2.8 Hz, 1H), 5.40 (d, J=4.0 Hz, 1H), 4.80 (d, J=2.8 Hz, 1H) 4.70 (s, 1H), 4.58 (d, J=1.6 Hz, 2H), 4.14 (m, 1H), 3.45 (m, 2H), 3.22 (s, 1H), 2.34 (m, 1H), 1.82 (m, 1H).

Example 27A: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27

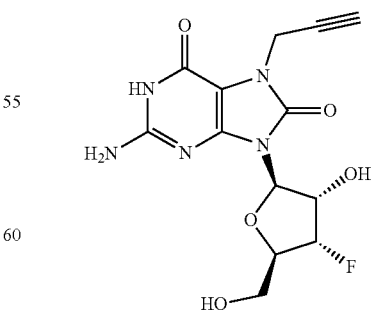

Using the same general procedure as described for Example 5A, Compound 27 was also synthesized according to the following alternative multi-step procedure.

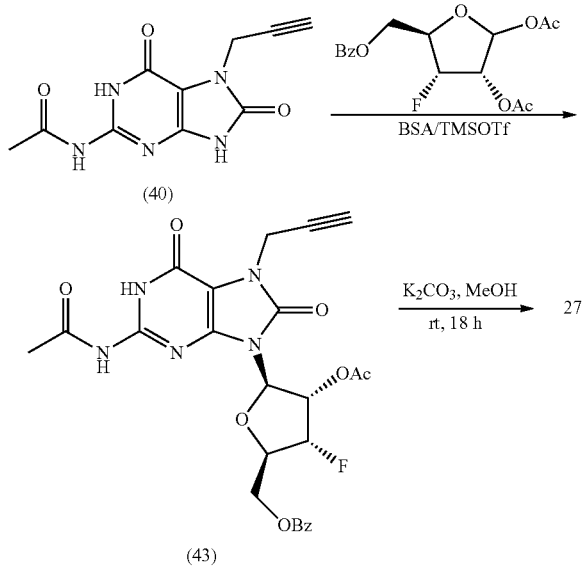

Step-1: ((2R,3R,4S,5R)-5-(2-Acetamido-6,8-dioxo-7-(prop-2-yn-1-yl)-1,6,7,8-tetrahydro-9H-purin-9-yl)-4-acetoxy-3-fluorotetrahydrofuran-2-yl)methyl benzoate (43)

N-(6,8-Dioxo-7-(prop-2-yn-1-yl)-6,7,8,9-tetrahydro-1H-purin-2-yl)acetamide (500 mg, 2.042 mmol), (2S,3S,4R,5R)-5-((benzoyloxy)methyl)-4-fluorotetrahydrofuran-2,3-diyl diacetate (See R. F. Schinazi, et al, *Het. Comm*, 2015, 21, p. 315) (1.376 g, 4.04 mmol) and BSA (331 mg, 2.2 mmol) in 1,2-dichloroethane (50 mL) were stirred vigorously for 45 min at 70° C. until a homogeneous solution formed. The reaction mixture was cooled to room temperature and concentrated under vacuum. The crude concentrate was dissolved in MeCN (50 mL) then charged with TMSOTf (0.186 mL, 0.81 mmol) and placed into a pre-heated oil bath at 90° C. After 16 h the reaction was cooled to room temperature and the solvent was removed by rotary evaporation. The resultant solid was dissolved in ethyl acetate (200 mL) and extracted with saturated aqueous NaHCO$_3$ (2×50 mL). The organic layer was dried with Na$_2$SO$_4$ and concentrated. The crude product was purified by column chromatography (SiO$_2$, 0 to 40% ethyl acetate-pet-ether) to afford 200 mg (18.25%) of ((2R,3R,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)methyl benzoate as a light yellow solid. ES+, m/z 528.1 [M+H]$^+$; C$_{24}$H$_{22}$FN$_5$O$_8$. $^1$H NMR (400 MHz, DMSO-d$_6$): δ 11.80 (s, 1H), 9.32 (s, 1H), 8.03 (d, J=7.2 Hz, 2H), 7.64-7.60 (t, J=7.2 Hz, 1H), 7.49-7.45 (t, J=8.0 Hz, 2H), 6.22 (d, J=5.6 Hz, 1H), 5.93-5.87 (m, 1H), 5.53-5.48 (m, 1H), 5.14-5.09 (m, 1H), 4.82 (s, 2H), 4.75-4.69 (m, 1H), 4.68-4.54 (m, 1H), 2.33 (s, 3H), 2.29 (m, 1H), 2.14 (s, 3H).

Step-2: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27

To ((2R,3R,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)methyl benzoate (500 mg, 0.948 mmol) dissolved in MeOH (10 mL) was added K$_2$CO$_3$ (131 mg, 0.948 mmol). The reaction mixture was stirred for 16 h room temperature. Acetic acid (114 mg, 1.896 mmol) was added, and the reaction mixture was concentrated via rotary evaporation. The crude product was purified by GRACE reverse phase purification (MeCN-0.01% of HCO$_2$H in H$_2$O), and obtained 120 mg (37.38%) of 2-amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione, Compound 27 as a light brown solid. ES+, m/z 340.1 [M+H]$^+$; C$_{13}$H$_{14}$FN$_5$O$_5$. $^1$H NMR (400 MHz, DMSO-d6): δ 11.00 (s, 1H), 6.59 (s, 2H), 5.79 (d, J=6.4 Hz, 1H), 5.62 (d, J=7.6 Hz, 1H), 5.24-5.17 (m, 1H), 5.09 (d, J=3.6 Hz, 1H), 4.96-4.93 (t, J=6.8 Hz, 1H), 4.60 (s, 2H), 4.15-4.16 (m, 1H), 3.59-3.50 (m, 2H), 3.24 (s, 1H).

Alternative Synthetic Procedures for Compound 32.

Example 32A: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, Compound 32

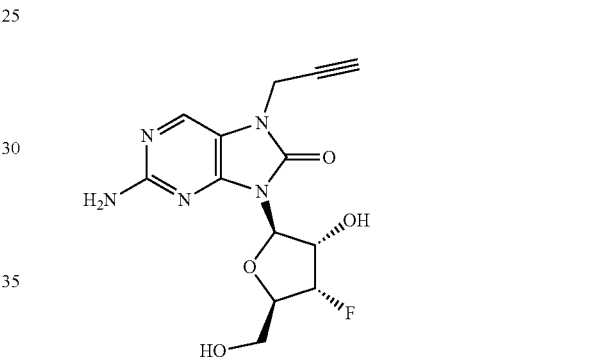

Compound 32 was also synthesized according to the following alternative multi-step procedure.

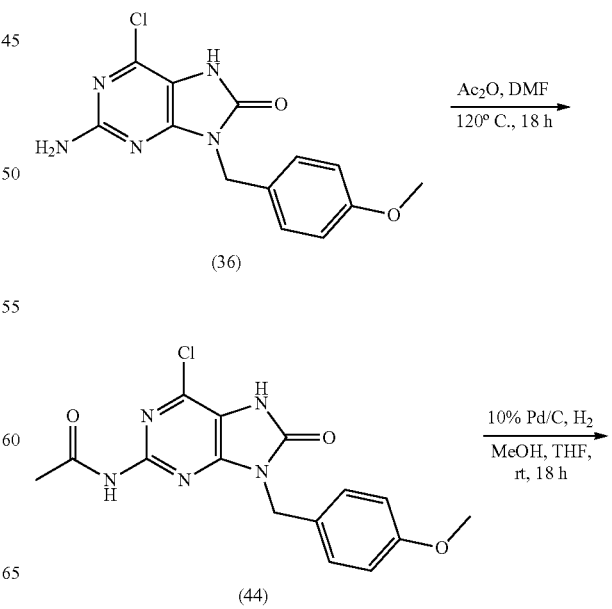

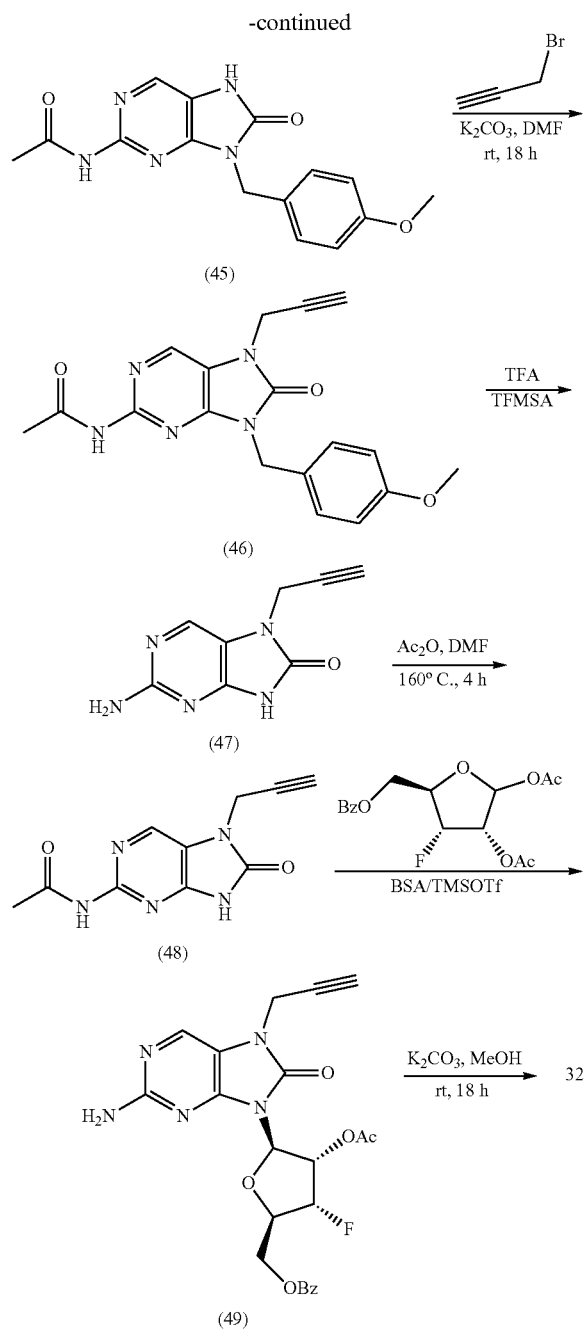

Step-1: N-(6-Chloro-9-(4-methoxybenzyl)-8-oxo-8,9-dihydro-7H-purin-2-yl)acetamide (44)

Acetic anhydride (13.04 ml, 85.224 mmol) was added to a solution of 2-amino-6-chloro-9-(4-methoxybenzyl)-7,9-dihydro-8H-purin-8-one (36) (13.0 g, 42.622 mmol) in DMF (100 mL) at room temperature under argon atmosphere and the resulting reaction mixture was stirred at 140° C. for 18 h. The reaction mixture was cooled to 0° C. (solid was formed under stirring) and stirred for 30 minutes. The product was filtered, washed with water and dried under vacuum to afford N-(6-chloro-9-(4-methoxybenzyl)-8-oxo-8,9-dihydro-7H-purin-2-yl)acetamide (9.0 g, 60.85%) as an brown solid; ES+, m/z 348.1 [M+H]+, $C_{15}H_{14}C_1N_5O_3$; $^1$H NMR (400 MHz, DMSO-d$_6$): δ 11.90 (s, 1H), 10.55 (s, 1H), 7.33 (d, J=8.8 Hz, 2H), 6.87 (d, J=8.4 Hz, 2H), 4.87 (s, 2H), 3.71 (s, 3H), 2.13 (s, 3H).

Step-2: N-(9-(4-Methoxybenzyl)-8-oxo-8,9-dihydro-7H-purin-2-yl)acetamide (45)

10% Pd/C (3.5 g) was added to a solution of N-(6-chloro-9-(4-methoxybenzyl)-8-oxo-8,9-dihydro-7H-purin-2-yl)acetamide (15.0 g, 28.81 mmol) in methanol (200 mL) and THF (400 mL). The reaction mixture was hydrogenated with H$_2$ gas at 80 psi of pressure in a Parr shaker vial at room temperature for 24 h. The reaction mixture was filtered through celite pad and the filtrate was evaporated to give a crude solid. The solids were taken into in diethyl ether and stirred for 15 min filtered and repeated. The solids were dried under vacuum to N-(9-(4-methoxybenzyl)-8-oxo-8,9-dihydro-7H-purin-2-yl)acetamide (10.5 g, 77.6%) as pale brown solid. $^1$H NMR and LC-MS indicated acetylated (37%) ES+, m/z 314.2 [M+H]+; $C_{15}H_{15}N_5O_3$; and deacetylated (43%) ES+, m/z 272.2 [M+H]+; $C_{13}H_{13}N_5O_2$; compounds. The crude mixture may be used in next step. $^1$H NMR (400 MHz, DMSO-d$_6$): δ 10.55 (s, 1H), 8.09 (s, 1H), 7.33 (d, J=8.8 Hz, 2H), 6.87 (d, J=8.8 Hz, 2H), 4.93 (s, 2H), 3.72 (s, 3H), 2.24 (s, 3H).

Step-3: N-(9-(4-Methoxybenzyl)-8-oxo-7-(prop-2-yn-1-yl)-8,9-dihydro-7H-purin-2-yl)acetamide (46)

Propargyl bromide (6.0 mL, 40.255 mmol) was added to a suspension of N-(9-(4-methoxybenzyl)-8-oxo-8,9-dihydro-7H-purin-2-yl)acetamide (45) (10.5 g, 33.546 mmol) and K$_2$CO$_3$ (6.95 g, 50.319 mmol) in DMF (50 mL) at 0° C. and stirred at room temperature for 18 h. The reaction mixture was quenched with ice water (200 mL), diethyl ether (150 mL) was added and stirred for 15 min. The resulting precipitated solid was filtered, washed with water and dried to afford N-(9-(4-methoxybenzyl)-8-oxo-7-(prop-2-yn-1-yl)-8,9-dihydro-7H-purin-2-yl)acetamide (8.5 g, 72.21%) as a brown solid. ES+, m/z 352.2 [M+H]+; $C_{18}H_{17}N_5O_3$; $^1$H NMR (400 MHz, DMSO-d$_6$): δ 10.41 (s, 1H), 8.32 (s, 1H), 7.35 (d, J=8.4 Hz, 2H), 6.88 (d, J=8.4 Hz, 2H), 4.92 (s, 2H), 4.73 (s, 2H), 3.71 (s, 3H), 3.42 (s, 1H), 2.15 (s, 3H).

Step-4: 2-Amino-7-(prop-2-yn-1-yl)-7,9-dihydro-8H-purin-8-one (47)

Trifluoromethanesulfonic acid (4.5 ml) was added to a suspension of N-(9-(4-methoxybenzyl)-8-oxo-7-(prop-2-yn-1-yl)-8,9-dihydro-7H-purin-2-yl)acetamide (4.5 g, 12.82 mmol) in triflouroacetic acid (4.5 mL) at 0° C. under argon atmosphere and the resulting reaction mixture was stirred at room temperature for 18 h. The reaction mixture was quenched with ice cold water, basified with sat NaHCO$_3$ solution under vigorous stirring and filtered. The residual solid was taken into ethyl acetate, stirred for 30 min, filtered and dried to afford 2-amino-7-(prop-2-yn-1-yl)-7,9-dihydro-8H-purin-8-one (2.0 g, 82.64%) as a brown solid. ES+, m/z 190.1 [M+H]+; $C_8H_7N_5O_2$; $^1$H NMR (400 MHz, DMSO-d$_6$): δ 11.32 (s, 1H), 7.57 (s, 1H), 5.60 (s, 2H), 4.46 (s, 2H), 3.22 (s, 1H).

Step-5: N-(8-Oxo-7-(prop-2-yn-1-yl)-8,9-dihydro-7H-purin-2-yl)acetamide (48)

Acetic anhydride (7 mL, 68.78 mmol) was added to a solution of 2-amino-7-(prop-2-yn-1-yl)-7,9-dihydro-8H-purin-8-one (6.5 g, 34.39 mmol) in DMF (65 mL) at room temperature under argon atmosphere and the resulting reaction mixture was stirred at 140° C. for 18 h. The reaction mixture was cooled to 0° C. and stirred for 30 minutes whereupon solids formed. The product was filtered, washed with water and dried under vacuum to afford N-(8-oxo-7-(prop-2-yn-1-yl)-8,9-dihydro-7H-purin-2-yl)acetamide (4 g, 50.34%) as an brown solid; $C_{10}H_9N_5O_3$; ¹H NMR (500 MHz, DMSO-$d_6$): δ 9.80 (s, 1H), 7.76 (s, 1H), 6.17 (s, 1H), 4.53 (s, 2H), 3.24 (s, 1H), 2.11 (s, 3H).

Step-6: ((2R,3R,4S,5R)-5-(2-Acetamido-8-oxo-7-(prop-2-yn-1-yl)-7,8-dihydro-9H-purin-9-yl)-4-acetoxy-3-fluorotetrahydrofuran-2-yl)methyl Benzoate (49)

N-(8-Oxo-7-(prop-2-yn-1-yl)-8,9-dihydro-7H-purin-2-yl)acetamide (2.0 g, 8.65 mmol), (2S,3S,4R,5R)-5-((benzoyloxy)methyl)-4-fluorotetrahydrofuran-2,3-diyl diacetate (5.887 g, 17.316 mmol), BSA (5.283 g, 25.974 mmol) and dichloro ethane (50 mL). The resulting reaction mixture was stirred at 80° C. for 30 min under argon. The reaction mixture was concentrated under reduced pressure, the residue was diluted with ACN (100 mL) and then charged with TMSOTf (2.886 g, 12.987 mmol) and placed into a preheated oil bath at 80° C. After 18 h the reaction was cooled to room temperature and the solvent was removed by rotary evaporation. The resultant solid was dissolved in ethyl acetate (100 mL) and washed with saturated aqueous NaHCO₃ (2×30 mL). The organic phase was dried over Na₂SO₄ and concentrated. The crude product was purified by column chromatography (SiO₂, 0 to 40% ethyl acetate-Pet-ether), to get (2 g, 47.16%) of ((2R,3R,4S,5R)-5-(2-acetamido-8-oxo-7-(prop-2-yn-1-yl)-7,8-dihydro-9H-purin-9-yl)-4-acetoxy-3-fluorotetrahydrofuran-2-yl)methyl benzoate as a light yellow solid. ES+, m/z 512.2 [M+H]⁺; $C_{24}H_{22}FN_5O_7$; LC-MS indicated 83.5% of desired m/z and ¹H-NMR indicated desired signals along with some solvent residues. The crude compound was used next without isolation.

Step-7: 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, Compound 32

((2R,3R,4S,5R)-5-(2-Acetamido-8-oxo-7-(prop-2-yn-1-yl)-7,8-dihydro-9H-purin-9-yl)-4-acetoxy-3-fluorotetrahydrofuran-2-yl)methyl benzoate (5.0 g, 11.13 mmol) was dissolved in methanolic ammonia (7M) (500 mL) in sealed vessel. The reaction was stirred at room temperature for 5 days. The reaction mixture was concentrated via rotary evaporation to afford a thick solid. This solid was dissolved in minimum amount of methanol and acetonitrile (50 mL), was added and stirred for 2 h. The solids were filtered to yield (1.4 g, 38.93%) of 2-amino-9-((2R,3S,4S,5R)-4-fluoro-3-hydroxy-5-(hydroxymethyl)tetrahydrofuran-2-yl)-7-(prop-2-yn-1-yl)-7,9-dihydro-8H-purin-8-one, Compound 32 as a pale brown solid. ES+, m/z 324.1 [M+H]⁺; $C_{13}H_{14}N_5O_4$; ¹H NMR (500 MHz, DMSO-$d_6$): δ 8.05 (s, 1H), 6.42 (s, 2H), 5.84 (d, J=6 Hz, 1H), 5.71 (d, J=7.5 Hz, 1H), 5.32-5.27 (m, 1H),), 5.12-5.01 (m, 1H), 4.96-4.93 (t, J=6 Hz, 1H), 4.65 (s, 2H), 4.17-4.10 (m, 1H), 3.63-3.51 (m, 2H), 3.40 (s, 1H).

Example 33: 2-Amino-7-benzyl-9-((2R,3R,5S)-3-hydroxy-5-(hydroxymethyl)tetrahydrofuran-2-yl)-7,9-dihydro-1H-purine-6,8-dione, Compound 33

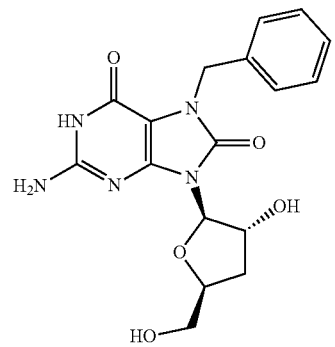 [SMILES: Nc1nc2c(c(=O)[nH]1)n(Cc1ccccc1)c(=O)n2[C@@H]1O[C@H](CO)C[C@H]1O]

Using the same general procedure as described for Example 5A, Compound 33 was synthesized according to the following multi-step procedure.

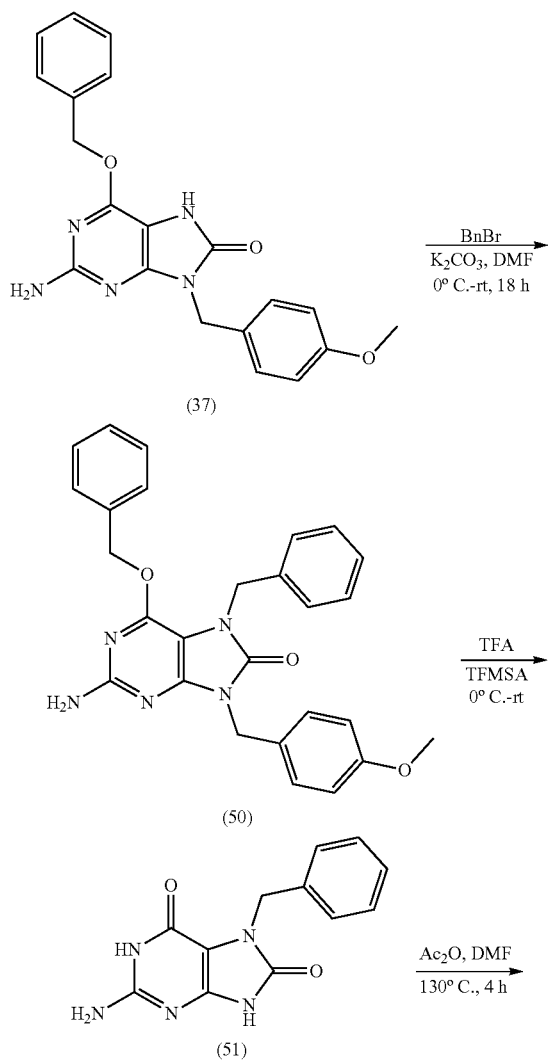

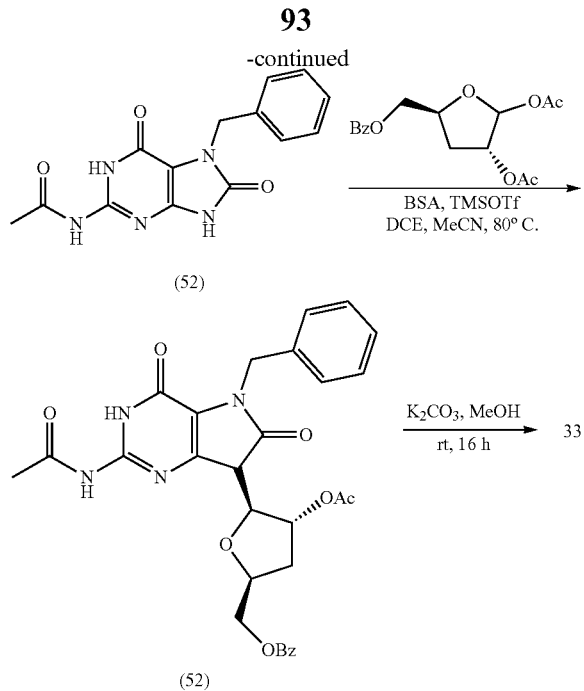

Step-1: 2-Amino-7-benzyl-6-(benzyloxy)-9-(4-methoxybenzyl)-7,9-dihydro-8H-purin-8-one (50)

Benzyl bromide (1.36 g, 7.95 mmol) was added to a suspension of 2-amino-6-(benzyloxy)-9-(4-methoxybenzyl)-7,9-dihydro-8H-purin-8-one (2 g, 5.305 mmol) and $K_2CO_3$ (2.1 g, 15.91 mmol) in DMF (20 mL) at 0° C. and stirred at room temperature for 18 h. The reaction mixture was quenched with ice water (120 mL), diluted with diethyl ether (80 mL) and stirred for 15 min. The resulting precipitated solid was filtered, washed with water and dried to afford 2-amino-7-benzyl-6-(benzyloxy)-9-(4-methoxybenzyl)-7,9-dihydro-8H-purin-8-one (2.0 g, 83%) as an off-white solid; ES+, m/z 468.2 [M+H]$^+$; $C_{27}H_{25}N_5O_3$; $^1$H NMR (400 MHz, DMSO-$d_6$): δ 7.32-7.20 (m, 10H), 7.12-7.09 (m, 2H), 6.87 (d, J=12 Hz, 2H), 6.41 (s, 2H), 5.34 (s, 2H), 4.95 (s, 2H), 4.85 (s, 2H), 3.71 (s, 3H).

Step-2: 2-Amino-7-benzyl-7,9-dihydro-1H-purine-6,8-dione (51)

Trifluoromethane sulfonic acid (2.2 mL, 25.64 mmol) was added to a suspension of 2-amino-7-benzyl-6-(benzyloxy)-9-(4-methoxybenzyl)-7,9-dihydro-8H-purin-8-one (2 g, 4.28 mmol) in trifluoroacetic acid (2.09 mL, 25.64 mmol) at 0° C. under argon atmosphere and the resulting reaction mixture was slowly warmed to room temperature and stirred for 3 h. The reaction mixture was quenched with ice cold water, basified with sat $NaHCO_3$ solution under vigorous stirring and filtered. The residual solid was taken into ethyl acetate, stirred for 30 min and filtered and dried to afford 2-amino-7-benzyl-7,9-dihydro-1H-purine-6,8-dione (0.5 g, 45%) as a brown solid. ES+, m/z 258.1 [M+H]$^+$; $C_{12}H_{11}N_5O_2$; $^1$H NMR (400 MHz, DMSO-$d_6$): $^1$H NMR: δ 11.16 (s, 1H), 10.64 (s, 1H), 7.30-7.22 (s, 5H), 6.37 (s, 2H), 4.93 (s, 2H).

Step-3: N-(7-Benzyl-6,8-dioxo-6,7,8,9-tetrahydro-1H-purin-2-yl)acetamide (52)

Acetic anhydride (0.28 mL, 5.36 mmol) was added to a solution 2-amino-7-benzyl-7,9-dihydro-1H-purine-6,8-dione (0.500 g, 1.945 mmol) in DMF (5 mL) at ambient temperature under argon atmosphere and the resulting reaction mixture was heated at 130° C. for 3 h under argon atmosphere. The reaction mixture was cooled to 0° C. (solid was formed under stirring) and stirred for 30 minutes. The product was filtered, washed with ethanol and dried under vacuum to afford N-(7-benzyl-6,8-dioxo-6,7,8,9 tetrahydro-1H-purin-2-yl)acetamide (0.3 g, 51%) as a brown solid. This crude compound was directly used for next step. $C_{14}H_{13}N_5O_3$; $^1$H NMR (400 MHz, DMSO-$d_6$): δ 12.01 (s, 1H), 11.76 (s, 1H), 11.65 (s, 1H), 7.32-7.31 (m, 5H), 5.01 (s, 2H), 2.14 (s, 3H).

Step-4: ((2S,4R,5R)-5-(2-Acetamido-7-benzyl-6,8-dioxo-1,6,7,8-tetrahydro-9H-purin-9-yl)-4-acetoxytetrahydrofuran-2-yl)methyl benzoate (53)

N-(7-Benzyl-6,8-dioxo-6,7,8,9-tetrahydro-1H-purin-2-yl)acetamide (300 mg, 1.0 mmol), (3R,5S)-5-((benzoyloxy)methyl)tetrahydrofuran-2,3-diyl diacetate (387.6 mg, 1.204 mmol), BSA (0.76 mL, 3.010 mmol) dissolved in 1,2-dichloroethane (10 mL) was stirred at 80° C. for 30 min under argon. The reaction mixture was concentrated under reduced pressure, the residue was diluted with dry acetonitrile (10 mL) and to the solution was added TMSOTf (0.12 mL, 0.707 mmol). The reaction mixture was placed into a pre-heated oil bath at 80° C. and stirred. After 3 h the reaction mixture was cooled to room temperature and the solvent was removed under reduced pressure. The resultant solid was dissolved in ethyl acetate (80 mL) and the solution was stirred with saturated aqueous $NaHCO_3$ (2×30 mL). The organic phase was separated, dried over $Na_2SO_4$ and concentrated. The crude compound was purified by column chromatography ($SiO_2$, 0 to 60% ethyl acetate-pet-ether) to afford ((2S,4R,5R)-5-(2-acetamido-7-benzyl-6,8-dioxo-1,6,7,8-tetrahydro-9H-purin-9-yl)-4-acetoxytetrahydrofuran-2-yl)methyl benzoate (100 mg, 17%) as an off-white solid; ES+, m/z 262.2 [M+H]$^+$; $C_{28}H_{27}N_5O_8$.

Step-5: 2-Amino-7-benzyl-9-((2R,3R,5S)-3-hydroxy-5-(hydroxymethyl)tetrahydrofuran-2-yl)-7,9-dihydro-1H-purine-6,8-dione, Compound 33

To a solution of ((2S,4R,5R)-5-(2-acetamido-7-benzyl-6,8-dioxo-1,6,7,8-tetrahydro-9H-purin-9-yl)-4-acetoxytetrahydrofuran-2-yl)methyl benzoate (0.1 g, 0.178 mmol) in methanol (5 mL) at room temperature was added $K_2CO_3$ (122.9 mg, 0.891 mmol) and the reaction mixture was stirred at room temperature for 16 h. The reaction progress was monitored by LC-MS. After complete consumption of starting material, the reaction mixture was concentrated under reduced pressure. The crude product was purified by Grace flash chromatography using methanol and dichloromethane to get 40 mg of product in 92% by LC-MS. The compound was further dissolved in 1 mL of methanol and stirred for 20 min. The precipitated compound was collected by filtration and dried to afford 2-amino-7-benzyl-9-((2R,3R,5S)-3-hydroxy-5-(hydroxymethyl)tetrahydrofuran-2-yl)-7,9-dihydro-1H-purine-6,8-dione, Compound 33 (15 mg, 22%), as an off-white solid. ES+, m/z 374.2 [M+H]$^+$; $C_{17}H_{19}N_5O_5$; $^1$H NMR (500 MHz, DMSO-$d_6$): δ 10.97 (s, 1H), 7.32-7.31 (s, 5H), 6.52 (s, 2H), 5.52 (d, J=5 Hz, 1H), 5.35 (d, J=5 Hz, 1H), 4.98 (s, 2H), 4.82-4.78 (m 1H), 4.69 (t, J=10 Hz, 1H), 4.14-412 (m, 1H), 3.48-3.41 (m, 2H), 2.37-2.32 (m, 1H), 1.84-1.79 (m, 1H).

Example 34: 2-Amino-7-(3-fluorobenzyl)-9-((2R,3R,5S)-3-hydroxy-5-(hydroxymethyl)tetrahydrofuran-2-yl)-7,9-dihydro-1H-purine-6,8-dione, Compound 34

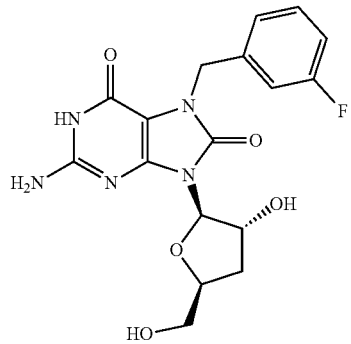 [SMILES: Nc1nc2c(c(=O)[nH]1)n(Cc1cccc(F)c1)c(=O)n2[C@@H]1O[C@H](CO)C[C@H]1O]

Using the same general procedure as described for Example 5A, Compound 34 was synthesized according to the following multi-step procedure.

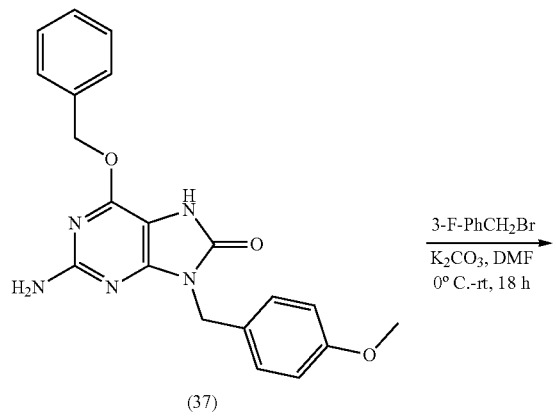

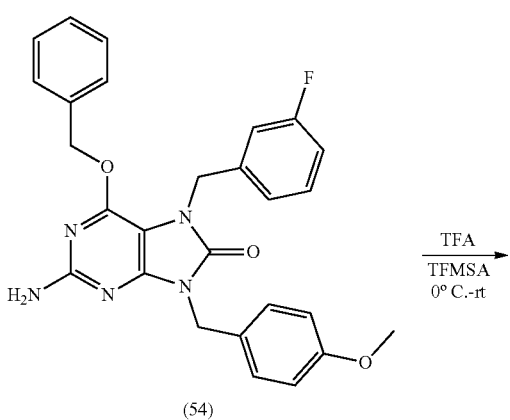

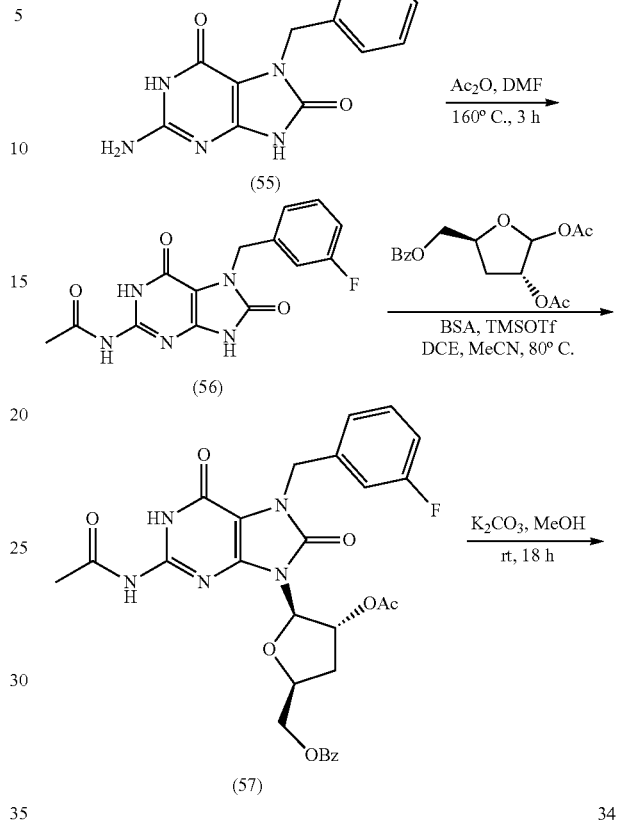

Step-1: 2-Amino-6-(benzyloxy)-7-(3-fluorobenzyl)-9-(4-methoxybenzyl)-7,9-dihydro-8H-purin-8-one (54)

3-Fluorobenzyl bromide (0.75 ml, 5.96 mmol) was added to a suspension of 2-amino-6-(benzyloxy)-9-(4-methoxybenzyl)-7,9-dihydro-8H-purin-8-one (2 g, 5.305 mmol) (1.5 g, 3.97 mmol), $K_2CO_3$ (1.64 g, 11.93 mmol) in DMF (20 mL) at 0° C. and stirred at room temperature for 18 h. The reaction mixture was quenched with ice water (120 mL), diluted with diethyl ether (80 mL) and stirred for 15 min. The resulting precipitated solid was filtered, washed with water and dried to afford 2-amino-6-(benzyloxy)-7-(3-fluorobenzyl)-9-(4-methoxybenzyl)-7,9-dihydro-8H-purin-8-one (1.7 g, 89%) as an off-white solid; ES+, m/z 486.1 [M+H]$^+$; $C_{27}H_{24}FN_5O_3$; $^1$H NMR (400 MHz, DMSO-d$_6$): δ 7.31-7.29 (m 4H), 7.26-7.21 (m, 4H), 7.09-7.04 (m 1H), 6.93-6.87 (m, 4H), 6.44 (s, 1H), 5.33 (s, 2H), 4.96 (s, 2H), 4.86 (s, 2H), 3.71 (s, 3H).

Step-2: 2-Amino-7-(3-fluorobenzyl)-7,9-dihydro-1H-purine-6,8-dione (55)

Trifluoromethanesulfonic acid (1.85 mL, 21.03 mmol) was added to a suspension of 2-amino-6-(benzyloxy)-7-(3-fluorobenzyl)-9-(4-methoxybenzyl)-7,9-dihydro-8H-purin-8-one (1.7 g, 3.50 mmol) in triflouroacetic acid (1.7 mL, 21.03 mmol) at 0° C. under argon atmosphere and the resulting reaction mixture was slowly warmed to room temperature and stirred for 3 h. The reaction mixture was quenched with ice cold water, basified with sat NaHCO$_3$ solution under vigorous stirring and filtered. The residual solid was taken into ethyl acetate, stirred for 30 min, filtered and dried to afford 2-amino-7-(3-fluorobenzyl)-7,9-dihydro-1H-purine-6,8-dione (0.7 g, 72%) as a brown solid; ES+, m/z 276.1 [M+H]$^+$; C$_{12}$H$_{10}$FN$_5$O$_2$; $^1$H NMR (400 MHz, DMSO-d$_6$): δ 11.2 (s, 1H), 10.67 (s, 1H), 7.36-7.33 (m, 1H), 7.13-7.05 (m, 4H), 6.39 (s, 2H), 4.94 (s, 2H).

Step-3: N-(7-(3-Fluorobenzyl)-6,8-dioxo-6,7,8,9-tetrahydro-1H-purin-2-yl)acetamide (56)

Acetic anhydride (0.76 mL, 7.63 mmol) was added to a solution of 2-amino-7-(3-fluorobenzyl)-7,9-dihydro-1H-purine-6,8-dione (0.7 g, 2.545 mmol) in DMF (10 mL) at ambient temperature under argon atmosphere and the resulting reaction mixture was stirred at 130° C. for 3 h under argon atmosphere. The reaction mixture was cooled down to 0° C. (solid was formed under stirring) and stirred for 30 minutes. The product was filtered, washed with ethanol and dried under vacuum to afford N-(7-(3-fluorobenzyl)-6,8-dioxo-6,7,8,9 tetrahydro-1H-purin-2-yl)acetamide (600 mg, 75%) as a brown solid. This crude compound was directly used for next step. ES−, m/z 316.1 [M−H]$^-$; C$_{14}$H$_{12}$FN$_5$O$_3$; $^1$H NMR (400 MHz, DMSO-d$_6$): δ 12.02 (s, 1H), 11.80 (s, 1H), 11.66 (s, 1H), 7.38-7.34 (m, 1H), 7.16-7.07 (m, 4H), 5.02 (s, 2H), 2.14 (s, 3H).

Step-4: ((2S,4R,5R)-5-(2-Acetamido-7-(3-fluorobenzyl)-6,8-dioxo-1,6,7,8-tetrahydro-9H-purin-9-yl)-4-acetoxytetrahydrofuran-2-yl)methyl benzoate (57)

N-(7-3-Fluorobenzyl)-6,8-dioxo-6,7,8,9 tetrahydro-1H-purin-2-yl)acetamide (440 mg, 1.338 mmol), (3R,5S)-5-((benzoyloxy)methyl)tetrahydrofuran-2,3-diyl diacetate (536 mg, 1.66 mmol), BSA (1.0 mL, 4.16 mmol) were dissolved in 1,2-dichloromethane (10 mL), the resulting reaction mixture was stirred at 80° C. for 30 min under argon. The reaction mixture was concentrated under reduced pressure, the residue was diluted with acetonitrile (10 mL), and TMSOTf (0.17 mL, 0.97 mmol) was added. The reaction mixture was placed into a pre-heated oil bath at 80° C. and stirred. After 3 h the reaction mixture was cooled to room temperature and the solvent was removed under reduced pressure. The resultant solid was dissolved in ethyl acetate (80 mL) and the solution was stirred with saturated aqueous NaHCO$_3$ (2×30 mL). The organic phase was separated, dried over Na$_2$SO$_4$ and concentrated. The crude compound was purified by column chromatography (SiO$_2$, 0 to 60% ethyl acetate-pet-ether) to ((2S,4R,5R)-5-(2-acetamido-7-(3-fluorobenzyl)-6,8-dioxo-1,6,7,8-tetrahydro-9H-purin-9-yl)-4-acetoxytetrahydrofuran-2-yl)methyl benzoate (150 mg, 18%) as an off-white solid; ES+, m/z 580.1 [M+H]$^+$; C$_{28}$H$_{26}$FN$_5$O$_8$; $^1$H NMR (400 MHz, DMSO-d$_6$): δ 12.1 (s, 1H), 11.55 (s, 1H), 7.88 (d, J=8 Hz, 2H), 7.64-7.60 (m, 2H), 7.44 (t, J=8 Hz, 3H), 7.16-7.07 (m, 3H), 5.76-5.72 (m, 2H), 5.05 (S, 2H), 4.51 (d, J=8 Hz, 2H), 4.40-4.36 (m, 1H), 3.16 (d, J=4, 1H), 2.17 (s, 3H), 2.15 (s, 3H).

Step-5: 2-Amino-7-(3-fluorobenzyl)-9-((2R,3R,5S)-3-hydroxy-5-(hydroxymethyl)tetrahydrofuran-2-yl)-7,9-dihydro-1H-purine-6,8-dione, Compound 34

To a solution of ((2S,4R,5R)-5-(2-acetamido-7-(3-fluorobenzyl)-6,8-dioxo-1,6,7,8-tetrahydro-9H-purin-9-yl)-4-acetoxytetrahydrofuran-2-yl)methyl benzoate (150 mg, 0.259 mmol) in methanol (5 mL) at room temperature, was added K$_2$CO$_3$ (177.4 mg, 1.295 mmol), the reaction mixture was stirred at room temperature for 16 h. The reaction progress was monitored by LC-MS. After completion of the reaction, solvent was removed under reduced pressure. The resulting crude compound was purified by GRACE flash chromatography using methanol and dichloromethane and obtained 50 mg of product. LC-MS showed 75% of product. The impure product was dissolved in 1 mL of methanol stirred for 20 minutes, then filtered and dried to afford 2-amino-7-(3-fluorobenzyl)-9-((2R,3R,5S)-3-hydroxy-5-(hydroxymethyl)tetrahydrofuran-2-yl)-7,9-dihydro-1H-purine-6,8-dione (Compound 34) (16 mg, 22%), as an off-white solid; ES+, m/z 392.1 [M+H]$^+$; C$_{17}$H$_{18}$FN$_5$O$_5$; $^1$H NMR (500 MHz, DMSO-d$_6$): δ 10.87 (s, 1H), 7.39-7.35 (m, 1H), 7.15-7.08 (m, 3H), 6.52 (s, 2H), 5.52 (d, J=5 Hz, 1H), 5.36 (d, J=5 Hz, 1H), 4.99 (s, 2H), 4.82-4.79 (s, 1H), 4.67 (t, J=10 Hz, 1H), 4.15-4.11 (m, 1H), 3.48-3.39 (m, 2H), 2.36-2.32 (m, 1H), 1.84-1.80 (m, 1H).

Example 35: 2-Amino-9-((2R,3R,5S)-3-hydroxy-5-(hydroxymethyl)tetrahydrofuran-2-yl)-7-(4-(trifluoromethyl)benzyl)-7,9-dihydro-1H-purine-6,8-dione, Compound 35

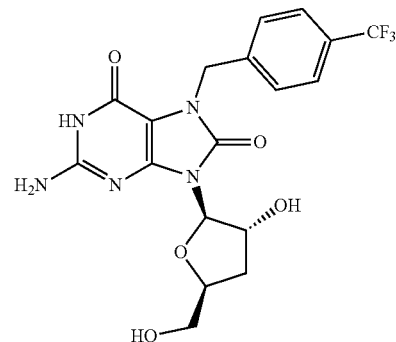 [SMILES: Nc1nc2c(c(=O)[nH]1)n(Cc1ccc(C(F)(F)F)cc1)c(=O)n2[C@@H]1O[C@H](CO)C[C@H]1O]

Using the same general procedure as described for Example 5A, Compound 35 was synthesized according to the following multi-step procedure.

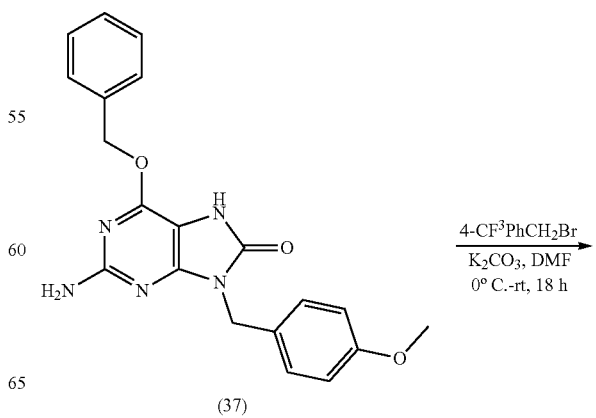

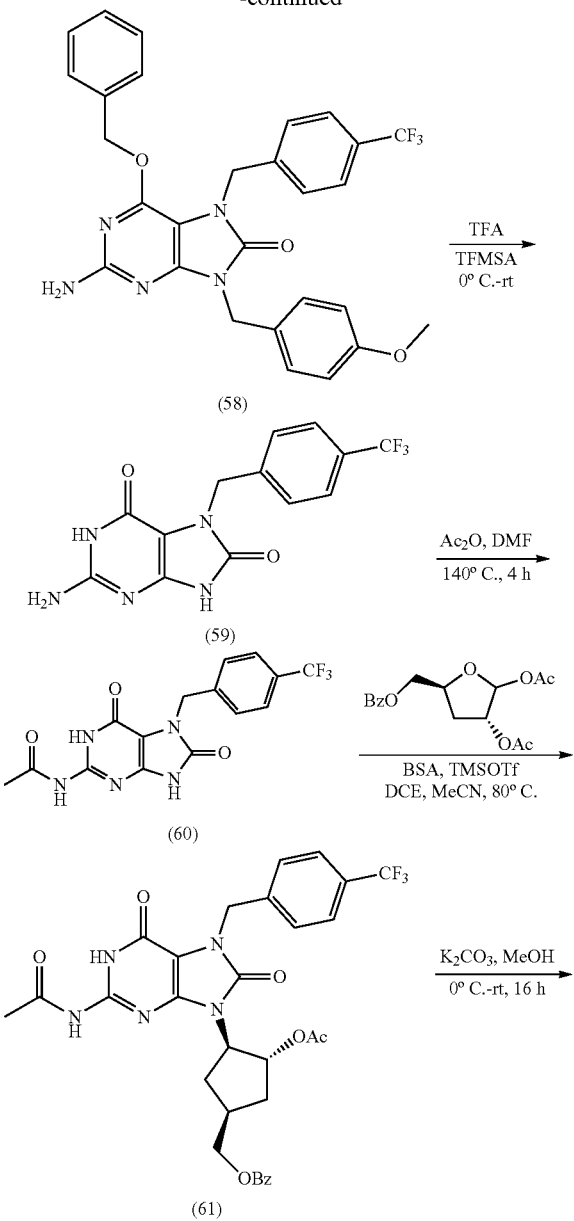

Step-1: 2-Amino-6-(benzyloxy)-9-(4-methoxybenzyl)-7-(4-(trifluoromethyl)benzyl)-7,9-dihydro-8H-purin-8-one (58)

1-(Bromomethyl)-4-(trifluoromethyl)benzene (2.28 g, 9.54 mmol) was added to a suspension of 2-amino-6-(benzyloxy)-9-(4-methoxybenzyl)-7,9-dihydro-8H-purin-8-one (3 g, 7.95 mmol), $K_2CO_3$ (1.64 g, 11.93 mmol) in DMF (30 mL) at 0° C. and stirred at room temperature for 16 h. The reaction mixture was quenched with ice water (120 mL), diluted with diethyl ether (80 mL) and stirred for 15 min. The resulting precipitate was collected by filtration, washed with water and dried to afford 2-amino-6-(benzyloxy)-9-(4-methoxybenzyl)-7-(4-(trifluoromethyl)benzyl)-7,9-dihydro-8H-purin-8-one (3.8 g, 90%) as an off-white solid; ES+, m/z 536.2 [M+H]$^+$; $C_{28}H_{24}F_3N_5O_3$; $^1$HNMR (400 MHz, DMSO-d$_6$): δ 7.60 (d, J=8.4 Hz, 2H), 7.31-7.21 (m, 7H), 7.16 (d, J=6.4 Hz, 2H), 6.89 (d, J=8.8 Hz, 2H), 6.45 (s, 2H), 5.31 (s, 2H), 5.04 (s, 2H), 4.87 (s, 2H), 3.71 (s, 3H).

Step-2: 2-Amino-7-(4-(trifluoromethyl)benzyl)-7,9-dihydro-1H-purine-6,8-dione (59)

Trifluoromethanesulfonic acid (1.97 mL, 22.42 mmol) was added to a suspension of 2-amino-6-(benzyloxy)-9-(4-methoxybenzyl)-7-(4-(trifluoromethyl)benzyl)-7,9-dihydro-8H-purin-8-one (2 g, 3.73 mmol) in trifluoroacetic acid (1.7 mL, 3.73 mmol) at 0° C. under argon atmosphere and the resulting reaction mixture was slowly warmed to room temperature and stirred for 3 h. The reaction mixture was quenched with ice cold water, basified with a sat. NaHCO$_3$ solution under vigorous stirring and filtered. The residual solid was taken into diethyl ether (100 mL), stirred for 30 min, filtered and dried to afford 2-amino-7-(4-(trifluoromethyl)benzyl)-7,9-dihydro-1H-purine-6,8-dione (1 g; 83%) as an off-white solid: ES+, m/z 326.1 [M+H]$^+$; $C_{13}H_{10}F_3N_5O_2$; $^1$H NMR (400 MHz, DMSO-d$_6$): δ 11.24 (s, 1H), 10.67 (s, 1H), 7.69 (d, J=8.4 Hz, 2H), 7.48 (d, J=8 Hz, 2H), 6.40 (s, 2H), 5.02 (s, 2H).

Step-3: N-(6,8-dioxo-7-(4-(Trifluoromethyl)benzyl)-6,7,8,9-tetrahydro-1H-purin-2-yl)acetamide (60)

Acetic anhydride (2 mL) was added to a solution of 2-amino-7-(4-(trifluoromethyl)benzyl)-7,9-dihydro-1H-purine-6,8-dione (1.4 g, 4.30 mmol) in DMF (20 mL) at ambient temperature under argon atmosphere and the resulting reaction mixture was heated at 140° C. for 3 h. The reaction mixture was cooled to 0° C. with stirring whereupon a solid formed. Stirring was continued for 30 minutes, the product was filtered, and dried under vacuum to afford N-(6,8-dioxo-7-(4-(trifluoromethyl)benzyl)-6,7,8,9-tetrahydro-1H-purin-2-yl)acetamide (1 g, 63%) as an off-white solid: ES+, m/z 368.1 [M+H]$^+$; $C_{15}H_{12}F_3N_5O_3$; $^1$H NMR (400 MHz, DMSO-d$_6$): δ 12.36 (s, 1H), 11.44 (s, 1H), 7.70 (d, J=8 Hz, 2H), 7.57 (d, J=8.4 Hz, 2H), 6.98 (br s, 1H), 5.19 (s, 2H), 2.17 (s, 3H).

Step-4: ((2S,4R,5R)-5-(2-Acetamido-6,8-dioxo-7-(4-(trifluoromethyl)benzyl)-1,6,7,8-tetrahydro-9H-purin-9-yl)-4-acetoxytetrahydrofuran-2-yl)methyl benzoate (61)

N-(6,8-Dioxo-7-(4-(trifluoromethyl)benzyl)-6,7,8,9-tetrahydro-1H-purin-2-yl)acetamide (350 mg, 0.953 mmol), (3R,5S)-5-((benzoyloxy)methyl)tetrahydrofuran-2,3-diyl diacetate (368 mg, 1.143 mmol), and BSA (0.72 mL, 2.859 mmol) were dissolved in 1,2-dichloroethane (10 mL) and the resulting reaction mixture was stirred at 80° C. for 30 min under argon. The reaction mixture was allowed cooled to room temperature and TMSOTf (0.12 mL, 0.667 mmol) was added. The reaction mixture was maintained at 80° C. for 3 h and then cooled to room temperature, diluted with water and extracted with CH$_2$Cl$_2$ (3×100 mL). The combined organic layers were washed with water (100 mL), brine (100 mL), dried over Na$_2$SO$_4$ and concentrated under reduced pressure. The crude compound was purified by flash chromatography (SiO$_2$, 0 to 60% EtOAc-pet-ether) to afford ((2S,4R,5R)-5-(2-acetamido-6,8-dioxo-7-(4-(trifluoromethyl)benzyl)-1,6,7,8-tetrahydro-9H-purin-9-yl)-4-acetoxytetrahydrofuran-2-yl)methyl benzoate (70 mg, 11%) as an off-white solid: $C_{29}H_{26}F_3N_5O_8$: LC-MS indicated 84% of desired mass; ES+, m/z 368.1 [M+H]$^+$.

Step-5: 2-Amino-9-((2R,3R,5S)-3-hydroxy-5-(hydroxymethyl)tetrahydrofuran-2-yl)-7-(4-(trifluoromethyl)benzyl)-7,9-dihydro-1H-purine-6,8-dione, Compound 35

To a solution of ((2S,4R,5R)-5-(2-acetamido-6,8-dioxo-7-(4-(trifluoromethyl)benzyl)-1,6,7,8-tetrahydro-9H-purin-9-yl)-4-acetoxytetrahydrofuran-2-yl)methyl benzoate (70 mg, 0.111 mmol) in methanol (5 mL) was added K$_2$CO$_3$ (61 mg, 0.445 mmol) at 0° C., the reaction mixture was stirred at room temperature for 16 h. The reaction mixture was directly purified by RP flash chromatography and the prep-fractions were lyophilized to afford 2-amino-9-((2R,3R,5S)-3-hydroxy-5-(hydroxymethyl)tetrahydrofuran-2-yl)-7-(4-(trifluoromethyl)benzyl)-7,9-dihydro-1H-purine-6,8-dione (Compound 35) (25 mg, 51%), as a white solid; ES+, m/z 442.1 [M+H]$^+$; $C_{18}H_{18}F_3N_5O_5$: $^1$H NMR (500 MHz, DMSO-d$_6$): δ 10.95 (s, 1H), 7.70 (d, J=8.5 Hz, 2H), 7.51 (d, J=8 Hz, 2H), 6.58 (s, 2H), 5.54 (d, J=3 Hz, 1H), 5.37 (d, J=4.5 Hz, 1H), 5.07 (s, 2H), 4.82-4.80 (m, 1H), 4.69-4.67 (m, 1H), 4.15-4.13 (m, 1H), 3.47-3.40 (s, 2H), 2.38-2.32 (m, 1H), 1.84-1.80 (m, 1H).

Example 36: 7-Allyl-2-amino-9-((2R,3R,5S)-3-hydroxy-5-(hydroxymethyl)tetrahydrofuran-2-yl)-7,9-dihydro-1H-purine-6,8-dione, Compound 36

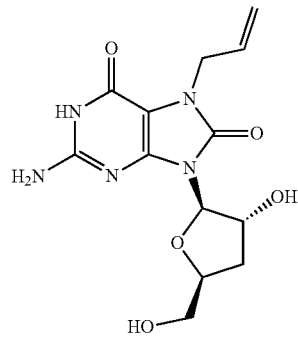 [SMILES: C=CCn1c(=O)n([C@@H]2O[C@H](CO)C[C@H]2O)c2nc(N)[nH]c(=O)c21]

Using the same general procedure as described for Example 5A, Compound 36 was synthesized according to the following multi-step procedure.

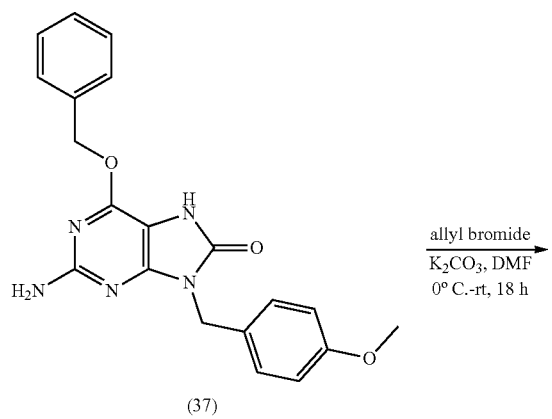

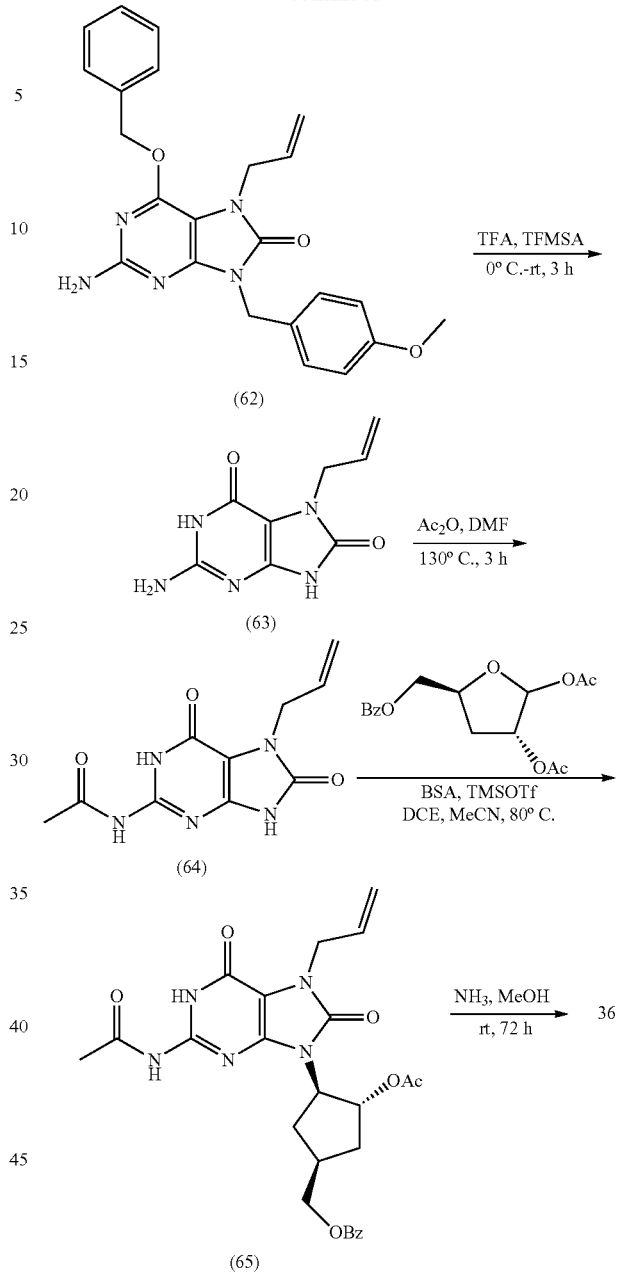

Step-1: 7-Allyl-2-amino-6-(benzyloxy)-9-(4-methoxybenzyl)-7,9-dihydro-8H-purin-8-one (62)

Allyl bromide (0.767 g, 5.30 mmol) was added to a suspension 2-amino-6-(benzyloxy)-9-(4-methoxybenzyl)-7,9-dihydro-8H-purin-8-one (2 g, 5.298 mmol), K$_2$CO$_3$ (1.09 g, 7.95 mmol) in DMF (20 mL) at 0° C. and stirred at room temperature for 18 h. The reaction mixture was quenched with ice water (120 mL), diluted with diethyl ether (80 mL) and stirred for 15 min. The resulting precipitated solid was collected by filtration, washed with water and dried to afford 7-allyl-2-amino-6-(benzyloxy)-9-(4-methoxybenzyl)-7,9-dihydro-8H-purin-8-one (2.0 g, 76%) as an off-white solid; ES+, m/z 418.1 [M+H]$^+$; $C_{23}H_{23}N_5O_3$; $^1$H NMR (400 MHz, DMSO-d$_6$): δ 7.44 (d, J=7.5 Hz, 2H), 7.40-7.36 (m, 2H), 7.30 (d, J=4.5 Hz, 1H), 7.21 (d, J=8.5 Hz, 2H), 6.8 (d, J=8.5 Hz, 2H), 6.40 (s, 2H), 5.89-5.82 (m, 1H), 5.37 (s, 2H), 5.05 (d, J=10 Hz, 1H), 5.04 (d, J=15 Hz, 1H), 4.83 (s, 2H), 4.37 (d, J=5 Hz, 2H), 3.71 (s, 3H).

Step-2: 7-Allyl-2-amino-7,9-dihydro-1H-purine-6,8-dione (63)

Trifluoromethanesulfonic acid (1.268 mL, 14.37 mmol) was added to a suspension of 7-allyl-2-amino-6-(benzyloxy)-9-(4-methoxybenzyl)-7,9-dihydro-8H-purin-8-one (2 g, 4.79 mmol) in triflouroacetic acid (1.09 mL, 14.37 mmol) at 0° C. under argon atmosphere and the resulting reaction mixture was slowly warmed to room temperature with stirring for 3 h. The reaction mixture was quenched with ice cold water, basified with sat. NaHCO$_3$ solution under vigorous stirring and filtered. The residual solid was taken into ethyl acetate, stirred for 30 min and filtered; the residue was dried to afford 7-allyl-2-amino-7,9-dihydro-1H-purine-6,8-dione (0.54 g, 56%) as a brown solid. ES+, m/z 208.1 [M+H]$^+$; C$_8$H$_9$N$_5$O$_2$; $^1$H NMR (400 MHz, DMSO-d$_6$): $^1$H NMR (500 MHz, DMSO-d$_6$): δ 11.15 (s, 1H), 10.81 (s, 1H), 6.36 (s, 2H), 5.92-5.85 (m, 1H), 5.07 (d, J=12.5 Hz, 1H), 5.04 (d, J=478 Hz, 1H), 4.33 (d, J=5.5 Hz, 2H).

Step-3: N-(7-Allyl-6,8-dioxo-6,7,8,9-tetrahydro-1H-purin-2-yl)acetamide (64)

Acetic anhydride (0.74 mL) was added to a solution of 7-allyl-2-amino-7,9-dihydro-1H-purine-6,8-dione (0.54 g, 7.82 mmol) in DMF (5 mL) at ambient temperature under argon atmosphere and the resulting reaction mixture was heated at 130° C. for 3 h under argon atmosphere. The reaction mixture was cooled down to 0° C. whereupon a solid was formed under stirring after 30 minutes. The product was collected by filtration, washed with ethanol and dried under vacuum to afford N-(7-allyl-6,8-dioxo-6,7,8,9-tetrahydro-1H-purin-2-yl)acetamide (0.50 g, 61%) as an brown solid. This crude compound was directly used for next step. ES+, m/z 250.1 [M+H]$^+$; C$_{10}$H$_{11}$N$_5$O$_3$; $^1$H NMR (400 MHz, DMSO-d$_6$): δ 11.99 (s, 1H), 11.74 (s, 1H), 11.67 (s, 1H), 5.96-5.87 (m, 1H), 5.10 (d, J=1.6 Hz, 1H), 5.04 (d, J=1.6 Hz, 1H), 4.4 (d, J=5.6 Hz, 2H), 2.19 (s, 3H).

Step-4: ((2S,4R,5R)-5-(2-Acetamido-7-allyl-6,8-dioxo-1,6,7,8-tetrahydro-9H-purin-9-yl)-4-acetoxytetrahydrofuran-2-yl)methyl benzoate (65)

N-(7-Allyl-6,8-dioxo-6,7,8,9-tetrahydro-1H-purin-2-yl)acetamide (500 mg, 2.01 mmol), (3R,5S)-5-((benzoyloxy)methyl)tetrahydrofuran-2,3-diyl diacetate (969 mg, 3.01 mmol), BSA (1.47 mL, 6.08 mmol) were dissolved in ACN (10 mL). The resulting reaction mixture was stirred at 80° C. for 30 min under argon. The reaction mixture was concentrated under reduced pressure, the residue was diluted with acetonitrile (9.5 mL) and TMSOTf (0.254 mL, 1.40 mmol) was added. The reaction mixture was placed into a preheated oil bath at 80° C. and stirred. After 3 h the reaction mixture was cooled to room temperature and the solvent was removed under reduced pressure. The resultant solid was dissolved in ethyl acetate (80 mL) and the solution was shaken with saturated aqueous NaHCO$_3$ (2×30 mL). The organic phase was separated, dried over Na$_2$SO$_4$ and concentrated. The crude compound was purified by column chromatography (SiO$_2$, 0 to 60% EtOAc-pet-ether) to afford ((2S,4R,5R)-5-(2-acetamido-7-allyl-6,8-dioxo-1,6,7,8-tetrahydro-9H-purin-9-yl)-4-acetoxytetrahydrofuran-2-yl) methyl benzoate (180 mg, 24%) as an off-white solid. $^1$H NMR (500 MHz, DMSO-d$_6$): δ 12.1 (s, 1H), 11.51 (s, 1H), 7.90 (d, J=10 Hz, 2H), 7.65-7.61 (m, 1H), 7.46 (t, J=8.5 Hz, 2H), 5.87-5.75 (m, 1H), 5.75-5.72 (m, 2H), 5.11-5.01 (m, 2H), 4.53 (d, J=5 Hz, 2H), 4.46 (d, J=2.5 Hz, 2H), 4.40-4.36 (m, 1H), 2.92 (m, 1H), 2.14 (s, 3H), 2.10 (m, 1H), 2.08 (s, 3H).

Step-5: 7-Allyl-2-amino-9-((2R,3R,5S)-3-hydroxy-5-(hydroxymethyl)tetrahydrofuran-2-yl)-7,9-dihydro-1H-purine-6,8-dione, Compound 36

A solution of afford ((2S,4R,5R)-5-(2-acetamido-7-allyl-6,8-dioxo-1,6,7,8-tetrahydro-9H-purin-9-yl)-4-acetoxytetrahydrofuran-2-yl)methyl benzoate (180 mg, 0.352 mmol) in 7 M ammonia in methanol (5 mL) taken in a sealed vessel was stirred at room temperature for 72 h. The reaction progress was monitored by LC-MS. After complete consumption of starting material, the reaction mixture was concentrated under reduced pressure. The resultant thick solid was dissolved in minimum amount of methanol and diethyl ether (10 mL) was added, stirred for 30 minutes and filtered. Upon drying 7-allyl-2-amino-9-((2R,3R,5S)-3-hydroxy-5-(hydroxymethyl)tetrahydrofuran-2-yl)-7,9-dihydro-1H-purine-6,8-dione (Compound 36) (60 mg, 51%) was isolated as an off-white solid. ES+, m/z 324.1 [M+H]$^+$; C$_{13}$H$_{17}$N$_5$O$_5$; $^1$H NMR (500 MHz, DMSO-d$_6$): δ 10.91 (s, 1H), 6.51 (s, 2H), 5.90 (m, 1H), 5.53 (d, J=2.5 Hz, 1H), 5.37 (d, J=4 Hz, 1H), 5.06 (dd, J=10 Hz, 2H), 4.72 (bs, 2H), 4.39 (d, J=4 Hz, 2H), 4.14 (s, 1H), 3.44 (m, 2H), 2.35 (m, 1H), 1.82 (m, 1H). m.p.=199-203° C.

Example 37: 2-Amino-7-butyl-9-((2R,3R,5S)-3-hydroxy-5-(hydroxymethyl)tetrahydrofuran-2-yl)-7,9-dihydro-1H-purine-6,8-dione, Compound 37

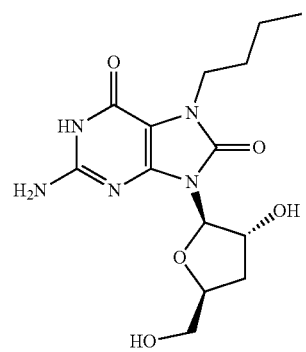 [SMILES: CCCCn1c(=O)n([C@@H]2O[C@H](CO)C[C@H]2O)c2nc(N)[nH]c(=O)c21]

Using the same general procedure as described for Example 5A, Compound 37 was synthesized according to the following multi-step procedure.

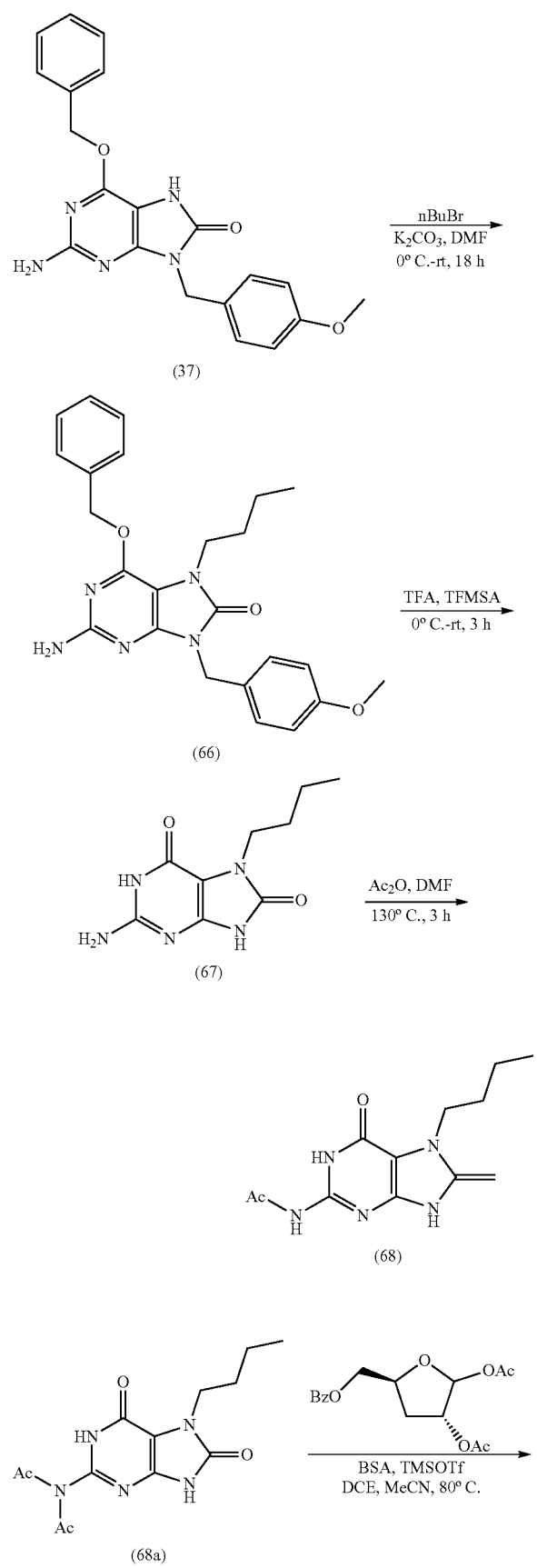

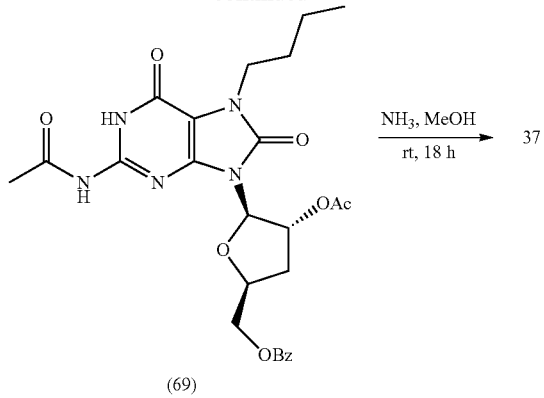

Step-1: 2-Amino-6-(benzyloxy)-7-butyl-9-(4-methoxybenzyl)-7,9-dihydro-8H-purin-8-one (66)

Butyl bromide (0.43 ml 3.183 mmol) was added to a suspension of 2-amino-6-(benzyloxy)-9-(4-methoxybenzyl)-7,9-dihydro-8H-purin-8-one (1 g, 2.65 mmol) and $K_2CO_3$ (0.548 g, 3.97 mmol) in DMF (10 mL) at 0° C. and stirred at room temperature for 18 h. The reaction mixture was quenched with ice water (120 mL), diluted with diethyl ether (80 mL) and stirred for 15 min. The resulting precipitated solid was collected by filtration, washed with water and dried to afford 2-amino-6-(benzyloxy)-7-butyl-9-(4-methoxybenzyl)-7,9-dihydro-8H-purin-8-one (0.80 g, 69%) as a brown solid; ES+, m/z 433.1 [M+H]$^+$; $C_{24}H_{27}N_5O_3$; $^1$H NMR (400 MHz, DMSO-$d_6$): δ 7.4 (d, J=6.8 Hz, 2H), 7.34-7.41 (m, 3H), 7.20 (d, J=8 Hz, 2H), 6.8 (d, J=8.8 Hz, 2H), 6.4 (s, 2H), 5.4 (s, 2H), 4.8 (s, 2H), 3.7 (t, J=15.6 Hz, 5H), 1.5 (t, J=14.4 Hz, 2H), 1.11-1.17 (m, 2H), 0.76 (t, J=14.8 Hz, 3H).

Step-2: 2-Amino-7-butyl-7,9-dihydro-1H-purine-6,8-dione (67)

Trifluoromethanesulfonic acid (1.03 g, 6.89 mmol) was added to a suspension of 2-amino-6-(benzyloxy)-7-butyl-9-(4-methoxybenzyl)-7,9-dihydro-8H-purin-8-one (1.0 g, 2.30 mmol) in trifluoroacetic acid (0.786 mL, 6.89 mmol) at 0° C. under argon atmosphere. The reaction mixture was slowly warmed to room temperature and stirred for 3 h. The reaction mixture was quenched with ice cold water, and a sat. $NaHCO_3$ solution was added under vigorous stirring. The solids were filtered, was taken into ethyl acetate, stirred for 30 min., filtered and dried to afford 2-amino-7-butyl-7,9-dihydro-1H-purine-6,8-dione (0.30 g, 58%) as a brown solid. ES+, m/z 224.1 [M+H]$^+$; $C_9H_{13}N_5O_2$; $^1$H NMR (400 MHz, DMSO-$d_6$): δ 11.0 (s, 1H), 10.6 (s, 1H), 6.3 (s, 2H), 3.7 (t, J=16 Hz, 2H), 1.5-1.6 (m, 2H), 1.25-1.20 (m, 2H), 0.8 (t, J=12 Hz, 3H).

Step-3: N-(7-Butyl-6,8-dioxo-6,7,8,9-tetrahydro-1H-purin-2-yl)acetamide (68) and N-Acetyl-N-(7-butyl-6,8-dioxo-6,7,8,9-tetrahydro-1H-purin-2-yl)acetamide (68a)

Acetic anhydride (0.20 ml, 2.01 mmol) was added to a solution of 2-amino-7-butyl-7,9-dihydro-1H-purine-6,8-dione (0.300 g, 1.345 mmol) in DMF (5 mL) at ambient temperature under argon atmosphere. The resulting reaction mixture was stirred at 130° C. for 3 h under argon atmosphere. The reaction mixture was cooled down to 0° C. (solid was formed under stirring) and stirred for 30 minutes. The product was filtered, washed with ethanol and dried under vacuum to afford a mixture of N-(7-butyl-6,8-dioxo-6,7,8,9-tetrahydro-1H-purin-2-yl)acetamide (68) and N-acetyl-N-(7-butyl-6,8-dioxo-6,7,8,9-tetrahydro-1H-purin-2-yl)acetamide (68a) (0.150 g, 42%) as an brown solid. LC-MS indicated 20% of (68); ES+, m/z 266.1 [M+H]$^+$; $C_{11}H_{15}N_5O_3$; and 49% of (68a); ES+, m/z 308.1 [M+H]$^+$; $C_{13}H_{17}N_5O_4$; This mixture was used directly in the next step.

Step-4: ((2S,4R,5R)-5-(2-Acetamido-7-butyl-6,8-dioxo-1,6,7,8-tetrahydro-9H-purin-9-yl)-4-acetoxytetrahydrofuran-2-yl)methyl benzoate (69)

A mixture of N-(7-butyl-6,8-dioxo-6,7,8,9-tetrahydro-1H-purin-2-yl)acetamide (68) and N-acetyl-N-(7-butyl-6,8-dioxo-6,7,8,9-tetrahydro-1H-purin-2-yl)acetamide (68a) (1.433 mmol), (2S,3R,5S)-5-((benzoyloxy)methyl)tetrahydrofuran-2,3-diyl diacetate (0.692 g, 2.150 mmol) and BSA (0.58 g, 2.86 mmol) were dissolved in dichloroethane (9.5 mL) and stirred at 80° C. for 30 min under argon. The reaction mixture was concentrated under reduced pressure and the residue was diluted with dry acetonitrile (9.5 mL) and TMSOTf (0.2 g, 0.931 mmol) was added. The reaction mixture was placed into a pre-heated oil bath at 80° C. and stirred. After 3 h the reaction mixture was cooled to room temperature and the solvent was removed under reduced pressure. The resultant solid was dissolved in ethyl acetate (80 mL) and the solution was shaken with saturated aqueous NaHCO$_3$ (2×30 mL). The organic phase was dried over Na$_2$SO$_4$ and concentrated. The crude compound was purified by column chromatography (SiO$_2$, 0 to 60% EtOAc-pet-ether as eluent) to yield 200 mg (26%) of ((2S,4R,5R)-5-(2-acetamido-7-butyl-6,8-dioxo-1,6,7,8-tetrahydro-9H-purin-9-yl)-4-acetoxytetrahydrofuran-2-yl)methyl benzoate as a pale yellow solid (78% pure by LC/MS); ES+, m/z 528.2 [M+H]$^+$; $C_{25}H_{29}N_5O_8$.

Step-5: 2-Amino-7-butyl-9-((2R,3R,5S)-3-hydroxy-5-(hydroxymethyl)tetrahydrofuran-2-yl)-7,9-dihydro-1H-purine-6,8-dione, Compound 37

((2S,4R,5R)-5-(2-Acetamido-7-butyl-6,8-dioxo-1,6,7,8-tetrahydro-9H-purin-9-yl)-4-acetoxytetrahydrofuran-2-yl) methyl benzoate (0.150 g, 0.285 mmol) was dissolved in methanolic ammonia (10 mL) and the reaction mixture was stirred for 18 h at room temperature. The reaction mixture was concentrated under reduced pressured. The crude product was purified by GRACE reverse phase purification system (MeCN-0.01% of HCO$_2$H in H$_2$O as eluent) and 0.060 g (62%) of 2-amino-7-butyl-9-((2R,3R,5S)-3-hydroxy-5-(hydroxymethyl)tetrahydrofuran-2-yl)-7,9-dihydro-1H-purine-6,8-dione (Compound 37) was obtained as a white solid. ES+, m/z 340.2 [M+H]$^+$, $C_{14}H_{21}N_5O_5$; $^1$H NMR (400 MHz, DMSO-d$_6$): δ 10.87 (s, 1H), 6.4 (s, 2H), 5.5 (d, J=4 Hz, 1H), 5.3 (d, J=4 Hz, 1H), 4.70-4.8 (m, 1H), 4.7 (t, J=12 Hz, 1H), 4.1 (t, J=12 Hz, 1H), 3.7 (t, J=16 Hz, 2H), 3.3-3.4 (m, 2H), 2.3-2.5 (m, 1H), 1.7-1.8 (m, 1H), 1.5-1.6 (m, 2H), 1.21-1.27 (m, 2H), 0.8 (t, J=16 Hz 3H).

Preparation of Intermediates (70), (71), (72), (73), and (74)

Intermediate compounds (70-74) were synthesized according to the following multi-step procedure.

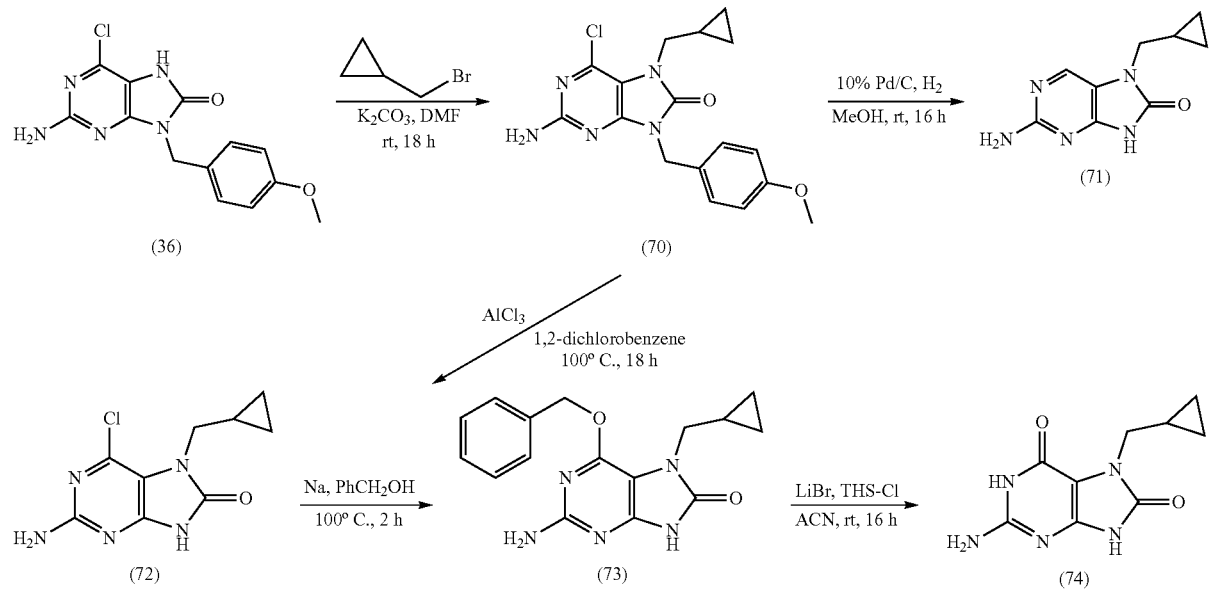

Step-1: 2-Amino-6-chloro-7-(cyclopropylmethyl)-9-(4-methoxybenzyl)-7,9-dihydro-8H-purin-8-one (70)

Cyclopropyl methyl bromide (32.9 g, 24.39 mol) was added to a suspension of 2-amino-6-chloro-9-(4-methoxybenzyl)-7,9-dihydro-8H-purin-8-one (36) (62 g, 20.32 mol), K$_2$CO$_3$ (42 g, 30.49 mol) in DMF (500 mL) at 0° C. and then stirred at room temperature for 18 h. The reaction mixture was poured on to ice cold water and stirred for 30 mins at room temperature. The precipitated solid product was collected by filteration and dried under vacuum to afforded 2-amino-6-chloro-7-(cyclopropylmethyl)-9-(4-methoxybenzyl)-7,9-dihydro-8H-purin-8-one (70) (60 g, 82%) as a brown solid. TLC: 30% Ethyl acetate in hexane; R$_f$: 0.4; ES+, m/z 360.1 [M+H]$^+$; $C_{17}H_{18}ClN_5O_2$; $^1$H NMR (400 MHz, DMSO-d$_6$): δ 7.23 (d, J=8.4 Hz, 2H), 6.89 (d, J=8.8

Hz, 2H), 6.75 (s, 2H), 4.86 (s, 2H), 3.80 (d, J=6.8 Hz, 2H), 3.71 (s, 3H), 1.21-1.17 (m, 1H), 0.50-0.46 (m, 2H), 0.37-0.34 (m, 2H).

Step-2: 2-Amino-7-(cyclopropylmethyl)-7,9-dihydro-8H-purin-8-one (71)

10% Pd—C (5.0 g) was added to a solution of 2-amino-6-chloro-7-(cyclopropylmethyl)-9-(4-methoxybenzyl)-7,9-dihydro-8H-purin-8-one (70) (20 g, mmol) in methanol (500 mL). The reaction mixture was hydrogenated with $H_2$ gas at 80 psi of pressure in a Parr shaker vial at room temperature for 24 h. The reaction mixture was filtered through a celite pad and the filtrate was evaporated to give crude product. To the crude compound was added acetonitrile with stirred for 15 min, filtered. This step was repeated and the solid was dried under vacuum to afford 2-amino-7-(cyclopropylmethyl)-7,9-dihydro-8H-purin-8-one (71) (11 g, 64%) as an off white solid. TLC: 70% Ethyl acetate in hexane; $R_f$: 0.2; ES+, m/z 206.2 [M+H]$^+$; $C_9H_{11}N_5O$. $^1$H NMR (500 MHz, DMSO-$d_6$): δ 12.68 (s, 1H), 8.11 (s, 1H), 7.87 (s, 2H), 3.60-3.59 (d, J=7.5 Hz, 2H), 1.18-1.12 (m, 1H), 0.50-0.46 (m, 2H), 0.37-0.34 (m, 2H). m.p. 245-249° C.

Step-3: 2-Amino-6-chloro-7-(cyclopropylmethyl)-7,9-dihydro-8H-purin-8-one (72)

Anhydrous $AlCl_3$ powder (25 g, 187 mmol) was added to a stirred solution of 2-amino-6-chloro-7-(cyclopropylmethyl)-9-(4-methoxybenzyl)-7,9-dihydro-8H-purin-8-one (70) (50 g, 139.2 mmol) in 1,2-dichloro benzene (250 mL) at room temperature under argon atmosphere and the resulting reaction mixture was stirred at 100° C. for 18 h under argon atmosphere. The reaction mixture was cooled to room temperature and quenched with ice cold water, basified with a sat. $NaHCO_3$ solution under vigorous stirring and filtered. The filtered solid was taken into 10% MeOH in dichloromethane, stirred for 30 min and filtered (repeated thrice with volume of 1.0 L solvent). The filterate was passed through a pad of celite and concentrated under reduced pressure. The solid thus obtained was washed twice with 10% methanol in dichloromethane and filtered. The filtered solid was again washed with twice acetonitrile, filtered and dried to afford 2-amino-6-chloro-7-(cyclopropylmethyl)-7,9-dihydro-8H-purin-8-one (72) (12 g, 36%) as a brown solid. TLC: 50% Ethyl acetate in hexane; $R_f$: 0.3; ES+, m/z 240.1 [M+H]$^+$; $C_9H_{10}ClN_5O$. $^1$H NMR (500 MHz, DMSO-$d_6$): δ 11.81 (s, 1H), 6.58 (s, 2H), 3.73-3.72 (d, J=7.0 Hz, 2H), 1.21-1.17 (m, 1H), 0.50-0.46 (m, 2H), 0.37-0.34 (m, 2H). m.p. 286-290° C.

Step-4: 2-Amino-6-(benzyloxy)-7-(cyclopropylmethyl)-7,9-dihydro-8H-purin-8-one (73)

Sodium metal (1.43 g, 62.6 mmol) was added to benzyl alcohol (25.0 mL) for 1 h (until all the sodium dissolved). The resulting viscous liquid was cooled to rt and 2-amino-6-chloro-7-(cyclopropylmethyl)-7,9-dihydro-8H-purin-8-one (72) (5.0 g, 20.86 mmol) was added. The resulting reaction mixture was stirred at 100° C. for 1 h and quenched with ice water (200 mL). Diethyl ether (150 mL) was added and stirred for 15 min. The resulting precipitated solid was filtered, washed with water and dried. The solid was dissolved in 15% methanol-dichloromethane (500 mL), filtered through celite pad, washed with brine and concentrated. The resulting solid was washed with diethyl ether and filtered to afford 2-amino-6-(benzyloxy)-7-(cyclopropylmethyl)-7,9-dihydro-8H-purin-8-one (73) (3.5 g, 54%) as an off white solid. TLC: 70% Ethyl acetate in pet ether; $R_f$: 0.6; ES+, m/z 312.2 [M+H]$^+$; $C_{16}H_{17}N_5O_2$. $^1$H NMR (500 MHz, DMSO-$d_6$): δ 11.30 (brs, 1H), 7.48-7.46 (m, 2H), 7.41-7.38 (m, 2H), 7.35-7.30 (m, 1H), 6.15 (s, 2H), 5.41 (s, 2H), 3.56 (d, J=7.0 Hz, 2H), 1.14-1.10 (m, 1H), 0.36-0.32 (m, 2H), 0.23-0.21 (m, 2H). m.p. 238-242° C.

Step-5: 2-Amino-7-(cyclopropylmethyl)-7,9-dihydro-1H-purine-6,8-dione (74)

A suspension of 2-amino-6-(benzyloxy)-7-(cyclopropylmethyl)-7,9-dihydro-8H-purin-8-one (73) (10.0 g, 32.15 mmol), anhydrous LiBr (3.34 g, 38.58 mmol), chlorotrimethylsilane (4.53 g, 108.6 mmol) in acetonitrile (700 mL) were stirred at room temperature for 16 h. Methanol (60 mL) was added to the reaction mixture and stirred for 30 min. The solvent was distilled off to a reduced volume of ~100 mL and filtered. The filter cake was washed with acetonitrile and dried. The solid was taken into a sat. $NaHCO_3$ solution (200 mL), stirred for 1 h, filtered, washed with water and dried. The solid was stirred in 10% methanol/dichloromethane (50 mL), filtered and dried to afford 2-amino-7-(cyclopropylmethyl)-7,9-dihydro-1H-purine-6,8-dione (74) (8.5 g, 80%) as a pale brown solid. TLC: 10% methanol in dichloromethane; $R_f$: 0.4; ES+, m/z 222.1 [M+H]$^+$; $C_9H_{11}N_5O_2$. $^1$H NMR (500 MHz, DMSO-$d_6$): δ 11.06 (s, 1H), 10.68 (s, 1H), 6.36 (s, 2H), 3.58 (d, J=7.0 Hz, 2H), 1.19-1.14 (m, 1H), 0.40-0.36 (m, 2H), 0.33-0.30 (m, 2H). m.p. 364-368° C.

Example 31S: ((2R,3S,4S,5R)-4-Acetoxy-5-(2-amino-8-oxo-7-(prop-2-yn-1-yl)-7,8-dihydro-9H-purin-9-yl)-3-fluorotetrahydrofuran-2-yl)methyl acetate (Compound 31S)

Compound 31S can be prepared using the procedure described in Example 31, substituting (18) with (23).

Example 32S: 2-Amino-9-((2R,3S,4R,5R)-4-fluoro-3-hydroxy-5-(hydroxymethyl)tetrahydrofuran-2-yl)-7-(prop-2-yn-1-yl)-7,9-dihydro-8H-purin-8-one (Compound 32S)

Compound 32S can be prepared from Compound 31S using the procedure described in Example 32.

Example 38: 2-Amino-7-(4-fluorobenzyl)-9-((2R,3R,5S)-3-hydroxy-5-(hydroxymethyl)tetrahydrofuran-2-yl)-7,9-dihydro-1H-purine-6,8-dione, Compound 38

Compound 38 can be prepared according to the procedure in either Example 26 or Examples 5A and 26A with 4-fluorobenzyl bromide.

Example 39: 2-Amino-7-(3,4-difluorobenzyl)-9-((2R,3R,5S)-3-hydroxy-5-(hydroxymethyl)tetrahydrofuran-2-yl)-7,9-dihydro-1H-purine-6,8-dione, Compound 39

Compound 39 can be prepared according to the procedure in either Example 26 or Examples 5A and 26A with 3,4-difluorobenzyl bromide.

Example 40: 2-Amino-7-(4-chlorobenzyl)-9-((2R,3R,5S)-3-hydroxy-5-(hydroxymethyl)tetrahydrofuran-2-yl)-7,9-dihydro-1H-purine-6,8-dione, Compound 40

Compound 40 can be prepared according to the procedure in either Example 26 or Examples 5A and 26A with 4-chlorobenzyl bromide.

Example 41: 2-Amino-7-(3-chlorobenzyl)-9-((2R,3R,5S)-3-hydroxy-5-(hydroxymethyl)tetrahydrofuran-2-yl)-7,9-dihydro-1H-purine-6,8-dione, Compound 41

Compound 41 can be prepared according to the procedure in either Example 26 or Examples 5A and 26A with 3-chlorobenzyl bromide.

Example 42: 2-Amino-7-(3,4-dichlorobenzyl)-9-((2R,3R,5S)-3-hydroxy-5-(hydroxymethyl)tetrahydrofuran-2-yl)-7,9-dihydro-1H-purine-6,8-dione, Compound 42

Compound 42 can be prepared according to the procedure in either Example 26 or Examples 5A and 26A with 3,4-dichlorobenzyl bromide.

Example 43: 4-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzonitrile, Compound 43

Compound 43 can be prepared according to the procedure in either Example 26 or Examples 5A and 26A with 4-cyanobenzyl bromide.

Example 44: 3-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzonitrile, Compound 44

Compound 44 can be prepared according to the procedure in either Example 26 or Examples 5A and 26A with 3-cyanobenzyl bromide.

Example 45: Methyl 4-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoate, Compound 45

Compound 45 can be prepared according to the procedure in either Example 26 or Examples 5A and 26A with methyl 4-(bromomethyl)benzoate.

Example 46: 4-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoic acid, Compound 46

Compound 46 can be prepared by the ester hydrolysis of Compound 45.

Example 47: Methyl 3-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoate, Compound 47

Compound 47 can be prepared according to the procedure in either Example 26 or Examples 5A and 26A with methyl 3-(bromomethyl)benzoate.

Example 48: 3-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoic acid, Compound 48

Compound 48 can be prepared by the ester hydrolysis of Compound 47.

Example 49: Methyl 2-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoate, Compound 49

Compound 49 can be prepared according to the procedure in either Example 26 or Examples 5A and 26A with methyl 2-(bromomethyl)benzoate.

Example 50: 2-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzoic acid, Compound 50

Compound 50 can be prepared by the ester hydrolysis of Compound 49.

Example 51: 2-Amino-7-(E)-cinnamyl-9-((2R,3R,5S)-3-hydroxy-5-(hydroxymethyl)tetrahydrofuran-2-yl)-7,9-dihydro-1H-purine-6,8-dione, Compound 51

Compound 51 can be prepared according to the procedure in either Example 26 or Examples 5A and 26A with (E)-cinnamyl bromide.

Example 52: 7-((1H-Pyrazol-5-yl)methyl)-2-amino-9-((2R,3R,5S)-3-hydroxy-5-(hydroxymethyl)tetrahydrofuran-2-yl)-7,9-dihydro-1H-purine-6,8-dione, Compound 52

Compound 52 can be prepared according to the procedure in either Example 26 or Examples 5A and 26A with tert-butyl 5-(bromomethyl)-1H-pyrazole-1-carboxylate [1001096-27-0] or 5-(bromomethyl)-1-(4-methoxybenzyl)-1H-pyrazole [1313409-97-0] or the mesylate of (1-(tetrahydro-2H-pyran-2-yl)-1H-pyrazol-5-yl)methanol [1823866-20-1].

Example 53: 2-Amino-9-((2R,3R,5S)-3-hydroxy-5-(hydroxymethyl)tetrahydrofuran-2-yl)-7-((1-methyl-1H-pyrazol-3-yl)methyl)-7,9-dihydro-1H-purine-6,8-dione, Compound 53

Compound 53 can be prepared according to the procedure in either Example 26 or Examples 5A and 26A with 3-(bromomethyl)-1-methyl-1H-pyrazole [102846-13-9].

Example 54: 2-Amino-9-((2R,3R,5S)-3-hydroxy-5-(hydroxymethyl)tetrahydrofuran-2-yl)-7-(thiophen-2-ylmethyl)-7,9-dihydro-1H-purine-6,8-dione, Compound 54

Compound 54 can be prepared according to the procedure in either Example 26 or Examples 5A and 26A with 2-(bromomethyl)-thiophene.

Example 55: 2-Amino-9-((2R,3R,5S)-3-hydroxy-5-(hydroxymethyl)tetrahydrofuran-2-yl)-7-(thiophen-3-ylmethyl)-7,9-dihydro-1H-purine-6,8-dione, Compound 55

Compound 55 can be prepared according to the procedure in either Example 26 or Examples 5A and 26A with 3-(bromomethyl)-thiophene.

Example 56: 2-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)acetic acid, Compound 56

Compound 56 can be prepared according to the procedure in either Example 26 or Examples 5A and 26A with methyl 2-bromoacetate and subsequent ester hydrolysis.

Example 57: 2-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)acetaldehyde, Compound 57

Compound 57 can be prepared according to the procedure in Example 26 with 2-bromo-1,1-dimethoxyethane.

Example 58: 2-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)acetonitrile, Compound 58

Compound 58 can be prepared from Compound 57 by conversion of the aldehyde to the corresponding oxime and subsequent dehydration of the oxime.

Example 59: 7-((1H-Tetrazol-5-yl)methyl)-2-amino-9-((2R,3R,5S)-3-hydroxy-5-(hydroxymethyl)tetrahydrofuran-2-yl)-7,9-dihydro-1H-purine-6,8-dione, Compound 59

Compound 59 can be prepared according to the procedure in either Example 26 or Examples 5A and 26A with 5-(chloromethyl)-1H-tetrazole [55408-11-2].

Example 60: 2-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)-N-(methylsulfonyl)acetamide, Compound 60

Compound 60 can be prepared from Compound 56 and methanesulfonamide.

Example 61: 2-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)-N-hydroxyacetamide, Compound 61

Compound 61 can be prepared from Compound 56 and hydroxylamine.

Example 62: 2-Amino-9-((2R,3R,5S)-3-hydroxy-5-(hydroxymethyl)tetrahydrofuran-2-yl)-7-((3-hydroxyisoxazol-5-yl)methyl)-7,9-dihydro-1H-purine-6,8-dione, Compound 62

Compound 62 can be prepared according to the procedure in either Example 26 or Examples 5A and 26A with the mesylate of (3-((4-methoxybenzyl)oxy)isoxazol-5-yl)methanol.

Example 63: Methyl 5-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-2-carboxylate, Compound 63

Compound 63 can be prepared according to the procedure in either Example 26 or Examples 5A and 26A with methyl 5-(bromomethyl)thiophene-2-carboxylate [108499-32-7].

Example 64: 5-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid, Compound 64

Compound 64 can be prepared from Compound 63 by ester hydrolysis.

Example 65: Ethyl 5-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-3-carboxylate, Compound 65

Compound 65 can be prepared according to the procedure in either Example 26 or Examples 5A and 26A with ethyl 5-(bromomethyl)thiophene-3-carboxylate [206860-16-4].

Example 66: 5-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-3-carboxylic acid, Compound 66

Compound 66 can be prepared from Compound 65 by ester hydrolysis.

Example 67: Methyl 4-((2-amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-2-carboxylate, Compound 67

Compound 67 can be prepared according to the procedure in either Example 26 or Examples 5A and 26A with methyl 4-(bromomethyl)thiophene-2-carboxylate [54796-51-9].

Example 68: 4-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid, Compound 68

Compound 68 can be prepared from Compound 67 by ester hydrolysis.

Example 69: (1R,2R)-2-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid, Compound 69

Compound 69 can be prepared according to the procedure in either Example 26 or Examples 5A and 26A with the mesylate of ethyl (1R,2R)-2-(hydroxymethyl)cyclopropane-1-carboxylate followed by ester hydrolysis.

Example 70: 7-((E)-3-(1H-tetrazol-5-yl)allyl)-2-amino-9-((2R,3R,5S)-3-hydroxy-5-(hydroxymethyl)tetrahydrofuran-2-yl)-7,9-dihydro-1H-purine-6,8-dione, Compound 70

Compound 70 can be prepared from Compound 36 and 5-vinyl-1H-tetrazole [18755-47-0].

Example 71: 4-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)benzaldehyde, Compound 71

Compound 71 can be prepared according to the procedure in either Example 26 or Examples 5A and 26A with methyl 4-(bromomethyl)benzaldehyde.

Example 72: 2-Amino-9-((2R,3R,5S)-3-hydroxy-5-(hydroxymethyl)tetrahydrofuran-2-yl)-7-(4-methoxybenzyl)-7,9-dihydro-1H-purine-6,8-dione, Compound 72

Compound 72 can be prepared according to the procedure in either Example 26 or Examples 5A and 26A with 4-methoxy-benzylbromide.

Example 73: 2-Amino-9-((2R,3R,5S)-3-hydroxy-5-(hydroxymethyl)tetrahydrofuran-2-yl)-7-(3-methoxybenzyl)-7,9-dihydro-1H-purine-6,8-dione, Compound 73

Compound 73 can be prepared according to the procedure in either Example 26 or Examples 5A and 26A with 3-methoxy-benzylbromide.

Example 74: 2-Amino-9-((2R,3R,5S)-3-hydroxy-5-(hydroxymethyl)tetrahydrofuran-2-yl)-7-(3-hydroxybenzyl)-7,9-dihydro-1H-purine-6,8-dione, Compound 74

Compound 74 can be prepared by demethylation of Compound 73 with $BBr_3$.

Example 75: 2-Amino-9-((2R,3R,5S)-3-hydroxy-5-(hydroxymethyl)tetrahydrofuran-2-yl)-7-(pyridin-3-ylmethyl)-7,9-dihydro-1H-purine-6,8-dione, Compound 75

Compound 75 can be prepared according to the procedure in either Example 26 or Examples 5A and 26A with 3-bromomethyl pyridine.

Example 76: 2-Amino-9-((2R,3R,5S)-3-hydroxy-5-(hydroxymethyl)tetrahydrofuran-2-yl)-7-(2-oxo-2-(pyrrolidin-1-yl)ethyl)-7,9-dihydro-1H-purine-6,8-dione, Compound 76

Compound 76 can be prepared according to the procedure in either Example 26 or Examples 5A and 26A with bromoacetopyrrolidine [90892-09-4].

Example 77: 2-Amino-7-(cyclopropylmethyl)-9-((2R,3R,5S)-3-hydroxy-5-(hydroxymethyl)tetrahydrofuran-2-yl)-7,9-dihydro-1H-purine-6,8-dione, Compound 77

Compound 77 can be prepared according to the procedure in Example 1 replacing 2-amino-9-((2R,3R,4R,5R)-3,4-dihydroxy-5-(hydroxymethyl)tetrahydrofuran-2-yl)-19-dihydro-6H-purin-6-one (1) [27462-39-1] with 3'-deoxyguanosine [3608-58-0] or according to the procedure in Example 26A replacing (40) with (74).

Example 78: 2-Amino-9-((2R,3R,5S)-3-hydroxy-5-(hydroxymethyl)tetrahydrofuran-2-yl)-7-(methoxymethyl)-7,9-dihydro-1H-purine-6,8-dione, Compound 78

Compound 78 can be prepared according to the procedure in Example 26 with chloromethyl methyl ether.

Example 79: 2-Amino-9-((2R,3R,5S)-3-hydroxy-5-(hydroxymethyl)tetrahydrofuran-2-yl)-7-((methylthio)methyl)-7,9-dihydro-1H-purine-6,8-dione, Compound 79

Compound 79 can be prepared according to the procedure in Example 26 with chloromethyl methyl sulfide.

Example 80: 2-Amino-9-((2R,3R,5S)-3-hydroxy-5-(hydroxymethyl)tetrahydrofuran-2-yl)-7-(2,2,2-trifluoroethyl)-7,9-dihydro-1H-purine-6,8-dione, Compound 80

Compound 80 can be prepared according to the procedure in either Example 26 or Examples 5A and 26A with 2-bromo-1,1,1-trifluoroethane [421-06-7].

Example 81: 2-Amino-7-(2,2-difluoroethyl)-9-((2R,3R,5S)-3-hydroxy-5-(hydroxymethyl)tetrahydrofuran-2-yl)-7,9-dihydro-1H-purine-6,8-dione, Compound 81

Compound 81 can be prepared according to the procedure in either Example 26 or Examples 5A and 26A with 2-bromo-1,1-difluoroethane [359-07-9].

Example 82: 2-Amino-9-((2R,3R,5S)-3-hydroxy-5-(hydroxymethyl)tetrahydrofuran-2-yl)-7-(3,3,3-trifluoropropyl)-7,9-dihydro-1H-purine-6,8-dione, Compound 82

Compound 82 can be prepared according to the procedure in either Example 26 or Examples 5A and 26A with 3-bromo-1,1,1-trifluoropropane [460-32-2].

Example 83: 2-Amino-9-((2R,3R,5S)-3-hydroxy-5-(hydroxymethyl)tetrahydrofuran-2-yl)-7-(2,2,3,3,3-pentafluoropropyl)-7,9-dihydro-1H-purine-6,8-dione, Compound 83

Compound 83 can be prepared according to the procedure in either Example 26 or Examples 5A and 26A with 3-bromo-1,1,1,2,2-pentafluoropropane [422-01-5] or 2,2,3,3,3-pentafluoropropyl methanesulfonate [813-31-0].

Example 84: 2-Amino-9-((2R,3R,5S)-3-hydroxy-5-(hydroxymethyl)tetrahydrofuran-2-yl)-7-(4,4,4-trifluorobutyl)-7,9-dihydro-1H-purine-6,8-dione, Compound 84

Compound 84 can be prepared according to the procedure in either Example 26 or Examples 5A and 26A with 4-bromo-1,1,1-trifluorobutane [406-81-5].

Example 85: 2-Amino-9-((2R,3R,5S)-3-hydroxy-5-(hydroxymethyl)tetrahydrofuran-2-yl)-7-(3,3,4,4,4-pentafluorobutyl)-7,9-dihydro-1H-purine-6,8-dione, Compound 85

Compound 85 can be prepared according to the procedure in either Example 26 or Examples 5A and 26A with 1,1,1,2,2-pentafluoro-4-bromobutane [52671-70-2].

Example 86: 3-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)propanenitrile, Compound 86

Compound 86 can be prepared according to the procedure in either Example 26 or Examples 5A and 26A with 3-bromopropanenitrile [2417-90-5].

Example 87: 4-(2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)butanenitrile, Compound 87

Compound 87 can be prepared according to the procedure in either Example 26 or Examples 5A and 26A with 4-bromobutanenitrile [5332-06-9].

Example 88: 2-Amino-9-((2R,3R,5S)-3-hydroxy-5-(hydroxymethyl)tetrahydrofuran-2-yl)-7-isobutyl-7,9-dihydro-1H-purine-6,8-dione, Compound 88

Compound 88 can be prepared according to the procedure in either Example 26 or Examples 5A and 26A with 1-bromo-2-methylpropane.

Example 89: 1-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)cyclopropane-1-carbonitrile, Compound 89

Compound 89 can be prepared according to the procedure in either Example 26 or Examples 5A and 26A with the mesylate of 1-(hydroxymethyl)cyclopropane-1-carbonitrile [98730-77-9].

Example 90: 1-((2-Amino-9-((2R,3R,5S)-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid, Compound 90

Compound 90 can be prepared according to the procedure in either Example 26 or Examples 5A and 26A with the mesylate of ethyl 1-(hydroxymethyl)cyclopropane-1-carboxylate [3697-68-5].

Example 91: 2-Amino-9-((2R,3R,5S)-3-hydroxy-5-(hydroxymethyl)tetrahydrofuran-2-yl)-7-((1-(trifluoromethyl)cyclopropyl)methyl)-7,9-dihydro-1H-purine-6,8-dione, Compound 91

Compound 91 can be prepared according to the procedure in either Example 26 or Examples 5A and 26A with the mesylate of (1-(trifluoromethyl)cyclopropyl)methanol [371917-17-8].

Example 92: 2-Amino-7-benzyl-9-((2R,3S,4S,5R)-4-fluoro-3-hydroxy-5-(hydroxymethyl)tetrahydrofuran-2-yl)-7,9-dihydro-1H-purine-6,8-dione, Compound 92

Compound 92 can be prepared according to the procedure in either Example 27 or Examples 5A and 27A with benzyl bromide.

Example 93: 2-Amino-9-((2R,3S,4S,5R)-4-fluoro-3-hydroxy-5-(hydroxymethyl)tetrahydrofuran-2-yl)-7-(4-fluorobenzyl)-7,9-dihydro-1H-purine-6,8-dione, Compound 93

Compound 93 can be prepared according to the procedure in either Example 27 or Examples 5A and 27A with 4-fluorobenzyl bromide.

Example 94: 2-Amino-9-((2R,3S,4S,5R)-4-fluoro-3-hydroxy-5-(hydroxymethyl)tetrahydrofuran-2-yl)-7-(3-fluorobenzyl)-7,9-dihydro-1H-purine-6,8-dione, Compound 94

Compound 94 can be prepared according to the procedure in either Example 27 or Examples 5A and 27A with 3-fluorobenzyl bromide.

Example 95: 2-Amino-7-(3,4-difluorobenzyl)-9-((2R,3S,4S,5R)-4-fluoro-3-hydroxy-5-(hydroxymethyl)tetrahydrofuran-2-yl)-7,9-dihydro-1H-purine-6,8-dione, Compound 95

Compound 95 can be prepared according to the procedure in either Example 27 or Examples 5A and 27A with 3,4-difluorobenzyl bromide.

Example 96: 2-Amino-7-(4-chlorobenzyl)-9-((2R,3S,4S,5R)-4-fluoro-3-hydroxy-5-(hydroxymethyl)tetrahydrofuran-2-yl)-7,9-dihydro-1H-purine-6,8-dione, Compound 96

Compound 96 can be prepared according to the procedure in either Example 27 or Examples 5A and 27A with 4-chlorobenzyl bromide.

Example 97: 2-Amino-7-(3-chlorobenzyl)-9-((2R,3S,4S,5R)-4-fluoro-3-hydroxy-5-(hydroxymethyl)tetrahydrofuran-2-yl)-7,9-dihydro-1H-purine-6,8-dione, Compound 97

Compound 97 can be prepared according to the procedure in either Example 27 or Examples 5A and 27A with 3-chlorobenzyl bromide.

Example 98: 2-Amino-7-(3,4-dichlorobenzyl)-9-((2R,3S,4S,5R)-4-fluoro-3-hydroxy-5-(hydroxymethyl)tetrahydrofuran-2-yl)-7,9-dihydro-1H-purine-6,8-dione, Compound 98

Compound 98 can be prepared according to the procedure in either Example 27 or Examples 5A and 27A with 3,4-dichlorobenzyl bromide.

Example 99: 4-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzonitrile, Compound 99

Compound 99 can be prepared according to the procedure in either Example 27 or Examples 5A and 27A with 4-cyanobenzyl bromide.

Example 100: 3-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzonitrile, Compound 100

Compound 100 can be prepared according to the procedure in either Example 27 or Examples 5A and 27A with 3-cyanobenzyl bromide.

Example 101: Methyl 4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate, Compound 101

Compound 101 can be prepared according to the procedure in either Example 27 or Examples 5A and 27A with methyl 4-(bromomethyl)benzoate.

Example 102: 4-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid, Compound 102

Compound 102 can be prepared by the ester hydrolysis of Compound 101.

Example 103: Methyl 3-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate, Compound 103

Compound 103 can be prepared according to the procedure in either Example 27 or Examples 5A and 27A with methyl 3-(bromomethyl)benzoate.

Example 104: 3-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid, Compound 104

Compound 104 can be prepared by the ester hydrolysis of Compound 103.

Example 105: Methyl 2-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate, Compound 104

Compound 104 can be prepared according to the procedure in either Example 27 or Examples 5A and 27A with methyl 2-(bromomethyl)benzoate.

Example 105: 2-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid, Compound 105

Compound 105 can be prepared by the ester hydrolysis of Compound 104.

Example 106: 2-Amino-7-(E)-cinnamyl-9-((2R,3S,4S,5R)-4-fluoro-3-hydroxy-5-(hydroxymethyl)tetrahydrofuran-2-yl)-7,9-dihydro-1H-purine-6,8-dione, Compound 106

Compound 106 can be prepared according to the procedure in either Example 27 or Examples 5A and 27A with (E)-cinnamyl bromide.

Example 107: 7-((1H-Pyrazol-5-yl)methyl)-2-amino-9-((2R,3S,4S,5R)-4-fluoro-3-hydroxy-5-(hydroxymethyl)tetrahydrofuran-2-yl)-7,9-dihydro-1H-purine-6,8-dione, Compound 107

Compound 107 can be prepared according to the procedure in either Example 27 or Examples 5A and 27A with tert-butyl 5-(bromomethyl)-1H-pyrazole-1-carboxylate [1001096-27-0] or 5-(bromomethyl)-1-(4-methoxybenzyl)-1H-pyrazole [1313409-97-0] or the mesylate of (1-(tetrahydro-2H-pyran-2-yl)-1H-pyrazol-5-yl)methanol [1823866-20-1].

Example 108: 2-Amino-9-((2R,3S,4S,5R)-4-fluoro-3-hydroxy-5-(hydroxymethyl)tetrahydrofuran-2-yl)-7-((1-methyl-1H-pyrazol-3-yl)methyl)-7,9-dihydro-1H-purine-6,8-dione, Compound 108

Compound 108 can be prepared according to the procedure in either Example 27 or Examples 5A and 27A and 26A with 3-(bromomethyl)-1-methyl-1H-pyrazole [102846-13-9].

Example 109: 2-Amino-9-((2R,3S,4S,5R)-4-fluoro-3-hydroxy-5-(hydroxymethyl)tetrahydrofuran-2-yl)-7-(thiophen-2-ylmethyl)-7,9-dihydro-1H-purine-6,8-dione, Compound 109

Compound 109 can be prepared according to the procedure in either Example 27 or Examples 5A and 27A and 26A with 2-(bromomethyl)-thiophene.

Example 110: 2-Amino-9-((2R,3S,4S,5R)-4-fluoro-3-hydroxy-5-(hydroxymethyl)tetrahydrofuran-2-yl)-7-(thiophen-3-ylmethyl)-7,9-dihydro-1H-purine-6,8-dione, Compound 110

Compound 110 can be prepared according to the procedure in either Example 27 or Examples 5A and 27A and 26A with 3-(bromomethyl)-thiophene.

Example 111: 2-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetic acid, Compound 111

Compound 111 can be prepared according to the procedure in either Example 27 or Examples 5A and 27A and 26A with methyl 2-bromoacetate and subsequent ester hydrolysis.

Example 112: 2-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetaldehyde, Compound 112

Compound 112 can be prepared according to the procedure in either Example 27 with 2-bromo-1,1-dimethoxyethane.

Example 113: 2-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetonitrile, Compound 113

Compound 113 can be prepared from Compound 112 by conversion of the aldehyde to the corresponding oxime and subsequent dehydration of the oxime.

Example 114: 7-((1H-Tetrazol-5-yl)methyl)-2-amino-9-((2R,3S,4S,5R)-4-fluoro-3-hydroxy-5-(hydroxymethyl)tetrahydrofuran-2-yl)-7,9-dihydro-1H-purine-6,8-dione, Compound 114

Compound 114 can be prepared according to the procedure in either Example 27 or Examples 5A and 27A and 26A with 5-(chloromethyl)-1H-tetrazole [5540811-2].

Example 115: 2-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)-N-(methylsulfonyl)acetamide, Compound 115

Compound 115 can be prepared from Compound 111 and methanesulfonamide.

Example 116: 2-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)-N-hydroxyacetamide, Compound 116

Compound 116 can be prepared from Compound 111 and hydroxylamine.

Example 117: 2-Amino-9-((2R,3S,4S,5R)-4-fluoro-3-hydroxy-5-(hydroxymethyl)tetrahydrofuran-2-yl)-7-((3-hydroxyisoxazol-5-yl)methyl)-7,9-dihydro-1H-purine-6,8-dione, Compound 117

Compound 117 can be prepared according to the procedure in either Example 27 or Examples 5A and 27A and 26A with the mesylate of (3-((4-methoxybenzyl)oxy)isoxazol-5-yl)methanol.

Example 118: Methyl 5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylate, Compound 118

Compound 118 can be prepared according to the procedure in either Example 27 or Examples 5A and 27A and 26A with methyl 5-(bromomethyl)thiophene-2-carboxylate [108499-32-7].

Example 119: 5-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid, Compound 119

Compound 119 can be prepared by the ester hydrolysis of Compound 118.

Example 120: Ethyl 5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-3-carboxylate, Compound 120

Compound 120 can be prepared according to the procedure in either Example 27 or Examples 5A and 27A and 26A with ethyl 5-(bromomethyl)thiophene-3-carboxylate [206860-16-4].

Example 121: 5-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-3-carboxylic acid, Compound 121

Compound 121 can be prepared by the ester hydrolysis of Compound 120.

Example 122: Methyl 4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylate, Compound 122

Compound 122 can be prepared according to the procedure in either Example 27 or Examples 5A and 27A and 26A with methyl 4-(bromomethyl)thiophene-2-carboxylate [54796-51-9].

Example 123: 4-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid, Compound 123

Compound 123 can be prepared by the ester hydrolysis of Compound 122.

Example 124: (1R,2R)-2-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid, Compound 124

Compound 124 can be prepared according to the procedure in either Example 27 or Examples 5A and 27A and 26A with the mesylate of ethyl (1R,2R)-2-(hydroxymethyl)cyclopropane-1-carboxylate followed by ester hydrolysis.

Example 125: 7-((E)-3-(1H-Tetrazol-5-yl)allyl)-2-amino-9-((2R,3S,4S,5R)-4-fluoro-3-hydroxy-5-(hydroxymethyl)tetrahydrofuran-2-yl)-7,9-dihydro-1H-purine-6,8-dione, Compound 125

Compound 125 can be prepared from 7-allyl-2-amino-9-((2R,3S,4S,5R)-4-fluoro-3-hydroxy-5-(hydroxymethyl)tetrahydrofuran-2-yl)-7,9-dihydro-1H-purine-6,8-dione and 5-vinyl-1H-tetrazole [18755-47-0].

Example 126: 4-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzaldehyde, Compound 126

Compound 126 can be prepared according to the procedure in either Example 27 or Examples 5A and 27A and 26A with methyl 4-(bromomethyl)benzaldehyde.

Example 127: 2-Amino-9-((2R,3S,4S,5R)-4-fluoro-3-hydroxy-5-(hydroxymethyl)tetrahydrofuran-2-yl)-7-(4-methoxybenzyl)-7,9-dihydro-1H-purine-6,8-dione, Compound 127

Compound 127 can be prepared according to the procedure in either Example 26 or Examples 5A and 27A and 26A with 4-methoxy-benzylbromide.

Example 128: 2-Amino-9-((2R,3S,4S,5R)-4-fluoro-3-hydroxy-5-(hydroxymethyl)tetrahydrofuran-2-yl)-7-(3-methoxybenzyl)-7,9-dihydro-1H-purine-6,8-dione, Compound 128

Compound 128 can be prepared according to the procedure in either Example 26 or Examples 5A and 27A and 26A with 3-methoxy-benzylbromide.

Example 129: 2-Amino-9-((2R,3S,4S,5R)-4-fluoro-3-hydroxy-5-(hydroxymethyl)tetrahydrofuran-2-yl)-7-(3-hydroxybenzyl)-7,9-dihydro-1H-purine-6,8-dione, Compound 129

Compound 129 can be prepared by demethylation of Compound 128 with BBr$_3$.

Example 130: 2-Amino-9-((2R,3S,4S,5R)-4-fluoro-3-hydroxy-5-(hydroxymethyl)tetrahydrofuran-2-yl)-7-(4-(trifluoromethyl)benzyl)-7,9-dihydro-1H-purine-6,8-dione, Compound 130

Compound 130 can be prepared using the same general procedure as described for Example 35 (Compound 35) from 2-amino-7-(4-(trifluoromethyl)benzyl)-7,9-dihydro-1H-purine-6,8-dione and (2S,3S,4R,5R)-5-((benzoyloxy)methyl)-4-fluorotetrahydrofuran-2,3-diyl diacetate.

Example 131: 2-Amino-9-((2R,3S,4S,5R)-4-fluoro-3-hydroxy-5-(hydroxymethyl)tetrahydrofuran-2-yl)-7-(pyridin-3-ylmethyl)-7,9-dihydro-1H-purine-6,8-dione, Compound 131

Compound 131 can be prepared according to the procedure in either Example 27 or Examples 5A and 27A and 26A with 3-bromomethyl pyridine.

Example 132: 2-Amino-9-((2R,3S,4S,5R)-4-fluoro-3-hydroxy-5-(hydroxymethyl)tetrahydrofuran-2-yl)-7-(2-oxo-2-(pyrrolidin-1-yl)ethyl)-7,9-dihydro-1H-purine-6,8-dione, Compound 132

Compound 132 can be prepared according to the procedure in either Example 27 or Examples 5A and 27A and 26A with bromoacetopyrrolidine [90892-09-4].

Example 133: 7-Allyl-2-amino-9-((2R,3S,4S,5R)-4-fluoro-3-hydroxy-5-(hydroxymethyl)tetrahydrofuran-2-yl)-7,9-dihydro-1H-purine-6,8-dione, Compound 133

Compound 133 can be prepared using the same general procedure as described for Example 36, (Compound 36) from N-(7-allyl-6,8-dioxo-6,7,8,9-tetrahydro-1H-purin-2-yl)acetamide and (2S,3S,4R,5R)-5-((benzoyloxy)methyl)-4-fluorotetrahydrofuran-2,3-diyl diacetate.

Example 134: 2-Amino-7-(cyclopropylmethyl)-9-((2R,3S,4S,5R)-4-fluoro-3-hydroxy-5-(hydroxymethyl)tetrahydrofuran-2-yl)-7,9-dihydro-1H-purine-6,8-dione, Compound 134

Compound 134 can be prepared according to the procedure in Example 1 replacing 2-amino-9-((2R,3R,4R,5R)-3,4-dihydroxy-5-(hydroxymethyl)tetrahydrofuran-2-yl)-1,9-dihydro-6H-purin-6-one (1) [27462-39-1] with 3'-deoxy-(3'S)-fluoro-guanosine [123402-21-1] or according to the procedure in Example 27A replacing (40) with (74).

Example 135: 2-Amino-7-butyl-9-((2R,3S,4S,5R)-4-fluoro-3-hydroxy-5-(hydroxymethyl)tetrahydrofuran-2-yl)-7,9-dihydro-1H-purine-6,8-dione, Compound 135

Compound 135 can be prepared using the same general procedure as described for Example 37, (Compound 37) from N-(7-butyl-6,8-dioxo-6,7,8,9-tetrahydro-1H-purin-2-yl)acetamide (68) and/or N-acetyl-N-(7-butyl-6,8-dioxo-6,7,8,9-tetrahydro-1H-purin-2-yl)acetamide (68a) and (2S,3S,4R,5R)-5-((benzoyloxy)methyl)-4-fluorotetrahydrofuran-2,3-diyl diacetate.

Example 136: 2-Amino-9-((2R,3S,4S,5R)-4-fluoro-3-hydroxy-5-(hydroxymethyl)tetrahydrofuran-2-yl)-7-(methoxymethyl)-7,9-dihydro-1H-purine-6,8-dione, Compound 136

Compound 136 can be prepared according to the procedure in Example 27 with chloromethyl methyl ether.

Example 137: 2-Amino-9-((2R,3S,4S,5R)-4-fluoro-3-hydroxy-5-(hydroxymethyl)tetrahydrofuran-2-yl)-7-((methylthio)methyl)-7,9-dihydro-1H-purine-6,8-dione, Compound 137

Compound 137 can be prepared according to the procedure in Example 27 with chloromethyl methyl sulfide.

Example 138: 2-Amino-9-((2R,3S,4S,5R)-4-fluoro-3-hydroxy-5-(hydroxymethyl)tetrahydrofuran-2-yl)-7-(2,2,2-trifluoroethyl)-7,9-dihydro-1H-purine-6,8-dione, Compound 138

Compound 138 can be prepared according to the procedure in either Example 27 or Examples 5A and 27A and 26A with 2-bromo-1,1,1-trifluoroethane [421-06-7].

Example 139: 2-Amino-7-(2,2-difluoroethyl)-9-((2R,3S,4S,5R)-4-fluoro-3-hydroxy-5-(hydroxymethyl)tetrahydrofuran-2-yl)-7,9-dihydro-1H-purine-6,8-dione, Compound 139

Compound 139 can be prepared according to the procedure in either Example 27 or Examples 5A and 27A and 26A with 2-bromo-1,1-difluoroethane [359-07-9].

Example 140: 2-Amino-9-((2R,3S,4S,5R)-4-fluoro-3-hydroxy-5-(hydroxymethyl)tetrahydrofuran-2-yl)-7-(3,3,3-trifluoropropyl)-7,9-dihydro-1H-purine-6,8-dione, Compound 140

Compound 140 can be prepared according to the procedure in either Example 26 or Examples 5A and 27A and 26A with 3-bromo-1,1,1-trifluoropropane [460-32-2].

Example 141: 2-Amino-9-((2R,3S,4S,5R)-4-fluoro-3-hydroxy-5-(hydroxymethyl)tetrahydrofuran-2-yl)-7-(2,2,3,3,3-pentafluoropropyl)-7,9-dihydro-1H-purine-6,8-dione, Compound 141

Compound 141 can be prepared according to the procedure in either Example 27 or Examples 5A and 27A and 26A with 3-bromo-1,1,1,2,2-pentafluoropropane [422-01-5] or 2,2,3,3,3-pentafluoropropyl methanesulfonate [813-31-0].

Example 142: 2-Amino-9-((2R,3S,4S,5R)-4-fluoro-3-hydroxy-5-(hydroxymethyl)tetrahydrofuran-2-yl)-7-(4,4,4-trifluorobutyl)-7,9-dihydro-1H-purine-6,8-dione, Compound 142

Compound 142 can be prepared according to the procedure in either Example 27 or Examples 5A and 27A and 26A with 4-bromo-1,1,1-trifluorobutane [406-81-5].

Example 143: 2-Amino-9-((2R,3S,4S,5R)-4-fluoro-3-hydroxy-5-(hydroxymethyl)tetrahydrofuran-2-yl)-7-(3,3,4,4,4-pentafluorobutyl)-7,9-dihydro-1H-purine-6,8-dione, Compound 143

Compound 143 can be prepared according to the procedure in either Example 27 or Examples 5A and 27A and 26A with 1,1,1,2,2-pentafluoro-4-bromobutane [52671-70-2].

Example 144: 3-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)propanenitrile, Compound 144

Compound 144 can be prepared according to the procedure in either Example 27 or Examples 5A and 27A and 26A with 3-bromopropanenitrile [2417-90-5].

Example 145: 4-(2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)butanenitrile, Compound 145

Compound 145 can be prepared according to the procedure in either Example 27 or Examples 5A and 27A and 26A with 3-bromobutanenitrile [5332-06-9].

Example 146: 2-Amino-9-((2R,3S,4S,5R)-4-fluoro-3-hydroxy-5-(hydroxymethyl)tetrahydrofuran-2-yl)-7-isobutyl-7,9-dihydro-1H-purine-6,8-dione, Compound 146

Compound 146 can be prepared according to the procedure in either Example 27 or Examples 5A and 27A and 26A with 1-bromo-2-methylpropane.

Example 147: 1-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carbonitrile, Compound 147

Compound 147 can be prepared according to the procedure in either Example 27 or Examples 5A and 27A and 26A with the mesylate of 1-(hydroxymethyl)cyclopropane-1-carbonitrile [98730-77-9].

Example 148: 1-((2-Amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid, Compound 148

Compound 148 can be prepared according to the procedure in either Example 27 or Examples 5A and 27A and 26A with the mesylate of ethyl 1-(hydroxymethyl)cyclopropane-1-carboxylate [3697-68-5].

Example 149: 2-Amino-9-((2R,3S,4S,5R)-4-fluoro-3-hydroxy-5-(hydroxymethyl)tetrahydrofuran-2-yl)-7-((1-(trifluoromethyl)cyclopropyl)methyl)-7,9-dihydro-1H-purine-6,8-dione, Compound 149

Compound 149 can be prepared according to the procedure in either Example 27 or Examples 5A and 27A and 26A with (1-(trifluoromethyl)cyclopropyl)methanol [371917-17-8].

Example 150: ((2S,4R,5R)-4-Acetoxy-5-(2-amino-7-benzyl-8-oxo-7,8-dihydro-9H-purin-9-yl)tetrahydrofuran-2-yl)methyl acetate, Compound 150

Compound 150 can be prepared according to the procedure outlined in Example 29 substituting propargyl bromide with benzyl bromide.

Example 151: 2-Amino-7-benzyl-9-((2R,3R,5S)-3-hydroxy-5-(hydroxymethyl)tetrahydrofuran-2-yl)-7,9-dihydro-8H-purin-8-one, Compound 151

Compound 151 can be prepared by ester hydrolysis of Compound 150 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with benzyl bromide.

Example 152: ((2S,4R,5R)-4-Acetoxy-5-(2-amino-7-(4-fluorobenzyl)-8-oxo-7,8-dihydro-9H-purin-9-yl)tetrahydrofuran-2-yl)methyl acetate, Compound 152

Compound 152 can be prepared according to the procedure outlined in Example 29 substituting propargyl bromide with 4-fluorobenzyl bromide.

Example 153: 2-Amino-7-(4-fluorobenzyl)-9-((2R,3R,5S)-3-hydroxy-5-(hydroxymethyl)tetrahydrofuran-2-yl)-7,9-dihydro-8H-purin-8-one, Compound 153

Compound 153 can be prepared by ester hydrolysis of Compound 152 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)

methyl)tetrahydrofuran-2,3-diyl diacetate substituting propargyl bromide with 4-fluorobenzyl bromide.

Example 154: ((2S,4R,5R)-4-Acetoxy-5-(2-amino-7-(3-fluorobenzyl)-8-oxo-7,8-dihydro-9H-purin-9-yl)tetrahydrofuran-2-yl)methyl acetate, Compound 154

Compound 154 can be prepared according to the procedure outlined in Example 29 substituting propargyl bromide with 3-fluorobenzyl bromide.

Example 155: 2-Amino-7-(3-fluorobenzyl)-9-((2R,3R,5S)-3-hydroxy-5-(hydroxymethyl)tetrahydrofuran-2-yl)-7,9-dihydro-8H-purin-8-one, Compound 155

Compound 155 can be prepared by ester hydrolysis of Compound 154 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-fluorobenzyl bromide.

Example 156: ((2S,4R,5R)-4-Acetoxy-5-(2-amino-7-(3,4-difluorobenzyl)-8-oxo-7,8-dihydro-9H-purin-9-yl)tetrahydrofuran-2-yl)methyl acetate, Compound 156

Compound 156 can be prepared according to the procedure outlined in Example 29 substituting propargyl bromide with 3,4-difluorobenzyl bromide.

Example 157: 2-Amino-7-(3,4-difluorobenzyl)-9-((2R,3R,5S)-3-hydroxy-5-(hydroxymethyl)tetrahydrofuran-2-yl)-7,9-dihydro-8H-purin-8-one, Compound 157

Compound 157 can be prepared by ester hydrolysis of Compound 156 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3,4-difluorobenzyl bromide.

Example 158: ((2S,4R,5R)-4-Acetoxy-5-(2-amino-7-(4-chlorobenzyl)-8-oxo-7,8-dihydro-9H-purin-9-yl)tetrahydrofuran-2-yl)methyl acetate, Compound 158

Compound 158 can be prepared according to the procedure outlined in Example 29 substituting propargyl bromide with 4-chlorobenzyl bromide.

Example 159: 2-Amino-7-(4-chlorobenzyl)-9-((2R,3R,5S)-3-hydroxy-5-(hydroxymethyl)tetrahydrofuran-2-yl)-7,9-dihydro-8H-purin-8-one, Compound 159

Compound 159 can be prepared by ester hydrolysis of Compound 158 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 4-chlorobenzyl bromide.

Example 160: ((2S,4R,5R)-4-Acetoxy-5-(2-amino-7-(3-chlorobenzyl)-8-oxo-7,8-dihydro-9H-purin-9-yl)tetrahydrofuran-2-yl)methyl acetate, Compound 160

Compound 160 can be prepared according to the procedure outlined in Example 29 substituting propargyl bromide with 3-chlorobenzyl bromide.

Example 161: 2-Amino-7-(3-chlorobenzyl)-9-((2R,3R,5S)-3-hydroxy-5-(hydroxymethyl)tetrahydrofuran-2-yl)-7,9-dihydro-8H-purin-8-one, Compound 161

Compound 161 can be prepared by ester hydrolysis of Compound 160 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-chlorobenzyl bromide.

Example 162: ((2S,4R,5R)-4-Acetoxy-5-(2-amino-7-(3,4-dichlorobenzyl)-8-oxo-7,8-dihydro-9H-purin-9-yl)tetrahydrofuran-2-yl)methyl acetate, Compound 162

Compound 162 can be prepared according to the procedure outlined in Example 29 substituting propargyl bromide with 3,4-dichlorobenzyl bromide.

Example 163: 2-Amino-7-(3,4-dichlorobenzyl)-9-((2R,3R,5S)-3-hydroxy-5-(hydroxymethyl)tetrahydrofuran-2-yl)-7,9-dihydro-8H-purin-8-one, Compound 163

Compound 163 can be prepared by ester hydrolysis of Compound 162 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3,4-dichlorobenzyl bromide.

Example 164: ((2S,4R,5R)-4-Acetoxy-5-(2-amino-7-(4-cyanobenzyl)-8-oxo-7,8-dihydro-9H-purin-9-yl)tetrahydrofuran-2-yl)methyl acetate, Compound 164

Compound 164 can be prepared according to the procedure outlined in Example 29 substituting propargyl bromide with 4-cyanobenzyl bromide.

Example 165: 4-((2-Amino-9-((2R,3R,5S)-3-hydroxy-5-(hydroxymethyl)tetrahydrofuran-2-yl)-8-oxo-8,9-dihydro-7H-purin-7-yl)methyl)benzonitrile, Compound 165

Compound 165 can be prepared by ester hydrolysis of Compound 164 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)

methyl)tetrahydrofuran-2,3-diyl diacetate substituting propargyl bromide with 4-cyanobenzyl bromide.

Example 166: ((2S,4R,5R)-4-Acetoxy-5-(2-amino-7-(3-cyanobenzyl)-8-oxo-7,8-dihydro-9H-purin-9-yl)tetrahydrofuran-2-yl)methyl acetate, Compound 166

Compound 166 can be prepared according to the procedure outlined in Example 29 substituting propargyl bromide with 3-cyanobenzyl bromide.

Example 167: 3-((2-Amino-9-((2R,3R,5S)-3-hydroxy-5-(hydroxymethyl)tetrahydrofuran-2-yl)-8-oxo-8,9-dihydro-7H-purin-7-yl)methyl)benzonitrile, Compound 167

Compound 167 can be prepared by ester hydrolysis of Compound 166 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-cyanobenzyl bromide.

Example 168: Methyl 4-((9-((2R,3R,5S)-3-acetoxy-5-(acetoxymethyl)tetrahydrofuran-2-yl)-2-amino-8-oxo-8,9-dihydro-7H-purin-7-yl)methyl)benzoate, Compound 168

Compound 168 can be prepared according to the procedure outlined in Example 29 substituting propargyl bromide with methyl 4-bromomethyl benzoate.

Example 168a: Methyl 4-((2-amino-9-((2R,3R,5S)-3-hydroxy-5-(hydroxymethyl)tetrahydrofuran-2-yl)-8-oxo-8,9-dihydro-7H-purin-7-yl)methyl)benzoate, Compound 168a Compound 168a can be prepared by exposure of Compound 168 to potassium carbonate in dry methanol.

Example 169: 4-((2-Amino-9-((2R,3R,5S)-3-hydroxy-5-(hydroxymethyl)tetrahydrofuran-2-yl)-8-oxo-8,9-dihydro-7H-purin-7-yl)methyl)benzoic acid, Compound 169

Compound 169 can be prepared by ester hydrolysis of Compound 168 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with methyl 4-bromomethyl benzoate.

Example 170: Methyl 3-((9-((2R,3R,5S)-3-acetoxy-5-(acetoxymethyl)tetrahydrofuran-2-yl)-2-amino-8-oxo-8,9-dihydro-7H-purin-7-yl)methyl)benzoate, Compound 170

Compound 170 can be prepared according to the procedure outlined in Example 29 substituting propargyl bromide with methyl 3-bromomethyl benzoate.

Example 170a: Methyl 3-((2-amino-9-((2R,3R,5S)-3-hydroxy-5-(hydroxymethyl)tetrahydrofuran-2-yl)-8-oxo-8,9-dihydro-7H-purin-7-yl)methyl)benzoate, Compound 170a Compound 170a can be prepared by exposure of Compound 170 to potassium carbonate in dry methanol.

Example 171: 3-((2-Amino-9-((2R,3R,5S)-3-hydroxy-5-(hydroxymethyl)tetrahydrofuran-2-yl)-8-oxo-8,9-dihydro-7H-purin-7-yl)methyl)benzoic acid, Compound 171

Compound 171 can be prepared by ester hydrolysis of Compound 170 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with methyl 3-bromomethyl benzoate.

Example 172: Methyl 2-((9-((2R,3R,5S)-3-acetoxy-5-(acetoxymethyl)tetrahydrofuran-2-yl)-2-amino-8-oxo-8,9-dihydro-7H-purin-7-yl)methyl)benzoate, Compound 172

Compound 172 can be prepared according to the procedure outlined in Example 29 substituting propargyl bromide with methyl 2-bromomethyl benzoate.

Example 172a: Methyl 2-((2-amino-9-((2R,3R,5S)-3-hydroxy-5-(hydroxymethyl)tetrahydrofuran-2-yl)-8-oxo-8,9-dihydro-7H-purin-7-yl)methyl)benzoate, Compound 172a Compound 172a can be prepared by exposure of Compound 172 to potassium carbonate in dry methanol.

Example 173: 2-((2-Amino-9-((2R,3R,5S)-3-hydroxy-5-(hydroxymethyl)tetrahydrofuran-2-yl)-8-oxo-8,9-dihydro-7H-purin-7-yl)methyl)benzoic acid, Compound 173

Compound 173 can be prepared by ester hydrolysis of Compound 172 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with methyl 2-bromomethyl benzoate.

Example 174: ((2S,4R,5R)-4-Acetoxy-5-(2-amino-7-(E)-cinnamyl-8-oxo-7,8-dihydro-9H-purin-9-yl)tetrahydrofuran-2-yl)methyl acetate, Compound 174

Compound 174 can be prepared according to the procedure outlined in Example 29 substituting propargyl bromide with (E)-cinnamyl bromide.

Example 175: 2-Amino-7-(E)-cinnamyl-9-((2R,3R,5S)-3-hydroxy-5-(hydroxymethyl)tetrahydrofuran-2-yl)-7,9-dihydro-8H-purin-8-one, Compound 175

Compound 175 can be prepared by ester hydrolysis of Compound 174 according to the procedure outlined in Example 30 or using the procedure described in Example 32A from N-(9-(4-methoxybenzyl)-8-oxo-8,9-dihydro-7H- purin-2-yl)acetamide and (2S,3R,5S)-5-((benzoyloxy) methyl)tetrahydrofuran-2,3-diyl diacetate substituting propargyl bromide with (E)-cinnamyl bromide.

Example 176: ((2S,4R,5R)-5-(7-((1H-Pyrazol-5-yl) methyl)-2-amino-8-oxo-7,8-dihydro-9H-purin-9-yl)-4-acetoxytetrahydrofuran-2-yl)methyl acetate, Compound 176

Compound 176 can be prepared according to the procedure outlined in Example 29 substituting propargyl bromide with tert-butyl 5-(bromomethyl)-1H-pyrazole-1-carboxylate [1001096-27-0] or 5-(bromomethyl)-1-(4-methoxybenzyl)-1H-pyrazole [1313409-97-0] or the mesylate of (1-(tetrahydro-2H-pyran-2-yl)-1H-pyrazol-5-yl)methanol [1823866-20-1].

Example 177: 7-((1H-Pyrazol-5-yl)methyl)-2-amino-9-((2R,3R,5S)-3-hydroxy-5-(hydroxymethyl) tetrahydrofuran-2-yl)-7,9-dihydro-8H-purin-8-one, Compound 177

Compound 177 can be prepared by ester hydrolysis of Compound 176 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with tert-butyl 5-(bromomethyl)-1H-pyrazole-1-carboxylate or 5-(bromomethyl)-1-(4-methoxybenzyl)-1H-pyrazole or the mesylate of (1-(tetrahydro-2H-pyran-2-yl)-1H-pyrazol-5-yl)methanol.

Example 178: ((2S,4R,5R)-4-Acetoxy-5-(2-amino-7-((1-methyl-1H-pyrazol-3-yl)methyl)-8-oxo-7,8-dihydro-9H-purin-9-yl)tetrahydrofuran-2-yl)methyl acetate, Compound 178

Compound 178 can be prepared according to the procedure outlined in Example 29 substituting propargyl bromide with 3-(bromomethyl)-1-methyl-1H-pyrazole [102846-13-9].

Example 179: 2-Amino-9-((2R,3R,5S)-3-hydroxy-5-(hydroxymethyl)tetrahydrofuran-2-yl)-7-((1-methyl-1H-pyrazol-3-yl)methyl)-7,9-dihydro-8H-purin-8-one, Compound 179

Compound 179 can be prepared by ester hydrolysis of Compound 178 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 3-(bromomethyl)-1-methyl-1H-pyrazole.

Example 180: ((2S,4R,5R)-4-Acetoxy-5-(2-amino-8-oxo-7-(thiophen-2-ylmethyl)-7,8-dihydro-9H-purin-9-yl)tetrahydrofuran-2-yl)methyl acetate, Compound 180

Compound 180 can be prepared according to the procedure outlined in Example 29 substituting propargyl bromide with 2-(bromomethyl)-thiophene.

Example 181: 2-Amino-9-((2R,3R,5S)-3-hydroxy-5-(hydroxymethyl)tetrahydrofuran-2-yl)-7-(thiophen-2-ylmethyl)-7,9-dihydro-8H-purin-8-one, Compound 181

Compound 181 can be prepared by ester hydrolysis of Compound 180 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 2-(bromomethyl)-thiophene.

Example 182: ((2S,4R,5R)-4-Acetoxy-5-(2-amino-8-oxo-7-(thiophen-3-ylmethyl)-7,8-dihydro-9H-purin-9-yl)tetrahydrofuran-2-yl)methyl acetate, Compound 182

Compound 182 can be prepared according to the procedure outlined in Example 29 substituting propargyl bromide with 3-(bromomethyl)-thiophene.

Example 183: 2-Amino-9-((2R,3R,5S)-3-hydroxy-5-(hydroxymethyl)tetrahydrofuran-2-yl)-7-(thiophen-3-ylmethyl)-7,9-dihydro-8H-purin-8-one, Compound 183

Compound 183 can be prepared by ester hydrolysis of Compound 182 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 3-(bromomethyl)-thiophene.

Example 184: Methyl 2-(9-((2R,3R,5S)-3-acetoxy-5-(acetoxymethyl)tetrahydrofuran-2-yl)-2-amino-8-oxo-8,9-dihydro-7H-purin-7-yl)acetate, Compound 184

Compound 184 can be prepared according to the procedure outlined in Example 29 substituting propargyl bromide with methyl 2-bromoacetate.

Example 184a: Methyl 2-(2-amino-9-((2R,3R,5S)-3-hydroxy-5-(hydroxymethyl)tetrahydrofuran-2-yl)-8-oxo-8,9-dihydro-7H-purin-7-yl)acetate Compound 184a Compound 184a can be prepared by exposure of Compound 184 to potassium carbonate in dry methanol.

Example 185: 2-(2-Amino-9-((2R,3R,5S)-3-hydroxy-5-(hydroxymethyl)tetrahydrofuran-2-yl)-8-oxo-8,9-dihydro-7H-purin-7-yl)acetic acid, Compound 185

Compound 185 can be prepared by ester hydrolysis of Compound 184 under aqueous conditions using a modified procedure outlined in Example 30 or using the procedure described in Example 32A from N-(9-(4-methoxybenzyl)-8-oxo-8,9-dihydro-7H-purin-2-yl)acetamide and (2S,3R, 5S)-5-((benzoyloxy)methyl)tetrahydrofuran-2,3-diyl diacetate substituting propargyl bromide with methyl 2-bromoacetate and subsequent ester hydrolysis.

Example 186: ((2S,4R,5R)-4-Acetoxy-5-(2-amino-8-oxo-7-(2-oxoethyl)-7,8-dihydro-9H-purin-9-yl)tetrahydrofuran-2-yl)methyl acetate, Compound 186

Compound 186 can be prepared according to the general procedure outlined in Example 29 substituting propargyl bromide with 2-bromo-1,1-dimethoxyethane followed by aqueous acid treatment.

Example 187: 2-(2-Amino-9-((2R,3R,5S)-3-hydroxy-5-(hydroxymethyl)tetrahydrofuran-2-yl)-8-oxo-8,9-dihydro-7H-purin-7-yl)acetaldehyde, Compound 187

Compound 187 can be prepared by base hydrolysis of Compound 186 or using the general procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 2-bromo-1,1-dimethoxyethane and subsequent acetal and ester hydrolysis.

Example 188: ((2S,4R,5R)-4-Acetoxy-5-(2-amino-7-(cyanomethyl)-8-oxo-7,8-dihydro-9H-purin-9-yl)tetrahydrofuran-2-yl)methyl acetate, Compound 188

Compound 188 can be prepared according to the general procedure outlined in Example 29 substituting propargyl bromide with 2-bromoacetonitrile.

Example 189: 2-(2-Amino-9-((2R,3R,5S)-3-hydroxy-5-(hydroxymethyl)tetrahydrofuran-2-yl)-8-oxo-8,9-dihydro-7H-purin-7-yl)acetonitrile, Compound 189

Compound 189 can be prepared by hydrolysis of Compound 188 or from Compound 187 by conversion of the aldehyde to the corresponding oxime and subsequent dehydration of the oxime.

Example 190: ((2S,4R,5R)-5-(7-((1H-Tetrazol-5-yl)methyl)-2-amino-8-oxo-7,8-dihydro-9H-purin-9-yl)-4-acetoxytetrahydrofuran-2-yl)methyl acetate, Compound 190

Compound 190 can be prepared according to the procedure outlined in Example 29 substituting propargyl bromide with 5-(chloromethyl)-1H-tetrazole [55408-11-2].

Example 191: 7-((1H-Tetrazol-5-yl)methyl)-2-amino-9-((2R,3R,5S)-3-hydroxy-5-(hydroxymethyl)tetrahydrofuran-2-yl)-7,9-dihydro-8H-purin-8-one, Compound 191

Compound 191 can be prepared by ester hydrolysis of Compound 190 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 5-(chloromethyl)-1H-tetrazole.

Example 192: 2-(2-Amino-9-((2R,3R,5S)-3-hydroxy-5-(hydroxymethyl)tetrahydrofuran-2-yl)-8-oxo-8,9-dihydro-7H-purin-7-yl)-N-(methylsulfonyl)acetamide, Compound 192

Compound 192 can be prepared from Compound 185 and methanesulfonamide.

Example 193: 2-(2-Amino-9-((2R,3R,5S)-3-hydroxy-5-(hydroxymethyl)tetrahydrofuran-2-yl)-8-oxo-8,9-dihydro-7H-purin-7-yl)-N-hydroxyacetamide, Compound 193

Compound 193 can be prepared from Compound 185 and hydroxylamine.

Example 194: ((2S,4R,5R)-4-Acetoxy-5-(2-amino-7-((3-hydroxyisoxazol-5-yl)methyl)-8-oxo-7,8-dihydro-9H-purin-9-yl)tetrahydrofuran-2-yl)methyl acetate, Compound 194

Compound 194 can be prepared according to the procedure outlined in Example 29 with the mesylate of (3-((4-methoxybenzyl)oxy)isoxazol-5-yl)methanol.

Example 195: 2-Amino-9-((2R,3R,5S)-3-hydroxy-5-(hydroxymethyl)tetrahydrofuran-2-yl)-7-((3-hydroxyisoxazol-5-yl)methyl)-7,9-dihydro-8H-purin-8-one, Compound 195

Compound 195 can be prepared by ester hydrolysis of Compound 194 according to the procedure outlined in Example 30.

Example 196: Methyl 5-((9-((2R,3R,5S)-3-acetoxy-5-(acetoxymethyl)tetrahydrofuran-2-yl)-2-amino-8-oxo-8,9-dihydro-7H-purin-7-yl)methyl)thiophene-2-carboxylate, Compound 196

Compound 196 can be prepared according to the procedure outlined in Example 29 with methyl 5-(bromomethyl)thiophene-2-carboxylate [108499-32-7].

Example 196a: Methyl 5-((2-amino-9-((2R,3R,5S)-3-hydroxy-5-(hydroxymethyl)tetrahydrofuran-2-yl)-8-oxo-8,9-dihydro-7H-purin-7-yl)methyl)thiophene-2-carboxylate, Compound 196a Compound 196a can be prepared by exposure of Compound 196 to potassium carbonate in dry methanol.

Example 197: 5-((2-Amino-9-((2R,3R,5S)-3-hydroxy-5-(hydroxymethyl)tetrahydrofuran-2-yl)-8-oxo-8,9-dihydro-7H-purin-7-yl)methyl)thiophene-2-carboxylic acid, Compound 197

Compound 197 can be prepared by ester hydrolysis of Compound 196 according to the procedure outlined in Example 30.

Example 198: Ethyl 5-((9-((2R,3R,5S)-3-acetoxy-5-(acetoxymethyl)tetrahydrofuran-2-yl)-2-amino-8-oxo-8,9-dihydro-7H-purin-7-yl)methyl)thiophene-3-carboxylate, Compound 198

Compound 198 can be prepared according to the procedure outlined in Example 29 with ethyl 5-(bromomethyl)thiophene-3-carboxylate [206860-16-4].

Example 198a: Ethyl 5-((2-amino-9-((2R,3R,5S)-3-hydroxy-5-(hydroxymethyl)tetrahydrofuran-2-yl)-8-oxo-8,9-dihydro-7H-purin-7-yl)methyl)thiophene-3-carboxylate, Compound 198a Compound 198a can be prepared by exposure of Compound 198 to potassium carbonate in dry ethanol.

Example 199: 5-((2-Amino-9-((2R,3R,5S)-3-hydroxy-5-(hydroxymethyl)tetrahydrofuran-2-yl)-8-oxo-8,9-dihydro-7H-purin-7-yl)methyl)thiophene-3-carboxylic acid, Compound 199

Compound 199 can be prepared by ester hydrolysis of Compound 198 according to the procedure outlined in Example 30.

Example 200: Methyl 4-((9-((2R,3R,5S)-3-acetoxy-5-(acetoxymethyl)tetrahydrofuran-2-yl)-2-amino-8-oxo-8,9-dihydro-7H-purin-7-yl)methyl)thiophene-2-carboxylate, Compound 200

Compound 200 can be prepared according to the procedure outlined in Example 29 with methyl 4-(bromomethyl)thiophene-2-carboxylate [54796-51-9].

Example 200a: Methyl 4-((2-amino-9-((2R,3R,5S)-3-hydroxy-5-(hydroxymethyl)tetrahydrofuran-2-yl)-8-oxo-8,9-dihydro-7H-purin-7-yl)methyl)thiophene-2-carboxylate, Compound 200a Compound 200a can be prepared by exposure of Compound 200 to potassium carbonate in dry methanol.

Example 201: 4-((2-Amino-9-((2R,3R,5S)-3-hydroxy-5-(hydroxymethyl)tetrahydrofuran-2-yl)-8-oxo-8,9-dihydro-7H-purin-7-yl)methyl)thiophene-2-carboxylic acid, Compound 201

Compound 201 can be prepared by ester hydrolysis of Compound 200 according to the procedure outlined in Example 30.

Example 202: Ethyl (1R,2R)-2-((9-((2R,3R,5S)-3-acetoxy-5-(acetoxymethyl)tetrahydrofuran-2-yl)-2-amino-8-oxo-8,9-dihydro-7H-purin-7-yl)methyl)cyclopropane-1-carboxylate, Compound 202

Compound 202 can be prepared according to the procedure outlined in Example 29 with the mesylate of ethyl (1R,2R)-2-(hydroxymethyl)cyclopropane-1-carboxylate.

Example 202a: Ethyl (1R,2R)-2-((2-amino-9-((2R,3R,5S)-3-hydroxy-5-(hydroxymethyl)tetrahydrofuran-2-yl)-8-oxo-8,9-dihydro-7H-purin-7-yl)methyl)cyclopropane-1-carboxylate, Compound 202a Compound 202a can be prepared by exposure of Compound 202 to potassium carbonate in dry ethanol.

Example 203: (1R,2R)-2-((2-Amino-9-((2R,3R,5S)-3-hydroxy-5-(hydroxymethyl)tetrahydrofuran-2-yl)-8-oxo-8,9-dihydro-7H-purin-7-yl)methyl)cyclopropane-1-carboxylic acid, Compound 203

Compound 203 can be prepared by ester hydrolysis of Compound 202 according to the procedure outlined in Example 30.

Example 204: ((2S,4R,5R)-5-(7-((E)-3-(1H-Tetrazol-5-yl)allyl)-2-amino-8-oxo-7,8-dihydro-9H-purin-9-yl)-4-acetoxytetrahydrofuran-2-yl)methyl acetate, Compound 204

Compound 204 can be prepared from ((2S,4R,5R)-4-acetoxy-5-(7-allyl-2-amino-8-oxo-7,8-dihydro-9H-purin-9-yl)tetrahydrofuran-2-yl)methyl acetate and 5-vinyl-1H-tetrazole [18755-47-0] by an olefin metathesis-type reaction.

Example 205: 7-((E)-3-(1H-Tetrazol-5-yl)allyl)-2-amino-9-((2R,3R,5S)-3-hydroxy-5-(hydroxymethyl)tetrahydrofuran-2-yl)-7,9-dihydro-8H-purin-8-one, Compound 205

Compound 205 can be prepared by ester hydrolysis of Compound 204 according to the procedure outlined in Example 30.

Example 206: ((2S,4R,5R)-4-Acetoxy-5-(2-amino-7-(4-formylbenzyl)-8-oxo-7,8-dihydro-9H-purin-9-yl)tetrahydrofuran-2-yl)methyl acetate, Compound 206

Compound 206 can be prepared according to the procedure outlined in Example 29 substituting propargyl bromide with 4-(bromomethyl)benzaldehyde.

Example 207: 4-((2-Amino-9-((2R,3R,5S)-3-hydroxy-5-(hydroxymethyl)tetrahydrofuran-2-yl)-8-oxo-8,9-dihydro-7H-purin-7-yl)methyl)benzaldehyde, Compound 207

Compound 207 can be prepared by ester hydrolysis of Compound 206 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 4-(bromomethyl)benzaldehyde.

Example 208: ((2S,4R,5R)-4-Acetoxy-5-(2-amino-7-(4-methoxybenzyl)-8-oxo-7,8-dihydro-9H-purin-9-yl)tetrahydrofuran-2-yl)methyl acetate, Compound 208

Compound 208 can be prepared according to the procedure outlined in Example 29 substituting propargyl bromide with 4-methoxy-benzylbromide.

Example 209: 2-Amino-9-((2R,3R,5S)-3-hydroxy-5-(hydroxymethyl)tetrahydrofuran-2-yl)-7-(4-methoxybenzyl)-7,9-dihydro-8H-purin-8-one, Compound 209

Compound 209 can be prepared by ester hydrolysis of Compound 208 according to the procedure outlined in Example 30.

Example 210: ((2S,4R,5R)-4-Acetoxy-5-(2-amino-7-(3-methoxybenzyl)-8-oxo-7,8-dihydro-9H-purin-9-yl)tetrahydrofuran-2-yl)methyl acetate, Compound 210

Compound 210 can be prepared according to the procedure outlined in Example 29 substituting propargyl bromide with 3-methoxy-benzylbromide.

Example 211: 2-Amino-9-((2R,3R,5S)-3-hydroxy-5-(hydroxymethyl)tetrahydrofuran-2-yl)-7-(3-methoxybenzyl)-7,9-dihydro-8H-purin-8-one, Compound 211

Compound 211 can be prepared by ester hydrolysis of Compound 210 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 3-methoxy-benzylbromide.

Example 212: ((2S,4R,5R)-4-Acetoxy-5-(2-amino-7-(3-hydroxybenzyl)-8-oxo-7,8-dihydro-9H-purin-9-yl)tetrahydrofuran-2-yl)methyl acetate, Compound 212

Compound 212 can be prepared by demethylation of Compound 211 with BBr$_3$.

Example 213: 2-Amino-9-((2R,3R,5S)-3-hydroxy-5-(hydroxymethyl)tetrahydrofuran-2-yl)-7-(3-hydroxy-benzyl)-7,9-dihydro-8H-purin-8-one, Compound 213

Compound 213 can be prepared by ester hydrolysis of Compound 212 according to the procedure outlined in Example 30.

Example 214: ((2S,4R,5R)-4-Acetoxy-5-(2-amino-8-oxo-7-(4-(trifluoromethyl)benzyl)-7,8-dihydro-9H-purin-9-yl)tetrahydrofuran-2-yl)methyl acetate, Compound 214

Compound 214 can be prepared according to the procedure outlined in Example 29 substituting propargyl bromide with 4-trifluoromethyl-benzylbromide.

Example 215: 2-Amino-9-((2R,3R,5S)-3-hydroxy-5-(hydroxymethyl)tetrahydrofuran-2-yl)-7-(4-(trifluoromethyl)benzyl)-7,9-dihydro-8H-purin-8-one, Compound 215

Compound 215 can be prepared by ester hydrolysis of Compound 214 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 4-trifluoromethyl-benzylbromide.

Example 216: ((2S,4R,5R)-4-Acetoxy-5-(2-amino-8-oxo-7-(pyridin-3-ylmethyl)-7,8-dihydro-9H-purin-9-yl)tetrahydrofuran-2-yl)methyl acetate, Compound 216

Compound 216 can be prepared according to the procedure outlined in Example 29 substituting propargyl bromide with 3-(bromomethyl)pyridine.

Example 217: 2-Amino-9-((2R,3R,5S)-3-hydroxy-5-(hydroxymethyl)tetrahydrofuran-2-yl)-7-(pyridin-3-ylmethyl)-7,9-dihydro-8H-purin-8-one, Compound 217

Compound 217 can be prepared by ester hydrolysis of Compound 216 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with 3-(bromomethyl)pyridine.

Example 218: ((2S,4R,5R)-4-Acetoxy-5-(2-amino-8-oxo-7-(2-oxo-2-(pyrrolidin-1-yl)ethyl)-7,8-dihydro-9H-purin-9-yl)tetrahydrofuran-2-yl)methyl acetate, Compound 218

Compound 218 can be prepared according to the procedure outlined in Example 29 substituting propargyl bromide with bromoacetopyrrolidine [90892-09-4].

Example 219: 2-Amino-9-((2R,3R,5S)-3-hydroxy-5-(hydroxymethyl)tetrahydrofuran-2-yl)-7-(2-oxo-2-(pyrrolidin-1-yl)ethyl)-7,9-dihydro-8H-purin-8-one, Compound 219

Compound 219 can be prepared by ester hydrolysis of Compound 218 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with bromoacetopyrrolidine.

Example 220: ((2S,4R,5R)-4-acetoxy-5-(7-allyl-2-amino-8-oxo-7,8-dihydro-9H-purin-9-yl)tetrahydrofuran-2-yl)methyl acetate, Compound 220

Compound 220 can be prepared according to the procedure outlined in Example 29 substituting propargyl bromide with allyl bromide.

Example 221: 7-Allyl-2-amino-9-((2R,3R,5S)-3-hydroxy-5-(hydroxymethyl)tetrahydrofuran-2-yl)-7,9-dihydro-8H-purin-8-one, Compound 221

Compound 221 can be prepared by ester hydrolysis of Compound 220 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy) methyl)tetrahydrofuran-2,3-diyl diacetate substituting propargyl bromide with allyl bromide.

Example 222: ((2S,4R,5R)-4-Acetoxy-5-(2-amino-7-(cyclopropylmethyl)-8-oxo-7,8-dihydro-9H-purin-9-yl)tetrahydrofuran-2-yl)methyl acetate, Compound 222

Compound 222 can be prepared according to the procedure outlined in Example 29 substituting propargyl bromide with (bromomethyl)cyclopropane.

Example 223: 2-Amino-7-(cyclopropylmethyl)-9-((2R,3R,5S)-3-hydroxy-5-(hydroxymethyl)tetrahydrofuran-2-yl)-7,9-dihydro-8H-purin-8-one Compound 223

Compound 223 can be prepared by ester hydrolysis of Compound 222 according to the procedure outlined in Example 30 or using the procedure described in Example 32A from (2S,3R,5S)-5-((benzoyloxy)methyl)tetrahydrofuran-2,3-diyl diacetate and substituting (45) with (71).

Example 224: ((2S,4R,5R)-4-Acetoxy-5-(2-amino-7-butyl-8-oxo-7,8-dihydro-9H-purin-9-yl)tetrahydrofuran-2-yl)methyl acetate, Compound 224

Compound 224 can be prepared according to the procedure outlined in Example 29 substituting propargyl bromide with n-butyl bromide.

Example 225: 2-Amino-7-butyl-9-((2R,3R,5S)-3-hydroxy-5-(hydroxymethyl)tetrahydrofuran-2-yl)-7,9-dihydro-8H-purin-8-one, Compound 225

Compound 225 can be prepared by ester hydrolysis of Compound 224 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with n-butyl bromide.

Example 226: ((2S,4R,5R)-4-Acetoxy-5-(2-amino-7-(methoxymethyl)-8-oxo-7,8-dihydro-9H-purin-9-yl)tetrahydrofuran-2-yl)methyl acetate, Compound 226

Compound 226 can be prepared according to the procedure outlined in Example 29 substituting propargyl bromide with chloromethyl methyl ether.

Example 227: 2-Amino-9-((2R,3R,5S)-3-hydroxy-5-(hydroxymethyl)tetrahydrofuran-2-yl)-7-(methoxymethyl)-7,9-dihydro-8H-purin-8-one, Compound 227

Compound 227 can be prepared by ester hydrolysis of Compound 226 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with chloromethyl methyl ether.

Example 228: ((2S,4R,5R)-4-Acetoxy-5-(2-amino-7-((methylthio)methyl)-8-oxo-7,8-dihydro-9H-purin-9-yl)tetrahydrofuran-2-yl)methyl acetate, Compound 228

Compound 228 can be prepared according to the procedure outlined in Example 29 substituting propargyl bromide with chloromethyl methyl sulfide.

Example 229: 2-Amino-9-((2R,3R,5S)-3-hydroxy-5-(hydroxymethyl)tetrahydrofuran-2-yl)-7-((methylthio)methyl)-7,9-dihydro-8H-purin-8-one, Compound 229

Compound 229 can be prepared by ester hydrolysis of Compound 228 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with chloromethyl methyl sulfide.

Example 230: ((2S,4R,5R)-4-Acetoxy-5-(2-amino-8-oxo-7-(2,2,2-trifluoroethyl)-7,8-dihydro-9H-purin-9-yl)tetrahydrofuran-2-yl)methyl acetate, Compound 230

Compound 230 can be prepared according to the procedure outlined in Example 29 substituting propargyl bromide with 2-bromo-1,1,1-trifluoroethane [421-06-7].

Example 231: 2-Amino-9-((2R,3R,5S)-3-hydroxy-5-(hydroxymethyl)tetrahydrofuran-2-yl)-7-(2,2,2-trifluoroethyl)-7,9-dihydro-8H-purin-8-one, Compound 231

Compound 231 can be prepared by ester hydrolysis of Compound 230 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 2-bromo-1,1,1-trifluoroethane.

Example 232: ((2S,4R,5R)-4-Acetoxy-5-(2-amino-7-(2,2-difluoroethyl)-8-oxo-7,8-dihydro-9H-purin-9-yl)tetrahydrofuran-2-yl)methyl acetate, Compound 232

Compound 232 can be prepared according to the procedure outlined in Example 29 substituting propargyl bromide with 2-bromo-1,1-difluoroethane [359-07-9].

Example 233: 2-Amino-7-(2,2-difluoroethyl)-9-((2R,3R,5S)-3-hydroxy-5-(hydroxymethyl)tetrahydrofuran-2-yl)-7,9-dihydro-8H-purin-8-one, Compound 233

Compound 233 can be prepared by ester hydrolysis of Compound 232 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 2-bromo-1,1-difluoroethane.

Example 234: ((2S,4R,5R)-4-acetoxy-5-(2-amino-8-oxo-7-(3,3,3-trifluoropropyl)-7,8-dihydro-9H-purin-9-yl)tetrahydrofuran-2-yl)methyl acetate, Compound 234

Compound 234 can be prepared according to the procedure outlined in Example 29 substituting propargyl bromide with 3-bromo-1,1,1-trifluoropropane [460-32-2].

Example 235: 2-Amino-9-((2R,3R,5S)-3-hydroxy-5-(hydroxymethyl)tetrahydrofuran-2-yl)-7-(3,3,3-trifluoropropyl)-7,9-dihydro-8H-purin-8-one, Compound 235

Compound 235 can be prepared by ester hydrolysis of Compound 234 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-bromo-1,1,1-trifluoropropane.

Example 236: ((2S,4R,5R)-4-Acetoxy-5-(2-amino-8-oxo-7-(2,2,3,3,3-pentafluoropropyl)-7,8-dihydro-9H-purin-9-yl)tetrahydrofuran-2-yl)methyl acetate, Compound 236

Compound 236 can be prepared according to the procedure outlined in Example 29 substituting propargyl bromide with 3-bromo-1,1,1,2,2-pentafluoropropane [422-01-5] or 2,2,3,3,3-pentafluoropropyl methanesulfonate [813-31-0].

Example 237: 2-Amino-9-((2R,3R,5S)-3-hydroxy-5-(hydroxymethyl)tetrahydrofuran-2-yl)-7-(2,2,3,3,3-pentafluoropropyl)-7,9-dihydro-8H-purin-8-one, Compound 237

Compound 237 can be prepared by ester hydrolysis of Compound 236 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-bromo-1,1,1,2,2-pentafluoropropane or 2,2,3,3,3-pentafluoropropyl methanesulfonate.

Example 238: ((2S,4R,5R)-4-Acetoxy-5-(2-amino-8-oxo-7-(4,4,4-trifluorobutyl)-7,8-dihydro-9H-purin-9-yl)tetrahydrofuran-2-yl)methyl acetate, Compound 238

Compound 238 can be prepared according to the procedure outlined in Example 29 substituting propargyl bromide with 4-bromo-1,1,1-trifluorobutane [406-81-5].

Example 239: 2-Amino-9-((2R,3R,5S)-3-hydroxy-5-(hydroxymethyl)tetrahydrofuran-2-yl)-7-(4,4,4-trifluorobutyl)-7,9-dihydro-8H-purin-8-one, Compound 239

Compound 239 can be prepared by ester hydrolysis of Compound 238 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 4-bromo-1,1,1-trifluorobutane.

Example 240: ((2S,4R,5R)-4-Acetoxy-5-(2-amino-8-oxo-7-(3,3,4,4,4-pentafluorobutyl)-7,8-dihydro-9H-purin-9-yl)tetrahydrofuran-2-yl)methyl acetate Compound 240

Compound 240 can be prepared according to the procedure outlined in Example 29 substituting propargyl bromide with 1,1,1,2,2-pentafluoro-4-bromobutane [52671-70-2].

Example 241: 2-Amino-9-((2R,3R,5S)-3-hydroxy-5-(hydroxymethyl)tetrahydrofuran-2-yl)-7-(3,3,4,4,4-pentafluorobutyl)-7,9-dihydro-8H-purin-8-one, Compound 241

Compound 241 can be prepared by ester hydrolysis of Compound 240 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 1,1,1,2,2-pentafluoro-4-bromobutane.

Example 242: ((2S,4R,5R)-4-Acetoxy-5-(2-amino-7-(2-cyanoethyl)-8-oxo-7,8-dihydro-9H-purin-9-yl)tetrahydrofuran-2-yl)methyl acetate, Compound 242

Compound 242 can be prepared according to the procedure outlined in Example 29 substituting propargyl bromide with 3-bromopropanenitrile [2417-90-5].

Example 243: 3-(2-Amino-9-((2R,3R,5S)-3-hydroxy-5-(hydroxymethyl)tetrahydrofuran-2-yl)-8-oxo-8,9-dihydro-7H-purin-7-yl)propanenitrile, Compound 243

Compound 243 can be prepared by ester hydrolysis of Compound 242 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 3-bromopropanenitrile.

Example 244: ((2S,4R,5R)-4-acetoxy-5-(2-amino-7-(3-cyanopropyl)-8-oxo-7,8-dihydro-9H-purin-9-yl)tetrahydrofuran-2-yl)methyl acetate, Compound 244

Compound 244 can be prepared according to the procedure outlined in Example 29 substituting propargyl bromide with 4-bromobutanenitrile [5332-06-9].

Example 245: 4-(2-Amino-9-((2R,3R,5S)-3-hydroxy-5-(hydroxymethyl)tetrahydrofuran-2-yl)-8-oxo-8,9-dihydro-7H-purin-7-yl)butanenitrile, Compound 245

Compound 245 can be prepared by ester hydrolysis of Compound 244 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 4-bromobutanenitrile.

Example 246: ((2S,4R,5R)-4-Acetoxy-5-(2-amino-7-isobutyl-8-oxo-7,8-dihydro-9H-purin-9-yl)tetrahydrofuran-2-yl)methyl acetate, Compound 246

Compound 246 can be prepared according to the procedure outlined in Example 29 substituting propargyl bromide with 1-bromo-2-methylpropane.

Example 247: 2-Amino-9-((2R,3R,5S)-3-hydroxy-5-(hydroxymethyl)tetrahydrofuran-2-yl)-7-isobutyl-7,9-dihydro-8H-purin-8-one, Compound 247

Compound 247 can be prepared by ester hydrolysis of Compound 246 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with 1-bromo-2-methylpropane.

Example 248: ((2S,4R,5R)-4-Acetoxy-5-(2-amino-7-((1-cyanocyclopropyl)methyl)-8-oxo-7,8-dihydro-9H-purin-9-yl)tetrahydrofuran-2-yl)methyl acetate, Compound 248

Compound 248 can be prepared according to the procedure outlined in Example 29 substituting propargyl bromide with the mesylate of 1-(hydroxymethyl)cyclopropane-1-carbonitrile [98730-77-9].

Example 249: 1-((2-Amino-9-((2R,3R,5S)-3-hydroxy-5-(hydroxymethyl)tetrahydrofuran-2-yl)-8-oxo-8,9-dihydro-7H-purin-7-yl)methyl)cyclopropane-1-carbonitrile, Compound 249

Compound 249 can be prepared by ester hydrolysis of Compound 248 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with mesylate of 1-(hydroxymethyl)cyclopropane-1-carbonitrile.

Example 250: Ethyl 1-((9-((2R,3R,5S)-3-acetoxy-5-(acetoxymethyl)tetrahydrofuran-2-yl)-2-amino-8-oxo-8,9-dihydro-7H-purin-7-yl)methyl)cyclopropane-1-carboxylate, Compound 250

Compound 250 can be prepared according to the procedure outlined in Example 29 the mesylate of ethyl 1-(hydroxymethyl)cyclopropane-1-carboxylate [3697-68-5].

Example 250a: Ethyl 1-((2-amino-9-((2R,3R,5S)-3-hydroxy-5-(hydroxymethyl)tetrahydrofuran-2-yl)-8-oxo-8,9-dihydro-7H-purin-7-yl)methyl)cyclopropane-1-carboxylate, Compound 250a Compound 250a can be prepared by exposure of Compound 250 to potassium carbonate in dry ethanol.

Example 251: 1-((2-Amino-9-((2R,3R,5S)-3-hydroxy-5-(hydroxymethyl)tetrahydrofuran-2-yl)-8-oxo-8,9-dihydro-7H-purin-7-yl)methyl)cyclopropane-1-carboxylic acid, Compound 251

Compound 251 can be prepared by ester hydrolysis of Compound 250 according to the procedure outlined in Example 30.

Example 252: ((2S,4R,5R)-4-Acetoxy-5-(2-amino-8-oxo-7-((1-(trifluoromethyl)cyclopropyl)methyl)-7,8-dihydro-9H-purin-9-yl)tetrahydrofuran-2-yl)methyl acetate, Compound 252

Compound 252 can be prepared according to the procedure outlined in Example 29 substituting propargyl bromide with the mesylate of (1-(trifluoromethyl)cyclopropyl)methanol [371917-17-8].

Example 253: 2-Amino-9-((2R,3R,5S)-3-hydroxy-5-(hydroxymethyl)tetrahydrofuran-2-yl)-7-((1-(trifluoromethyl)cyclopropyl)methyl)-7,9-dihydro-8H-purin-8-one, Compound 253

Compound 253 can be prepared by ester hydrolysis of Compound 252 according to the procedure outlined in Example 30 or using the procedure described in Example 32A from N-(9-(4-methoxybenzyl)-8-oxo-8,9-dihydro-7H-purin-2-yl)acetamide and (2S,3R,5S)-5-((benzoyloxy)methyl)tetrahydrofuran-2,3-diyl diacetate substituting propargyl bromide with the mesylate of (1-(trifluoromethyl)cyclopropyl)methanol.

Example 254: ((2R,3R,4S,5R)-4-Acetoxy-5-(2-amino-7-benzyl-8-oxo-7,8-dihydro-9H-purin-9-yl)-3-fluorotetrahydrofuran-2-yl)methyl acetate, Compound 254

Compound 254 can be prepared according to the procedure outlined in Example 31 substituting propargyl bromide with benzyl bromide.

Example 255: 2-Amino-7-benzyl-9-((2R,3S,4S,5R)-4-fluoro-3-hydroxy-5-(hydroxymethyl)tetrahydrofuran-2-yl)-7,9-dihydro-8H-purin-8-one, Compound 255

Compound 255 can be prepared by ester hydrolysis of Compound 254 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with benzyl bromide.

Example 256: ((2R,3R,4S,5R)-4-Acetoxy-5-(2-amino-7-(4-fluorobenzyl)-8-oxo-7,8-dihydro-9H-purin-9-yl)-3-fluorotetrahydrofuran-2-yl)methyl acetate, Compound 256

Compound 256 can be prepared according to the procedure outlined in Example 31 substituting propargyl bromide with 4-fluorobenzyl bromide.

Example 257: 2-Amino-9-((2R,3S,4S,5R)-4-fluoro-3-hydroxy-5-(hydroxymethyl)tetrahydrofuran-2-yl)-7-(4-fluorobenzyl)-7,9-dihydro-8H-purin-8-one, Compound 257

Compound 257 can be prepared by ester hydrolysis of Compound 256 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-fluorobenzyl bromide.

Example 258: ((2R,3R,4S,5R)-4-Acetoxy-5-(2-amino-7-(3-fluorobenzyl)-8-oxo-7,8-dihydro-9H-purin-9-yl)-3-fluorotetrahydrofuran-2-yl)methyl acetate, Compound 258

Compound 258 can be prepared according to the procedure outlined in Example 31 substituting propargyl bromide with 3-fluorobenzyl bromide.

Example 259: 2-Amino-9-((2R,3S,4S,5R)-4-fluoro-3-hydroxy-5-(hydroxymethyl)tetrahydrofuran-2-yl)-7-(3-fluorobenzyl)-7,9-dihydro-8H-purin-8-one, Compound 259

Compound 259 can be prepared by ester hydrolysis of Compound 258 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-fluorobenzyl bromide.

Example 260: ((2R,3R,4S,5R)-4-Acetoxy-5-(2-amino-7-(3,4-difluorobenzyl)-8-oxo-7,8-dihydro-9H-purin-9-yl)-3-fluorotetrahydrofuran-2-yl)methyl acetate, Compound 260

Compound 260 can be prepared according to the procedure outlined in Example 31 substituting propargyl bromide with 3,4-difluorobenzyl bromide.

Example 261: 2-Amino-9-((2R,3S,4S,5R)-4-fluoro-3-hydroxy-5-(hydroxymethyl)tetrahydrofuran-2-yl)-7-(3,4-difluorobenzyl)-7,9-dihydro-8H-purin-8-one, Compound 261

Compound 261 can be prepared by ester hydrolysis of Compound 260 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3,4-difluorobenzyl bromide.

Example 262: ((2R,3R,4S,5R)-4-Acetoxy-5-(2-amino-7-(4-chlorobenzyl)-8-oxo-7,8-dihydro-9H-purin-9-yl)-3-fluorotetrahydrofuran-2-yl)methyl acetate, Compound 262

Compound 262 can be prepared according to the procedure outlined in Example 31 substituting propargyl bromide with 4-chlorobenzyl bromide.

Example 263: 2-Amino-9-((2R,3S,4S,5R)-4-fluoro-3-hydroxy-5-(hydroxymethyl)tetrahydrofuran-2-yl)-7-(4-chlorobenzyl)-7,9-dihydro-8H-purin-8-one, Compound 263

Compound 263 can be prepared by ester hydrolysis of Compound 262 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-chlorobenzyl bromide.

Example 264: ((2R,3R,4S,5R)-4-Acetoxy-5-(2-amino-7-(3-chlorobenzyl)-8-oxo-7,8-dihydro-9H-purin-9-yl)-3-fluorotetrahydrofuran-2-yl)methyl acetate, Compound 264

Compound 264 can be prepared according to the procedure outlined in Example 31 substituting propargyl bromide with 3-chlorobenzyl bromide.

Example 265: 2-Amino-9-((2R,3S,4S,5R)-4-fluoro-3-hydroxy-5-(hydroxymethyl)tetrahydrofuran-2-yl)-7-(3-chlorobenzyl)-7,9-dihydro-8H-purin-8-one, Compound 265

Compound 265 can be prepared by ester hydrolysis of Compound 264 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-chlorobenzyl bromide.

Example 266: ((2R,3R,4S,5R)-4-Acetoxy-5-(2-amino-7-(3,4-dichlorobenzyl)-8-oxo-7,8-dihydro-9H-purin-9-yl)-3-fluorotetrahydrofuran-2-yl)methyl acetate, Compound 266

Compound 266 can be prepared according to the procedure outlined in Example 31 substituting propargyl bromide with 3,4-dichlorobenzyl bromide.

Example 267: 2-Amino-9-((2R,3S,4S,5R)-4-fluoro-3-hydroxy-5-(hydroxymethyl)tetrahydrofuran-2-yl)-7-(3,4-dichlorobenzyl)-7,9-dihydro-8H-purin-8-one, Compound 267

Compound 267 can be prepared by ester hydrolysis of Compound 266 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3,4-dichlorobenzyl bromide.

Example 268: ((2R,3R,4S,5R)-4-Acetoxy-5-(2-amino-7-(4-cyanobenzyl)-8-oxo-7,8-dihydro-9H-purin-9-yl)-3-fluorotetrahydrofuran-2-yl)methyl acetate, Compound 268

Compound 268 can be prepared according to the procedure outlined in Example 31 substituting propargyl bromide with 4-cyanobenzyl bromide.

Example 269: 4-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzonitrile, Compound 269

Compound 269 can be prepared by ester hydrolysis of Compound 268 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-cyanobenzyl bromide.

Example 270: ((2R,3R,4S,5R)-4-Acetoxy-5-(2-amino-7-(3-cyanobenzyl)-8-oxo-7,8-dihydro-9H-purin-9-yl)-3-fluorotetrahydrofuran-2-yl)methyl acetate, Compound 270

Compound 270 can be prepared according to the procedure outlined in Example 31 substituting propargyl bromide with 3-cyanobenzyl bromide.

Example 271: 3-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzonitrile, Compound 271

Compound 271 can be prepared by ester hydrolysis of Compound 270 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-cyanobenzyl bromide.

Example 272: Methyl 4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate, Compound 272

Compound 272 can be prepared according to the procedure outlined in Example 31 substituting propargyl bromide with methyl 4-bromomethyl benzoate.

Example 273: Methyl 4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate, Compound 273

Compound 273 can be prepared by exposure of Compound 272 to potassium carbonate in dry methanol.

Example 274: 4-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid, Compound 274

Compound 274 can be prepared by ester hydrolysis of Compound 272 according to the procedure outlined in Example 32 or using the procedure described in Example 32A from N-(9-(4-methoxybenzyl)-8-oxo-8,9-dihydro-7H-purin-2-yl)acetamide substituting propargyl bromide with methyl 4-bromomethyl benzoate.

Example 275: Methyl 3-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate, Compound 275

Compound 275 can be prepared according to the procedure outlined in Example 31 substituting propargyl bromide with methyl 3-bromomethyl benzoate.

Example 276: Methyl 3-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate, Compound 276

Compound 276 can be prepared by exposure of Compound 275 to potassium carbonate in dry methanol.

Example 277: 3-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid, Compound 277

Compound 277 can be prepared by ester hydrolysis of Compound 275 according to the procedure outlined in Example 32 or using the procedure described in Example 32A from N-(9-(4-methoxybenzyl)-8-oxo-8,9-dihydro-7H-purin-2-yl)acetamide substituting propargyl bromide with methyl 3-bromomethyl benzoate.

Example 278: Methyl 2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate, Compound 278

Compound 278 can be prepared according to the procedure outlined in Example 31 substituting propargyl bromide with methyl 2-bromomethyl benzoate.

Example 279: Methyl 2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate, Compound 279

Compound 279 can be prepared by exposure of Compound 278 to potassium carbonate in dry methanol.

Example 280: 2-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid, Compound 280

Compound 280 can be prepared by ester hydrolysis of Compound 278 according to the procedure outlined in Example 32 or using the procedure described in Example 32A from N-(9-(4-methoxybenzyl)-8-oxo-8,9-dihydro-7H-purin-2-yl)acetamide substituting propargyl bromide with methyl 2-bromomethyl benzoate.

Example 281: ((2R,3R,4S,5R)-4-Acetoxy-5-(2-amino-7-(E)-cinnamyl-8-oxo-7,8-dihydro-9H-purin-9-yl)-3-fluorotetrahydrofuran-2-yl)methyl acetate, Compound 281

Compound 281 can be prepared according to the procedure outlined in Example 31 substituting propargyl bromide with (E)-cinnamyl bromide.

Example 282: 2-Amino-7-(E)-cinnamyl-9-((2R,3S,4S,5R)-4-fluoro-3-hydroxy-5-(hydroxymethyl)tetrahydrofuran-2-yl)-7,9-dihydro-8H-purin-8-one, Compound 282

Compound 282 can be prepared by ester hydrolysis of Compound 281 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with (E)-cinnamyl bromide.

Example 283: ((2R,3R,4S,5R)-5-(7-((1H-Pyrazol-5-yl)methyl)-2-amino-8-oxo-7,8-dihydro-9H-purin-9-yl)-4-acetoxy-3-fluorotetrahydrofuran-2-yl)methyl acetate, Compound 283

Compound 283 can be prepared according to the procedure outlined in Example 31 substituting propargyl bromide with tert-butyl 5-(bromomethyl)-1H-pyrazole-1-carboxylate [1001096-27-0] or 5-(bromomethyl)-1-(4-methoxybenzyl)-1H-pyrazole [1313409-97-0] or the mesylate of (1-(tetrahydro-2H-pyran-2-yl)-1H-pyrazol-5-yl)methanol [1823866-20-1].

Example 284: 7-((1H-Pyrazol-5-yl)methyl)-2-amino-9-((2R,3S,4S,5R)-4-fluoro-3-hydroxy-5-(hydroxymethyl)tetrahydrofuran-2-yl)-7,9-dihydro-8H-purin-8-one, Compound 284

Compound 284 can be prepared by ester hydrolysis of Compound 283 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with tert-butyl 5-(bromomethyl)-1H-pyrazole-1-carboxylate or Example 285: ((2R,3R,4S,5R)-4-Acetoxy-5-(2-amino-7-((1-methyl-1H-pyrazol-3-yl)methyl)-8-oxo-7,8-dihydro-9H-purin-9-yl)-3-fluorotetrahydrofuran-2-yl)methyl acetate, Compound 285

Compound 285 can be prepared according to the procedure outlined in Example 31 substituting propargyl bromide with 3-(bromomethyl)-1-methyl-1H-pyrazole [102846-13-9].

Example 286: 2-Amino-9-((2R,3S,4S,5R)-4-fluoro-3-hydroxy-5-(hydroxymethyl)tetrahydrofuran-2-yl)-7-((1-methyl-1H-pyrazol-3-yl)methyl)-7,9-dihydro-8H-purin-8-one, Compound 286

Compound 286 can be prepared by ester hydrolysis of Compound 285 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-(bromomethyl)-1-methyl-1H-pyrazole.

Example 287: ((2R,3R,4S,5R)-4-Acetoxy-5-(2-amino-8-oxo-7-(thiophen-2-ylmethyl)-7,8-dihydro-9H-purin-9-yl)-3-fluorotetrahydrofuran-2-yl)methyl acetate, Compound 287

Compound 287 can be prepared according to the procedure outlined in Example 31 substituting propargyl bromide with 2-(bromomethyl)-thiophene.

Example 288: 2-Amino-9-((2R,3S,4S,5R)-4-fluoro-3-hydroxy-5-(hydroxymethyl)tetrahydrofuran-2-yl)-7-(thiophen-2-ylmethyl)-7,9-dihydro-8H-purin-8-one, Compound 288

Compound 288 can be prepared by ester hydrolysis of Compound 287 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 2-(bromomethyl)-thiophene.

Example 289: ((2R,3R,4S,5R)-4-Acetoxy-5-(2-amino-8-oxo-7-(thiophen-3-ylmethyl)-7,8-dihydro-9H-purin-9-yl)-3-fluorotetrahydrofuran-2-yl)methyl acetate, Compound 289

Compound 289 can be prepared according to the procedure outlined in Example 31 substituting propargyl bromide with 3-(bromomethyl)-thiophene.

Example 290: 2-Amino-9-((2R,3S,4S,5R)-4-fluoro-3-hydroxy-5-(hydroxymethyl)tetrahydrofuran-2-yl)-7-(thiophen-3-ylmethyl)-7,9-dihydro-8H-purin-8-one, Compound 290

Compound 290 can be prepared by ester hydrolysis of Compound 289 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-(bromomethyl)-thiophene.

Example 291: Methyl 2-(9-((2R,3S,4R,5R)-3-acetoxy-5-(acetoxymethyl)-4-fluorotetrahydrofuran-2-yl)-2-amino-8-oxo-8,9-dihydro-7H-purin-7-yl)acetate, Compound 291

Compound 291 can be prepared according to the procedure outlined in Example 31 substituting propargyl bromide with methyl 2-bromoacetate.

Example 292: Methyl 2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetate, Compound 292

Compound 292 can be prepared by exposure of Compound 291 to potassium carbonate in dry methanol.

Example 293: 2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetic acid, Compound 293

Compound 293 can be prepared by ester hydrolysis of Compound 291 under aqueous conditions using a modified procedure outlined in Example 32 or using the procedure described in Example 32A from N-(9-(4-methoxybenzyl)-8-oxo-8,9-dihydro-7H-purin-2-yl)acetamide and substituting propargyl bromide with methyl 2-bromoacetate and subsequent ester hydrolysis.

Example 294: ((2R,3R,4S,5R)-4-Acetoxy-5-(2-amino-8-oxo-7-(2-oxoethyl)-7,8-dihydro-9H-purin-9-yl)-3-fluorotetrahydrofuran-2-yl)methyl acetate, Compound 294

Compound 294 can be prepared according to the general procedure outlined in Example 31 substituting propargyl bromide with 2-bromo-1,1-dimethoxyethane followed by aqueous acid treatment.

Example 295: 2-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetaldehyde, Compound 295

Compound 295 can be prepared by base hydrolysis of Compound 294 or using the general procedure described in Example 32A from N-(9-(4-methoxybenzyl)-8-oxo-8,9-dihydro-7H-purin-2-yl)acetamide substituting propargyl bromide with 2-bromo-1,1-dimethoxyethane and subsequent acetal and ester hydrolysis.

Example 296: ((2R,3R,4S,5R)-4-Acetoxy-5-(2-amino-7-(cyanomethyl)-8-oxo-7,8-dihydro-9H-purin-9-yl)-3-fluorotetrahydrofuran-2-yl)methyl acetate, Compound 296

Compound 296 can be prepared according to the general procedure outlined in Example 31 substituting propargyl bromide with 2-bromoacetonitrile.

Example 297: 2-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetonitrile, Compound 297

Compound 297 can be prepared by hydrolysis of Compound 296 or from Compound 295 by conversion of the aldehyde to the corresponding oxime and subsequent dehydration of the oxime.

Example 298: ((2R,3R,4S,5R)-5-(7-((1H-Tetrazol-5-yl)methyl)-2-amino-8-oxo-7,8-dihydro-9H-purin-9-yl)-4-acetoxy-3-fluorotetrahydrofuran-2-yl)methyl acetate, Compound 298

Compound 298 can be prepared according to the procedure outlined in Example 31 substituting propargyl bromide with 5-(chloromethyl)-1H-tetrazole [55408-11-2].

Example 299: 7-((1H-Tetrazol-5-yl)methyl)-2-amino-9-((2R,3S,4S,5R)-4-fluoro-3-hydroxy-5-(hydroxymethyl)tetrahydrofuran-2-yl)-7,9-dihydro-8H-purin-8-one, Compound 298

Compound 299 can be prepared by ester hydrolysis of Compound 298 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 5-(chloromethyl)-1H-tetrazole.

Example 300: 2-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)-N-(methylsulfonyl)acetamide, Compound 300

Compound 300 can be prepared from Compound 293 and methanesulfonamide.

Example 301: 2-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)-N-hydroxyacetamide, Compound 301

Compound 301 can be prepared from Compound 293 and hydroxylamine.

Example 302: ((2R,3R,4S,5R)-4-Acetoxy-5-(2-amino-7-((3-hydroxyisoxazol-5-yl)methyl)-8-oxo-7,8-dihydro-9H-purin-9-yl)-3-fluorotetrahydrofuran-2-yl)methyl acetate, Compound 302

Compound 302 can be prepared according to the procedure outlined in Example 31 substituting propargyl bromide with the mesylate of (3-((4-methoxybenzyl)oxy)isoxazol-5-yl)methanol.

Example 303: 2-Amino-9-((2R,3S,4S,5R)-4-fluoro-3-hydroxy-5-(hydroxymethyl)tetrahydrofuran-2-yl)-7-((3-hydroxyisoxazol-5-yl)methyl)-7,9-dihydro-8H-purin-8-one, Compound 303

Compound 303 can be prepared by ester hydrolysis of Compound 302 according to the procedure outlined in Example 32.

Example 304: Methyl 2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate, Compound 304

Compound 304 can be prepared according to the procedure outlined in Example 31 substituting propargyl bromide with methyl 5-(bromomethyl)thiophene-2-carboxylate [108499-32-7].

Example 305: Methyl 2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate, Compound 305

Compound 305 can be prepared by exposure of Compound 304 to potassium carbonate in dry methanol.

Example 306: 2-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid, Compound 306

Compound 306 can be prepared by ester hydrolysis of Compound 304 according to the procedure outlined in Example 32.

Example 307: Ethyl 5-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-3-carboxylate, Compound Compound 307 can be prepared according to the procedure outlined in Example 31 substituting propargyl bromide with ethyl 5-(bromomethyl)thiophene-3-carboxylate [206860-16-4].

Example 308: Ethyl 5-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-3-carboxylate, Compound 308

Compound 308 can be prepared by exposure of Compound 307 to potassium carbonate in dry ethanol.

Example 309: 5-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-3-carboxylic acid, Compound 309

Compound 309 can be prepared by ester hydrolysis of Compound 307 according to the procedure outlined in Example 32.

Example 310: Methyl 4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-2-carboxylate, Compound 310

Compound 310 can be prepared according to the procedure outlined in Example 31 substituting propargyl bromide with methyl 4-(bromomethyl)thiophene-2-carboxylate [54796-51-9].

Example 311: Methyl 4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylate, Compound 311

Compound 311 can be prepared by exposure of Compound 310 to potassium carbonate in dry methanol.

Example 312: 4-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylic acid, Compound 312

Compound 312 can be prepared by ester hydrolysis of Compound 310 according to the procedure outlined in Example 32.

Example 313: Ethyl (1R,2R)-2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)cyclopropane-1-carboxylate, Compound 313

Compound 313 can be prepared according to the procedure outlined in Example 31 substituting propargyl bromide with the mesylate of ethyl (1R,2R)-2-(hydroxymethyl)cyclopropane-1-carboxylate.

Example 314: Ethyl (1R,2R)-2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylate, Compound 314

Compound 314 can be prepared by exposure of Compound 313 to potassium carbonate in dry ethanol.

Example 315: (1R,2R)-2-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylic acid, Compound 315

Compound 315 can be prepared by ester hydrolysis of Compound 313 according to the procedure outlined in Example 32.

Example 316: ((2R,3R,4S,5R)-5-(7-((E)-3-(1H-Tetrazol-5-yl)allyl)-2-amino-8-oxo-7,8-dihydro-9H-purin-9-yl)-4-acetoxy-3-fluorotetrahydrofuran-2-yl)methyl acetate, Compound 316

Compound 316 can be prepared from ((2R,3R,4S,5R)-4-acetoxy-5-(7-allyl-2-amino-8-oxo-7,8-dihydro-9H-purin-9-yl)-3-fluorotetrahydrofuran-2-yl)methyl acetate and 5-vinyl-1H-tetrazole [18755-47-0] by an olefin metathesis-type reaction.

Example 317: 7-((E)-3-(1H-Tetrazol-5-yl)allyl)-2-amino-9-((2R,3S,4S,5R)-4-fluoro-3-hydroxy-5-(hydroxymethyl)tetrahydrofuran-2-yl)-7,9-dihydro-8H-purin-8-one, Compound 317

Compound 317 can be prepared by ester hydrolysis of Compound 316 according to the procedure outlined in Example 32.

Example 318: ((2R,3R,4S,5R)-4-Acetoxy-5-(2-amino-7-(4-formylbenzyl)-8-oxo-7,8-dihydro-9H-purin-9-yl)-3-fluorotetrahydrofuran-2-yl)methyl acetate, Compound 318

Compound 318 can be prepared according to the procedure outlined in Example 31 substituting propargyl bromide with 4-(bromomethyl)benzaldehyde.

Example 319: 4-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzaldehyde, Compound 319

Compound 319 can be prepared by ester hydrolysis of Compound 318 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-(bromomethyl)benzaldehyde.

Example 320: ((2R,3R,4S,5R)-4-Acetoxy-5-(2-amino-7-(4-methoxybenzyl)-8-oxo-7,8-dihydro-9H-purin-9-yl)-3-fluorotetrahydrofuran-2-yl)methyl acetate, Compound 320

Compound 320 can be prepared according to the procedure outlined in Example 31 substituting propargyl bromide with 4-methoxybenzyl bromide.

Example 321: 2-Amino-9-((2R,3S,4S,5R)-4-fluoro-3-hydroxy-5-(hydroxymethyl)tetrahydrofuran-2-yl)-7-(4-methoxybenzyl)-7,9-dihydro-8H-purin-8-one, Compound 321

Compound 321 can be prepared by ester hydrolysis of Compound 320 according to the procedure outlined in Example 32.

Example 322: ((2R,3R,4S,5R)-4-Acetoxy-5-(2-amino-7-(3-methoxybenzyl)-8-oxo-7,8-dihydro-9H-purin-9-yl)-3-fluorotetrahydrofuran-2-yl)methyl acetate, Compound 322

Compound 322 can be prepared according to the procedure outlined in Example 31 substituting propargyl bromide with 3-methoxybenzyl bromide.

Example 323: 2-Amino-9-((2R,3S,4S,5R)-4-fluoro-3-hydroxy-5-(hydroxymethyl)tetrahydrofuran-2-yl)-7-(3-methoxybenzyl)-7,9-dihydro-8H-purin-8-one, Compound 323

Compound 323 can be prepared by ester hydrolysis of Compound 322 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-methoxybenzyl bromide.

Example 324: ((2R,3R,4S,5R)-4-Acetoxy-5-(2-amino-7-(3-hydroxybenzyl)-8-oxo-7,8-dihydro-9H-purin-9-yl)-3-fluorotetrahydrofuran-2-yl)methyl acetate, Compound 324

Compound 324 can be prepared by demethylation of Compound 322 with $BBr_3$.

Example 325: 2-Amino-9-((2R,3S,4S,5R)-4-fluoro-3-hydroxy-5-(hydroxymethyl)tetrahydrofuran-2-yl)-7-(3-hydroxybenzyl)-7,9-dihydro-8H-purin-8-one, Compound 325

Compound 325 can be prepared by ester hydrolysis of Compound 324 according to the procedure outlined in Example 32.

Example 326: ((2R,3R,4S,5R)-4-Acetoxy-5-(2-amino-7-(4-trifluoromethylbenzyl)-8-oxo-7,8-dihydro-9H-purin-9-yl)-3-fluorotetrahydrofuran-2-yl)methyl acetate, Compound 326

Compound 326 can be prepared according to the procedure outlined in Example 31 substituting propargyl bromide with 4-trifluoromethyl-benzylbromide.

Example 327: 2-Amino-9-((2R,3S,4S,5R)-4-fluoro-3-hydroxy-5-(hydroxymethyl)tetrahydrofuran-2-yl)-7-(4-trifluoromethylbenzyl)-7,9-dihydro-8H-purin-8-one, Compound 327

Compound 327 can be prepared by ester hydrolysis of Compound 326 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-trifluoromethyl-benzylbromide.

Example 328: ((2R,3R,4S,5R)-4-Acetoxy-5-(2-amino-8-oxo-7-(pyridin-3-ylmethyl)-7,8-dihydro-9H-purin-9-yl)-3-fluorotetrahydrofuran-2-yl)methyl acetate, Compound 328

Compound 328 can be prepared according to the procedure outlined in Example 31 substituting propargyl bromide with 3-(bromomethyl)pyridine.

Example 329: 2-Amino-9-((2R,3S,4S,5R)-4-fluoro-3-hydroxy-5-(hydroxymethyl)tetrahydrofuran-2-yl)-7-(pyridin-3-ylmethyl)-7,9-dihydro-8H-purin-8-one, Compound 329

Compound 329 can be prepared by ester hydrolysis of Compound 328 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-(bromomethyl)pyridine.

Example 330: ((2R,3R,4S,5R)-4-Acetoxy-5-(2-amino-8-oxo-7-(2-oxo-2-(pyrrolidin-1-yl)ethyl)-7,8-dihydro-9H-purin-9-yl)-3-fluorotetrahydrofuran-2-yl)methyl acetate, Compound 330

Compound 330 can be prepared according to the procedure outlined in Example 31 substituting propargyl bromide with bromoacetopyrrolidine [90892-09-4].

Example 331: 2-Amino-9-((2R,3S,4S,5R)-4-fluoro-3-hydroxy-5-(hydroxymethyl)tetrahydrofuran-2-yl)-7-(2-oxo-2-(pyrrolidin-1-yl)ethyl)-7,9-dihydro-8H-purin-8-one, Compound 331

Compound 331 can be prepared by ester hydrolysis of Compound 330 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with bromoacetopyrrolidine.

Example 332: ((2R,3R,4S,5R)-4-Acetoxy-5-(7-allyl-2-amino-8-oxo-7,8-dihydro-9H-purin-9-yl)-3-fluorotetrahydrofuran-2-yl)methyl acetate, Compound 332

Compound 332 can be prepared according to the procedure outlined in Example 31 substituting propargyl bromide with allyl bromide.

Example 333: 7-Allyl-2-amino-9-((2R,3S,4S,5R)-4-fluoro-3-hydroxy-5-(hydroxymethyl)tetrahydrofuran-2-yl)-7,9-dihydro-8H-purin-8-one, Compound 333

Compound 333 can be prepared by ester hydrolysis of Compound 332 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with allyl bromide.

Example 334: ((2R,3R,4S,5R)-4-Acetoxy-5-(2-amino-7-(cyclopropylmethyl)-8-oxo-7,8-dihydro-9H-purin-9-yl)-3-fluorotetrahydrofuran-2-yl)methyl acetate, Compound 334

Compound 334 can be prepared according to the procedure outlined in Example 29 substituting propargyl bromide with (bromomethyl)cyclopropane.

Example 335: 2-Amino-7-(cyclopropylmethyl)-9-((2R,3S,4S,5R)-4-fluoro-3-hydroxy-5-(hydroxymethyl)tetrahydrofuran-2-yl)-7,9-dihydro-8H-purin-8-one Compound 335

Compound 335 can be prepared by ester hydrolysis of Compound 334 according to the procedure outlined in Example 32 or using the procedure described in Example 32A substituting (45) with (71).

Example 336: ((2R,3R,4S,5R)-4-Acetoxy-5-(2-amino-7-butyl-8-oxo-7,8-dihydro-9H-purin-9-yl)-3-fluorotetrahydrofuran-2-yl)methyl acetate, Compound 336

Compound 336 can be prepared according to the procedure outlined in Example 31 substituting propargyl bromide with n-butyl bromide.

Example 337: 2-Amino-7-butyl-9-((2R,3S,4S,5R)-4-fluoro-3-hydroxy-5-(hydroxymethyl)tetrahydrofuran-2-yl)-7,9-dihydro-8H-purin-8-one, Compound 337

Compound 337 can be prepared by ester hydrolysis of Compound 336 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with n-butyl bromide.

Example 338: ((2R,3R,4S,5R)-4-Acetoxy-5-(2-amino-7-(methoxymethyl)-8-oxo-7,8-dihydro-9H-purin-9-yl)-3-fluorotetrahydrofuran-2-yl)methyl acetate, Compound 338

Compound 338 can be prepared according to the procedure outlined in Example 31 substituting propargyl bromide with chloromethyl methyl ether.

Example 339: 2-Amino-9-((2R,3S,4S,5R)-4-fluoro-3-hydroxy-5-(hydroxymethyl)tetrahydrofuran-2-yl)-7-(methoxymethyl)-7,9-dihydro-8H-purin-8-one, Compound 339

Compound 339 can be prepared by ester hydrolysis of Compound 338 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with chloromethyl methyl ether.

Example 340: ((2R,3R,4S,5R)-4-Acetoxy-5-(2-amino-7-((methylthio)methyl)-8-oxo-7,8-dihydro-9H-purin-9-yl)-3-fluorotetrahydrofuran-2-yl)methyl acetate, Compound 340

Compound 340 can be prepared according to the procedure outlined in Example 31 substituting propargyl bromide with chloromethyl methyl sulfide.

Example 341: 2-Amino-9-((2R,3S,4S,5R)-4-fluoro-3-hydroxy-5-(hydroxymethyl)tetrahydrofuran-2-yl)-7-((methylthio)methyl)-7,9-dihydro-8H-purin-8-one, Compound 341

Compound 341 can be prepared by ester hydrolysis of Compound 340 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with chloromethyl methyl sulfide.

Example 342: ((2R,3R,4S,5R)-4-Acetoxy-5-(2-amino-8-oxo-7-(2,2,2-trifluoroethyl)-7,8-dihydro-9H-purin-9-yl)-3-fluorotetrahydrofuran-2-yl)methyl acetate, Compound 342

Compound 342 can be prepared according to the procedure outlined in Example 31 substituting propargyl bromide with 2-bromo-1,1,1-trifluoroethane [421-06-7].

Example 343: 2-Amino-9-((2R,3S,4S,5R)-4-fluoro-3-hydroxy-5-(hydroxymethyl)tetrahydrofuran-2-yl)-7-(2,2,2-trifluoroethyl)-7,9-dihydro-8H-purin-8-one, Compound 343

Compound 343 can be prepared by ester hydrolysis of Compound 342 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 2-bromo-1,1,1-trifluoroethane.

Example 344: ((2R,3R,4S,5R)-4-Acetoxy-5-(2-amino-7-(2,2-difluoroethyl)-8-oxo-7,8-dihydro-9H-purin-9-yl)-3-fluorotetrahydrofuran-2-yl)methyl acetate, Compound 344

Compound 344 can be prepared according to the procedure outlined in Example 31 substituting propargyl bromide with 2-bromo-1,1-difluoroethane [359-07-9].

Example 345: 2-Amino-7-(2,2-difluoroethyl)-9-((2R,3S,4S,5R)-4-fluoro-3-hydroxy-5-(hydroxymethyl)tetrahydrofuran-2-yl)-7,9-dihydro-8H-purin-8-one, Compound 345

Compound 345 can be prepared by ester hydrolysis of Compound 344 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 2-bromo-1,1-difluoroethane.

Example 346: ((2R,3R,4S,5R)-4-Acetoxy-5-(2-amino-8-oxo-7-(3,3,3-trifluoropropyl)-7,8-dihydro-9H-purin-9-yl)-3-fluorotetrahydrofuran-2-yl)methyl acetate, Compound 346

Compound 346 can be prepared according to the procedure outlined in Example 31 substituting propargyl bromide with 3-bromo-1,1,1-trifluoropropane [460-32-2].

Example 347: 2-Amino-9-((2R,3S,4S,5R)-4-fluoro-3-hydroxy-5-(hydroxymethyl)tetrahydrofuran-2-yl)-7-(3,3,3-trifluoropropyl)-7,9-dihydro-8H-purin-8-one, Compound 347

Compound 347 can be prepared by ester hydrolysis of Compound 346 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-bromo-1,1,1-trifluoropropane.

Example 348: ((2R,3R,4S,5R)-4-Acetoxy-5-(2-amino-8-oxo-7-(2,2,3,3,3-pentafluoropropyl)-7,8-dihydro-9H-purin-9-yl)-3-fluorotetrahydrofuran-2-yl)methyl acetate, Compound 348

Compound 348 can be prepared according to the procedure outlined in Example 31 substituting propargyl bromide with 3-bromo-1,1,1,2,2-pentafluoropropane [422-01-5] or 2,2,3,3,3-pentafluoropropyl methanesulfonate [813-31-0].

Example 349: 2-Amino-9-((2R,3S,4S,5R)-4-fluoro-3-hydroxy-5-(hydroxymethyl)tetrahydrofuran-2-yl)-7-(2,2,3,3,3-pentafluoropropyl)-7,9-dihydro-8H-purin-8-one, Compound 349

Compound 349 can be prepared by ester hydrolysis of Compound 348 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-bromo-1,1,1,2,2-pentafluoropropane or 2,2,3,3,3-pentafluoropropyl methanesulfonate.

Example 350: ((2R,3R,4S,5R)-4-Acetoxy-5-(2-amino-8-oxo-7-(4,4,4-trifluorobutyl)-7,8-dihydro-9H-purin-9-yl)-3-fluorotetrahydrofuran-2-yl)methyl acetate, Compound 350

Compound 350 can be prepared according to the procedure outlined in Example 31 substituting propargyl bromide with 4-bromo-1,1,1-trifluorobutane [406-81-5].

Example 351: 2-Amino-9-((2R,3S,4S,5R)-4-fluoro-3-hydroxy-5-(hydroxymethyl)tetrahydrofuran-2-yl)-7-(4,4,4-trifluorobutyl)-7,9-dihydro-8H-purin-8-one, Compound 351

Compound 351 can be prepared by ester hydrolysis of Compound 350 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-bromo-1,1,1-trifluorobutane.

Example 352: ((2R,3R,4S,5R)-4-Acetoxy-5-(2-amino-8-oxo-7-(3,3,4,4,4-pentafluorobutyl)-7,8-dihydro-9H-purin-9-yl)-3-fluorotetrahydrofuran-2-yl)methyl acetate, Compound 352

Compound 352 can be prepared according to the procedure outlined in Example 31 substituting propargyl bromide with 1,1,1,2,2-pentafluoro-4-bromobutane [52671-70-2].

Example 353: 2-Amino-9-((2R,3S,4S,5R)-4-fluoro-3-hydroxy-5-(hydroxymethyl)tetrahydrofuran-2-yl)-7-(3,3,4,4,4-pentafluorobutyl)-7,9-dihydro-8H-purin-8-one, Compound 353

Compound 353 can be prepared by ester hydrolysis of Compound 352 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 1,1,1,2,2-pentafluoro-4-bromobutane.

Example 354: ((2R,3R,4S,5R)-4-Acetoxy-5-(2-amino-7-(2-cyanoethyl)-8-oxo-7,8-dihydro-9H-purin-9-yl)-3-fluorotetrahydrofuran-2-yl)methyl acetate, Compound 354

Compound 354 can be prepared according to the procedure outlined in Example 31 substituting propargyl bromide with 3-bromopropanenitrile [2417-90-5].

Example 355: 3-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)propanenitrile, Compound 355

Compound 355 can be prepared by ester hydrolysis of Compound 354 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 3-bromopropanenitrile.

Example 356: ((2R,3R,4S,5R)-4-Acetoxy-5-(2-amino-7-(3-cyanopropyl)-8-oxo-7,8-dihydro-9H-purin-9-yl)-3-fluorotetrahydrofuran-2-yl)methyl acetate, Compound 356

Compound 356 can be prepared according to the procedure outlined in Example 31 substituting propargyl bromide with 4-bromobutanenitrile [5332-06-9].

Example 357: 4-(2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)butanenitrile, Compound 357

Compound 357 can be prepared by ester hydrolysis of Compound 356 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 4-bromobutanenitrile.

Example 358: ((2R,3R,4S,5R)-4-acetoxy-5-(2-amino-7-isobutyl-8-oxo-7,8-dihydro-9H-purin-9-yl)-3-fluorotetrahydrofuran-2-yl)methyl acetate, Compound 358

Compound 358 can be prepared according to the procedure outlined in Example 31 substituting propargyl bromide with 1-bromo-2-methylpropane.

Example 359: 2-Amino-9-((2R,3S,4S,5R)-4-fluoro-3-hydroxy-5-(hydroxymethyl)tetrahydrofuran-2-yl)-7-isobutyl-7,9-dihydro-8H-purin-8-one, Compound 359

Compound 359 can be prepared by ester hydrolysis of Compound 358 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with 1-bromo-2-methylpropane.

Example 360: ((2R,3R,4S,5R)-4-Acetoxy-5-(2-amino-7-((1-cyanocyclopropyl)methyl)-8-oxo-7,8-dihydro-9H-purin-9-yl)-3-fluorotetrahydrofuran-2-yl)methyl acetate, Compound 360

Compound 360 can be prepared according to the procedure outlined in Example 31 substituting propargyl bromide with the mesylate of 1-(hydroxymethyl)cyclopropane-1-carbonitrile [98730-77-9].

Example 361: 1-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carbonitrile, Compound 361

Compound 361 can be prepared by ester hydrolysis of Compound 360 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with the mesylate of 1-(hydroxymethyl)cyclopropane-1-carbonitrile.

Example 362: Ethyl 1-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)cyclopropane-1-carboxylate, Compound 362

Compound 362 can be prepared according to the procedure outlined in Example 31 substituting propargyl bromide with the mesylate of ethyl 1-(hydroxymethyl)cyclopropane-1-carboxylate [3697-68-5].

Example 363: Ethyl 1-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylate, Compound 363

Compound 363 can be prepared by exposure of Compound 362 to potassium carbonate in dry ethanol.

Example 364: 1-((2-Amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylic acid, Compound 364

Compound 364 can be prepared by ester hydrolysis of Compound 362 according to the procedure outlined in Example 32.

Example 365: ((2R,3R,4S,5R)-4-Acetoxy-5-(2-amino-8-oxo-7-((1-(trifluoromethyl)cyclopropyl)methyl)-7,8-dihydro-9H-purin-9-yl)-3-fluorotetrahydrofuran-2-yl)methyl acetate, Compound 365

Compound 365 can be prepared according to the procedure outlined in Example 31 substituting propargyl bromide with the mesylate of (1-(trifluoromethyl)cyclopropyl)methanol [371917-17-8].

Example 366: 2-Amino-9-((2R,3S,4S,5R)-4-fluoro-3-hydroxy-5-(hydroxymethyl)tetrahydrofuran-2-yl)-7-((1-(trifluoromethyl)cyclopropyl)methyl)-7,9-dihydro-8H-purin-8-one, Compound 366

Compound 366 can be prepared by ester hydrolysis of Compound 365 according to the procedure outlined in Example 32 or using the procedure described in Example 32A from N-(9-(4-methoxybenzyl)-8-oxo-8,9-dihydro-7H-purin-2-yl)acetamide, substituting propargyl bromide with the mesylate of (1-(trifluoromethyl)cyclopropyl)methanol.

Example 367. Activity of Compounds as TLR7 and TLR8 Agonists as Measured in Reporter Cell Assays The engagement of TLRs by cognate ligands triggers downstream signaling cascades, leading to the activation of NF-κB and other transcription factors which initiate various immunomodulatory effects. The human embryonic kidney cell line, HEK293, is essentially non-responsive to TLR agonists, but ectopic expression of TLRs in these cells allows cognate agonists to activate endogenous NF-κB. Accordingly, the HEK293-TLR-NF-κB inducible reporter system is used to assay TLR agonists. HEK293 cell lines stably expressing human TLR7 or TLR8 together with an NF-κB-driven-secreted alkaline phosphatase (SEAP) reporter were invented at InvivoGen (San Diego, CA, USA) and used to assess compounds of the present invention for TLR7 and TLR8 agonist activities. Cells were seeded at $2-5 \times 10^4$ cells/well in 96 well plates (200 μl/well) and treated with various concentrations of compound (10 μl) for 15-24 hours. SEAP activity was determined by measuring OD at 650 nm; the media used to culture the cell lines contains the reagents required for SEAP detection. The $EC_{50}$ values in Table 2 are calculated from fitting the dose response of measured SEAP activity for each compound to the following equation: $Y = y_{max} * c^{nh}/(EC_{50}{}^{nh} + c^{nh}) + blank$ where Y is the experimentally measured $OD_{650}$ at concentration c of test article, blank is the observed $OD_{650}$ in the absence of TLR7 agonist, $y_{max}$ is the difference between the measured $OD_{650}$ in the presence of either 28.5 μM resiquimod or 1.675 μM CL307 and the blank and values of $EC_{50}$ and nh are determined by nonlinear least squares analysis.

The results of testing of selected compounds in TLR7 reporter cells are shown in Table 2.

TABLE 2

| TLR7 Reporter Assay | |
|---|---|
| Compound | TLR7 Reporter $EC_{50}$ (μM) |
| loxoribine | 322 |
| 1 | 188 |
| 2 | 298 |
| 5 | 292 |
| 6 | 835 |
| 7 | 535 |
| 8 | 413 |
| 9 | 15 |
| 10 | 248 |
| 11 | 249 |
| 12 | 407 |
| 13 | 151 |
| 14 | 180 |
| 15 | >500* |
| 16 | 534 |
| 17 | 337 |
| 18 | 330 |
| 19 | 491 |
| 20 | 79 |
| 21 | 520 |
| 22 | 567 |
| 23 | >>500* |
| 26 | 519 |
| 27 | 376 |
| 28 | 470 |
| 33 | 688 |
| 34 | 512 |
| 35 | 1155 |
| 36 | 1208 |
| 37 | 564 |

*Measurable activity above baseline but <10% of $y_{max}$ was observed with compound 15 at 500 μM. No activity was observed at the same concentration with Compound 23. For all other compounds, activity at 500 μM was at least 15% of $y_{max}$.

None of the compounds listed in Table 2 displayed significant (>2.5% of $y_m$ax for TLR8 as measured at 28.5 μM resiquimod) activity in the TLR8 reporter cell assay at concentrations up to 500 μM. Substantial induction of SEAP production in the TLR8 reporter cell assay was observed upon incubation with resiquimod which is a known agonist of both TLR7 and TLR8.

Example 368. Induction of Interferon-α Production in hPBMCs (Human Peripheral Blood Mononuclear Cells)

Treatment of hPBMCs with a TLR7 agonist typically induces substantial production of interferon-α as well as lesser amounts of a variety of other cytokines and chemokines. A typical experiment uses hPBMCs isolated from a healthy donor and placed in replicate cell culture wells; typically $1.0-7.5 \times 10^6$ cells are placed in each well. Test compound is added and the cells cultured for 24 hours at 37° C. in a humidified atmosphere containing 5% $CO_2$ post-addition; untreated controls are included. Secreted interferon-α production is measured using an a multisubtype interferon-α ELISA kit like those from PBL Assay Sciences or specifically as $IFN\alpha_{2a}$ as part of a panel of cytokines and chemokines using luminex methodologies. The minimal effective concentration (MEC) is the minimum concentration in a dose response curve where a significant increase in interferon-α production (generally at least 20 pg/ml) is observed above baseline. MEC values for each compound are determined for at least three donors. The weighted MEC for each compound is the geometric mean of all individual MECs across all donors. Concentrations tested typically consist of a two-fold dilution series starting at 100 μM. In the calculation of weighted MEC, any value >100 μM is arbitrarily set to 200 μM unless all MECs for a compound exceed 100 μM When hPBMCs were treated with TLR7 agonists of the present invention and loxoribine, several induced interferon-α production as shown in Table 3. Compounds 5, 18, 26, 27, 28 and 34, all with weighted MEC values less than or equal to 40 μM and with all individual MEC values <100 μM, are of particular interest.

TABLE 3

Weighted MEC values from interferon-α production from hPBMCs in vitro upon incubation with TLR7 agonists

| Example | Weighted MEC (μM) |
| --- | --- |
| loxoribine | 136* |
| 1 | 66* |
| 2 | 79 |
| 5 | 34 |
| 6 | 79 |
| 7 | 63 |
| 8 | >100* |
| 9 | >100* |
| 10 | >100* |
| 11 | 79 |
| 12 | >100* |
| 13 | 66* |
| 14 | 100* |
| 16 | >100* |
| 17 | 100* |
| 18 | 37 |
| 19 | >100* |
| 20 | >100* |
| 21 | >100* |
| 22 | >100* |
| 26 | 31 |
| 27 | 23 |
| 28 | 33 |
| 33 | 79* |
| 34 | 40 |
| 35 | 79* |
| 36 | 100 |
| 37 | 50 |

*For loxoribine, 5 of 9 individual MEC values exceeded 100 μM. For Compound 1, 1 of 15 individual MEC values exceeded 100 μM. For Compound 13, 1 of 5 individual MEC values exceeded 100 μM. For Compounds 14, 33 and 35, 1 of 3 individual MEC values exceeded 100 μM. For Compound 17, 2 of 6 individual MEC values exceeded 100 μM. For compounds 8, 9, 10, 12, 16, 19, 20, 21 and 22, all individual MEC values exceeded 100 μM.

Example 369. Oral Bioavailability in Cynomolgus Monkeys

From two to four male or female cynomolgus monkeys were used for animal testing studies. The study compounds were formulated in a vehicle (e.g. 50 mM Phosphate Buffered Saline, pH 7.4) appropriate for animal oral or intravenous administration. Parent compounds 1, 5, 26 and 27 were administered at 1 mg/kg by IV administration whereas prodrugs of the corresponding compounds were administered at 2 mg/kg. After dosing, 0.5 mL blood samples were collected typically at 0.083, 0.33, 1, 2, 4, 6, 8, 12 and 24 hours post-dosing (iv administration) or 0.25, 0.5, 1, 2, 4, 6, 8, 12 and 24 hours post-dosing (oral administration). Plasma was separated from blood and analyzed for the active agonists by well-known LC-MS techniques. Area-under-the-curve (AUC) values were calculated for the time period 0-24 hrs and normalized for applied dose. Percent bioavailability (F %) of compounds when administered orally as prodrug was calculated from the ratio of dose-normalized AUC of parent from oral prodrug administration to that of dose-normalized parent AUC from IV parent administration and reported in Table 4.

Systemic delivery of compounds 1, 26 and 27 by prodrugs is substantially greater than loxoribine either administered orally as loxoribine itself or as prodrugs as described in Table 4. This is at least in part a function of the underlying agonist structure since the prodrug approach used with 7-allyl-2-amino-9-β-D-ribofuranosyl-7,9-dihydropurin-8-one is identical to that with prodrugs 4, 25, 30 and 32 herein.

TABLE 4

Percent bioavailability of TLR7 agonists administered as prodrugs (weight/weight basis)

| Parent TLR7 Agonist (Compound) | Corresponding Prodrug (Compound) | % F |
| --- | --- | --- |
| loxoribine[a] | N/A | 2%[b] |
| loxoribine[a] | 7-allyl-2-amino-9-β-D-ribofuranosyl-7,9-dihydropurin-8-one | 13% |
|  | 7-allyl-2-amino-6-ethoxy-9-β-D-ribofuranosyl-7,9-dihydropurin-8-one | 9% |
| 1 | 3 | 24% |
| 1 | 4 | 29% |
| 5 | 24 | 14% |
| 5 | 25 | 14% |
| 26 | 29 | 73% |
| 26 | 30 | 83% |
| 27 | 31 | 88% |
| 27 | 32 | 104% |

[a]Values from Table 23 of U.S. Pat. No. 7,575,068 B2
[b]Intrinsic bioavailability of loxoribine in cynomolgus monkeys.

Example 370. Antitumor Activity in Rodent Model

B16-F10 rodent melanoma tumor cells were injected into the flank of 32 mice in a syngenic model. The mice were divided into four treatment groups of eight animals each: (i) control (untreated) group (ii) Compound 5 (40 mg/kg, IV by tail vein, BID for five consecutive days with doses on each day administered ~8 hours apart; 10 total doses), (iii) Compound 5 (40 mg/kg, IV by tail vein, BID every other day with doses on each dosing day administered ~8 hours apart; 10 total doses), (iv) bropirimine (40 mg/kg by oral gavage, BID for five consecutive days with doses on each day administered ~8 hours apart, 10 total doses). Animals were randomized to groups when the average tumor volume was ~100 mm$^3$ (actual mean, 99 mm$^3$; minimum value, 60 mm$^3$; maximum size, 150 mm$^3$). Administration of the drugs was initiated on the following day. Tumor volumes were monitored for two weeks. Mean tumor growth inhibition (% TGI) versus the control group two weeks after randomization were 40%, 64% and 61% for groups (ii), (iii) and (iv), respectively. Mean % TGI was calculated from the following equation: Mean % TGI=[1−(T−T0)/(C−C0)]*100% where T=mean group tumor volume at D14, T0=mean group tumor volume at D0, C=mean control group tumor volume at D14 and C0=mean control group tumor volume at D0. Animal weight gain during the course of the study was normal and no adverse events were observed.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A compound having the structure of Formula I:

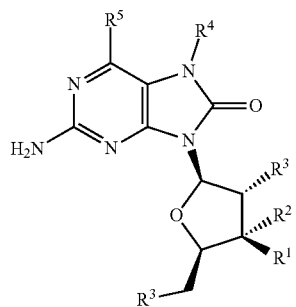

I or a pharmaceutically acceptable salt, solvate or hydrate thereof,
wherein:
$R^1$ is —H, —F, —OH, or —OC(O)$R^6$;
$R^2$ is —F;
$R^3$ is —OH or —OC(O)$R^7$;
$R^4$ is —$C_1$-$C_8$ alkyl, —$C_2$-$C_8$ alkenyl, —$C_2$-$C_8$ alkynyl, —$(CH_2)_nC(O)OR^6$, —$(CH_2)_n$cycloalkyl, —$(CH_2)_n$heterocyclyl, —$(CH_2)_n$aryl, or —$(CH_2)_n$heteroaryl;
    wherein the —$C_1$-$C_8$ alkyl, —$C_2$-$C_8$ alkenyl, or —$C_2$-$C_8$ alkynyl is optionally substituted with one or more substituents independently selected from halogen, —CN, —$NO_2$, —C(O)$R^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl, —O(alkylene)-aryl, —O(alkylene)-heteroaryl, —S$C_1$-$C_8$ alkyl, —S(O)alkyl, —S(O)$_2$alkyl, aryl, and heteroaryl;
    wherein the cycloalkyl of —$(CH_2)_n$cycloalkyl, heterocyclyl of —$(CH_2)_n$heterocyclyl, aryl of —$(CH_2)_n$aryl, or heteroaryl of —$(CH_2)_n$heteroaryl is optionally substituted with one or more substituents independently selected from halogen, —CN, —$NO_2$, —$C_1$-$C_3$ alkyl, —$C_1$-$C_3$ haloalkyl, alkenyl, alkynyl, —C(O)R$^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl,
—O(alkylene)-aryl, —O(alkylene)-heteroaryl, —S$C_1$-$C_8$ alkyl, —S(O)alkyl, —S(O)$_2$alkyl, aryl, and heteroaryl;
$R^5$ is —H, —Cl, —OH, —OCH$_3$, or —SH;
each $R^6$ is independently —$C_1$-$C_8$ alkyl or aryl;
    wherein each —$C_1$-$C_8$ alkyl is optionally and independently substituted with one or more substituents independently selected from halogen, —CN, —$NO_2$, —C(O)R$^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl, —O(alkylene)-aryl, —O(alkylene)-heteroaryl, —S$C_1$-$C_8$ alkyl, —S(O)alkyl, —S(O)$_2$alkyl, aryl, and heteroaryl; and
    wherein each aryl is optionally and independently substituted with one or more substituents independently selected from halogen, —CN, —$NO_2$, —$C_1$-$C_3$ alkyl, —$C_1$-$C_3$ haloalkyl, alkenyl, alkynyl, —C(O)R$^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl, —O(alkylene)-aryl, —O(alkylene)-heteroaryl, —S$C_1$-$C_8$ alkyl, —S(O)alkyl, —S(O)$_2$alkyl, aryl, and heteroaryl;
$R^7$ is —$C_1$-$C_8$ alkyl or aryl;
    wherein the —$C_1$-$C_8$ alkyl is optionally substituted with one or more substituents independently selected from halogen, —CN, —$NO_2$, —C(O)R$^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl, —O(alkylene)-aryl, —O(alkylene)-heteroaryl, —S$C_1$-$C_8$ alkyl, —S(O)alkyl, —S(O)$_2$alkyl, aryl, and heteroaryl; and
    wherein the aryl is optionally substituted with one or more substituents independently selected from halogen, —CN, —$NO_2$, —$C_1$-$C_3$ alkyl, —$C_1$-$C_3$ haloalkyl, alkenyl, alkynyl, —C(O)R$^8$, —C(O)NR$^8$R$^8$, —C(O)NR$^8$S(O)$_2$alkyl, —C(O)OR$^8$, —NR$^8$R$^8$, —NHC(O)R$^8$, —NR$^8$C(O)OR$^8$, —NHS(O)$_2$alkyl, —NHS(O)$_2$NR$^8$R$^8$, —OH, —O$C_1$-$C_3$ alkyl, —O(alkylene)-aryl, —O(alkylene)-heteroaryl, —S$C_1$-$C_8$ alkyl, —S(O)alkyl, —S(O)$_2$alkyl, aryl, and heteroaryl;
each $R^8$ is independently —H, —$C_1$-$C_8$ alkyl, —OH, cycloalkyl, or heterocyclyl; or
$R^8$ and $R^8$, together with the nitrogen atom to which they are attached, form a heterocyclyl; and
n is an integer 1, 2, 3, 4, or 5.

2. The compound of claim 1, or a pharmaceutically acceptable salt, solvate or hydrate thereof, wherein $R^1$ is —H.

3. The compound of claim 2, or a pharmaceutically acceptable salt, solvate or hydrate thereof, wherein:
$R^3$ is —OH; and
$R^5$ is —H or —OH.

4. The compound of claim 2, or a pharmaceutically acceptable salt, solvate or hydrate thereof, wherein:
$R^3$ is —OC(O)$R^7$;
$R^5$ is —H; and
$R^7$ is —CH$_3$.

5. The compound of claim 1, or a pharmaceutically acceptable salt, solvate or hydrate thereof, wherein $R^4$ is —$(CH_2)_n$aryl or —$(CH_2)_n$heteroaryl.

6. The compound of claim 1, or a pharmaceutically acceptable salt, solvate or hydrate thereof, wherein $R^4$ is —$(CH_2)_n$aryl.

7. The compound of claim 1, or a pharmaceutically acceptable salt, solvate or pharmaceutically acceptable hydrate thereof, wherein $R^4$ is —$CH_2CH_2CH_2CH_3$, —$CH_2CF_3$, —$CH_2C\equiv CH$, or —$CH_2$-cyclopropyl.

8. The compound of claim 1, or a pharmaceutically acceptable salt, solvate or hydrate thereof, wherein each $R^8$ is independently —H, —$CH_3$, —$CH_2CH_3$, or —OH.

9. The compound of claim 1, or a pharmaceutically acceptable salt, solvate or hydrate thereof, wherein the compound is selected from the group consisting of:

2-amino-7-benzyl-9-((2R,3S,4S,5R)-4-fluoro-3-hydroxy-5-(hydroxymethyl)tetrahydrofuran-2-yl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(4-fluorobenzyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(3-fluorobenzyl)-7,9-dihydro-1H-purine-6,8-dione;

2-amino-7-(3,4-difluorobenzyl)-9-((2R,3S,4S,5R)-4-fluoro-3-hydroxy-5-(hydroxymethyl)tetrahydrofuran-2-yl)-7,9-dihydro-1H-purine-6,8-dione;

2-amino-7-(4-chlorobenzyl)-9-((2R,3S,4S,5R)-4-fluoro-3-hydroxy-5-(hydroxymethyl)tetrahydrofuran-2-yl)-7,9-dihydro-1H-purine-6,8-dione;

2-amino-7-(3-chlorobenzyl)-9-((2R,3S,4S,5R)-4-fluoro-3-hydroxy-5-(hydroxymethyl)tetrahydrofuran-2-yl)-7,9-dihydro-1H-purine-6,8-dione;

2-amino-7-(3,4-dichlorobenzyl)-9-((2R,3S,4S,5R)-4-fluoro-3-hydroxy-5-(hydroxymethyl)tetrahydrofuran-2-yl)-7,9-dihydro-1H-purine-6,8-dione;

4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzonitrile;

3-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzonitrile;

4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid;

methyl 4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate;

3-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid;

methyl 3-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate;

2-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoic acid;

methyl 2-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzoate;

2-amino-7-(E)-cinnamyl-9-((2R,3S,4S,5R)-4-fluoro-3-hydroxy-5-(hydroxymethyl)tetrahydrofuran-2-yl)-7,9-dihydro-1H-purine-6,8-dione;

7-((1H-pyrazol-5-yl)methyl)-2-amino-9-((2R,3S,4S,5R)-4-fluoro-3-hydroxy-5-(hydroxymethyl)tetrahydrofuran-2-yl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-((1-methyl-1H-pyrazol-3-yl)methyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(thiophen-2-ylmethyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(thiophen-3-ylmethyl)-7,9-dihydro-1H-purine-6,8-dione;

2-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetic acid;

2-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetonitrile;

2-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)acetaldehyde;

7-((1H-tetrazol-5-yl)methyl)-2-amino-9-((2R,3S,4S,5R)-4-fluoro-3-hydroxy-5-(hydroxymethyl)tetrahydrofuran-2-yl)-7,9-dihydro-1H-purine-6,8-dione;

2-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)-N-(methylsulfonyl)acetamide;

2-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)-N-hydroxyacetamide;

2-amino-9-((2R,3S,4S,5R)-4-fluoro-3-hydroxy-5-(hydroxymethyl)tetrahydrofuran-2-yl)-7-((3-hydroxyisoxazol-5-yl)methyl)-7,9-dihydro-1H-purine-6,8-dione;

5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid;

methyl 5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylate;

5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-3-carboxylic acid;

ethyl 5-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-3-carboxylate;

4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylic acid;

methyl 4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)thiophene-2-carboxylate;

(1R,2R)-2-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid;

7-((E)-3-(1H-tetrazol-5-yl)allyl)-2-amino-9-((2R,3S,4S,5R)-4-fluoro-3-hydroxy-5-(hydroxymethyl)tetrahydrofuran-2-yl)-7,9-dihydro-1H-purine-6,8-dione;

4-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)benzaldehyde;

2-amino-9-((2R,3S,4S,5R)-4-fluoro-3-hydroxy-5-(hydroxymethyl)tetrahydrofuran-2-yl)-7-(4-methoxybenzyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(3-methoxybenzyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(3-hydroxybenzyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(4-(trifluoromethyl)benzyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(pyridin-3-ylmethyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(2-oxo-2-(pyrrolidin-1-yl)ethyl)-7,9-dihydro-1H-purine-6,8-dione;

7-allyl-2-amino-9-((2R,3S,4S,5R)-4-fluoro-3-hydroxy-5-(hydroxymethyl)tetrahydrofuran-2-yl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(methoxymethyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-((methylthio)methyl)-7,9-dihydro-1H-purine-6,8-dione;

2-amino-7-(2,2-difluoroethyl)-9-((2R,3S,4S,5R)-4-fluoro-3-hydroxy-5-(hydroxymethyl)tetrahydrofuran-2-yl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(3,3,3-trifluoropropyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(2,2,3,3,3-pentafluoropropyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(4,4,4-trifluorobutyl)-7,9-dihydro-1H-purine-6,8-dione;

2-amino-9-((2R,3S,4S,5R)-4-fluoro-3-hydroxy-5-(hydroxymethyl)tetrahydrofuran-2-yl)-7-(3,3,4,4,4-pentafluorobutyl)-7,9-dihydro-1H-purine-6,8-dione;

3-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)propanenitrile;

4-(2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)butanenitrile;

2-amino-9-((2R,3S,4S,5R)-4-fluoro-3-hydroxy-5-(hydroxymethyl)tetrahydrofuran-2-yl)-7-isobutyl-7,9-dihydro-1H-purine-6,8-dione;

1-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carbonitrile;

1-((2-amino-9-((2R,3S,4S,5R)-4-fluoro-3-hydroxy-5-(hydroxymethyl)tetrahydrofuran-2-yl)-6,8-dioxo-1,6,8,9-tetrahydro-7H-purin-7-yl)methyl)cyclopropane-1-carboxylic acid;

2-amino-9-((2R,3S,4S,5R)-4-fluoro-3-hydroxy-5-(hydroxymethyl)tetrahydrofuran-2-yl)-7-((1-(trifluoromethyl)cyclopropyl)methyl)-7,9-dihydro-1H-purine-6,8-dione;

((2R,3R,4S,5R)-4-acetoxy-5-(2-amino-7-benzyl-8-oxo-7,8-dihydro-9H-purin-9-yl)-3-fluorotetrahydrofuran-2-yl)methyl acetate;

2-amino-7-benzyl-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(4-fluorobenzyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(4-fluorobenzyl)-7,9-dihydro-8H-purin-8-one;

((2R,3R,4S,5R)-4-acetoxy-5-(2-amino-7-(3-fluorobenzyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(3-fluorobenzyl)-7,9-dihydro-8H-purin-8-one;

((2R,3R,4S,5R)-4-acetoxy-5-(2-amino-7-(3,4-difluorobenzyl)-8-oxo-7,8-dihydro-9H-purin-9-yl)-3-fluorotetrahydrofuran-2-yl)methyl acetate;

2-amino-7-(3,4-difluorobenzyl)-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(4-chlorobenzyl)-8-oxo-7,8-dihydro-9H-purin-9-yl)-3-fluorotetrahydrofuran-2-yl)methyl acetate;

2-amino-7-(4-chlorobenzyl)-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(3-chlorobenzyl)-8-oxo-7,8-dihydro-9H-purin-9-yl)-3-fluorotetrahydrofuran-2-yl)methyl acetate;

2-amino-7-(3-chlorobenzyl)-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(3,4-dichlorobenzyl)-8-oxo-7,8-dihydro-9H-purin-9-yl)-3-fluorotetrahydrofuran-2-yl)methyl acetate;

2-amino-7-(3,4-dichlorobenzyl)-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(4-cyanobenzyl)-8-oxo-7,8-dihydro-9H-purin-9-yl)-3-fluorotetrahydrofuran-2-yl)methyl acetate;

4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzonitrile;

((2R,3R,4S,5R)-4-acetoxy-5-(2-amino-7-(3-cyanobenzyl)-8-oxo-7,8-dihydro-9H-purin-9-yl)-3-fluorotetrahydrofuran-2-yl)methyl acetate;

3-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzonitrile;

4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoic acid;

4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid;

methyl 4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate;

methyl 4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate;

3-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoic acid;

3-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid;

methyl 3-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate;

methyl 3-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate;

2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoic acid;

2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoic acid;

methyl 2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)benzoate;

methyl 2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzoate;

((2R,3R,4S,5R)-4-acetoxy-5-(2-amino-7-(E)-cinnamyl-8-oxo-7,8-dihydro-9H-purin-9-yl)-3-fluorotetrahydrofuran-2-yl)methyl acetate;

2-amino-7-(E)-cinnamyl-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-5-(7-((1H-pyrazol-5-yl)methyl)-2-amino-8-oxo-7,8-dihydro-9H-purin-9-yl)-4-acetoxy-3-fluorotetrahydrofuran-2-yl)methyl acetate;

7-((1H-pyrazol-5-yl)methyl)-2-amino-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-((1-methyl-1H-pyrazol-3-yl)methyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-((1-methyl-1H-pyrazol-3-yl)methyl)-7,9-dihydro-8H-purin-8-one;

((2R,3R,4S,5R)-4-acetoxy-5-(2-amino-8-oxo-7-(thiophen-2-ylmethyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(thiophen-2-ylmethyl)-7,9-dihydro-8H-purin-8-one;

((2R,3R,4S,5R)-4-acetoxy-5-(2-amino-8-oxo-7-(thiophen-3-ylmethyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(thiophen-3-ylmethyl)-7,9-dihydro-8H-purin-8-one;

methyl 2-(9-((2R,3S,4R,5R)-3-acetoxy-5-(acetoxymethyl)-4-fluorotetrahydrofuran-2-yl)-2-amino-8-oxo-8,9-dihydro-7H-purin-7-yl)acetate;

methyl 2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetate;

2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetic acid;

((2R,3R,4S,5R)-4-acetoxy-5-(2-amino-7-(cyanomethyl)-8-oxo-7,8-dihydro-9H-purin-9-yl)-3-fluorotetrahydrofuran-2-yl)methyl acetate;

2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetonitrile;

((2R,3R,4S,5R)-4-acetoxy-5-(2-amino-8-oxo-7-(2-oxoethyl)-7,8-dihydro-9H-purin-9-yl)-3-fluorotetrahydrofuran-2-yl)methyl acetate;

2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)acetaldehyde;

((2R,3R,4S,5R)-5-(7-((1H-tetrazol-5-yl)methyl)-2-amino-8-oxo-7,8-dihydro-9H-purin-9-yl)-4-acetoxy-3-fluorotetrahydrofuran-2-yl)methyl acetate;

7-((1H-tetrazol-5-yl)methyl)-2-amino-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(2-(methylsulfonamido)-2-oxoethyl)-8-oxo-7,8-dihydro-9H-purin-9-yl)-3-fluorotetrahydrofuran-2-yl)methyl acetate;

2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)-N-(methylsulfonyl)acetamide;

((2R,3R,4S,5R)-4-acetoxy-5-(2-amino-7-(2-(hydroxyamino)-2-oxoethyl)-8-oxo-7,8-dihydro-9H-purin-9-yl)-3-fluorotetrahydrofuran-2-yl)methyl acetate;

2-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)-N-hydroxyacetamide;

((2R,3R,4S,5R)-4-acetoxy-5-(2-amino-7-((3-hydroxyisoxazol-5-yl)methyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-((3-hydroxyisoxazol-5-yl)methyl)-7,9-dihydro-8H-purin-8-one;

5-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-2-carboxylic acid;

5-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylic acid;

methyl 5-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-2-carboxylate;

methyl 5-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylate;

5-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-3-carboxylic acid;

5-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-3-carboxylic acid;

ethyl 5-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-3-carboxylate;

ethyl 5-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-3-carboxylate;

4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-2-carboxylic acid;

4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylic acid;

methyl 4-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)thiophene-2-carboxylate;

methyl 4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)thiophene-2-carboxylate;

ethyl (1R,2R)-2-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)cyclopropane-1-carboxylate;

ethyl (1R,2R)-2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylate;

(1R,2R)-2-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylic acid;

((2R,3R,4S,5R)-5-(7-((E)-3-(1H-tetrazol-5-yl)allyl)-2-amino-8-oxo-7,8-dihydro-9H-purin-9-yl)-4-acetoxy-3-fluorotetrahydrofuran-2-yl)methyl acetate;

7-((E)-3-(1H-tetrazol-5-yl)allyl)-2-amino-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(4-formylbenzyl)-8-oxo-7,8-dihydro-9H-purin-9-yl)-3-fluorotetrahydrofuran-2-yl)methyl acetate;

4-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)benzaldehyde;

((2R,3R,4S,5R)-4-acetoxy-5-(2-amino-7-(4-methoxybenzyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(4-methoxybenzyl)-7,9-dihydro-8H-purin-8-one;

((2R,3R,4S,5R)-4-acetoxy-5-(2-amino-7-(3-methoxybenzyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(3-methoxybenzyl)-7,9-dihydro-8H-purin-8-one;

((2R,3R,4S,5R)-4-acetoxy-5-(2-amino-7-(3-hydroxybenzyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(3-hydroxybenzyl)-7,9-dihydro-8H-purin-8-one;

((2R,3R,4S,5R)-4-acetoxy-5-(2-amino-8-oxo-7-(4-(trifluoromethyl)benzyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(4-(trifluoromethyl)benzyl)-7,9-dihydro-8H-purin-8-one;

((2R,3R,4S,5R)-4-acetoxy-5-(2-amino-8-oxo-7-(pyridin-3-ylmethyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(pyridin-3-ylmethyl)-7,9-dihydro-8H-purin-8-one;

((2R,3R,4S,5R)-4-acetoxy-5-(2-amino-8-oxo-7-(2-oxo-2-(pyrrolidin-1-yl)ethyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(2-oxo-2-(pyrrolidin-1-yl)ethyl)-7,9-dihydro-8H-purin-8-one;

((2R,3R,4S,5R)-4-acetoxy-5-(7-allyl-2-amino-8-oxo-7,8-dihydro-9H-purin-9-yl)-3-fluorotetrahydrofuran-2-yl)methyl acetate;

7-allyl-2-amino-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-7-(methoxymethyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(methoxymethyl)-7,9-dihydro-8H-purin-8-one;

((2R,3R,4S,5R)-4-acetoxy-5-(2-amino-7-((methylthio)methyl)-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-((methylthio)methyl)-7,9-dihydro-8H-purin-8-one;

((2R,3R,4S,5R)-4-acetoxy-5-(2-amino-7-(2,2-difluoroethyl)-8-oxo-7,8-dihydro-9H-purin-9-yl)-3-fluorotetrahydrofuran-2-yl)methyl acetate;

2-amino-7-(2,2-difluoroethyl)-9-((2R,3S,4S,5R)-4-fluoro-3-hydroxy-5-(hydroxymethyl)tetrahydrofuran-2-yl)-7,9-dihydro-8H-purin-8-one;

((2R,3R,4S,5R)-4-acetoxy-5-(2-amino-8-oxo-7-(3,3,3-trifluoropropyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(3,3,3-trifluoropropyl)-7,9-dihydro-8H-purin-8-one;

((2R,3R,4S,5R)-4-acetoxy-5-(2-amino-8-oxo-7-(2,2,3,3,3-pentafluoropropyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(2,2,3,3,3-pentafluoropropyl)-7,9-dihydro-8H-purin-8-one;

((2R,3R,4S,5R)-4-acetoxy-5-(2-amino-8-oxo-7-(4,4,4-trifluorobutyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(4,4,4-trifluorobutyl)-7,9-dihydro-8H-purin-8-one;

((2R,3R,4S,5R)-4-acetoxy-5-(2-amino-8-oxo-7-(3,3,4,4,4-pentafluorobutyl)-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-(3,3,4,4,4-pentafluorobutyl)-7,9-dihydro-8H-purin-8-one;

((2R,3R,4S,5R)-4-acetoxy-5-(2-amino-7-(2-cyanoethyl)-8-oxo-7,8-dihydro-9H-purin-9-yl)-3-fluorotetrahydrofuran-2-yl)methyl acetate;

3-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)propanenitrile;

((2R,3R,4S,5R)-4-acetoxy-5-(2-amino-7-(3-cyanopropyl)-8-oxo-7,8-dihydro-9H-purin-9-yl)-3-fluorotetrahydrofuran-2-yl)methyl acetate;

4-(2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)butanenitrile;

((2R,3R,4S,5R)-4-acetoxy-5-(2-amino-7-isobutyl-8-oxo-7,8-dihydro-9H-purin-9-yl)-3-fluorotetrahydrofuran-2-yl)methyl acetate;

2-amino-9-((2R,3S,4S,5R)-4-fluoro-3-hydroxy-5-(hydroxymethyl)tetrahydrofuran-2-yl)-7-isobutyl-7,9-dihydro-8H-purin-8-one;

((2R,3R,4S,5R)-4-acetoxy-5-(2-amino-7-((1-cyanocyclopropyl)methyl)-8-oxo-7,8-dihydro-9H-purin-9-yl)-3-fluorotetrahydrofuran-2-yl)methyl acetate;

1-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carbonitrile;

ethyl 1-((9-((2R,3S,4R,5R)-3-acetoxy-5-(acetoxymethyl)-4-fluorotetrahydrofuran-2-yl)-2-amino-8-oxo-8,9-dihydro-7H-purin-7-yl)methyl)cyclopropane-1-carboxylate;

ethyl 1-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylate;

1-((2-amino-9-((2R,3S,4S,5R)-4-fluoro-3-hydroxy-5-(hydroxymethyl)tetrahydrofuran-2-yl)-8-oxo-8,9-dihydro-7H-purin-7-yl)methyl)cyclopropane-1-carboxylic acid;

((2R,3R,4S,5R)-4-acetoxy-5-(2-amino-8-oxo-7-((1-(trifluoromethyl)cyclopropyl)methyl)-7,8-dihydro-9H-purin-9-yl)-3-fluorotetrahydrofuran-2-yl)methyl acetate; and, 2-amino-9-((2R,3S,4S,5R)-4-fluoro-3-hydroxy-5-(hydroxymethyl)tetrahydrofuran-2-yl)-7-((1-(trifluoromethyl)cyclopropyl)methyl)-7,9-dihydro-8H-purin-8-one.

10. A pharmaceutical composition comprising a compound of claim 1, or a pharmaceutically acceptable salt, solvate, or hydrate thereof, and a pharmaceutically acceptable excipient.

11. The pharmaceutical composition of claim 10 further comprising one or more additional agents, wherein the one or more additional agents are selected from a 4-1BB agonist, a glucocorticoid-induced tumor necrosis factor receptor-related protein (GITR) agonist, an immune checkpoint inhibitor, an inducible T-cell co-stimulator (ICOS) agonist, an interleukin-2 (IL-2) receptor agonist and an OX40 agonist.

12. The pharmaceutical composition of claim 11, wherein the one or more additional agents are selected from a cluster of a differentiation 47 (CD47) inhibitor, a cytotoxic T-lymphocyte-associated protein 4 (CTLA4) inhibitor, a lymphocyte-activation gene 3 (LAG3) inhibitor, a programmed cell death ligand 1 (PD-L1) inhibitor, a programmed cell death protein 1 (PD-1) inhibitor, a signal-regulatory protein α (SIRPα) inhibitor and a T-cell immunoglobulin domain and mucin domain-containing protein 3 (TIM3) inhibitor.

13. The pharmaceutical composition of claim 10 further comprising one or more additional agents, wherein the one or more additional agents are independently an antibody mediated by antibody-dependent cellular cytotoxicity (ADCC).

14. The pharmaceutical composition of claim 13, wherein the antibody mediated by ADCC is selected from alemtuzumab, rituximab and trastuzumab.

* * * * *